US012662475B2

(12) United States Patent
Chovatia et al.

(10) Patent No.: US 12,662,475 B2
(45) Date of Patent: Jun. 23, 2026

(54) DIFLUOROCYCLOHEXYL DERIVATIVES AS IL-17 MODULATORS

(71) Applicant: UCB BIOPHARMA SRL, Brussels (BE)

(72) Inventors: Prafulkumar Tulshibhai Chovatia, Abingdon (GB); Anne Marie Foley, Slough (GB); Martin Clive Hutchings, Slough (GB); James Andrew Johnson, Slough (GB); Fabien Claude Lecomte, Slough (GB); Nathaniel Julius Thomas Monck, Abingdon (GB); James Thomas Reuberson, Slough (GB); Adam Peter Smalley, Slough (GB); Darshan Gunvant Vaidya, Abingdon (GB)

(73) Assignee: UCB BIOPHARMA SRL, Brussels (BE)

( * ) Notice: Subject to any disclaimer, the term of this patent is extended or adjusted under 35 U.S.C. 154(b) by 719 days.

(21) Appl. No.: 17/995,495

(22) PCT Filed: Apr. 6, 2021

(86) PCT No.: PCT/EP2021/058940
§ 371 (c)(1),
(2) Date: Oct. 5, 2022

(87) PCT Pub. No.: WO2021/204801
PCT Pub. Date: Oct. 14, 2021

(65) Prior Publication Data

US 2023/0271951 A1 Aug. 31, 2023

(30) Foreign Application Priority Data

Apr. 7, 2020 (GB) .................................... 2005153
Jun. 24, 2020 (GB) .................................... 2009617

(51) Int. Cl.

| | |
|---|---|
| ***C07D 413/14*** | (2006.01) |
| ***A61K 45/06*** | (2006.01) |
| ***C07D 235/24*** | (2006.01) |
| ***C07D 403/12*** | (2006.01) |
| ***C07D 403/14*** | (2006.01) |
| ***C07D 413/12*** | (2006.01) |
| ***C07D 471/04*** | (2006.01) |

(52) U.S. Cl.
CPC ........... *C07D 413/14* (2013.01); *A61K 45/06* (2013.01); *C07D 235/24* (2013.01); *C07D 403/12* (2013.01); *C07D 403/14* (2013.01); *C07D 413/12* (2013.01); *C07D 471/04* (2013.01)

(58) Field of Classification Search
None
See application file for complete search history.

(56) References Cited

FOREIGN PATENT DOCUMENTS

| | | | |
|---|---|---|---|
| JP | 2011-507851 | 3/2011 | |
| JP | 2015-515976 | 6/2015 | |
| WO | 2009/089036 | 7/2009 | |
| WO | 2013/116682 | 8/2013 | |
| WO | 2014/066726 | 5/2014 | |
| WO | 2018/229079 | 12/2018 | |
| WO | 2019/138017 | 7/2019 | |
| WO | 2019/213470 | 11/2019 | |
| WO | 2019/223718 | 11/2019 | |
| WO | 2020/011731 | 1/2020 | |
| WO | 2020/120140 | 6/2020 | |
| WO | 2020/120141 | 6/2020 | |
| WO | 2020/260425 | 12/2020 | |
| WO | 2020/260426 | 12/2020 | |
| WO | 2020/261141 | 12/2020 | |
| WO | WO-2021027724 A1 * | 2/2021 | ........... C07D 405/04 |
| WO | WO2021/098844 * | 5/2021 | |
| WO | WO-2021098844 A1 * | 5/2021 | ........... C07D 409/12 |

OTHER PUBLICATIONS

The International Search Report (ISR) with Written Opinion for PCT/EP2021/058940 dated Apr. 23, 2021, pp. 1-11.
Faour, Wissam H. et al. "T-cell-derived Interleukin-17 Regulates the Level and Stability of Cyclooxygenase-2 (COX-2) mRNA through Restricted Activation of the p38 Mitogen-activated Protein Kinase Cascade" Journal of Biological Chemistry (2003) vol. 278(29), pp. 26897-26907.
Gaffen, Sarah L. "An overview of IL-17 function and signaling" Cytokine (2008) vol. 43, pp. 402-407.
Korn et al. "IL-17 and Th17 Cells" Annu. Rev. Immunol. (2009) vol. 27, pp. 485-517.
Moseley et al. "Interleukin-17 family and IL-17 receptors" Cytokine Growth Factor Rev. (2003) vol. 14, pp. 155-174.
Rouvier et al. "CTLA-8, cloned from an activated T cell, bearing AU-rich messenger RNA instability sequences, and homologous to a herpesvirus saimiri gene" J. Immunol. (1993) vol. 150, pp. 5445-5456,.
Wright et al. "The human IL17/IL-17A Heterodimeric Cytokine Signals through the IL-17RA/IL-17RC Receptor Complex" J. Immunol. (2008) vol. 181, pp. 2799-2805.
English Translation of Japanese Office Action for JP 2022-561194 dated Dec. 24, 2024, pp. 1-3.
Faour, Wissam H. et al. "T-cell-derived Interleukin-17 Regulates the Level and Stability of Cyclooxygenase-2 (COX-2) mRNA through Restricted Activation of the p38 Mitogen-activated Protein Kinase Cascade" The Journal of Biological Chemistry (2003) vol. 278(29), pp. 26897-26907.

* cited by examiner

*Primary Examiner* — Jeffrey S Lundgren
*Assistant Examiner* — Sara Elizabeth Townsley
(74) *Attorney, Agent, or Firm* — McDonnell Boehnen Hulbert & Berghoff LLP

(57) ABSTRACT

A series of substituted 4,4-difluorocyclohexyl derivatives as defined herein, being potent modulators of human IL-17 activity, are accordingly of benefit in the treatment and/or prevention of various human ailments, including inflammatory and autoimmune disorders.

9 Claims, No Drawings

DIFLUOROCYCLOHEXYL DERIVATIVES AS IL-17 MODULATORS

CROSS-REFERENCE TO RELATED APPLICATIONS

This application is a U.S. national phase of International Application No. PCT/EP2021/058940, filed Apr. 6, 2021, which claims priority from Great Britain Application No. 2005153.8, filed Apr. 7, 2020, and Great Britain Application No. 2009617.8, filed Jun. 24, 2020, the disclosure of each of which is hereby incorporated by reference in its entirety.

The present invention relates to heterocyclic compounds, and to their use in therapy. More particularly, this invention is concerned with pharmacologically active substituted 4,4-difluorocyclohexyl derivatives. These compounds act as modulators of IL-17 activity, and are accordingly of benefit as pharmaceutical agents for the treatment and/or prevention of pathological conditions, including adverse inflammatory and autoimmune disorders.

IL-17A (originally named CTLA-8 and also known as IL-17) is a pro-inflammatory cytokine and the founder member of the IL-17 family (Rouvier et al., *J. Immunol.,* 1993, 150, 5445-5456). Subsequently, five additional members of the family (IL-17B to IL-17F) have been identified, including the most closely related, IL-17F (ML-1), which shares approximately 55% amino acid sequence homology with IL-17A (Moseley et al., *Cytokine Growth Factor Rev.,* 2003, 14, 155-174). IL-17A and IL-17F are expressed by the recently defined autoimmune related subset of T helper cells, Th17, that also express IL-21 and IL-22 signature cytokines (Korn et al., *Ann. Rev. Immunol.,* 2009, 27, 485-517). IL-17A and IL-17F are expressed as homodimers, but may also be expressed as the IL-17A/F heterodimer (Wright et al., *J. Immunol.,* 2008, 181, 2799-2805). IL-17A and F signal through the receptors IL-17R, IL-17RC or an IL-17RA/RC receptor complex (Gaffen, *Cytokine,* 2008, 43, 402-407). Both IL-17A and IL-17F have been associated with a number of autoimmune diseases.

The compounds in accordance with the present invention, being potent modulators of human IL-17 activity, are therefore beneficial in the treatment and/or prevention of various human ailments, including inflammatory and autoimmune disorders.

Furthermore, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/116682 and WO 2014/066726 relate to separate classes of chemical compounds that are stated to modulate the activity of IL-17 and to be useful in the treatment of medical conditions, including inflammatory diseases.

WO 2018/229079 and WO 2020/011731 describe spirocyclic molecules that are stated to act as modulators of IL-17 activity, and thus to be of benefit in the treatment of pathological conditions including adverse inflammatory and autoimmune disorders.

WO 2019/138017 describes a class of fused bicyclic imidazole derivatives, including benzimidazole derivatives and analogues thereof, that are stated to act as modulators of IL-17 activity, and thus to be of benefit in the treatment of pathological conditions including adverse inflammatory and autoimmune disorders.

WO 2019/223718 describes heterocyclic compounds, including benzimidazole derivatives, that are stated to inhibit IL-17A and to be useful as immunomodulators.

Co-pending international patent applications PCT/EP2019/082774 and PCT/EP2019/082779 (both published on 18 Jun. 2020 as WO 2020/120140 and WO 2020/120141 respectively), co-pending international patent applications PCT/IB2020/055970, PCT/EP2020/067758 and PCT/EP2020/067759 (all published on 30 Dec. 2020 as WO 2020/261141, WO 2020/260425 and WO 2020/260426 respectively, claiming priority from United Kingdom patent applications 1909190.9, 1909191.7 and 1909194.1 respectively), and co-pending international patent applications PCT/EP2021/054519 and PCT/EP2021/054523 (claiming earliest priority from United Kingdom patent applications 2002635.7 and 2002636.5 respectively), describe discrete classes of chemical compounds that are stated to act as modulators of IL-17 activity, and thus to be of benefit in the treatment of pathological conditions including adverse inflammatory and autoimmune disorders.

None of the prior art available to date, however, discloses or suggests the precise structural class of substituted 4,4-difluorocyclohexyl derivatives as provided by the present invention.

As well as being potent modulators of human IL-17 activity, the compounds in accordance with the present invention also possess other notable advantages. In particular, the compounds of the invention display valuable metabolic stability, as determined in either microsomal or hepatocyte incubations.

The present invention provides a compound of formula (I) or an N-oxide thereof, or a pharmaceutically acceptable salt thereof:

(I)

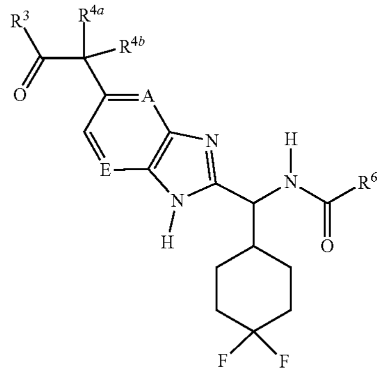

wherein

A represents C—$R^1$ or N;

E represents C—$R^2$ or N;

$R^1$ represents hydrogen or fluoro;

$R^2$ represents hydrogen or fluoro;

$R^3$ represents —$NR^{3a}R^{3b}$; or $R^3$ represents a group of formula (Wa):

(Wa)

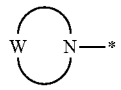

in which the asterisk (*) represents the point of attachment to the remainder of the molecule;

W represents the residue of an optionally substituted saturated monocyclic ring containing 3 to 6 carbon atoms, one nitrogen atom, and 0, 1, 2 or 3 additional heteroatoms independently selected from N, O and S, but containing no more than one O or S atom; or W represents the residue of an optionally substituted saturated bicyclic ring system containing 4 to 10 carbon atoms, one nitrogen atom, and 0, 1, 2 or 3 additional heteroatoms independently selected from N, O and S, but containing no more than one O or S atom; or W represents the residue of an optionally substituted saturated spirocyclic ring system containing 5 to 10 carbon atoms, one nitrogen atom, and 0, 1, 2 or 3 additional heteroatoms independently selected from N, O and S, but containing no more than one O or S atom;

$R^{3a}$ represents hydrogen or $C_{1-6}$ alkyl;

$R^{3b}$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^{4a}$ represents hydrogen, fluoro or hydroxy; or $R^{4a}$ represents $C_{1-6}$ alkyl, which group may be optionally substituted by one or more substituents; and $R^{4b}$ represents hydrogen, fluoro or $C_{1-6}$ alkyl; or $R^{4a}$ and $R^{4b}$, when taken together with the carbon atom to which they are both attached, represent $C_{3-9}$ cycloalkyl or $C_{3-7}$ heterocycloalkyl, either of which groups may be optionally substituted by one or more substituents;

$R^6$ represents —$OR^{6a}$ or —$NR^{6b}R^{6c}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents;

$R^{6a}$ represents $C_{1-6}$ alkyl; or $R^{6a}$ represents $C_{3-9}$ cycloalkyl, which group may be optionally substituted by one or more substituents;

$R^{6b}$ represents hydrogen or $C_{1-6}$ alkyl; and $R^{6c}$ represents hydrogen or $C_{1-6}$ alkyl; or $R^{6b}$ and $R^{6c}$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

The present invention also provides a compound of formula (I) as defined above, or a pharmaceutically acceptable salt thereof.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of IL-17 function is indicated.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of IL-17 function is indicated.

The present invention also provides a method for the treatment and/or prevention of disorders for which the administration of a modulator of IL-17 function is indicated which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Generally, such groups will be unsubstituted, or substituted by one, two, three or four substituents. Typically, such groups will be unsubstituted, or substituted by one, two or three substituents. Suitably, such groups will be unsubstituted, or substituted by one or two substituents.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of formula (I) include acid addition salts which may, for example, be formed by mixing a solution of a compound of formula (I) with a solution of a pharmaceutically acceptable acid.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkyl-sulphonyl" and "$C_{1-6}$ alkylamino" are to be construed accordingly.

The term "$C_{3-9}$ cycloalkyl" as used herein refers to monovalent groups of 3 to 9 carbon atoms derived from a saturated monocyclic hydrocarbon, and may comprise benzo-fused analogues thereof. Suitable $C_{3-9}$ cycloalkyl groups include cyclopropyl, cyclobutyl, benzocyclobutenyl, cyclopentyl, indanyl, cyclohexyl, cycloheptyl, cyclooctyl and cyclononanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]-pyrazinyl, homopiperazinyl, morpholinyl, benzoxazinyl, thiomorpholinyl, azepanyl, oxazepanyl, diazepanyl, thiadiazepanyl and azocanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b]-[1,4]dioxinyl, dibenzothienyl, pyrrolyl, indolyl, pyrrolo[2,3-b]pyridinyl, pyrrolo[3,2-c]-pyridinyl, pyrrolo[3,4-b]pyridinyl, pyrazolyl, pyrazolo[1,5-a]pyridinyl, 4,5,6,7-tetrahydropyrazolo[1,5-a]pyridinyl, pyrazolo[3,4-d]pyrimidinyl, pyrazolo[1,5-a]-pyrazinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]-thiazolyl, imidazo[1,2-a]pyridinyl, 5,6,7,8-tetrahydroimidazo[1,2-a]pyridinyl, imidazo-[4,5-b]pyridinyl, imidazo[1,2-b]pyridazinyl, purinyl, imidazo[1,2-a]pyrimidinyl, imidazo-[1,2-c]pyrimidinyl, imidazo[1,2-a]pyrazinyl, oxadiazolyl, thiadiazolyl, triazolyl, [1,2,4]triazolo[1,5-a]pyridinyl, [1,2,4]triazolo[4,3-a]pyridinyl, 5,6,7,8-tetrahydro-[1,2,4]triazolo[4,3-a]pyridinyl, [1,2,4]triazolo[1,5-a]pyrimidinyl, 6,8-dihydro-5H-[1,2,4]triazolo[4,3-a]pyrazinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C{=}O$)↔enol ($CH{=}CHOH$) tautomers or amide ($NHC{=}O$)↔hydroxyimine ($N{=}COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, A represents C—$R^1$. In another embodiment, A represents N.

In one embodiment, E represents C—$R^2$. In another embodiment, E represents N.

In a particular embodiment, A represents C—$R^1$ or N; and E represents C—$R^2$. In one aspect of that embodiment, A represents C—$R^1$; and E represents C—$R^2$.

Suitably, the present invention provides a compound of formula (I-1) or (I-2) or an N-oxide thereof, or a pharmaceutically acceptable salt thereof:

(I-1)

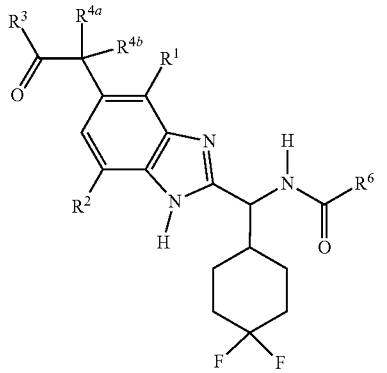

(I-2)

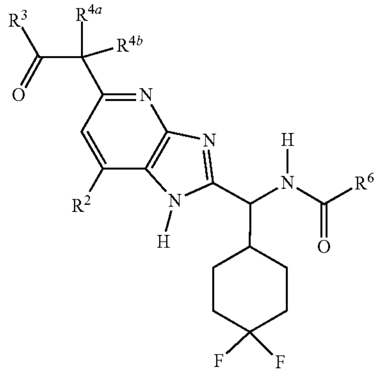

wherein $R^1$, $R^2$, $R^3$, $R^{4a}$, $R^{4b}$ and $R^6$ are as defined above.

In a first embodiment, $R^1$ represents hydrogen. In a second embodiment, $R^1$ represents fluoro.

In a first embodiment, $R^2$ represents hydrogen. In a second embodiment, $R^2$ represents fluoro.

In a first embodiment, $R^3$ represents —$NR^{3a}R^{3b}$. In a second embodiment, $R^3$ represents a group of formula (Wa) as defined above.

In a first embodiment, $R^{3a}$ represents hydrogen. In a second embodiment, $R^{3a}$ represents $C_{1-6}$ alkyl, especially methyl or ethyl. In a first aspect of that embodiment, $R^{3a}$ represents methyl. In a second aspect of that embodiment, $R^{3a}$ represents ethyl.

Typically, $R^{3b}$ represents $C_{1-6}$ alkyl, $C_{3-7}$ cycloalkyl ($C_{1-6}$)alkyl or heteroaryl, any of which groups may be optionally substituted by one or more substituents.

Suitably, $R^{3b}$ represents $C_{1-6}$ alkyl or $C_{3-7}$ cycloalkyl ($C_{1-6}$)alkyl, either of which groups may be optionally substituted by one or more substituents.

In a first embodiment, $R^{3b}$ represents optionally substituted $C_{1-6}$ alkyl. In a second embodiment, $R^{3b}$ represents optionally substituted $C_{3-7}$ cycloalkyl. In a third embodiment, $R^{3b}$ represents optionally substituted $C_{3-7}$ cycloalkyl ($C_{1-6}$)alkyl. In a fourth embodiment, $R^{3b}$ represents optionally substituted aryl. In a fifth embodiment, $R^{3b}$ represents optionally substituted aryl($C_{1-6}$)alkyl. In a sixth embodiment, $R^{3b}$ represents optionally substituted $C_{3-7}$ heterocycloalkyl. In a seventh embodiment, $R^{3b}$ represents optionally substituted $C_{3-7}$ heterocycloalkyl($C_{1-6}$)alkyl. In an eighth embodiment, $R^{3b}$ represents optionally substituted heteroaryl. In a ninth embodiment, $R^{3b}$ represents optionally substituted heteroaryl($C_{1-6}$)alkyl.

Typical values of $R^{3b}$ include ethyl, n-propyl, isopropyl, 2-methylpropyl, cyclopropylmethyl and pyridinyl, any of which groups may be optionally substituted by one or more substituents.

Illustrative values of $R^{3b}$ include ethyl, n-propyl, isopropyl, 2-methylpropyl and cyclopropylmethyl, any of which groups may be optionally substituted by one or more substituents.

Typical examples of optional substituents on $R^{3b}$ include one, two or three substituents independently selected from halogen, cyano, nitro, $C_{1-6}$ alkyl, trifluoromethyl, hydroxy, $C_{1-6}$ alkoxy, difluoromethoxy, difluoroethoxy, trifluoromethoxy, trifluoroethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl and di($C_{1-6}$)alkylsulfoximino.

Apposite examples of optional substituents on $R^{3b}$ include one, two or three substituents independently selected from halogen, $C_{1-6}$ alkyl, trifluoromethyl, $C_{1-6}$ alkylaminocarbonyl and di($C_{1-6}$)alkylaminocarbonyl.

Suitable examples of optional substituents on $R^{3b}$ include one, two or three substituents independently selected from halogen, $C_{1-6}$ alkylaminocarbonyl and di-($C_{1-6}$)alkylaminocarbonyl.

Typical examples of particular substituents on $R^{3b}$ include one, two or three substituents independently selected from fluoro, chloro, bromo, cyano, nitro, methyl, ethyl, trifluoromethyl, hydroxy, methoxy, isopropoxy, difluoromethoxy, difluoroethoxy, trifluoromethoxy, trifluoroethoxy, methylthio, methylsulfinyl, methylsulfonyl, ethylsulfonyl, amino, methylamino, dimethylamino, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl, dimethylaminosulfonyl and dimethylsulfoximino.

Apposite examples of particular substituents on $R^{3b}$ include one, two or three substituents independently selected from fluoro, methyl, trifluoromethyl, methylaminocarbonyl and dimethylaminocarbonyl.

Suitable examples of particular substituents on $R^{3b}$ include one, two or three substituents independently selected from fluoro, methylaminocarbonyl and dimethylaminocarbonyl.

Apposite values of $R^{3b}$ include trifluoroethyl, trifluoropropyl, trifluoroisopropyl, methylaminocarbonyl-2-methylpropyl, dimethylaminocarbonyl-2-methylpropyl, difluorocyclopropylmethyl and (methyl)(trifluoromethyl)pyridinyl. Additional values include difluoroethyl and (cyclopropyl)(trifluoromethyl)methyl. Additional values include difluoropropyl and (fluoro)(methyl)propyl.

Selected values of $R^{3b}$ include difluoroethyl, trifluoroethyl, difluoropropyl, trifluoropropyl, trifluoroisopropyl, (fluoro)(methyl)propyl, methylaminocarbonyl-2-methylpropyl, dimethylaminocarbonyl-2-methylpropyl, (cyclopropyl)(trifluoromethyl)-methyl and difluorocyclopropylmethyl.

Typical values of $R^{3b}$ include difluoroethyl, trifluoroethyl, trifluoropropyl, trifluoroisopropyl, methylaminocarbonyl-2-methylpropyl, dimethylaminocarbonyl-2-methylpropyl, (cyclopropyl)(trifluoromethyl)methyl and difluorocyclopropylmethyl.

Suitable values of $R^{3b}$ include trifluoroethyl, trifluoropropyl, trifluoroisopropyl, methylaminocarbonyl-2-methylpropyl, dimethylaminocarbonyl-2-methylpropyl and difluorocyclopropylmethyl.

In a first embodiment, W represents the residue of an optionally substituted saturated monocyclic ring containing 3 to 6 carbon atoms, one nitrogen atom, and 0, 1, 2 or 3 additional heteroatoms independently selected from N, O and S, but containing no more than one O or S atom. In a first aspect of that embodiment, W represents the residue of an optionally substituted saturated monocyclic ring containing 3 or 4 carbon atoms, one nitrogen atom, and 0, 1, 2 or 3 additional heteroatoms independently selected from N, O and S, but containing no more than one O or S atom.

In a second embodiment, W represents the residue of an optionally substituted saturated bicyclic ring system containing 4 to 10 carbon atoms, one nitrogen atom, and 0, 1, 2 or 3 additional heteroatoms independently selected from N, O and S, but containing no more than one O or S atom. In a first aspect of that embodiment, W represents the residue of an optionally substituted saturated bicyclic ring system containing 5, 6 or 7 carbon atoms, one nitrogen atom, and 0, 1, 2 or 3 additional heteroatoms independently selected from N, O and S, but containing no more than one O or S atom.

In a third embodiment, W represents the residue of an optionally substituted saturated spirocyclic ring system containing 5 to 10 carbon atoms, one nitrogen atom, and 0, 1, 2 or 3 additional heteroatoms independently selected from N, O and S, but containing no more than one O or S atom. In a first aspect of that embodiment, W represents the residue of an optionally substituted saturated spirocyclic ring system containing 5, 6 or 7 carbon atoms, one nitrogen atom, and 0, 1, 2 or 3 additional heteroatoms independently selected from N, O and S, but containing no more than one O or S atom.

Suitably, W represents the residue of an optionally substituted saturated monocyclic ring containing 3 or 4 carbon atoms, one nitrogen atom, and 0 or 1 oxygen atom(s). In a first embodiment, W represents the residue of an optionally substituted saturated monocyclic ring containing 3 or 4 carbon atoms and one nitrogen atom. In a first aspect of that embodiment, W represents the residue of an optionally substituted saturated monocyclic ring containing 3 carbon atoms and one nitrogen atom. In a second aspect of that embodiment, W represents the residue of an optionally substituted saturated monocyclic ring containing 4 carbon atoms and one nitrogen atom. In a second embodiment, W represents the residue of an optionally substituted saturated monocyclic ring containing 4 carbon atoms, one nitrogen atom, and one oxygen atom.

In a first embodiment, the group of formula (Wa) represents a saturated monocyclic ring containing one nitrogen atom and no additional heteroatoms (i.e. it is an optionally substituted azetidin-1-yl, pyrrolidin-1-yl, piperidin-1-yl or hexahydroazepin-1-yl ring). In a second embodiment, the group of formula (Wa) represents a saturated monocyclic ring containing one nitrogen atom and one additional heteroatom selected from N, O and S. In a first aspect of that embodiment, the group of formula (Wa) is an optionally substituted morpholin-4-yl moiety. In a third embodiment, the group of formula (Wa) represents a saturated monocyclic ring containing one nitrogen atom and two additional heteroatoms selected from N, O and S, of which not more than one is O or S. In a fourth embodiment, the group of formula (Wa) represents a saturated monocyclic ring containing one nitrogen atom and three additional heteroatoms selected from N, O and S, of which not more than one is O or S.

Typical values of the group of formula (Wa) include azetidin-1-yl, pyrrolidin-1-yl, oxazolidin-3-yl, thiazolidin-3-yl, isothiazolidin-2-yl, imidazolidin-1-yl, piperidin-1-yl, piperazin-1-yl, homopiperazin-1-yl, morpholin-4-yl, thiomorpholin-4-yl, azepan-1-yl, [1,4]oxazepan-4-yl, [1,4]diazepan-1-yl, [1,4]thiadiazepan-4-yl, azocan-1-yl, 3-azabicyclo-[3.1.0]hexan-3-yl, 2-oxa-5-azabicyclo[2.2.1]heptan-5-yl, 6-azabicyclo[3.2.0]heptan-6-yl, 3-azabicyclo[3.1.1]heptan-3-yl, 6-oxa-3-azabicyclo[3.1.1]heptan-3-yl, 3-azabicyclo-[4.1.0]heptan-3-yl, 2-oxa-5-azabicyclo[2.2.2]octan-5-yl, 3-azabicyclo[3.2.1]octan-3-yl, 8-azabicyclo[3.2.1]octan-8-yl, 3-oxa-8-azabicyclo[3.2.1]octan-8-yl, 3,8-diazabicyclo-[3.2.1]octan-3-yl, 3,8-diazabicyclo[3.2.1]octan-8-yl, 3,6-diazabicyclo[3.2.2]nonan-3-yl, 3,6-diazabicyclo[3.2.2]nonan-6-yl, 3-oxa-7-azabicyclo[3.3.1]nonan-7-yl, 3,7-dioxa-9-azabicyclo[3.3.1]nonan-9-yl, 3,9-diazabicyclo[4.2.1]nonan-3-yl, 3,9-diazabicyclo[4.2.1]-nonan-9-yl, 5-azaspiro[2.3]hexan-5-yl, 5-azaspiro[2.4]heptan-5-yl, 2-azaspiro[3.3]heptan-2-yl, 2-oxa-6-azaspiro[3.3]heptan-6-yl, 3-oxa-6-azaspiro[3.3]heptan-6-yl, 6-thia-2-azaspiro[3.3]heptan-2-yl, 2-oxa-6-azaspiro[3.4]octan-6-yl, 2-oxa-6-azaspiro[3.5]nonan-6-yl, 7-oxa-2-azaspiro[3.5]nonan-2-yl, 2-oxa-7-azaspiro[3.5]nonan-7-yl, 2,4,8-triazaspiro[4.5]-decan-2-yl, 2,4,8-triazaspiro[4.5]decan-4-yl and 2,4,8-triazaspiro[4.5]decan-8-yl, any of which groups may be optionally substituted by one or more substituents.

Apposite values of the group of formula (Wa) include azetidin-1-yl, pyrrolidin-1-yl and morpholin-4-yl, any of which rings may be optionally substituted by one or more substituents.

Suitable values of the group of formula (Wa) include azetidin-1-yl and pyrrolidin-1-yl, either of which rings may be optionally substituted by one or more substituents.

In a first embodiment, the group of formula (Wa) is unsubstituted. In a second embodiment, the group of formula (Wa) is substituted by one or more substituents, typically by one to six substituents, suitably by two to four substituents. In a first aspect of that embodiment, the group of formula (Wa) is substituted by one substituent. In a second aspect of that embodiment, the group of formula (Wa) is substituted by two substituents. In a third aspect of that embodiment, the group of formula (Wa) is substituted by three substituents. In a fourth aspect of that embodiment, the group of formula (Wa) is substituted by four substituents. In a fifth aspect of that embodiment, the group of formula (Wa) is substituted by five substituents. In a sixth aspect of that embodiment, the group of formula (Wa) is substituted by six substituents.

Typical examples of optional substituents on the group of formula (Wa) include halogen, $C_{1-6}$ alkyl, trifluoromethyl, hydroxy, hydroxy($C_{1-6}$)alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulfonyl, cyano, oxo, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, amino, amino($C_{1-6}$)alkyl, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, aminocarbonyl, $C_{1-6}$ alkylaminocarbonyl and di($C_{1-6}$)alkylaminocarbonyl.

Suitable examples of optional substituents on the group of formula (Wa) include halogen.

Typical examples of particular substituents on the group of formula (Wa) include fluoro, chloro, bromo, methyl, ethyl, isopropyl, trifluoromethyl, hydroxy, hydroxymethyl, hydroxyethyl, methoxy, isopropoxy, difluoromethoxy, trifluoromethoxy, methoxymethyl, methylthio, ethylthio, methylsulfonyl, cyano, oxo, formyl, acetyl, ethylcarbonyl, tert-butylcarbonyl, carboxy, carboxymethyl, methoxycarbonyl, ethoxycarbonyl, tert-butoxycarbonyl, methoxycarbonylmethyl, ethoxycarbonylmethyl, amino, aminomethyl, methylamino, ethylamino, dimethylamino, acetylamino, tert-butoxycarbonylamino, methylsulfonylamino, aminocarbonyl, methylaminocarbonyl and dimethylaminocarbonyl.

Suitable examples of particular substituents on the group of formula (Wa) include fluoro.

Apposite values of the group of formula (Wa) include difluoroazetidin-1-yl, tetrafluoropyrrolidin-1-yl and tetrafluoromorpholin-4-yl.

Typical values of the group of formula (Wa) include difluoroazetidin-1-yl and tetrafluoropyrrolidin-1-yl.

Generally, $R^{4a}$ represents hydrogen or fluoro; or $R^{4a}$ represents $C_{1-6}$ alkyl, which group may be optionally substituted by one or more substituents.

Typically, $R^{4a}$ represents hydrogen; or $R^{4a}$ represents $C_{1-6}$ alkyl, which group may be optionally substituted by one or more substituents.

Suitably, $R^{4a}$ represents $C_{1-6}$ alkyl, which group may be optionally substituted by one or more substituents.

In a first embodiment, $R^{4a}$ represents hydrogen. In a second embodiment, $R^{4a}$ represents fluoro. In a third embodiment, $R^{4a}$ represents hydroxy. In a fourth embodiment, $R^{4a}$ represents $C_{1-6}$ alkyl, especially methyl or ethyl, which group may be optionally substituted by one or more substituents. In a first aspect of that embodiment, $R^{4a}$ represents optionally substituted methyl. In a second aspect of that embodiment, $R^{4a}$ represents optionally substituted ethyl. In a third aspect of that embodiment, $R^{4a}$ represents optionally substituted propyl.

Typical examples of optional substituents on $R^{4a}$ include one, two or three substituents independently selected from halogen, cyano, nitro, hydroxy, $C_{1-6}$ alkoxy, difluoromethoxy, difluoroethoxy, trifluoromethoxy, trifluoroethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl and di($C_{1-6}$)alkylsulfoximino.

Selected examples of optional substituents on $R^{4a}$ include one, two or three substituents independently selected from halogen, $C_{1-6}$ alkoxy and $C_{1-6}$ alkylsulfonyl.

Apposite examples of optional substituents on $R^{4a}$ include one, two or three substituents independently selected from halogen and $C_{1-6}$ alkylsulfonyl.

Typical examples of particular substituents on $R^{4a}$ include one, two or three substituents independently selected from fluoro, chloro, bromo, cyano, nitro, hydroxy, methoxy, isopropoxy, difluoromethoxy, difluoroethoxy, trifluoromethoxy, trifluoroethoxy, methylthio, methylsulfinyl, methylsulfonyl, ethylsulfonyl, amino, methylamino, dimethylamino, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl, dimethylaminosulfonyl and dimethylsulfoximino.

Selected examples of particular substituents on $R^{4a}$ include one, two or three substituents independently selected from fluoro, methoxy and ethylsulfonyl.

Apposite examples of particular substituents on $R^{4a}$ include one, two or three substituents independently selected from fluoro and ethylsulfonyl.

Illustrative values of $R^{4a}$ include hydrogen, fluoro, hydroxy, methyl, difluoroethyl, trifluoroethyl and ethylsulfonylethyl. Additional values include methoxymethyl and difluoropropyl.

Selected values of $R^{4a}$ include methyl, methoxymethyl, difluoroethyl, trifluoroethyl, ethylsulfonylethyl and difluoropropyl.

Typical values of $R^{4a}$ include methyl, difluoroethyl, trifluoroethyl and ethylsulfonylethyl.

In a first embodiment, $R^{4b}$ represents hydrogen. In a second embodiment, $R^{4b}$ represents fluoro. In a third embodiment, $R^{4b}$ represents $C_{1-6}$ alkyl, especially methyl or ethyl. In a first aspect of that embodiment, $R^{4b}$ represents methyl. In a second aspect of that embodiment, $R^{4b}$ represents ethyl.

Typical values of $R^{4b}$ include hydrogen and fluoro, especially hydrogen.

Alternatively, $R^{4a}$ and $R^{4b}$ may together form an optionally substituted spiro linkage. Thus, $R^{4a}$ and $R^{4b}$, when taken together with the carbon atom to which they are both attached, may represent $C_{3-7}$ cycloalkyl or $C_{3-7}$ heterocycloalkyl, either of which groups may be unsubstituted, or substituted by one or more substituents, typically by one or two substituents.

In a first embodiment, $R^{4a}$ and $R^{4b}$, when taken together with the carbon atom to which they are both attached, may suitably represent $C_{3-7}$ cycloalkyl, which group may be unsubstituted, or substituted by one or more substituents, typically by one or two substituents. As a general illustration of that embodiment, $R^{4a}$ and $R^{4b}$, when taken together with the carbon atom to which they are both attached, may suitably represent cyclopropyl, cyclobutyl, cyclopentyl or cyclohexyl, any of which groups may be unsubstituted, or substituted by one or more substituents, typically by one or two substituents. As a particular illustration of that embodiment, $R^{4a}$ and $R^{4b}$, when taken together with the carbon atom to which they are both attached, may suitably represent cyclobutyl or cyclohexyl, either of which groups may be unsubstituted, or substituted by one or more substituents, typically by one or two substituents. In a first aspect of that embodiment, $R^{4a}$ and $R^{4b}$, when taken together with the carbon atom to which they are both attached, may suitably represent a cyclopropyl ring, which may be unsubstituted, or substituted by one or more substituents, typically by one or two substituents. In a second aspect of that embodiment, $R^{4a}$ and $R^{4b}$, when taken together with the carbon atom to which they are both attached, may suitably represent a cyclobutyl ring, which may be unsubstituted, or substituted by one or more substituents, typically by one or two substituents. In a third aspect of that embodiment, $R^{4a}$ and $R^{4b}$, when taken together with the carbon atom to which they are both attached, may suitably represent a cyclopentyl ring, which may be unsubstituted, or substituted by one or more substituents, typically by one or two substituents. In a fourth aspect of that embodiment, $R^{4a}$ and $R^{4b}$, when taken together with the carbon atom to which they are both attached, may suitably represent a cyclohexyl ring, which may be unsubstituted, or substituted by one or more substituents, typically by one or two substituents.

In a second embodiment, $R^{4a}$ and $R^{4b}$, when taken together with the carbon atom to which they are both attached, may suitably represent $C_{3-7}$ heterocycloalkyl, which group may be unsubstituted, or substituted by one or more substituents, typically by one or two substituents. As a general illustration of that embodiment, $R^{4a}$ and $R^{4b}$, when taken together with the carbon atom to which they are both attached, may suitably represent oxetanyl, pyrrolidinyl, tetrahydropyranyl or piperidinyl, any of which groups may be unsubstituted, or substituted by one or more substituents, typically by one or two substituents. As a particular illustration of that embodiment, $R^{4a}$ and $R^{4b}$, when taken together with the carbon atom to which they are both attached, may suitably represent pyrrolidinyl, tetrahydropyranyl or piperidinyl, any of which groups may be unsubstituted, or substituted by one or more substituents, typically by one or two substituents. In a first aspect of that embodiment, $R^{4a}$ and $R^{4b}$, when taken together with the carbon atom to which they are both attached, may suitably represent an oxetanyl ring, which may be unsubstituted, or substituted by one or more substituents, typically by one or two substituents. In a second aspect of that embodiment, $R^{4a}$ and $R^{4b}$, when taken together with the carbon atom to which they are both attached, may suitably represent a pyrrolidinyl ring, which may be unsubstituted, or substituted by one or more substituents, typically by one or two substituents. In a third aspect of that embodiment, $R^{4a}$ and $R^{4b}$, when taken together with the carbon atom to which they are both attached, may suitably represent a tetrahydropyranyl ring, which may be unsubstituted, or substituted by one or more substituents, typically by one or two substituents. In a fourth aspect of that embodiment, $R^{4a}$ and $R^{4b}$, when taken together with the carbon atom to which they are both attached, may suitably represent a piperidinyl ring, which may be unsubstituted, or substituted by one or more substituents, typically by one or two substituents.

Typically, $R^{4a}$ and $R^{4b}$, when taken together with the carbon atom to which they are both attached, may represent cyclopropyl, cyclobutyl, cyclopentyl, cyclohexyl, oxetanyl, pyrrolidinyl, tetrahydropyranyl or piperidinyl, any of which groups may be unsubstituted, or substituted by one or more substituents, typically by one or two substituents.

Appositely, $R^{4a}$ and $R^{4b}$, when taken together with the carbon atom to which they are both attached, may represent cyclobutyl, cyclohexyl, pyrrolidinyl, tetrahydropyranyl or piperidinyl, any of which groups may be unsubstituted, or substituted by one or more substituents, typically by one or two substituents.

Typical examples of optional substituents on the spirocycle formed by $R^{4a}$ and $R^{4b}$ include $C_{1-6}$ alkyl, halogen, cyano, trifluoromethyl, trifluoroethyl, hydroxy, $C_{1-6}$ alkoxy, $C_{1-6}$ alkylthio, $C_{1-6}$ alkylsulfinyl, $C_{1-6}$ alkylsulfonyl, $C_{2-6}$ alkylcarbonyl, $C_{2-6}$ alkoxycarbonyl, amino, $C_{1-6}$ alkylamino and di$(C_{1-6})$alkylamino.

Apposite examples of optional substituents on the spirocycle formed by $R^{4a}$ and $R^{4b}$ include $C_{1-6}$ alkyl, halogen, trifluoroethyl and $C_{2-6}$ alkoxycarbonyl, especially halogen.

Suitable examples of optional substituents on the spirocycle formed by $R^{4a}$ and $R^{4b}$ include halogen and $C_{2-6}$ alkoxycarbonyl.

Typical examples of particular substituents on the spirocycle formed by $R^{4a}$ and $R^{4b}$ include methyl, fluoro, chloro, bromo, cyano, trifluoromethyl, trifluoroethyl, hydroxy, methoxy, methylthio, methylsulfinyl, methylsulfonyl, acetyl, methoxycarbonyl, ethoxycarbonyl, amino, methylamino and dimethylamino.

Apposite examples of particular substituents on the spirocycle formed by $R^{4a}$ and $R^{4b}$ include methyl, fluoro, trifluoroethyl and methoxycarbonyl, especially fluoro.

Suitable examples of particular substituents on the spirocycle formed by $R^{4a}$ and $R^{4b}$ include fluoro and methoxycarbonyl.

Typical examples of the spirocycle formed by $R^{4a}$ and $R^{4b}$ include cyclopropyl, difluorocyclobutyl, cyclopentyl, difluorocyclohexyl, oxetanyl, methoxycarbonylpyrrolidinyl, tetrahydropyranyl, piperidinyl and methoxycarbonylpiperidinyl.

Apposite examples of the spirocycle formed by $R^{4a}$ and $R^{4b}$ include difluorocyclobutyl, difluorocyclohexyl, methoxycarbonylpyrrolidinyl, tetrahydropyranyl, piperidinyl and methoxycarbonylpiperidinyl.

Typically, $R^6$ represents —$OR^{6a}$ or —$NR^{6b}R^{6c}$; or $R^6$ represents $C_{1-6}$ alkyl, $C_{3-9}$ cycloalkyl, $C_{3-9}$ cycloalkyl($C_{1-6}$) alkyl, aryl, aryl($C_{1-6}$)alkyl, heteroaryl or heteroaryl-($C_{1-6}$) alkyl, any of which groups may be optionally substituted by one or more substituents.

More particularly, $R^6$ represents —$OR^{6a}$ or —$NR^{6b}R^{6c}$; or $R^6$ represents $C_{3-9}$ cycloalkyl, aryl or heteroaryl, any of which groups may be optionally substituted by one or more substituents.

Appositely, $R^6$ represents —$OR^{6a}$ or —$NR^{6b}R^{6c}$; or $R^6$ represents aryl or heteroaryl, either of which groups may be optionally substituted by one or more substituents.

Suitably, $R^6$ represents —$OR^{6a}$; or $R^6$ represents heteroaryl, which group may be optionally substituted by one or more substituents.

In a first embodiment, $R^6$ represents optionally substituted $C_{1-6}$ alkyl. In a second embodiment, $R^6$ represents optionally substituted $C_{3-9}$ cycloalkyl. In a third embodiment, $R^6$ represents optionally substituted $C_{3-9}$ cycloalkyl($C_{1-6}$)alkyl. In a fourth embodiment, $R^6$ represents optionally substituted aryl. In a fifth embodiment, $R^6$ represents optionally substituted aryl($C_{1-6}$)alkyl. In a sixth embodiment, $R^6$ represents optionally substituted $C_{3-7}$ heterocycloalkyl. In a seventh embodiment, $R^6$ represents optionally substituted $C_{3-7}$ heterocycloalkyl($C_{1-6}$)alkyl. In an eighth embodiment, $R^6$ represents optionally substituted heteroaryl. In a ninth embodiment, $R^6$ represents optionally substituted heteroaryl($C_{1-6}$) alkyl. In a tenth embodiment, $R^6$ represents —$OR^{6a}$. In an eleventh embodiment, $R^6$ represents —$NR^{6a}R^{6b}$.

Typical values of $R^6$ include —$OR^{6a}$ or —$NR^{6a}R^{6b}$; and methyl, ethyl, propyl, 2-methylpropyl, butyl, cyclopropyl, cyclobutyl, cyclohexyl, cyclohexylmethyl, phenyl, benzyl, phenylethyl, pyrazolyl, isoxazolyl, oxadiazolyl, pyridinyl, triazolylmethyl, benzotriazolylmethyl or pyridinylmethyl, any of which groups may be optionally substituted by one or more substituents. Additional values of $R^6$ include triazolyl, which group may be optionally substituted by one or more substituents.

Typical examples of $R^6$ include —$OR^{6a}$ or —$NR^{6a}R^{6b}$; and cyclopropyl, phenyl, pyrazolyl, isoxazolyl, oxadiazolyl or triazolyl, any of which groups may be optionally substituted by one or more substituents.

Representative values of $R^6$ include —$OR^{6a}$ or —$NR^{6a}R^{6b}$; and phenyl, pyrazolyl, isoxazolyl or oxadiazolyl, any of which groups may be optionally substituted by one or more substituents.

Illustrative values of $R^6$ include —$OR^{6a}$; and pyrazolyl, isoxazolyl or oxadiazolyl, any of which groups may be optionally substituted by one or more substituents.

Representative examples of $R^6$ include cyclopropyl, phenyl, pyrazolyl, isoxazolyl, oxadiazolyl and triazolyl, any of which groups may be optionally substituted by one or more substituents.

Selected examples of $R^6$ include cyclopropyl, phenyl, pyrazolyl, oxadiazolyl and triazolyl, any of which groups may be optionally substituted by one or more substituents.

Apt values of $R^6$ include phenyl, pyrazolyl, isoxazolyl and oxadiazolyl, any of which groups may be optionally substituted by one or more substituents.

More apt values of $R^6$ include phenyl, pyrazolyl and oxadiazolyl, any of which groups may be optionally substituted by one or more substituents.

Suitable values of $R^6$ include pyrazolyl, isoxazolyl and oxadiazolyl, any of which groups may be optionally substituted by one or more substituents.

Apposite values of $R^6$ include pyrazolyl and oxadiazolyl, either of which groups may be optionally substituted by one or more substituents.

Particular values of $R^6$ include oxadiazolyl, which group may be optionally substituted by one or more substituents.

Typical examples of optional substituents on $R^6$ include one, two or three substituents independently selected from halogen, cyano, nitro, $C_{1-6}$ alkyl, trifluoromethyl, phenyl, fluorophenyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$) alkyl, $C_{1-6}$ alkylamino, di($C_{1-6}$)alkylamino, pyrrolidinyl, tetrahydropyranyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl and di-($C_{1-6}$)alkylsulfoximinyl. Additional examples include cyclopropyl.

Selected examples of optional substituents on $R^6$ include one, two or three substituents independently selected from halogen, $C_{1-6}$ alkyl and cyclopropyl.

Apposite examples of optional substituents on $R^6$ include one, two or three substituents independently selected from halogen and $C_{1-6}$ alkyl.

Suitable examples of optional substituents on $R^6$ include one, two or three substituents independently selected from $C_{1-6}$ alkyl.

Typical examples of particular substituents on $R^6$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, tetrahydropyranyl, morpholinyl, piperazinyl, acetylamino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl, dimethylaminosulfonyl and dimethylsulfoximinyl. Additional examples include cyclopropyl.

Selected examples of particular substituents on $R^6$ include one, two or three substituents independently selected from fluoro, methyl, ethyl, isopropyl and cyclopropyl.

Apposite examples of particular substituents on $R^6$ include one, two or three substituents independently selected from fluoro, methyl and ethyl.

Suitable examples of particular substituents on $R^6$ include one, two or three substituents independently selected from methyl and ethyl.

Illustrative examples of particular values of $R^6$ include methyl, difluoromethyl, methylsulfonylmethyl, aminomethyl, methylaminomethyl, difluoroethyl, carboxyethyl, difluoropropyl, 2-methylpropyl, butyl, cyanocyclopropyl, methylcyclopropyl, ethyl-cyclopropyl, dimethylcyclopropyl, trifluoromethylcyclopropyl, phenylcyclopropyl, fluorophenylcyclopropyl, hydroxycyclopropyl, aminocyclopropyl, cyclobutyl, trifluoromethylcyclobutyl, cyclohexyl, cyclohexylmethyl, phenyl, fluorophenyl, chloro-phenyl, cyanophenyl, methylphenyl, hydroxyphenyl, methylsulfonylphenyl, dimethyl-sulfoximinylphenyl, benzyl, fluorobenzyl, difluorobenzyl, chlorobenzyl, (chloro)(fluoro)-benzyl, dichlorobenzyl, (chloro)(difluoro)benzyl, bromobenzyl, cyanobenzyl, methyl-benzyl, dimethylbenzyl, trifluoromethylbenzyl, phenylbenzyl, hydroxybenzyl, hydroxymethylbenzyl, benzoyl, methoxybenzyl, dimethoxybenzyl, trifluoromethoxy-benzyl, methylsulfonylbenzyl, aminomethylbenzyl, aminoethylbenzyl, dimethylamino-benzyl, pyrrolidinylbenzyl, (dimethyl)(pyrrolidinyl)benzyl, morpholinylbenzyl, (dimethyl)(morpholinyl)benzyl, piperazinylbenzyl, acetylaminoethylbenzyl, phenylethyl, chlorophenylethyl, methylpyrazolyl, ethylpyrazolyl, (methyl)(tetrahydropyranyl)-pyrazolyl, methylisoxazolyl, ethylisoxazolyl, methyloxadiazolyl, ethyloxadiazolyl, pyridinyl, triazolylmethyl, benzotriazolylmethyl, pyridinylmethyl and aminopyridinyl-methyl. Additional examples include fluorocyclopropyl, cyclopropyloxadiazolyl and isopropyltriazolyl.

Favoured values of $R^6$ include methylpyrazolyl, ethylpyrazolyl, methylisoxazolyl, ethylisoxazolyl, methyloxadiazolyl and ethyloxadiazolyl.

Selected values of $R^6$ include methylpyrazolyl, ethylpyrazolyl, methyloxadiazolyl and ethyloxadiazolyl.

Selected examples of particular values of $R^6$ include fluorocyclopropyl, fluorophenyl, methylpyrazolyl, methyloxadiazolyl, ethyloxadiazolyl, cyclopropyloxadiazolyl and isopropyltriazolyl.

Representative examples of particular values of $R^6$ include fluorophenyl, methylpyrazolyl, methyloxadiazolyl and ethyloxadiazolyl.

Notable values of $R^6$ include methylpyrazolyl, methyloxadiazolyl and ethyloxadiazolyl.

Particular examples of selected values of $R^6$ include methyloxadiazolyl and ethyloxadiazolyl.

In a first embodiment, $R^{6a}$ represents $C_{1-6}$ alkyl. In a second embodiment, $R^{6a}$ represents optionally substituted $C_{3-9}$ cycloalkyl.

Typically, $R^{6a}$ represents $C_{1-6}$ alkyl; or $R^{6a}$ represents cyclobutyl, which group may be optionally substituted by one or more substituents.

Typical examples of optional substituents on $R^{6a}$ include one, two or three substituents independently selected from halogen, cyano, nitro, $C_{1-6}$ alkyl, trifluoromethyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^{6a}$ include one, two or three substituents independently selected from halogen.

Typical examples of specific substituents on $R^{6a}$ include one, two or three substituents independently selected from fluoro, chloro, bromo, cyano, nitro, methyl, ethyl, isopropyl, tert-butyl, trifluoromethylhydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Suitable examples of specific substituents on $R^{6a}$ include one, two or three substituents independently selected from fluoro.

Illustrative examples of specific values of $R^{6a}$ include methyl, ethyl, n-propyl, isopropyl, n-butyl, tert-butyl, cyclobutyl and difluorocyclobutyl.

Typically, $R^{6a}$ represents cyclobutyl.

Typically, $R^{6b}$ represents hydrogen or methyl.

In a first embodiment, $R^{6b}$ represents hydrogen. In a second embodiment, $R^{6b}$ represents $C_{1-6}$ alkyl, especially methyl.

Typically, $R^{6c}$ represents hydrogen or methyl.

In a first embodiment, $R^{6c}$ represents hydrogen. In a second embodiment, $R^{6c}$ represents $C_{1-6}$ alkyl, especially methyl.

Alternatively, the moiety —$NR^{6b}R^{6c}$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^{6b}R^{6c}$ include $C_{1-6}$ alkyl, $C_{1-6}$ alkylsulfonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino and aminocarbonyl.

Selected examples of specific substituents on the heterocyclic moiety —$NR^{6b}R^{6c}$ include methyl, methylsulfonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulfonylamino and aminocarbonyl.

One sub-class of compounds according to the invention is represented by the compounds of formula (IIA) and N-oxides thereof, and pharmaceutically acceptable salts thereof:

(IIA)

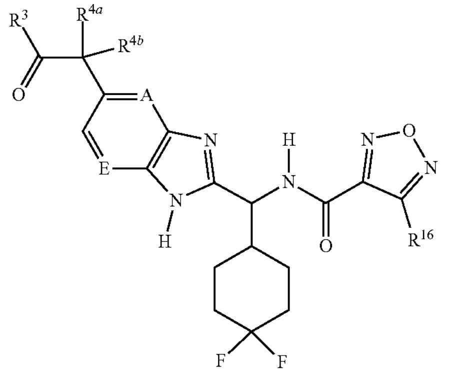

wherein $R^{16}$ represents methyl (including —$CD_3$), ethyl, isopropyl or cyclopropyl; and A, E, $R^3$, $R^{4a}$ and $R^{4b}$ are as defined above.

Generally, $R^{16}$ represents methyl (including —$CD_3$) or ethyl.

In a first embodiment, $R^{16}$ represents methyl. In a first aspect of that embodiment, $R^{16}$ represents —$CH_3$. In a second aspect of that embodiment, $R^{16}$ represents —$CD_3$. In a second embodiment, $R^{16}$ represents ethyl. In a third embodiment, $R^{16}$ represents isopropyl. In a fourth embodiment, $R^{16}$ represents cyclopropyl.

Another sub-class of compounds according to the invention is represented by the compounds of formula (IIB) and N-oxides thereof, and pharmaceutically acceptable salts thereof:

(IIB)

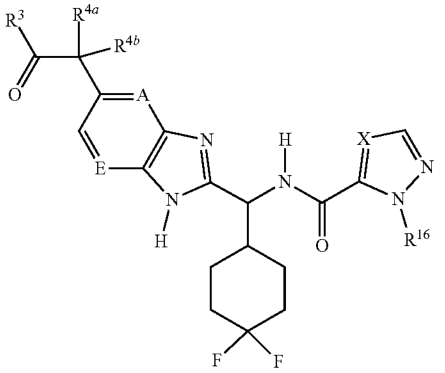

wherein

X represents CH or N; and

A, E, $R^3$, $R^{4a}$, $R^{4b}$ and $R^{16}$ are as defined above.

In a first embodiment, X represents CH. In a second embodiment, $R^{16}$ represents N.

Another sub-class of compounds according to the invention is represented by the compounds of formula (IIC) and N-oxides thereof, and pharmaceutically acceptable salts thereof:

(IIC)

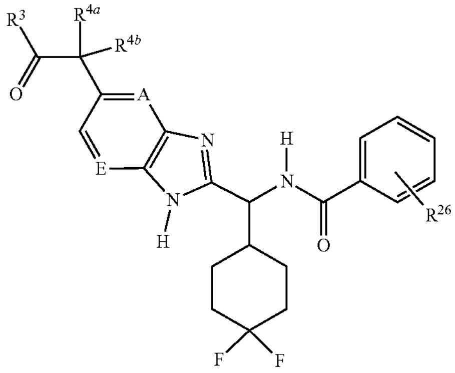

wherein $R^{26}$ represents halogen; and

A, E, $R^3$, $R^{4a}$ and $R^{4b}$ are as defined above.

Suitably, $R^{26}$ represents fluoro or chloro, especially fluoro.

In a first embodiment, $R^{26}$ represents fluoro. In a second embodiment, $R^{26}$ represents chloro.

Another sub-class of compounds according to the invention is represented by the compounds of formula (IID) and N-oxides thereof, and pharmaceutically acceptable salts thereof:

(IID)

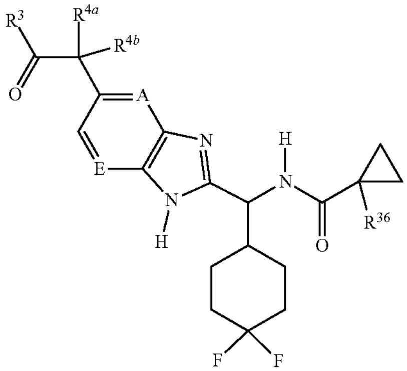

wherein $R^{36}$ represents halogen; and

A, E, $R^3$, $R^{4a}$ and $R^{4b}$ are as defined above.

Suitably, $R^{36}$ represents fluoro or chloro, especially fluoro.

In a first embodiment, $R^{36}$ represents fluoro. In a second embodiment, $R^{36}$ represents chloro.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments, including inflammatory and autoimmune disorders.

The compounds according to the present invention are useful in the treatment and/or prophylaxis of a pathological disorder that is mediated by a pro-inflammatory IL-17 cytokine or is associated with an increased level of a pro-inflammatory IL-17 cytokine. Generally, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bowel syndrome, ulcerative colitis, Castleman's disease, axial spondyloarthritis, ankylosing spondylitis and other spondyloarthropathies, dermatomyositis, myocarditis, uveitis, exophthalmos, autoimmune thyroiditis, Peyronie's Disease, coeliac disease, gall bladder disease, Pilonidal disease, peritonitis, psoriasis, atopic dermatitis, hidradenitis suppurativa, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis, hypochlorhydia and pain (particularly pain associated with inflammation).

WO 2009/089036 reveals that modulators of IL-17 activity may be administered to inhibit or reduce the severity of ocular inflammatory disorders, in particular ocular surface inflammatory disorders including Dry Eye Syndrome (DES). Consequently, the compounds in accordance with the present invention are useful in the treatment and/or prevention of an IL-17-mediated ocular inflammatory disorder, in particular an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, ocular autoimmune conditions, Pemphigoid syndrome, Stevens-Johnson syndrome, ocular allergy, severe allergic (atopic) eye disease, conjunctivitis and microbial keratitis. Particular categories of Dry Eye Syndrome include keratoconjunctivitis sicca (KCS), Sjögren syndrome, Sjögren syndrome-associated keratoconjunctivitis sicca, non-Sjögren syndrome-associated keratoconjunctivitis sicca, keratitis sicca, sicca syndrome, xerophthalmia, tear film disorder, decreased tear production, aqueous tear deficiency (ATD), meibomian gland dysfunction and evaporative loss.

Illustratively, the compounds of the present invention may be useful in the treatment and/or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, hidradenitis suppurativa, scleroderma, systemic sclerosis, lung fibrosis, inflammatory bowel diseases (including Crohn's disease and ulcerative colitis), axial spondyloarthritis, ankylosing spondylitis and other spondyloarthropathies, cancer and pain (particularly pain associated with inflammation).

Suitably, the compounds of the present invention are useful in the treatment and/or prophylaxis of psoriasis, psoriatic arthritis, hidradenitis suppurativa, axial spondyloarthritis or ankylosing spondylitis.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds according to the present invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds according to the present invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate.

Alternatively, for ophthalmic administration the compounds according to the present invention may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound according to the present invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above may be prepared by a process which comprises reacting a carboxylic acid of formula $R^6$—$CO_2H$ or a salt thereof, e.g. the lithium salt thereof, with a compound of formula (III):

(III)

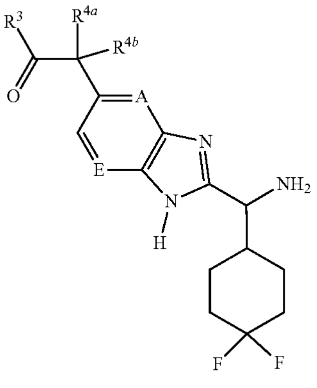

wherein A, E, $R^3$, $R^{4a}$, $R^{4b}$ and $R^6$ are as defined above.

The reaction is conveniently accomplished in the presence of a coupling agent and a base. Suitable coupling agents include 1-[bis(dimethylamino)methylene]-1H-1,2,3-triazolo [4,5-b]pyridinium 3-oxid hexafluorophosphate (HATU); and 2,4,6-tripropyl-1,3,5,2,4,6-trioxatriphosphorinane-2,4,6-trioxide. Suitable bases include organic amines, e.g. a trialkylamine such as N,N-diisopropylethylamine; or pyridine. The reaction is conveniently performed at ambient or elevated temperature in a suitable solvent, e.g. a cyclic ether such as tetrahydrofuran; or a dipolar aprotic solvent such as N,N-dimethylformamide or N,N-dimethylacetamide; or a chlorinated solvent such as dichloromethane; or an organic ester solvent such as ethyl acetate.

Where $R^6$ represents $C_{1-6}$ alkyl, e.g. methyl, the compounds of formula (I) above may be prepared by a process which comprises reacting a compound of formula $R^6$—COCl, e.g. acetyl chloride, with a compound of formula (III) as defined above. The reaction is conveniently accomplished in the presence of a base. Suitable bases include organic amines, e.g. a trialkylamine such as N,N-diisopropylethylamine. The reaction is conveniently performed at ambient temperature in a suitable solvent, e.g. a cyclic ether such as tetrahydrofuran.

Where $R^6$ represents —$OR^{6a}$, the compounds of formula (I) above may be prepared by a two-step process which comprises: (i) reacting a compound of formula $R^{6a}$—OH with N,N'-disuccinimidyl carbonate, ideally in the presence of a base, e.g. an organic amine such as triethylamine; and (ii) reacting the resulting material with a compound of formula (III) as defined above. Steps (i) and (ii) are conveniently performed at ambient temperature in a suitable solvent, e.g. a chlorinated solvent such as dichloromethane, or an organic nitrile solvent such as acetonitrile.

The intermediates of formula (III) above may be prepared by removal of the N-protecting group $R^p$ from a compound of formula (IV):

(IV)

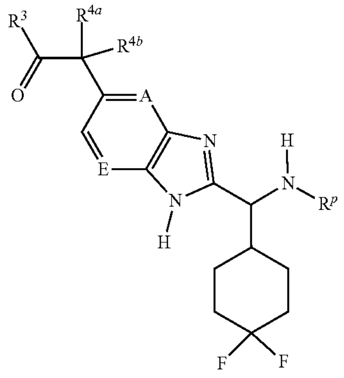

wherein A, E, $R^3$, $R^{4a}$ and $R^{4b}$ are as defined above, and $R^p$ represents a N-protecting group.

The N-protecting group $R^p$ will suitably be tert-butoxycarbonyl (BOC), in which case the removal thereof may conveniently be effected by treatment with an acid, e.g. a mineral acid such as hydrochloric acid, or an organic acid such as trifluoroacetic acid.

Alternatively, the N-protecting group $R^p$ may be benzyloxycarbonyl, in which case the removal thereof may conveniently be effected by catalytic hydrogenation, typically by treatment with hydrogen gas or ammonium formate in the presence of a hydrogenation catalyst, e.g. palladium on charcoal, or palladium hydroxide on charcoal.

In an alternative procedure, the compounds of formula (I) above may be prepared by a two-step process which comprises:

(i) saponifying a compound of formula (V):

(V)

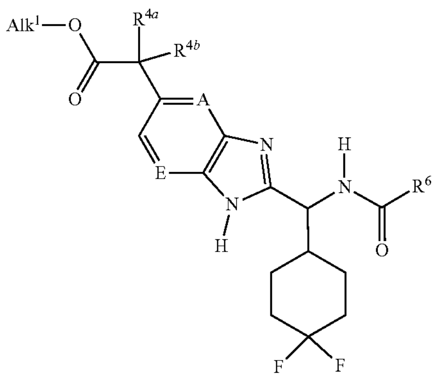

wherein A, E, $R^{4a}$, $R^{4b}$ and $R^6$ are as defined above, and $Alk^1$ represents $C_{1-4}$ alkyl, e.g. methyl, ethyl or tert-butyl; and (ii) reaction of the carboxylic acid derivative thereby obtained with a compound of formula $R^3$—H; under conditions analogous to those described above for the reaction between compound (III) and a carboxylic acid of formula $R^6$—$CO_2H$.

Where $Alk^1$ represents methyl or ethyl, the saponification reaction in step (i) will generally be effected by treatment with a base. Suitable bases include inorganic hydroxides, e.g. an alkali metal hydroxide such as lithium hydroxide or sodium hydroxide. The reaction is conveniently performed at ambient or elevated temperature in water and a suitable organic solvent, e.g. a cyclic ether such as tetrahydrofuran, or a $C_{1-4}$ alkanol such as methanol.

Alternatively, where $Alk^1$ represents tert-butyl, the saponification reaction in step (i) may generally be effected by treatment with an acid, e.g. an organic acid such as trifluoroacetic acid. The reaction is conveniently performed at ambient temperature in a suitable organic solvent, e.g. a chlorinated solvent such as dichloromethane.

Alternative coupling agents that may usefully be employed in step (ii) include 2-chloro-1-methylpyridinium iodide.

In another procedure, the compounds of formula (I) above may be prepared by a process which comprises cyclising a compound of formula (VIA) or (VIB):

(VIA)

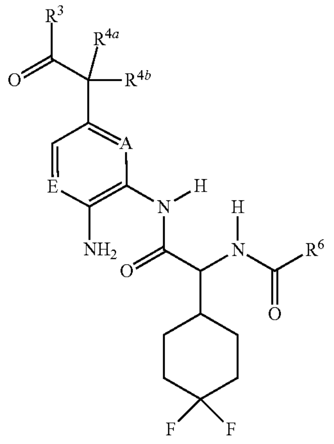

(VIB)

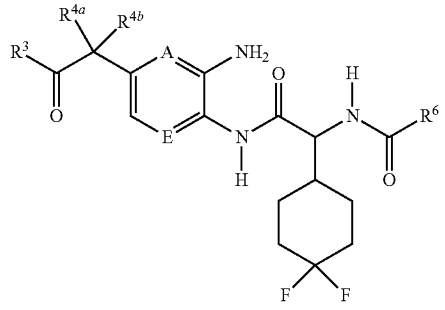

wherein A, E, $R^3$, $R^{4a}$, $R^{4b}$ and $R^6$ are as defined above.

Cyclisation of compound (VIA) or (VIB) is conveniently effected by heating in a suitable medium, e.g. acetic acid, or trifluoroacetic acid.

The intermediates of formula (VIA) or (VIB) above may be prepared by reacting a compound of formula (VII) with a carboxylic acid of formula (VIII) or a salt thereof, e.g. a lithium salt thereof:

(VII)

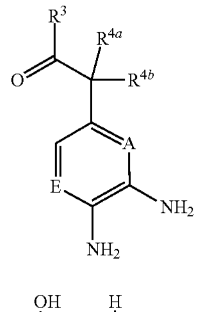

(VIII)

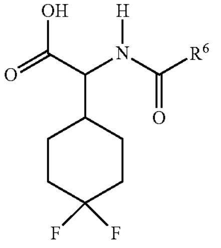

wherein A, E, $R^3$, $R^{4a}$, $R^{4b}$ and $R^6$ are as defined above; under conditions analogous to those described above for the reaction between compound (III) and a carboxylic acid of formula $R^6$—$CO_2H$.

The intermediates of formula (VIII) may be prepared by a two-step procedure which comprises: (i) reacting a carboxylic acid of formula $R^6$—$CO_2H$ with a compound of formula (IX):

(IX)

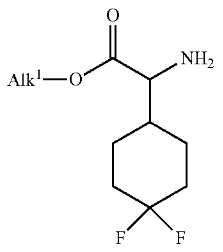

wherein $R^6$ and $Alk^1$ are as defined above; under conditions analogous to those described above for the reaction between compound (III) and a carboxylic acid of formula $R^6$—$CO_2H$; and (ii) saponification of the resulting material under conditions analogous to those described above for the saponification of compound (V).

Alternative coupling agents that may usefully be employed in step (i) include N-(3-dimethylaminopropyl)-N'-ethylcarbodiimide hydrochloride (EDC·HCl) and O-(benzotriazol-1-yl)-N,N,N',N'-tetramethyluronium hexafluorophosphate (HBTU).

The intermediates of formula (IV) above may be prepared by a two-step procedure which comprises the following steps:

(i) reacting a compound of formula (VII) as defined above with a compound of formula (X):

(X)

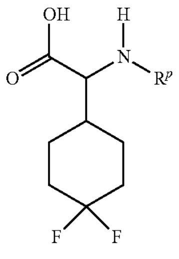

wherein $R^p$ is as defined above; under conditions analogous to those described above for the reaction between compounds (VII) and (VIII); and (ii) cyclisation of the resulting material under conditions analogous to those described above for the cyclisation of compound (VIA) or (VIB).

In the alternative, the intermediates of formula (III) above may be prepared by a procedure which comprises the following steps:

(i) reacting a compound of formula (XI) with the compound of formula (XII):

(XI)

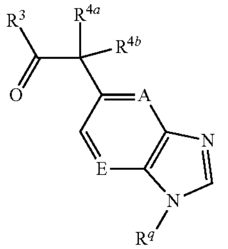

(XII)

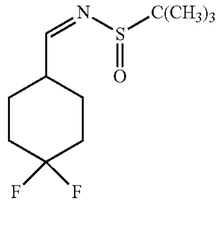

wherein A, E, $R^3$, $R^{4a}$ and $R^{4b}$ are as defined above, and $R^q$ represents a N-protecting group; to provide a compound of formula (XIII):

(XIII)

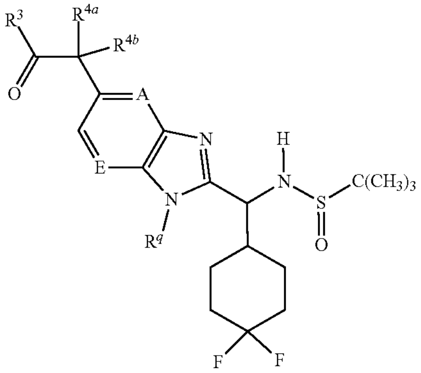

wherein A, E, $R^3$, $R^{4a}$, $R^{4b}$ and $R^q$ are as defined above; and (ii) removal of the tert-butylsulfinyl group and the N-protecting group $R^q$ from compound (XIII).

The N-protecting group $R^q$ will suitably be 2-(trimethylsilyl)ethoxymethyl.

Step (i) is suitably effected by treatment of compound (XI) with a base, e.g. an organic base such as n-butyllithium, followed by reaction with compound (XII). The reaction is conveniently accomplished in a suitable solvent, e.g. a cyclic ether such as tetrahydrofuran.

Where the N-protecting group $R^q$ is 2-(trimethylsilyl)ethoxymethyl, removal of the tert-butylsulfinyl group and the N-protecting group $R^q$ from compound (XIII) in step (ii) may both be accomplished by treatment with an acid, e.g. a mineral acid such as hydrochloric acid, or an organic acid such as trifluoroacetic acid.

Where the N-protecting group $R^q$ is 2-(trimethylsilyl)ethoxymethyl, the intermediates of formula (XI) above may be prepared by a procedure which comprises the following steps:

(i) reaction of a compound of formula (VII) as defined above with formic acid; and (ii) reaction of the material thereby obtained with 2-(trimethylsilyl)ethoxymethyl chloride.

Step (i) is conveniently carried out at an elevated temperature.

Step (ii) is suitably effected by treating the reactants with a base, e.g. an inorganic base such as sodium hydride, or an organic amine such as N,N-diisopropylethylamine.

The intermediate of formula (XII) above may be prepared by reacting 4,4-difluorocyclohexyl carboxaldehyde with 2-methyl-2-propanesulfinamide. The reaction is suitably effected in the presence of pyridinium p-toluenesulfonate and magnesium sulfate. The reaction is conveniently carried out at ambient temperature in a suitable solvent, e.g. a chlorinated solvent such as dichloromethane.

The intermediates of formula (V) above may be prepared by reacting a carboxylic acid of formula $R^6$—$CO_2H$ with a compound of formula (XIV):

(XIV)

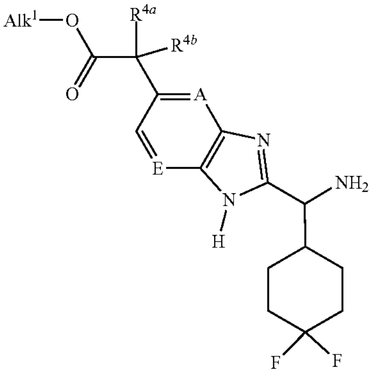

wherein A, E, $R^{4a}$, $R^{4b}$ and $Alk^1$ are as defined above; under conditions analogous to those described above for the reaction between compound (III) and a carboxylic acid of formula $R^6$—$CO_2H$.

The intermediates of formula (XIV) above may be prepared by a three-step procedure which comprises the following steps:

(i) reacting a compound of formula (X) as defined above with a compound of formula (XV):

(XV)

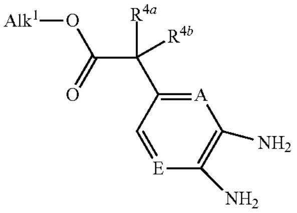

wherein A, E, $R^{4a}$, $R^{4b}$ and $Alk^1$ are as defined above; under conditions analogous to those described above for the reaction between compounds (VII) and (VIII);

(ii) cyclisation of the resulting material under conditions analogous to those described above for the cyclisation of compound (VIA) or (VIB); and (iii) removal of the N-protecting group $R^p$ from the material thereby obtained; under conditions analogous to those described above for the removal of the N-protecting group $R^p$ from compound (IV).

In an alternative method, the intermediates of formula (IV) above may be prepared by a four-step procedure which comprises the following steps:

(i) reacting a compound of formula (X) as defined above with a compound of formula (XV) as defined above under conditions analogous to those described above for the reaction between compounds (VII) and (VIII);

(ii) cyclisation of the resulting material under conditions analogous to those described above for the cyclisation of compound (VIA) or (VIB);

(iii) saponification of the resulting material under conditions analogous to those described above for the saponification of compound (V); and (iv) reaction of the carboxylic acid derivative thereby obtained with a compound of formula $R^3$—H; under conditions analogous to those described above for the reaction between compound (III) and a carboxylic acid of formula $R^6$—$CO_2H$.

Where they are not commercially available, the starting materials of formula (VII), (IX), (X) and (XV) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound comprising a N—BOC moiety (wherein BOC is an abbreviation for tert-butoxycarbonyl) may be converted into the corresponding compound comprising a N—H moiety by treatment with an acid, e.g. a mineral acid such as hydrochloric acid, or an organic acid such as trifluoroacetic acid.

A compound comprising a N—H functionality may be alkylated, e.g. methylated, by treatment with a suitable alkyl halide, e.g. iodomethane, typically in the presence of a base, e.g. an inorganic carbonate such as sodium carbonate.

A compound comprising a N—H functionality may be acylated, e.g. acetylated, by treatment with a suitable acyl halide, e.g. acetyl chloride, typically in the presence of a base, e.g. an organic base such as N,N-diisopropylethylamine or triethylamine. Similarly, a compound comprising a N—H functionality may be acylated, e.g. acetylated, by treatment with a suitable acyl anhydride, e.g. acetic anhydride, typically in the presence of a base, e.g. an organic base such as triethylamine.

Similarly, a compound comprising a N—H functionality may be converted into the corresponding compound comprising a N—$S(O)_2Alk^1$ functionality (wherein $Alk^1$ is as defined above) by treatment with the appropriate $C_{1-4}$ alkylsulfonyl chloride reagent, e.g. methylsulfonyl chloride, typically in the presence of a base, e.g. an organic base such as triethylamine.

Similarly, a compound comprising a N—H functionality may be converted into the corresponding compound comprising a carbamate or urea moiety respectively by treatment with the appropriate chloroformate or carbamoyl chloride reagent, typically in the presence of a base, e.g. an organic base such as triethylamine or N,N-diisopropylethylamine. Alternatively, a compound comprising a N—H functionality may be converted into the corresponding compound comprising a urea moiety by treatment with the appropriate amine-substituted (3-methylimidazol-3-ium-1-yl)methanone iodide derivative, typically in the presence of a base, e.g. an organic base such as triethylamine. Alternatively, a compound comprising a N—H functionality may be converted into the corresponding compound comprising a urea moiety N—C(O)N(H)$Alk^1$ (wherein $Alk^1$ is as defined above) by treatment with the appropriate isocyanate derivative $Alk^1$-N═C═O, typically in the presence of a base, e.g. an organic base such as triethylamine.

A compound comprising a N—H functionality may be converted into the corresponding compound comprising a N—C(H) functionality by treatment with the appropriate aldehyde or ketone in the presence of a reducing agent such as sodium triacetoxyborohydride.

A compound comprising a $C_{1-4}$ alkoxycarbonyl moiety —$CO_2Alk^1$ (wherein $Alk^1$ is as defined above) may be converted into the corresponding compound comprising a carboxylic acid (—$CO_2H$) moiety by treatment with a base, e.g. an alkali metal hydroxide salt such as lithium hydroxide. Alternatively, a compound comprising a tert-butoxycarbonyl moiety may be converted into the corresponding compound comprising a carboxylic acid (—$CO_2H$) moiety by treatment with trifluoroacetic acid.

A compound comprising a carboxylic acid (—$CO_2H$) moiety may be converted into the corresponding compound comprising an amide moiety by treatment with the appropriate amine, under conditions analogous to those described above for the reaction between compound (III) and a carboxylic acid of formula $R^6$—$CO_2H$.

A compound comprising a $C_{1-4}$ alkoxycarbonyl moiety —$CO_2Alk^1$ (wherein $Alk^1$ is as defined above) may be converted into the corresponding compound comprising a hydroxymethyl (—$CH_2OH$) moiety by treatment with a reducing agent such as lithium aluminium hydride.

A compound comprising a $C_{1-4}$ alkylcarbonyloxy moiety —OC(O)$Alk^1$ (wherein $Alk^1$ is as defined above), e.g. acetoxy, may be converted into the corresponding compound comprising a hydroxy (—OH) moiety by treatment with a base, e.g. an alkali metal hydroxide salt such as sodium hydroxide.

A compound comprising a halogen atom, e.g. bromo, may be converted into the corresponding compound comprising an optionally substituted aryl, heterocycloalkenyl or heteroaryl moiety by treatment with the appropriately substituted aryl, heterocycloalkenyl or heteroaryl boronic acid or a cyclic ester thereof formed with an organic diol, e.g. pinacol, 1,3-propanediol or neopentyl glycol. The reaction is typically effected in the presence of a transition metal catalyst, and a base. The transition metal catalyst may be [1,1'-bis(diphenylphosphino)ferrocene]dichloropalladium (II). In the alternative, the transition metal catalyst may be tris(dibenzylideneacetone)dipalladium(0), which may advantageously be employed in conjunction with 2-dicyclohexylphosphino-2',4',6'-triisopropylbiphenyl (XPhos). Suitably, the base may be an inorganic base such as sodium carbonate or potassium carbonate.

A compound comprising a halogen atom, e.g. bromo, may be converted into the corresponding compound comprising an optionally substituted aryl or heteroaryl moiety via a two-step procedure which comprises: (i) reaction with bis(pinacolato)diboron; and (ii) reaction of the compound thereby obtained with an appropriately substituted bromoaryl or bromoheteroaryl derivative. Step (i) is conveniently effected in the presence of a transition metal catalyst such as [1,1'-bis(diphenylphosphino)ferrocene]-dichloropalladium(II), and potassium acetate. Step (ii) is conveniently effected in the presence of a transition metal catalyst such as [1,1'-bis(diphenylphosphino)ferrocene]-dichloropalladium (II), and a base, e.g. an inorganic base such as sodium carbonate or potassium carbonate.

A compound comprising a cyano (—CN) moiety may be converted into the corresponding compound comprising a 1-aminoethyl moiety by a two-step process which comprises: (i) reaction with methylmagnesium chloride, ideally in the presence of titanium(IV) isopropoxide; and (ii) treatment of the resulting material with a reducing agent such as sodium borohydride. If an excess of methylmagnesium chloride is employed in step (i), the corresponding compound comprising a 1-amino-1-methylethyl moiety may be obtained.

A compound comprising the moiety —S— may be converted into the corresponding compound comprising the moiety —S(O)(NH)— by treatment with (diacetoxyiodo)benzene and ammonium carbamate.

A compound comprising a C═C double bond may be converted into the corresponding compound comprising a CH—CH single bond by treatment with gaseous hydrogen in the presence of a hydrogenation catalyst, e.g. palladium on charcoal.

A compound comprising an aromatic nitrogen atom may be converted into the corresponding compound comprising an N-oxide moiety by treatment with a suitable oxidising agent, e.g. 3-chloroperbenzoic acid.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode.
Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Greene's Protective Groups in Organic Synthesis*, ed. P. G. M. Wuts, John Wiley & Sons, $5^{th}$ edition, 2014. The protecting groups may be removed at any convenient subsequent stage utilising methods known from the art.

The compounds in accordance with this invention potently inhibit the ability of IL-17A to bind to IL-17RA. Thus, when tested in the IL-17 FRET assay described below, compounds of the present invention exhibit a $pIC_{50}$ value of 5.0 or more, generally of 6.0 or more, usually of 7.0 or more, typically of 7.2 or more, suitably of 7.5 or more, ideally of 7.8 or more, and preferably of 8.0 or more ($pIC_{50}$ equals $-\log_{10}[IC_{50}]$, in which $IC_{50}$ is expressed as a molar concentration, so the skilled person will appreciate that a higher $pIC_{50}$ figure denotes a more active compound).

Moreover, certain compounds in accordance with this invention potently inhibit IL-17 induced IL-6 release from human dermal fibroblasts. Indeed, when tested in the HDF cell line assay described below, compounds of the present invention exhibit a $pIC_{50}$ value of 5.0 or more, generally of 6.0 or more, usually of 7.0 or more, typically of 7.2 or more, suitably of 7.5 or more, ideally of 7.8 or more, and preferably of 8.0 or more (as before, the skilled person will appreciate that a higher $pIC_{50}$ figure denotes a more active compound).

IL-17 FRET Assay

The purpose of this assay is to test the ability of compounds to disrupt the interaction between IL-17A and soluble IL-17 Receptor A (IL-17RA). The ability of a compound to inhibit IL-17A binding to IL-17RA is measured in this assay.

An IL-17AA-TEV-Human Fc construct was expressed in a CHO SXE cell system and purified by protein A chromatography and size exclusion. The protein was labelled with an amine reactive AlexaFluor 647 dye (Thermo Fisher #A20006), as per manufacturer's instruction.

Soluble IL-17RA (33-317)-HKH-TEV-Fc was expressed in an Expi HEK293 cell system and purified by protein A chromatography and size exclusion. The Fc tag was cleaved by TEV, producing IL-17RA (33-317)-HKH, and the protein was labelled with amine reactive terbium (Thermo Fisher #PV3581).

In assay buffer [Dulbecco's PBS (Sigma #14190-094), 0.05% P20 (Thermo Scientific #28320), 1 mg/mL BSA (Sigma #A2153-500G)] the following solutions were prepared:

For IL-17A Assay

IL-17A-Fc-AF647 at 5 nM

IL-17RA-HKH-Tb at 5 nM

Compounds were serially diluted in DMSO before receiving an aqueous dilution into a 384 well dilution plate (Greiner #781281), to give a 25% DMSO solution.

IL-17A (10 μL) was added to a black low volume assay plate (Costar #4511) and diluted compound (5 μL) was transferred from the aqueous dilution plate. The cytokine and compound were allowed to incubate for 1 h, then IL-17RA (10 μL) was added. The plates were wrapped in foil and incubated at room temperature for 18-20 h with gentle shaking (<400 rpm) before being read on a Perkin Elmer Envision plate reader (Excitation: 330 nm; Emission 615/645 nm).

The final assay concentrations were IL-17A-AF647 2 nM and IL-17RA-Tb 2 nM, 5% DMSO.

When tested in the IL-17 FRET assay as described above, the compounds of the accompanying Examples were found to exhibit the following $pIC_{50}$ values.

| Example | $pIC_{50}$ |
|---|---|
| 1 | 7.4 |
| 2 | 7.4 |
| 3 | 7.6 |
| 4 | 7.4 |
| 5 | 5.8 |
| 6 | 7.1 |
| 7 | 7.8 |
| 8 | 7.0 |
| 9 | # |
| 10 | # |
| 11 | # |
| 12 | # |
| 13 | # |
| 14 | # |
| 15 | # |
| 16 | 6.9 |
| 17 | 7.3 |
| 18 | 6.8 |
| 19 | 7.9 |
| 20 | 7.0 |
| 21 | 7.6 |
| 22 | 6.5 |
| 23 | 7.7 |
| 24 | 7.6 |
| 25 | # |
| 26 | # |
| 27 | # |
| 28 | # |
| 29 | # |
| 30 | # |
| 31 | # |
| 32 | # |
| 33 | # |
| 34 | # |
| 35 | # |
| 36 | # |
| 37 | # |
| 38 | # |
| 39 | # |
| 40 | # |
| 41 | # |
| 42 | # |
| 43 | # |
| 44 | # |
| 45 | # |
| 46 | # |
| 47 | # |
| 48 | # |
| 49 | # |
| 50 | # |
| 51 | # |
| 52 | # |
| 53 | # |
| 54 | # |
| 55 | # |
| 56 | # |
| 57 | # |
| 58 | # |
| 59 | # |
| 60 | # |
| 61 | # |
| 62 | # |
| 63 | # |
| 64 | # |
| 65 | # |
| 66 | # |
| 67 | # |
| 68 | # |
| 69 | # |
| 70 | # |
| 71 | # |
| 72 | # |
| 73 | # |
| 74 | # |
| 75 | # |
| 76 | # |
| 77 | # |
| 78 | # |
| 79 | # |
| 80 | # |
| 81 | # |
| 82 | # |
| 83 | # |

-continued

| Example | $pIC_{50}$ |
|---|---|
| 84 | # |
| 85 | # |
| 86 | # |
| 87 | # |

#: -not determined

Inhibition of IL-17A Induced IL-6 Release from Dermal Fibroblast Cell Line

The purpose of this assay is to test the neutralising ability to IL-17 proteins, in a human primary cell system. Stimulation of normal human dermal fibroblasts (HDF) with IL-17 alone produces only a very weak signal but in combination with certain other cytokines, such as TNFα, a synergistic effect can be seen in the production of inflammatory cytokines, i.e. IL-6.

HDFs were stimulated with IL-17A (50 pM) in combination with TNF-α (25 pM). The resultant IL-6 response was then measured using a homogenous time-resolved FRET kit from Cisbio. The kit utilises two monoclonal antibodies, one labelled with Eu-Cryptate (Donor) and the second with d2 or XL665 (Acceptor). The intensity of the signal is proportional to the concentration of IL-6 present in the sample (Ratio is calculated by 665/620×104).

The ability of a compound to inhibit IL-17 induced IL-6 release from human dermal fibroblasts is measured in this assay.

HDF cells (Sigma #106-05n) were cultured in complete media (DMEM+10% FCS+2 mM L-glutamine) and maintained in a tissue culture flask using standard techniques. Cells were harvested from the tissue culture flask on the morning of the assay using TrypLE (Invitrogen #12605036). The TrypLE was neutralised using complete medium (45 mL) and the cells were centrifuged at 300×g for 3 minutes. The cells were re-suspended in complete media (5 mL) counted and adjusted to a concentration of $3.125\times10^4$ cells/mL before being added to the 384 well assay plate (Corning #3701) at 40 μL per well. The cells were left for a minimum of three hours, at 37° C./5% $CO_2$, to adhere to the plate.

Compounds were serially diluted in DMSO before receiving an aqueous dilution into a 384 well dilution plate (Greiner #781281), where 5 μL from the titration plate was transferred to 45 μL of complete media and mixed to give a solution containing 10% DMSO.

Mixtures of TNFα and IL-17 cytokine were prepared in complete media to final concentrations of TNFα 25 pM/IL-17A 50 pM, then 30 μL of the solution was added to a 384 well reagent plate (Greiner #781281).

10 μL from the aqueous dilution plate was transferred to the reagent plate containing 30 μL of the diluted cytokines, to give a 2.5% DMSO solution. The compounds were incubated with the cytokine mixtures for 1 h or 5 h at 37° C. (incubation times for specific test compounds are indicated in the Table below). After the incubation, 10 μL was transferred to the assay plate, to give a 0.500 DMSO solution, then incubated for 18-20 h at 37° C./5% $CO_2$.

From the Cisbio IL-6 FRET kit (Cisbio #62IL6PEB) europium cryptate and Alexa 665 were diluted in reconstitution buffer and mixed 1:1, as per kit insert. To a white low volume 384 well plate (Greiner #784075) were added FRET reagents (10 μL), then supernatant (10 μL) was transferred from the assay plate to Greiner reagent plate. The mixture was incubated at room temperature for 3 h with gentle shaking (<400 rpm) before being read on a Synergy Neo 2 plate reader (Excitation: 330 nm; Emission: 615/645 nm).

When tested in the HDF cell line assay as described above, the compounds of the accompanying Examples were found to exhibit the following $pIC_{50}$ values.

| Example | $pIC_{50}$ | Incubation Time (h) |
|---|---|---|
| 1 | 8.2 | 5 |
| 2 | 8.0 | 5 |
| 3 | 7.6 | 5 |
| 4 | 7.8 | 5 |
| 5 | 5.9 | 1 |
| 6 | 7.6 | 5 |
| 7 | 7.8 | 5 |
| 8 | 7.6 | 5 |
| 9 | 8.9 | 5 |
| 10 | 7.8 | 5 |
| 11 | 8.4 | 5 |
| 12 | 6.9 | 5 |
| 13 | 8.3 | 5 |
| 14 | 8.1 | 5 |
| 15 | 7.7 | 5 |
| 16 | 7.1 | 5 |
| 17 | 7.9 | 5 |
| 18 | 7.1 | 1 |
| 19 | 8.4 | 5 |
| 20 | 7.7 | 5 |
| 21 | 7.8 | 5 |
| 22 | 6.5 | 5 |
| 23 | 8.0 | 5 |
| 24 | 8.2 | 5 |
| 25 | 8.1 | 5 |
| 26 | 6.9 | 5 |
| 27 | 8.2 | 5 |
| 28 | 8.5 | 5 |
| 29 | 6.9 | 5 |
| 30 | 8.5 | 5 |
| 31 | 8.8 | 5 |
| 32 | 7.2 | 5 |
| 33 | 8.4 | 5 |
| 34 | 8.6 | 5 |
| 35 | 6.2 | 5 |
| 36 | 7.5 | 5 |
| 37 | 7.8 | 5 |
| 38 | 7.0 | 5 |
| 39 | 8.3 | 5 |
| 40 | 8.1 | 5 |
| 41 | 8.3 | 5 |
| 42 | 6.9 | 5 |
| 43 | 7.3 | 5 |
| 44 | 8.0 | 5 |
| 45 | 6.3 | 5 |
| 46 | 6.4 | 5 |
| 47 | 6.8 | 5 |
| 48 | 5.5 | 5 |
| 49 | 7.5 | 5 |
| 50 | 8.0 | 5 |
| 51 | 5.8 | 5 |
| 52 | 8.3 | 5 |
| 53 | 7.2 | 5 |
| 54 | 7.1 | 5 |
| 55 | 8.4 | 5 |
| 56 | | |
| 57 | 5.6 | 5 |
| 58 | 8.1 | 5 |
| 59 | 8.9 | 5 |
| 60 | 6.7 | 5 |
| 61 | 9.1 | 5 |
| 62 | 8.3 | 5 |
| 63 | 6.8 | 5 |
| 64 | 8.7 | 5 |
| 65 | 8.6 | 5 |
| 66 | 6.7 | 5 |
| 67 | 8.8 | 5 |
| 68 | 7.9 | 5 |
| 69 | 5.6 | 5 |
| 70 | 8.2 | 5 |
| 71 | 7.6 | 5 |

-continued

| Example | $pIC_{50}$ | Incubation Time (h) |
|---|---|---|
| 72 | 5.8 | 5 |
| 73 | 8.2 | 5 |
| 74 | 8.5 | 5 |
| 75 | 6.2 | 5 |
| 76 | 8.9 | 5 |
| 77 | 7.9 | 5 |
| 78 | 7.8 | 5 |
| 79 | 8.1 | 5 |
| 80 | 8.2 | 5 |
| 81 | 7.5 | 5 |
| 82 | 7.6 | 5 |
| 83 | 5.7 | 5 |
| 84 | 7.6 | 5 |
| 85 | 7.9 | 5 |
| 86 | 5.2 | 5 |
| 87 | 8.1 | 5 |

The following Examples illustrate the preparation of compounds according to the invention.

EXAMPLES

Abbreviations

DCM: dichloromethane THF: tetrahydrofuran

MeOH: methanol EtOH: ethanol

DMSO: dimethyl sulfoxide DIPEA: N,N-diisopropylethylamine

DMF: N,N-dimethylformamide DMA: N,N-dimethylacetamide

EtOAc: ethyl acetate TFA: trifluoroacetic acid

TBME: tert-butyl methyl ether DAST: (diethylamino) sulfur trifluoride

IPA: isopropyl alcohol DBU: 1,8-diazabicyclo[5.4.0]undec-7-ene

LiHMDS: lithium bis(trimethylsilyl)amide

T3P®: 2,4,6-tripropyl-1,3,5,2,4,6-trioxatriphosphorinane-2,4,6-trioxide

HATU: 1-[bis(dimethylamino)methylene]-1H-1,2,3-triazolo[4,5-b]pyridinium 3-oxid hexafluorophosphate XPhos: 2-dicyclohexylphosphino-2',4',6'-triisopropylbiphenyl $Pd_2(dba)_3$: tris(dibenzylideneacetone)dipalladium(0)

h: hour r.t.: room temperature

M: mass RT: retention time

HPLC: High Performance Liquid Chromatography

LCMS: Liquid Chromatography Mass Spectrometry

SFC: Supercritical Fluid Chromatography

Analytical and Preparative Methods

Method 1

Agilent, pH 3, 3 minute run.

Stationary Phase: X-Bridge C18 Waters (2.1×20 mm, 2.5 μm column)

Column Temperature: 40° C.

Mobile Phase A: 10 mM ammonium formate in water+0.1% formic acid

Mobile Phase B: acetonitrile+5% water+0.1% formic acid

Flow rate: 1 mL/minute

Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 2

Agilent, pH 3, 6 minute run.

Stationary Phase: X-Bridge C18 Waters (2.1×20 mm, 2.5 μm column)

Column Temperature: 40° C.

Mobile Phase A: 10 mM ammonium formate in water+0.1% formic acid

Mobile Phase B: acetonitrile+5% water+0.1% formic acid

Flow rate: 1 mL/minute

Gradient program:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 3

Agilent, pH 10, 3 minute run.

Stationary Phase: X-Bridge C18 Waters (2.1×20 mm, 2.5 μm column)

Mobile Phase A: 10 mM ammonium formate in water+0.1% ammonia solution

Mobile Phase B: acetonitrile+5% water+0.1% ammonia solution

Flow rate: Pump 1: 1 mL/minute

Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 4

MSQ1/MSQ2 low pH uPLC-MET-uHPLC-AB-101, 7 minute run.

Stationary Phase: Phenomenex Kinetix-XB C18 (2.1×100 mm, 1.7 μm column)

Column Temperature: 40° C.

Mobile Phase A: water+0.1% formic acid

Mobile Phase B: acetonitrile+0.1% formic acid

Flow rate: 0.6 mL/minute

Gradient program:

| Time | A % | B % |
|---|---|---|
| 0.00 | 95.00 | 5.00 |
| 5.30 | 0.00 | 100.00 |
| 5.80 | 0.00 | 100.00 |
| 5.82 | 95.00 | 5.00 |
| 7.00 | 95.0 | 5.00 |

Method 5

Gilson low pH prep method (Early Elute Method).

Stationary Phase: Waters Sunfire C18 (30×100 mm, 10 μm column) (part no. 186003971)

Mobile Phase A: water+0.1% formic acid
Mobile Phase B: acetonitrile+0.1% formic acid
Flow rate: 40 mL/minute
Gradient program:

| Time | A % | B % |
|---|---|---|
| 0.00 | 90 | 10 |
| 0.55 | 90 | 10 |
| 14.44 | 5 | 95 |
| 16.55 | 5 | 95 |
| 16.75 | 90 | 10 |

Method 6

MET/CR/1602—uPLC IPC high pH method; 1 μL injection volume.

Stationary Phase: Waters BEH C18 (30×2.1 mm, 1.7 μm column) (part no. 186002349)
Column Temperature: 40° C.
Mobile Phase A: 2 mM ammonium bicarbonate, buffered to pH10
Mobile Phase B: acetonitrile
Flow rate: 1 mL/minute
Gradient program:

| Time | A % | B % |
|---|---|---|
| 0.00 | 95 | 5 |
| 0.75 | 0 | 100 |
| 0.85 | 0 | 100 |
| 0.90 | 95 | 5 |
| 1.00 | 95 | 5 |

Method 7 pH 10.

Stationary Phase: Phenomenex Gemini NmX-C18 (2×20 mm, 3 μm column)
Mobile Phase A: 10 mM ammonium formate in water+0.1% ammonia solution
Mobile Phase B: acetonitrile+5% water+0.1% ammonia solution
Flow rate: 1 mL/minute
Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 8

MSDXT, pH 10.

Stationary Phase: Waters Acquity UPLC BEH C18 (2.1×50 mm, 1.7 μm column)
Mobile Phase A: 10 mM ammonium formate in water+0.1% ammonia solution
Mobile Phase B: acetonitrile+5% water+0.1% ammonia solution
Flow rate: 1.5 mL/minute
Gradient program:

| Time | A % | B % |
|---|---|---|
| 0.00 | 95.00 | 5.00 |
| 0.10 | 95.00 | 5.00 |

-continued

| Time | A % | B % |
|---|---|---|
| 3.50 | 5.00 | 95.00 |
| 4.00 | 5.00 | 95.00 |
| 4.05 | 95.00 | 5.00 |

Method 9 pH 10.

Stationary Phase: Phenomenex Gemini NX-C18 (2×20 mm, 3 μm column)
Mobile Phase A: 10 mM ammonium formate in water+0.1% ammonia solution
Mobile Phase B: acetonitrile+5% water+0.1% ammonia solution
Flow rate: 1 mL/minute
Gradient program:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 10

Chiral HPLC condition: Chiralpak AD-H (4.6×250 mm, 5 μm column)
85:15 heptane:EtOH (1 mL/minute)

Method 11

Purification was performed by SFC using a Chiralpak IB (250×20 mm, 5 μm column), flow rate 100 mL/minute, eluting with an isocratic 5% MeOH (+0.1% $NH_4OH$) method (ABPR 60 bar), using a 16 minute run time on a Waters Prep 100 fractionlynx system, in tandem with a Waters SQD2 mass spectrometer.

Method 12

Purification was performed by SFC using a Chiralcel OJ (250×20 mm, 5 μm column), flow rate 100 mL/minute, eluting with an isocratic 3% MeOH (+0.1% $NH_4OH$) method (ABPR 120 bar), using a 16 minute run time on a Waters Prep 100 fractionlynx system, in tandem with a Waters SQD2 mass spectrometer.

Method 13

Achiral purification was performed using a XBridge Prep Phenyl OBD (19×150 mm, 5 μm column), flow rate 20 mL/minute, eluting with a focus gradient of 45-60% over 15 minutes on a Waters FractionLynx Autopurification system, in tandem with a Waters SQD2 mass spectrometer.

Solvent A: 10 mM ammonium bicarbonate in water+0.1% ammonia solution
Solvent B: acetonitrile+5% water+0.1% ammonia solution Method 14

Gilson high pH prep method 1500 μL injection with UV detection (215 nM).

Stationary Phase: Waters Xbridge C18 (30×100 mm, 10 μm column) (part no. 186003930)
Mobile Phase A: water+0.2% ammonium hydroxide
Mobile Phase B: acetonitrile+0.2% ammonium hydroxide
Flow rate: 40 mL/minute Gradient program:

| Time | A % | B % |
|---|---|---|
| 0.00 | 70 | 30 |
| 0.55 | 70 | 30 |
| 11.00 | 5 | 95 |
| 13.10 | 5 | 95 |
| 13.31 | 70 | 30 |

Method 15

Chiral purification was performed using a Chiralpak-IB (250×21.2 mm, 5 μm column), flow rate 100 mL/minute, eluting with a 5% MeOH (+0.1% $NH_4OH$) isocratic method (ABPR 60 bar), using a 14 minute run time on a Waters Prep 100 fractionlynx system, in tandem with a Waters SQD2 mass spectrometer.

Method 16

Chiral analysis was performed using a Chiralpak-IB (150×4.6 mm, 3 μm column), flow rate 3 mL/minute, eluting with a 5% MeOH (+0.1% $NH_4OH$) isocratic method (ABPR 120 bar), using an 8 minute run time on a Waters UPC2 system, in tandem with a Waters QDa mass spectrometer.

Method 17

Chiral purification was performed using a Chiralpak IC (250×20 mm, 5 μm column), flow rate 100 mL/minute, eluting with an isocratic 10% MeOH (+0.1% $NH_4OH$) method (ABPR 120 bar), using a 7.5 minute run time on a Waters Prep 100 fractionlynx system, in tandem with a Waters SQD2 mass spectrometer.

Method 18

Chiral analysis was performed using a Chiralpak-IB (150×4.6 mm, 3 μm column), flow rate 3 mL/minute, eluting with a 10% MeOH (+0.1% $NH_4OH$) isocratic method (ABPR 120 bar), using a 6.5 minute run time on a Waters UPC2 system, in tandem with a Waters QDa mass spectrometer.

Method 19

Waters Prep SFC80 with a stationary phase of a Pirkle (R,R) Whelk-01 (5 mm, 250×21.1 mm column) and mobile phase of $CO_2$/MeOH (70/300), flow rate 50 mL/minute (100 bar) at 40° C.

Method 20

Preparative Chiral LC was carried out on a Gilson system with a 321/322 pump, GX-241 autosampler, 171/172 detector and prep FC fraction collector. Purity and/or enantiomeric purity determined by UV (210-400 nm) and identity confirmed by MS.

Stationary Phase: CSH 100×30 mm, 5 μm column

Flow Rate: 40 mL/minute

Gradient: 95:5 acetonitrile/$H_2O$ (+0.1% formic acid) to 5:95 acetonitrile/$H_2O$ (+0.1% formic acid) over 20 minutes.

Method 21

Gilson low pH prep method.

Stationary Phase: Waters Sunfire C18 (30×100 mm, 10 μm column) (part no. 186003971)

Mobile Phase A: water+0.1% formic acid

Mobile Phase B: acetonitrile+0.1% formic acid

Flow rate: 40 mL/minute

Gradient program:

| Time | A % | B % |
|---|---|---|
| 0.00 | 70 | 30 |
| 0.55 | 70 | 30 |
| 11.00 | 5 | 95 |

-continued

| Time | A % | B % |
|---|---|---|
| 13.10 | 5 | 95 |
| 16.31 | 70 | 30 |

Method 22

Preparative Chiral LC was carried out on Gilson system with a 321/322 pump, GX-241 autosampler, 171/172 detector and prep FC fraction collector. Purity and/or enantiomeric purity determined by UV (210-400 nm) and identity confirmed by MS.

Stationary Phase: Chiralpak AD-H, 4.6×250 mm, 5 μm column

Flow Rate: 40 mL/minute

Gradient: 90:10 heptane:ethanol

Method 23

Purification was performed using a Chiralpak IB, 250×21.2 mm, 5 μm column, flow rate 100 mL/minute, eluting with an isocratic 5% EtOH (+10 mM ammonium formate) method (ABPR 60 bar), using a 20-minute run time on a Waters Prep 100 fractionlynx system, in tandem with a Waters SQD2 mass spectrometer.

Method 24

Stationary Phase: Phenomenex Gemini NX-C18 (2×20 mm, 3 μm column)

Mobile Phase A: 10 mM ammonium formate in water+0.1% formic acid solution

Mobile Phase B: acetonitrile+5% water+0.1% formic acid solution

Flow rate: 1 mL/minute

Gradient program:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 25

Chiral purification performed by HPLC using a using a Regis (R,R)-Whelk-1 250×21.1 mm, 5 μm column (temperature 40° C.), eluting with a 3-40% MeOH (+0.1% $NH_4OH$) gradient (ABPR 60 bar) with a 7.5 minute run time, on a Waters Prep 150 fractionlynx system, in tandem with a Waters QDa mass spectrometer.

Method 26

Chiral analysis performed by HPLC using a Regis (R,R)-Whelk-1 250×4.6 mm, 5 μm column (temperature 40° C., eluting with a 3-40% MeOH (+0.1% $NH_4OH$) method (ABPR 120 bar) with a 6.5 minute run time on a Waters UPC2 Acquity system, in tandem with a Waters QDa mass spectrometer.

Method 27

Chiral purification performed by HPLC using a using a Regis (R,R)-Whelk-1 250×21.1 mm, 5 μm column (temperature 40° C.), eluting with a 3-40% EtOH (+0.1% $NH_4OH$) gradient (ABPR 60 bar) with a 7.5 minute run time, on a Waters Prep 150 fractionlynx system, in tandem with a Waters QDa mass spectrometer.

Method 28

Chiral analysis performed by HPLC using a Regis (R,R)-Whelk-1 250×4.6 mm, 5 μm column (temperature 40° C., eluting with a 3-40% EtOH (+0.1% $NH_4OH$) method (ABPR 120 bar) with a 6.5 minute run time on a Waters UPC2 Acquity system, in tandem with a Waters QDa mass spectrometer.

Method 29

Chiral purification performed by SFC using a Chiralpak AD-H, 10×250 mm, 5 μm column with a flow rate of 15 mL/minute, eluting with 5% MeOH and 95% $CO_2$.

Method 30

Chiral analysis performed by SFC using a Chiralpak AD-H, 4.6×250 mm, 5 μm column with with a flow rate of 4 mL/minute, eluting with 5% MeOH and 95% $CO_2$.

Method 31

Chiral purification performed by SFC Prep using a Kromasil 2EP column with a gradient of 3-40% MeOH+0.1% $NH_4OH$.

Method 32

Chiral analysis performed by HPLC using a Regis (R,R)-Whelk-1 250×4.6 mm, 5 μm column (temperature 35° C.), eluting with a 3-40% MeOH (+0.1% $NH_4OH$) method (ABPR 120 bar) with a 6.5 minute run time on a Waters UPC2 Acquity system, in tandem with a Waters QDa mass spectrometer.

Method 33

Chiral purification performed by SFC using a Chiralpak AD-H, 10×250 mm, 5 μm column, eluting with 10% EtOH and 90% $CO_2$, with a flow rate of 15 mL/minute.

Method 34

Chiral analysis performed by SFC using a Chiralpak AD-H, 4.6×250 mm, 5 μm column, eluting with 15% EtOH and 85% $CO_2$, with a flow rate of 4 mL/minute.

Method 35

Chiral purification performed by SFC using a Chiralpak AD-H, 10×250 mm, 5 μm column with a flow rate of 10 mL/minute and a run time of 15 minutes, eluting with 5% EtOH and 95% $CO_2$.

Method 36

Chiral analysis performed by SFC using a Chiralpak AD-H, 4.6×250 mm, 5 μm column with a flow rate of 4 mL/minute over a run time of 15 minutes, eluting with 5% EtOH and 95% $CO_2$.

Method 37

Chiral purification performed by SFC using a Chiralpak AD-H, 10×250 mm, 5 μm column with a flow rate of 15 mL/minute and a run time of 10 minutes, eluting with 5% EtOH and 95% $CO_2$.

Method 38

Chiral analysis performed by SFC using a Chiralpak AD-H, 4.6×250 mm, 5 μm column with a flow rate of 4 mL/minute and a run time of 10 minutes, eluting with 5% EtOH and 95% $CO_2$.

Method 39

Chiral purification performed by HPLC using a Chiralpak AD-H, 20×250 mm, 5 μm column with a flow rate of 18 mL/minute, eluting with 15% EtOH and 85% heptane.

Method 40

Chiral analysis performed by HPLC using a Chiralpak AD-H, 4.6×250 mm, 5 μm with flow rate of 1 mL/minute, eluting with 15% EtOH and 85% heptane.

Method 41

Chiral analysis performed by SFC using a Chiralpak AD-H, 4.6×250 mm, 5 μm column, eluting with 10% EtOH and 90% $CO_2$, with a flow rate of 4 mL/minute.

Intermediate 1

(2S)-2-(Benzyloxycarbonylamino)-2-(4,4-difluorocyclohexyl)acetic Acid

To a stirred solution of (2S)-2-amino-2-(4,4-difluorocyclohexyl)acetic acid hydrochloride (1.61 g, 6.66 mmol) and triethylamine (3.25 mL, 23.3 mmol) in DCM (26.6 mL) at 0° C. was added N-(benzyloxycarbonyloxy)succinimide (1.61 g, 6.33 mmol). The reaction mixture was warmed to room temperature and stirred for 4 h, then diluted with DCM (25 mL) and washed with 5% hydrochloric acid (50 mL) and water (50 mL). The organic extracts were combined, passed through a phase separator and concentrated. Trituration with hexane (50 mL) afforded the title compound (1.99 g, 91%) as a white solid. $\delta_H$ (300 MHz, DMSO-$d_6$) 12.70 (s, 1H), 7.09 (d, J 8.7 Hz, 1H), 7.43-7.26 (m, 5H), 5.04 (s, 2H), 4.00 (dd, J 8.7, 6.0 Hz, 1H), 2.12-1.55 (m, 7H), 1.52-1.19 (m, 2H).

Intermediate 2

(2S)-2-(tert-Butoxycarbonylamino)-2-(4,4-difluorocyclohexyl)acetic Acid

To a stirred solution of (2S)-2-amino-2-(4,4-difluorocyclohexyl)acetic acid hydrochloride (2.0 g, 8.71 mmol) in DCM (10 mL) were added triethylamine (4.3 mL, 30.5 mmol) and N-(tert-butoxycarbonyloxy)succinimide (1.72 g, 7.83 mmol). The resulting mixture was stirred at room temperature for 24 h, then diluted with DCM (200 mL), 5% hydrochloric acid (2×100 mL) and water (100 mL). The organic extracts were combined, passed through a phase separator and concentrated. Trituration with hexane (100 mL) afforded the title compound (2.0 g, 78%) as a white solid. $\delta_H$ (300 MHz, DMSO-$d_6$) 12.60 (s, 1H), 7.09 (d, J 8.7 Hz, 1H), 3.91 (dd, J 8.5, 6.2 Hz, 1H), 2.08-1.92 (m, 2H), 1.92-1.54 (m, 5H), 1.51-1.16 (m, 11H).

Intermediate 3

Bromo(2-tert-butoxy-2-oxoethyl)zinc tert-Butyl 2-bromoacetate (45.0 mL, 0.31 mol) was added dropwise over 1 h to a slurry of activated zinc (30.2 g, 0.46 mol) in THF (400 mL) at 60° C. An exotherm was observed. The reaction mixture was stirred at 65° C. for 1 h, then allowed to cool to r.t., with settling of the excess zinc. Conversion was assumed to be 100%, and the resulting yellow solution was assumed to be a 0.77M solution in THF.

Intermediate 4

N,N-Dibenzyl-3-bromo-2-fluoro-6-nitroaniline

To a stirred suspension of 1-bromo-2,3-difluoro-4-nitrobenzene (23.0 g, 96.6 mmol) and potassium carbonate (16.0 g, 116 mmol) in acetonitrile (250 mL) was added N-benzyl-1-phenylmethanamine (20.0 mL, 106 mmol). The suspension was stirred at 80° C. for 16 h, then re-treated with N-benzyl-1-phenylmethanamine (2.0 mL, 10.4 mmol) and stirred at 80° C. for 1 h. The mixture was filtered, then concentrated. The residue was purified by flash column chromatography, eluting with a gradient of ethyl acetate in heptanes, to afford the title compound (40.9 g, 85%) as an orange solid. $\delta_H$ (400 MHz, DMSO-$d_6$) 7.64 (dd, J 8.8, 6.5 Hz, 1H), 7.54 (dd, J 8.8, 1.6 Hz, 1H), 7.33-7.18 (m, 10H), 4.15 (s, 4H). LCMS (Method 1) $[M+H]^+$ m/z 415, 417, RT 2.25 minutes.

Intermediate 5 tert-Butyl 2-[3-(dibenzylamino)-2-fluoro-4-nitrophenyl]acetate

To a stirred solution of Intermediate 4 (63.0 g, 0.15 mol), XPhos (4.17 g, 8.74 mmol) and allyl(chloro)palladium dimer (1.61 g, 4.37 mmol) in THF (400 mL) under nitrogen was added Intermediate 3 (0.77M, 378 mL, 0.29 mol) dropwise. The mixture was stirred at 50° C. for 45 minutes, then cooled to 30° C. and quenched with saturated aqueous $NH_4Cl$ solution (200 mL), keeping the temperature between 20° C. and 30° C. The combined mixture was diluted with EtOAc (200 mL), and the phases were separated. The aqueous phase was extracted with EtOAc (50 mL). The organic fractions were combined, dried over $Na_2SO_4$ and concentrated in vacuo. The residue was purified by flash column chromatography, eluting with a gradient of DCM in heptanes, to afford the title compound (65 g, 94%) as a yellow powder. $\delta_H$ (400 MHz, DMSO-$d_6$) 7.47 (dd, J 8.3, 1.1 Hz, 1H), 7.30-7.18 (m, 11H), 4.11 (s, 4H), 3.68 (d, J 1.3 Hz, 2H), 1.41 (s, 9H). LCMS (Method 1): $[M+H]^+$ m/z 451, RT 2.27 minutes.

Intermediate 6 tert-Butyl 2-[3-(dibenzylamino)-2-fluoro-4-nitrophenyl]prop-2-enoate

To a solution of Intermediate 5 (5.00 g, 11.1 mmol) in DMSO (25 mL) was added N,N,N',N'-tetramethylmethanediamine (2.3 mL, 16.7 mmol), followed by acetic anhydride (3.5 mL, 36.6 mmol). The reaction mixture was stirred at r.t. for 21 h, then diluted with water (100 mL) and extracted with EtOAc (3×100 mL). The combined organic fractions were washed with water (3×50 mL), saturated aqueous $NaHCO_3$ solution (50 mL) and brine (50 mL), then dried over $Na_2SO_4$ and concentrated in vacuo. The residue was purified by flash column chromatography, eluting with a gradient of 0-100% EtOAc in heptanes, to afford the title compound (4.97 g, 97%) as a pale yellow solid. LCMS (Method 1): $[M+H]^+$ m/z 463.0, RT 2.32 minutes.

Intermediate 7 tert-Butyl 1-benzyl-3-[3-(dibenzylamino)-2-fluoro-4-nitrophenyl]pyrrolidine-3-carboxylate To a solution of Intermediate 6 (4.97 g, 10.7 mmol) and N-(methoxymethyl)-1-phenyl-N-(trimethylsilylmethyl) methanamine (4.1 mL, 16.1 mmol) in DCM (99 mL) was added TFA (81 μL, 1.09 mmol) at 0° C. The mixture was warmed to room temperature and stirred for 16 h, then concentrated in vacuo. The residue was purified by flash column chromatography, eluting with a gradient of 0-100% EtOAc in heptanes, to afford the title compound (6.30 g, 98%) as a pale yellow solid. LCMS (Method 1): $[M+H]^+$ m/z 596, RT 2.05 minutes.

Intermediate 8 tert-Butyl 3-[4-amino-3-(dibenzylamino)-2-fluorophenyl]pyrrolidine-3-carboxylate To a stirred solution of Intermediate 7 (3.00 g, 5.04 mmol) in EtOH (40 mL) was added 10% Pd/C (50% wet, 2.0 g, 0.94 mmol) in one portion. The reaction mixture was purged and stirred vigorously under a hydrogen atmosphere at r.t. for 18 h. The reaction mixture was filtered through a pad of Celite®, then washed with EtOH (2×10 mL) and concentrated in vacuo, to afford the title compound (1.60 g, 53%) as a light orange solid. $\delta_H$ (400 MHz, DMSO-$d_6$) 7.35-7.13 (m, 10H), 6.78 (t, J 8.5 Hz, 1H), 6.31 (d, J 8.5 Hz, 1H), 5.06 (br s, 2H), 4.13-3.88 (m, 4H), 3.57 (s, 1H), 3.09-2.81 (m, 3H), 2.43-2.31 (m, 1H), 2.08-1.92 (m, 1H), 1.33-1.24 (m, 9H). LCMS (Method 1): $[M+H]^+$ m/z 476, RT 1.80 minutes.

Intermediate 9

Di-tert-butyl 3-[4-amino-3-(dibenzylamino)-2-fluorophenyl]pyrrolidine-1,3-dicarboxylate To a stirred solution of Intermediate 8 (1.56 g, 2.62 mmol) in DCM (31 mL) was added DIPEA (884 μL, 5.06 mmol), followed by di-tert-butyl dicarbonate (572 mg, 2.62 mmol). The reaction mixture was stirred at r.t. for 1 h, then diluted with DCM (30 mL) and washed with saturated aqueous $NH_4Cl$ solution (30 mL). The organic fraction was dried over $Na_2SO_4$ and concentrated in vacuo. The residue was purified by flash column chromatography, eluting with a gradient of 0-100% EtOAc in heptanes, to afford the title compound (1.33 g, 88%) as a pale orange solid. LCMS (Method 1): $[M+H]^+$ m/z 576, RT 2.27 minutes.

Intermediate 10

Di-tert-butyl 3-(3,4-diamino-2-fluorophenyl)pyrrolidine-1,3-dicarboxylate

To a stirred solution of Intermediate 9 (1.33 g, 2.26 mmol) in EtOH (30 mL) was added 10% Pd/C (50% wet, 0.78 g, 0.366 mmol) in one portion. The reaction mixture was purged and stirred vigorously under a hydrogen atmosphere at r.t. for 5 h. The reaction mixture was filtered through a pad of Celite®, then washed with EtOH (2×10 mL) and concentrated in vacuo, to afford the title compound (0.769 g, 86%) as a beige solid. $\delta_H$ (500 MHz, DMSO-$d_6$) 6.29 (t, J 3.7 Hz, 2H), 4.80 (s, 2H), 4.41 (s, 2H), 4.14 (t, J 10.4 Hz, 1H), 3.29 (s, 1H), 3.26-3.14 (m, 2H), 2.55-2.51 (m, 1H), 2.20-2.10 (m, 1H), 1.40 (d, J 6.6 Hz, 9H), 1.31 (s, 9H). LCMS (Method 1): $[M-BOC-^tBu+H]^+$ m/z 240.2, RT 1.86 minutes.

Intermediate 11

Di-tert-butyl 3-{2-[(S)-benzyloxycarbonylamino(4,4-difluorocyclohexyl)methyl]-4-fluoro-1H-benzimidazol-5-yl}pyrrolidine-1,3-dicarboxylate To a stirred solution of Intermediate 1 (697 mg, 2.13 mmol) and HATU (810 mg, 2.16 mmol) in DCM (20 mL) at r.t. were added DIPEA (1.0 mL, 5.73 mmol) and Intermediate 10 (766 mg, 1.94 mmol). The reaction mixture was stirred for 3 h, then diluted with DCM (50 mL) and washed sequentially with saturated aqueous $NH_4Cl$ solution (50 mL), saturated aqueous $NaHCO_3$ solution (50 mL) and water (50 mL). The organic fractions were combined, dried over $Na_2SO_4$ and concentrated in vacuo. The residue was purified by flash column chromatography, eluting with a gradient of 0-100% EtOAc in heptanes. The resulting beige solid was dissolved in acetic acid (15 mL) and heated at 60° C. for 12 h. The reaction mixture was cooled to r.t. and concentrated in vacuo. The residue was purified by flash column chromatography, eluting with a gradient of 0-100% EtOAc in heptanes, to afford the title compound (1.10 g, 83%) as a beige solid. $\delta_H$ (500 MHz, $CD_3OD$) 7.50-6.86 (m, 7H), 5.24-4.99 (m, 2H), 4.80 (d, J 8.0 Hz, 1H), 4.46 (d, J 10.9 Hz, 1H), 3.61-3.37 (m, 3H), 2.86 (d, J 22.6 Hz, 1H), 2.48-2.31 (m, 1H), 2.24-2.09 (m, 1H), 2.09-1.89 (m, 3H), 1.89-1.66 (m, 2H), 1.50 (d, J 7.9 Hz, 11H), 1.38 (s, 10H). LCMS (Method 1): $[M+H]^+$ m/z 687.1, RT 2.09 minutes.

Intermediate 12

Di-tert-butyl 3-{2-[(S)-amino(4,4-difluorocyclohexyl)methyl]-4-fluoro-1H-benzimidazol-5-yl}pyrrolidine-1,3-dicarboxylate To a stirred solution of Intermediate 11 (1.10 g, 1.60 mmol) in EtOH (20 mL) was added 10% Pd/C (50% wet, 0.33 g, 0.155 mmol) in one portion. The reaction mixture was purged and stirred vigorously under a hydrogen atmosphere at r.t. for 1.5 h. The reaction mixture was filtered through a pad of Celite®, then washed with EtOH (2×20 mL) and concentrated in vacuo, to afford the title compound (0.88 g, 99%) as a beige solid. $\delta_H$ (500 MHz, $CD_3OD$) 7.34 (d, J 8.5 Hz, 1H), 7.23-7.17 (m, 1H), 4.51-4.42 (m, 1H), 3.95 (d, J 7.3 Hz, 1H), 3.57-3.36 (m, 3H), 2.94-2.81 (m, 1H), 2.46-2.34 (m, 1H), 2.16-1.97 (m, 3H), 1.97-1.87 (m, 1H), 1.87-1.62 (m, 3H), 1.50 (d, J 7.9 Hz, 10H), 1.37 (d, J 1.3 Hz, 11H). LCMS (Method 1): $[M+H]^+$ m/z 553.0, RT 1.76 minutes.

Intermediate 13

Di-tert-butyl 3-(2-{(S)-(4,4-difluorocyclohexyl)[(4-methyl-1,2,5-oxadiazole-3-carbonyl)-amino]methyl}-4-fluoro-1H-benzimidazol-5-yl)pyrrolidine-1,3-dicarboxylate To a stirred suspension of 4-methyl-1,2,5-oxadiazole-3-carboxylic acid (128 mg, 0.99 mmol) and HATU (404 mg, 1.06 mmol) in DCM (10 mL) at r.t. was added DIPEA (44 µL, 0.25 mmol), followed by Intermediate 12 (500 mg, 0.91 mmol). The reaction mixture was stirred for 2 h, then diluted sequentially with saturated aqueous $NH_4Cl$ solution (25 mL) and water (25 mL). The residue was extracted with EtOAc (2×50 mL). The combined organic fractions were washed with brine (50 mL), dried over $Na_2SO_4$ and concentrated in vacuo. The residue was purified by flash column chromatography, eluting with a gradient of 0-100% EtOAc in heptanes, to afford the title compound (411 mg, 69%) as an off-white solid. $\delta_H$ (500 MHz, $CD_3OD$) 7.41-7.32 (m, 1H), 7.26-7.19 (m, 1H), 5.27 (d, J 8.7 Hz, 1H), 4.46 (d, J 11.4 Hz, 1H), 3.55-3.38 (m, 3H), 2.93-2.83 (m, 1H), 2.53 (s, 3H), 2.44-2.28 (m, 2H), 2.19-1.99 (m, 3H), 1.94-1.70 (m, 3H), 1.50 (d, J 8.0 Hz, 11H), 1.37 (s, 9H). LCMS (Method 1): $[M+H]^+$ m/z 663.0, RT 2.06 minutes.

Intermediate 14 tert-Butyl 3-(2-{(S)-(4,4-difluorocyclohexyl)[(4-methyl-1,2,5-oxadiazole-3-carbonyl)-amino]methyl}-4-fluoro-1H-benzimidazol-5-yl)pyrrolidine-3-carboxylate To a stirred solution of Intermediate 13 (400 mg, 0.60 mmol) in DCM (8 mL) was added 4M HCl in 1,4-dioxane (700 µL, 2.80 mmol). The mixture was stirred at r.t. for 3.5 h, then quenched with saturated aqueous $NaHCO_3$ solution (25 mL) and extracted with 10% MeOH in DCM (3×20 mL). The organic fractions were combined, then dried over $Na_2SO_4$ and concentrated in vacuo, to afford the title compound (335 mg, 99%) as an off-white solid. $\delta_H$ (500 MHz, $CD_3OD$) 7.34 (d, J 8.5 Hz, 1H), 7.30-7.22 (m, 1H), 5.27 (d, J 8.7 Hz, 1H), 3.95-3.86 (m, 1H), 3.17-3.06 (m, 3H), 2.81-2.68 (m, 1H), 2.53 (s, 3H), 2.42-2.26 (m, 2H), 2.18-2.00 (m, 3H), 1.95-1.66 (m, 2H), 1.62-1.40 (m, 3H), 1.37 (d, J 1.3 Hz, 9H). LCMS (Method 1): $[M+H]^+$ m/z 563.0, RT 1.66 minutes.

Intermediate 15

3-tert-Butyl 1-methyl 3-(2-{(S)-(4,4-difluorocyclohexyl)[(4-methyl-1,2,5-oxadiazole-3-carbonyl)amino]methyl}-4-fluoro-1H-benzimidazol-5-yl)pyrrolidine-1,3-dicarboxylate To a stirred solution of Intermediate 14 (167 mg, 0.30 mmol) and DIPEA (104 µL, 0.59 mmol) in DCM (4 mL) at 0° C. was added a solution of methyl chloroformate (21 µL, 0.27 mmol) in DCM (2 mL) dropwise. The reaction mixture was stirred for 15 minutes. Additional methyl chloroformate (2.0 µL, 0.03 mmol) in DCM (0.2 mL) was added. The reaction mixture was stirred at 0° C. for 20 minutes, then diluted with DCM (5 mL) and washed with saturated aqueous $NaHCO_3$ solution (5 mL). The combined organic layers were dried over $Na_2SO_4$, then filtered and concentrated in vacuo. The residue was purified by flash column chromatography, eluting with a gradient of 0-100% EtOAc in heptanes, to afford the title compound (140 mg, 76%) as an off-white solid. LCMS (Method 1): $[M+H]^+$ m/z 621.0, RT 1.94 minutes.

Intermediate 16

3-(2-{(S)-(4,4-Difluorocyclohexyl)[(4-methyl-1,2,5-oxadiazole-3-carbonyl)amino]-methyl}-4-fluoro-1H-benzimidazol-5-yl)-1-(methoxycarbonyl)pyrrolidine-3-carboxylic Acid, Trifluoroacetate Salt Intermediate 15 (130 mg, 0.21 mmol) was stirred in DCM (0.7 mL) and TFA (0.7 mL) at r.t. for 2.5 h. The reaction mixture was concentrated in vacuo to afford the title compound (130 mg, 91%) as a beige solid. $\delta_H$ (500 MHz, $CD_3OD$) 7.38-7.31 (m, 1H), 7.31-7.22 (m, 1H), 5.19 (d, J 8.5 Hz, 1H), 4.47-4.38 (m, 1H), 3.66-3.57 (m, 3H), 3.54-3.43 (m, 2H), 3.42-3.35 (m, 1H), 2.89-2.78 (m, 1H), 2.40 (s, 3H), 2.38-2.31 (m, 1H), 2.31-2.18 (m, 1H), 2.08-1.90 (m, 3H), 1.83-1.62 (m, 2H), 1.55-1.28 (m, 3H). LCMS (Method 1): $[M+H]^+$ m/z 565.0, RT 1.74 minutes.

Intermediate 17 tert-Butyl 2-[3-(dibenzylamino)-2-fluoro-4-nitrophenyl]-4,4-difluorobutanoate

To a stirred solution of Intermediate 5 (1.00 g, 2.22 mmol) in THF (10 mL) at 5° C. was added NaH (60%, 98 mg, 2.45 mmol) in one portion. The reaction mixture was stirred for 15 minutes, then 2,2-difluoroethyl trifluoromethanesulfonate (308 µL, 2.33 mmol) was added dropwise. The reaction mixture was allowed to warm to r.t. and stirred for 2 h, then treated with additional 2,2-difluoroethyl trifluoromethanesulfonate (30 µL, 0.14 mmol) and stirred for 30 minutes. The resulting mixture was quenched with saturated aqueous $NH_4Cl$ solution (50 mL) and extracted with EtOAc (2×50 mL). The combined organic layers were washed with brine (50 mL) and dried over $Na_2SO_4$, then filtered and concentrated in vacuo. The residue was purified by flash column chromatography, eluting with a gradient of 0-10% EtOAc in heptanes, to afford the title compound (1.00 g, 79%) as a pale oil. $\delta_H$ (500 MHz, $CDCl_3$) 7.39-7.16 (m, 11H), 7.04 (dd, J 8.5, 6.7 Hz, 1H), 5.64 (tt, J 56.4, 4.6 Hz, 1H), 4.22 (s, 4H), 3.98 (t, J 7.5 Hz, 1H), 2.70-2.54 (m, 1H), 2.19-2.00 (m, 1H), 1.42 (s, 9H). LCMS (Method 2): $[M+H]^+$ m/z 515.0, RT 4.03 minutes.

Intermediate 18

2-[3-(Dibenzylamino)-2-fluoro-4-nitrophenyl]-4,4-difluorobutanoic Acid

Intermediate 17 (1.00 g, 1.94 mmol) was stirred in DCM (3.7 mL) and TFA (7.7 mL) at r.t. for 4 h. The reaction mixture was concentrated in vacuo to afford the title compound (0.89 g, 100%) as a pale orange oil. LCMS (Method 1): $[M+H]^+$ m/z 459.0, RT 2.05 minutes.

Intermediate 19

2-[3-(Dibenzylamino)-2-fluoro-4-nitrophenyl]-1-(3,3-difluoroazetidin-1-yl)-4,4-difluoro-butan-1-one To a stirred solution of Intermediate 18 (1.00 g, 1.96 mmol) and HATU (895 mg, 2.35 mmol) in DCM (10 mL) at r.t. was added DIPEA (1.6 mL, 9.16 mmol). The reaction mixture was stirred for 5 minutes, then 3,3-difluoroazetidine hydrochloride (305 mg, 2.35 mmol) was added. The reaction mixture was stirred for 1 h, then diluted with DCM (50 mL) and washed with saturated aqueous $NH_4Cl$ solution (25 mL). The organic layer was dried over $Na_2SO_4$, then filtered and concentrated in vacuo. The residue was purified by flash column chromatography, eluting with a gradient of 0-100% EtOAc in heptanes, to afford the title compound (700 mg, 67%) as an orange solid. $\delta_H$ (500 MHz, $CDCl_3$) 7.39 (dd, J 8.5, 1.4 Hz, 1H), 7.26 (s, 10H), 7.09 (dd, J 8.5, 6.6 Hz, 1H), 5.69 (tt, J 56.3, 4.3 Hz, 1H), 4.42-4.08 (m, 7H), 3.96-3.88 (m, 1H), 3.51 (q, J 11.1 Hz, 1H), 2.73-2.55 (m, 1H), 2.15-1.97 (m, 1H). LCMS (Method 1): $[M+H]^+$ m/z 534.0, RT 2.12 minutes.

Intermediate 20

2-(3,4-Diamino-2-fluorophenyl)-1-(3,3-difluoroazetidin-1-yl)-4,4-difluorobutan-1-one To a stirred solution of Intermediate 19 (700 mg, 1.31 mmol) in EtOH (10 mL) was added 10% Pd/C (50% wet, 0.28 g, 0.132 mmol) in one portion. The reaction mixture was purged and stirred vigorously under a hydrogen atmosphere at r.t. for 18 h. The reaction mixture was filtered through a pad of Celite®, then washed with EtOH (2×20 mL) and concentrated in vacuo, to afford the title compound (420 mg, 99%) as a light pink solid. LCMS (Method 1): $[M+H]^+$ m/z 324.0, RT 1.40 minutes.

Intermediate 21 tert-Butyl N—[(S)-{5-[1-(3,3-difluoroazetidine-1-carbonyl)-3,3-difluoropropyl]-4-fluoro-1H-benzimidazol-2-yl}(4,4-difluorocyclohexyl)methyl]carbamate To a stirred solution of Intermediate 2 (424 mg, 1.45 mmol) and HATU (555 mg, 1.45 mmol) in DCM (10 mL) at r.t. was added DIPEA (0.46 mL, 2.61 mmol), followed by Intermediate 20 (420 mg, 1.30 mmol). The reaction mixture was stirred for 1 h, then diluted with DCM (50 mL) and washed with saturated aqueous $NH_4Cl$ solution (50 mL). The combined organic phases were dried over $Na_2SO_4$, then filtered and concentrated in vacuo. The residue was purified by flash column chromatography, eluting with a gradient of 0-100% EtOAc in heptanes. The resulting pink solid was dissolved in acetic acid (6 mL) and heated at 60° C. for 14 h. The reaction mixture was cooled to r.t. and concentrated in vacuo. The residue was purified by flash column chromatography, eluting with a gradient of 0-100% EtOAc in heptanes, to afford the title compound (395 mg, 52%) as a beige solid. $\delta_H$ (500 MHz, $CD_3OD$) 7.35 (br s, 1H), 7.27-7.16 (m, 1H), 5.87 (tt, J 56.6, 4.5 Hz, 1H), 4.78-4.51 (m, 2H), 4.49-4.15 (m, 3H), 4.15-3.90 (m, 1H), 2.80-2.66 (m, 1H), 2.38-2.19 (m, 1H), 2.16-1.89 (m, 4H), 1.89-1.63 (m, 2H), 1.59-1.04 (m, 12H). LCMS (Method 1): $[M+H]^+$ m/z 581.0, RT 1.93 minutes.

Intermediate 22

2-{2-[(S)-Amino(4,4-difluorocyclohexyl)methyl]-4-fluoro-1H-benzimidazol-5-yl}-1-(3,3-difluoroazetidin-1-yl)-4,4-difluorobutan-1-one Intermediate 21 (395 mg, 0.680 mmol) was stirred in DCM (2 mL) and TFA (2 mL) at r.t. for 2 h. The reaction mixture was concentrated in vacuo. The residue was suspended in saturated aqueous $NaHCO_3$ solution and extracted with 10% MeOH in DCM (4×10 mL). The combined organic phases were dried over $Na_2SO_4$, then filtered and concentrated in vacuo, to afford the title compound (325 mg, 99%) as a beige solid. LCMS (Method 1): $[M+H]^+$ m/z 481.0, RT 1.54 minutes.

Intermediate 23 tert-Butyl 2-[3-(dibenzylamino)-2-fluoro-4-nitrophenyl]-4,4,4-trifluorobutanoate To a stirring mixture of KOH (0.12 g, 2.09 mmol), KOH in water (60%, 24 mL, 0.12 mol), Intermediate 5 and tetrabutylammonium bromide (0.67 g, 2.09 mmol) was added 1,1,1-trifluoro-2-iodoethane (0.41 mL, 4.17 mmol) in one portion. The reaction mixture was stirred at 40° C. for 6 h, then cooled to r.t. and partitioned between water (40 mL) and DCM (40 mL). The organic layers were combined, passed through a phase separator and concentrated in vacuo. The residue was purified by flash column chromatography, eluting with a gradient of 0-100% EtOAc in heptanes, to afford the title compound (1.04 g, 61%) as a yellow-orange solid. LCMS (Method 1): $[M+H]^+$ m/z 533, RT 2.33 minutes.

Intermediate 24

2-[3-(Dibenzylamino)-2-fluoro-4-nitrophenyl]-4,4,4-trifluorobutanoic Acid

Intermediate 23 (65%, 1.00 g, 1.22 mmol) was stirred in DCM (3 mL) and TFA (2.7 mL) at r.t. for 18 h. The reaction mixture was concentrated in vacuo to afford the title compound (1.77 g, 100%, 60% purity) as a yellow-orange gum. LCMS (Method 1): $[M+H]^+$ m/z 477, RT 2.05 minutes.

Intermediate 25

2-[3-(Dibenzylamino)-2-fluoro-4-nitrophenyl]-1-(3,3-difluoroazetidin-1-yl)-4,4,4-trifluorobutan-1-one To a stirred solution of Intermediate 24 (60% purity, 1.70 g, 2.14 mmol) and HATU (1.06 g, 2.80 mmol) in DCM (20 mL) at r.t. was added DIPEA (5.6 mL, 32.1 mmol). The reaction mixture was stirred for 15 minutes, then 3,3-difluoroazetidine hydrochloride (0.37 g, 2.89 mmol) was added. The reaction mixture was stirred for 18 h, then diluted with saturated aqueous $NaHCO_3$ solution (40 mL) and DCM (40 mL). The phases were separated, and the aqueous phase was extracted with DCM (2×40 mL). The combined organic phases were dried over $Na_2SO_4$, then filtered and concentrated in vacuo. The residue was purified by flash column chromatography, eluting with a gradient of 0-30% EtOAc in heptanes, to afford the title compound (0.56 g, 47%) as an orange solid. $\delta_H$ (500 MHz, DMSO-$d_6$) 7.57 (d, J 8.5 Hz, 1H), 7.34-7.16 (m, 11H), 4.68 (q, J 11.8 Hz, 1H), 4.33 (q, J 12.6 Hz, 1H), 4.28-4.10 (m, 6H), 3.57 (q, J 11.4 Hz, 1H), 3.08-2.91 (m, 1H), 2.73-2.59 (m, 1H). LCMS (Method 1): $[M+H]^+$ m/z 552, RT 2.16 minutes.

Intermediate 26

2-(3,4-Diamino-2-fluorophenyl)-1-(3,3-difluoroazetidin-1-yl)-4,4,4-trifluorobutan-1-one To a stirred solution of Intermediate 25 (550 mg, 1 mmol) in EtOH (10 mL) was added 10% Pd/C (50% wet, 1.63 g, 0.80 mmol) in one portion. The reaction mixture was purged and stirred vigorously under a hydrogen atmosphere at r.t. for 3 h. The reaction mixture was filtered through a pad of Celite®, then washed with EtOH (2×20 mL) and concentrated in vacuo, to afford the title compound (0.34 g, 81%) as a clear purple oil. $\delta_H$ (500 MHz, DMSO-$d_6$) 6.37-6.21 (m, 2H), 4.84 (s, 2H), 4.74 (q, J 11.7 Hz, 1H), 4.45 (s, 2H), 4.39-4.14 (m, 2H), 4.03-3.81 (m, 2H), 3.08-2.90 (m, 1H), 2.60-2.39 (m, 1H). LCMS (Method 1): $[M+H]^+$ m/z 342, RT 1.55 minutes.

Intermediate 27

Benzyl N-[(1S)-2-{2-amino-4-[1-(3,3-difluoroazetidine-1-carbonyl)-3,3,3-trifluoro-propyl]-3-fluoroanilino}-1-(4,4-difluorocyclohexyl)-2-oxoethyl]carbamate To a stirred suspension of Intermediate 1 (338 mg, 1.03 mmol) and HATU (393 mg, 1.03 mmol) in DCM (3.5 mL) at r.t. was added DIPEA (0.35 mL, 1.99 mmol). The reaction mixture was stirred at r.t. for 15 minutes, then Intermediate 26 (333 mg, 0.80 mmol) in DCM (3.5 mL) was added. The reaction mixture was stirred for 18 h, then diluted with saturated aqueous $NaHCO_3$ solution (30 mL) and DCM (30 mL). The phases were separated, and the aqueous phase was extracted with DCM (2×30 mL). The combined organic phases were dried over $Na_2SO_4$, then filtered and concentrated in vacuo. The residue was purified by flash column chromatography, eluting with a gradient of 0-100% EtOAc in heptanes, to afford the title compound (0.51 g, 99%) as a red-brown oil. $\delta_H$ (400 MHz, DMSO-$d_6$) 9.51 (d, J 4.5 Hz, 1H), 7.68 (d, J 7.9 Hz, 1H), 7.45-7.24 (m, 5H), 7.13-7.03 (m, 1H), 6.53 (t, J 8.0 Hz, 1H), 5.05 (s, 2H), 4.97 (s, 2H), 4.82 (q, J 11.9 Hz, 1H), 4.47-4.17 (m, 2H), 4.18-4.08 (m, 2H), 4.06-3.91 (m, 1H), 3.13-2.93 (m, 1H), 2.77-2.59 (m, 1H), 2.15-1.97 (m, 2H), 1.94-1.63 (m, 5H), 1.53-1.27 (m, 2H). LCMS (Method 1): $[M+H]^+$ m/z 651, RT 1.97 minutes.

Intermediate 28

Benzyl N—[(S)-{5-[1-(3,3-difluoroazetidine-1-carbonyl)-3,3,3-trifluoropropyl]-4-fluoro-1H-benzimidazol-2-yl}(4,4-difluorocyclohexyl)methyl]carbamate Intermediate 27 (0.513 g, 0.79 mmol) was stirred in acetic acid (10 mL) at 75° C. for 3 h. The reaction mixture was cooled to room temperature and concentrated in vacuo, then saturated aqueous $NaHCO_3$ solution (30 mL) was carefully added. The aqueous phase was extracted with DCM (3×30 mL). The organic phases were combined, passed through a phase separator and concentrated in vacuo. The residue was purified by flash column chromatography, eluting with a gradient of 0-20% MeOH in DCM, to afford the title compound (0.41 g, 82%) as a red solid. $\delta_H$ (400 MHz, DMSO-$d_6$) 12.70 (br s, 1H), 8.14-7.80 (m, 1H), 7.47-7.23 (m, 5H), 7.22-7.03 (m, 1H), 5.15-4.96 (m, 2H), 4.85 (q, J 12.3 Hz, 1H), 4.73 (t, J 8.2 Hz, 1H), 4.46-4.27 (m, 2H), 4.22 (q, J 11.8 Hz, 1H), 4.10-3.93 (m, 1H), 3.51-3.20 (m, 1H, obs.), 3.18-2.99 (m, 1H), 2.86-2.63 (m, 1H), 2.20-1.63 (m, 6H), 1.58-1.44 (m, 1H), 1.43-1.18 (m, 2H). LCMS (Method 1): $[M+H]^+$ m/z 633, RT 1.96 minutes.

Intermediate 29

2-{2-[(S)-Amino(4,4-difluorocyclohexyl)methyl]-4-fluoro-1H-benzimidazol-5-yl}-1-(3,3-difluoroazetidin-1-yl)-4,4,4-trifluorobutan-1-one To a stirred solution of Intermediate 28 (0.41 g, 0.65 mmol) in EtOH (5 mL) and THF (5 mL) was added 10% Pd/C (50% wet, 0.207 g, 0.19 mmol) in one portion. The reaction mixture was purged and stirred vigorously under a hydrogen atmosphere at r.t. for 2 h. The reaction mixture was filtered through a pad of Celite®, then washed with EtOH (2×10 mL) and concentrated in vacuo, to afford the title compound (0.35 g, 100%) as a purple oil. $\delta_H$ (400 MHz, DMSO-$d_6$) 12.53 (s, 1H), 7.30 (d, J 8.3 Hz, 1H), 7.10 (ddd, J 8.7, 6.6, 2.7 Hz, 1H), 4.84 (q, J 11.7 Hz, 1H), 4.53-4.28 (m, 2H), 4.30-4.14 (m, 1H), 4.04-3.89 (m, 1H), 3.88 (d, J 5.9 Hz, 1H), 3.14-2.98 (m, 1H), 2.84-2.63 (m, 1H), 2.11-1.92 (m, 2H), 1.94-1.65 (m, 4H), 1.61-1.47 (m, 1H), 1.42-1.24 (m, 2H). LCMS (Method 1): $[M+H]^+$ m/z 499, RT 1.59 minutes.

Intermediate 30 tert-Butyl 2-(3,4-diamino-2-fluorophenyl)-4,4,4-trifluorobutanoate

To a stirred solution of Intermediate 23 (3.05 g, 5.27 mmol) in EtOH (50 mL) was added 10% Pd/C (50% wet, 1.12 g, 1.05 mmol) in one portion. The reaction mixture was purged and stirred vigorously under a hydrogen atmosphere at r.t. for 18 h. The reaction mixture was filtered through a pad of Celite®, then washed with EtOH (2×50 mL) and concentrated in vacuo, to afford the title compound (1.91 g, 97%) as a purple-brown oil. $\delta_H$ (500 MHz, DMSO-$d_6$) 6.31 (s, 2H), 4.81 (s, 2H), 4.44 (s, 2H), 3.83 (dd, J 8.2, 5.9 Hz, 1H), 3.07-2.90 (m, 1H), 2.51 (dt, J 3.6, 1.8 Hz, 1H), 1.34 (s, 9H). LCMS (Method 1): $[M+H]^+$ m/z 323, RT 1.84 minutes.

Intermediate 31 tert-Butyl 2-(3-amino-4-{[(2S)-2-(benzyloxycarbonylamino)-2-(4,4-difluorocyclohexyl)-acetyl]amino}-2-fluorophenyl)-4,4,4-trifluorobutanoate To a stirred solution of Intermediate 1 (2.16 g, 6.59 mmol) and HATU (2.51 g, 6.59 mmol) in DCM (25 mL) at r.t. was added DIPEA (2.2 mL, 12.7 mmol). The reaction mixture was stirred for 15 minutes. Intermediate 30 (1.90 g, 5.07 mmol) was added as a solution in DCM (25 mL). The reaction mixture was stirred for 36 h, then diluted with saturated aqueous $NaHCO_3$ solution (30 mL) and DCM (30 mL). The phases were separated, and the aqueous phase was extracted with DCM (2×30 mL). The organic phases were combined, passed through a phase separator and concentrated in vacuo. The residue was purified by flash column chromatography, eluting with a gradient of 0-100% EtOAc in heptanes, to afford the title compound (3.4 g, 99%) as an orange-brown solid. $\delta_H$ (500 MHz, DMSO-$d_6$) 9.51 (s, 1H), 7.76-7.63 (m, 1H), 7.51-7.18 (m, 5H), 7.08 (d, J 8.4 Hz, 1H), 6.53 (t, J 7.9 Hz, 1H), 5.06 (s, 2H), 4.96 (s, 2H), 4.19-4.09 (m, 1H), 3.99 (t, J 7.3 Hz, 1H), 3.16-2.95 (m, 1H), 2.74-2.56 (m, 1H), 2.14-1.95 (m, 2H), 1.95-1.58 (m, 5H), 1.53-1.22 (m, 11H). LCMS (Method 1): $[M+H]^+$ m/z 632, RT 2.10 minutes.

Intermediate 32 tert-Butyl 2-{2-[(S)-benzyloxycarbonylamino(4,4-difluorocyclohexyl)methyl]-4-fluoro-1H-benzimidazol-5-yl}-4,4,4-trifluorobutanoate Intermediate 31 (3.35 g, 4.93 mmol) was stirred in DCM (30 mL) and TFA (0.73 mL, 9.87 mmol) at 40° C. for 16 h. The reaction mixture was cooled to r.t. and diluted with DCM (50 mL), then washed with 1M aqueous NaOH solution (50 mL). The layers were separated using a phase separator, and the organic phase was concentrated in vacuo. The residue was purified by flash column chromatography, eluting with a gradient of 0-100% EtOAc in heptanes, to afford the title compound (3.1 g, 93%) as a red-brown solid. $\delta_H$ (500 MHz, DMSO-$d_6$) 12.69 (s, 1H), 7.99 (s, 1H), 7.46-7.25 (m, 6H), 7.21-7.11 (m, 1H), 5.07 (d, J 12.6 Hz, 1H), 5.01 (d, J 12.6 Hz, 1H), 4.74 (t, J 8.1 Hz, 1H), 4.18 (t, J 7.1 Hz, 1H), 3.23-3.06 (m, 1H), 2.83-2.67 (m, 1H), 2.20-2.08 (m, 1H), 2.08-1.93 (m, 2H), 1.92-1.84 (m, 1H), 1.84-1.68 (m, 2H), 1.68-1.56 (m, 1H), 1.48 (d, J 10.5 Hz, 1H), 1.44-1.30 (m, 10H). LCMS (Method 1): $[M+H]^+$ m/z 614, RT 2.10 minutes.

Intermediate 33 tert-Butyl 2-{2-[(S)-amino(4,4-difluorocyclohexyl)methyl]-4-fluoro-1H-benzimidazol-5-yl}-4,4,4-trifluorobutanoate To a stirred solution of Intermediate 32 (2.40 g, 3.56 mmol) in EtOH (36 mL) was added 10% Pd/C (50% wet, 1.52 g, 0.1712 mmol) in one portion. The reaction mixture was purged and stirred vigorously under a hydrogen atmosphere at r.t for 18 h. The reaction mixture was filtered through a pad of Celite®, then washed with EtOH (2×20 mL) and concentrated in vacuo, to afford the title compound (1.92 g, 100%) as a pale brown foam. $\delta_H$ (500 MHz, DMSO-$d_6$) 12.46 (br s, 1H), 7.30 (d, J 8.3 Hz, 1H), 7.19-6.92 (m, 1H), 4.17 (t, J 6.5 Hz, 1H), 3.90 (d, J 5.9 Hz, 1H), 3.21-3.05 (m, 1H), 2.82-2.66 (m, 1H), 2.12-1.93 (m, 2H), 1.94-1.66 (m, 4H), 1.60-1.49 (m, 1H), 1.42-1.26 (m, 11H). LCMS (Method 1): $[M+H]^+$ m/z 480, RT 1.72 minutes.

Intermediate 34 tert-Butyl 2-(2-{(S)-(4,4-difluorocyclohexyl)[(4-methyl-1,2,5-oxadiazole-3-carbonyl)-amino]methyl}-4-fluoro-1H-benzimidazol-5-yl)-4,4,4-trifluorobutanoate To a stirred suspension of 4-methyl-1,2,5-oxadiazole-3-carboxylic acid (0.63 g, 4.9 mmol) and HATU (1.87 g, 4.93 mmol) in DCM (20 mL) at r.t. was added DIPEA (1.87 mL, 10.71 mmol). The reaction mixture was stirred for 15 minutes, then Intermediate 33 (1.90 g, 3.61 mmol) in DCM (20 mL) was added. The reaction mixture was stirred for 18 h, then quenched with saturated aqueous $NaHCO_3$ solution (40 mL) and stirred at r.t. for 20 minutes. The phases were separated using a phase separator, and the organic phase was concentrated in vacuo. The residue was purified by flash column chromatography, eluting with a gradient of 0-100% EtOAc in heptanes, to afford the title compound (2.0 g, 87%) as a yellow-orange oil. $\delta_H$ (500 MHz, DMSO-$d_6$) 12.79 (s, 1H), 9.68 (s, 1H), 7.60-7.26 (m, 1H), 7.25-7.00 (m, 1H), 5.20 (t, J 7.1 Hz, 1H), 4.18 (t, J 7.2 Hz, 1H), 3.22-3.04 (m, 1H), 2.84-2.67 (m, 1H), 2.49 (s, 3H), 2.39-2.24 (m, 1H), 2.16-1.93 (m, 3H), 1.91-1.72 (m, 2H), 1.69-1.54 (m, 1H), 1.49-1.21 (m, 11H). LCMS (Method 1): $[M+H]^+$ m/z 590, RT 2.16 minutes.

Intermediate 35

2-(2-{(S)-(4,4-Difluorocyclohexyl)[(4-methyl-1,2,5-oxadiazole-3-carbonyl)amino]-methyl}-4-fluoro-1H-benzimidazol-5-yl)-4,4,4-trifluorobutanoic Acid, Trifluoroacetate Salt Intermediate 34 (1.99 g, 3.11 mmol) was stirred in DCM (10 mL) and TFA (10 mL) at r.t. for 18 h. The reaction mixture was concentrated in vacuo to afford the title compound (2.52 g, 100%) as a light brown foam. $\delta_H$ (500 MHz, DMSO-$d_6$) 9.60 (d, J 8.4 Hz, 1H), 7.28 (d, J 8.4 Hz, 1H), 7.21-7.06 (m, 1H), 5.11 (t, J 8.3 Hz, 1H), 4.17-4.11 (m, 1H), 3.14-2.99 (m, 1H), 2.79-2.63 (m, 1H), 2.39 (s, 3H), 2.30-2.17 (m, 1H), 2.05-1.85 (m, 3H), 1.82-1.60 (m, 2H), 1.55-1.41 (m, 1H), 1.39-1.10 (m, 3H). LCMS (Method 1): $[M+H]^+$ m/z 534, RT 1.89 minutes.

Intermediate 36

Methyl (2R)-2-{[2-(2-{(S)-(4,4-difluorocyclohexyl)[(4-methyl-1,2,5-oxadiazole-3-carbonyl)amino]methyl}-4-fluoro-1H-benzimidazol-5-yl)-4,4,4-trifluorobutanoyl]-amino}-3-methylbutanoate To a stirred suspension of Intermediate 35 (200 mg, 0.29 mmol) and HATU (145 mg, 0.38 mmol) in DCM (2 mL) at r.t. was added DIPEA (256 μL, 1.47 mmol). The reaction mixture was stirred for 15 minutes, then methyl D-valinate hydrochloride (64 mg, 0.38 mmol) in DCM (2 mL) was added. The reaction mixture was stirred for 18 h, then quenched with saturated aqueous $NaHCO_3$ solution (4 mL) and stirred at r.t. for 20 minutes. The phases were separated using a phase separator, and the organic phase was concentrated in vacuo. The residue was purified by flash column chromatography, eluting with a gradient of 0-100% EtOAc in heptanes, to afford the title compound (1:1 mixture of diastereomers, 139 mg, 63%) as a white solid. $\delta_H$ (500 MHz, DMSO-$d_6$) 12.73 (s, 1H), 9.68 (s, 1H), 8.58 (dd, J 16.5, 8.1 Hz, 1H), 7.49-7.26 (m, 1H), 7.25-7.15 (m, 1H), 5.18 (d, J 6.4 Hz, 1H), 4.44 (ddd, J 16.5, 8.6, 5.1 Hz, 1H), 4.27-4.09 (m, 1H), 3.67-3.49 (m, 3H), 3.17-2.98 (m, 1H), 2.70-2.54 (m, 1H), 2.49-2.41 (m, 3H), 2.36-2.25 (m, 1H), 2.12-1.91 (m, 4H), 1.90-1.71 (m, 2H), 1.58-1.50 (m, 1H), 1.45-1.35 (m, 1H), 1.35-1.22 (m, 2H), 0.88 (d, J 6.9 Hz, 1H), 0.87 (d, J 6.9 Hz, 1H), 0.75-0.66 (m, 3H). LCMS (Method 4): $[M+H]^+$ m/z 647, RT 3.59, 3.70 minutes.

Intermediate 37

(2R)-2-{[2-(2-{(S)-(4,4-Difluorocyclohexyl)[(4-methyl-1,2,5-oxadiazole-3-carbonyl)-amino]methyl}-4-fluoro-1H-benzimidazol-5-yl)-4,4,4-trifluorobutanoyl]amino}-3-methylbutanoic Acid Intermediate 36 (135 mg, 0.18 mmol) was dissolved in THF (2.3 mL) and water (0.6 mL), and lithium hydroxide monohydrate (18.5 mg, 0.43 mmol) was added. The reaction mixture was stirred at r.t. for 18 h, then concentrated in vacuo, diluted with water (10 mL) and acidified to pH 2 with 1M HCl. The aqueous phase was extracted with DCM:isopropanol (4:1, 3×15 mL). The combined organic phases were dried over $MgSO_4$, then filtered and concentrated in vacuo, to afford the title compound (1:1 mixture of diastereomers, 125 mg, 100%) as an off-white foam. $\delta_H$ (500 MHz, DMSO-$d_6$) 12.51 (br s, 1H), 9.68 (dd, J 8.4, 3.9 Hz, 1H), 8.45 (dd, J 8.6, 5.9 Hz, 1H), 7.36-7.23 (m, 2H), 5.25-5.16 (m, 1H), 4.53-4.42 (m, 1H), 4.21-4.11 (m, 1H), 3.15-3.00 (m, 1H), 2.73-2.55 (m, 1H), 2.48 (s, 3H), 2.40-2.24 (m, 1H), 2.13-1.93 (m, 4H), 1.90-1.68 (m, 2H), 1.61-1.49 (m, 1H), 1.48-1.21 (m, 2H), 0.88 (d, J 6.8 Hz, 3H), 0.70 (dd, J 6.8, 3.7 Hz, 3H). LCMS (Method 1): $[M+H]^+$ m/z 633, RT 1.88, 1.92 minutes.

Intermediate 38

1-Benzyl-4-[3-(dibenzylamino)-2-fluoro-4-nitrophenyl]piperidine-4-carboxylate, Sodium Salt To a stirred mixture of KOH (4.21 g, 75.1 mmol), KOH in water (60%, 120 mL, 0.57 mol), Intermediate 5 (10 g, 20.90 mmol) and tetrabutylammonium bromide (10.12 g, 31.3 mmol) was added N-benzyl-2-chloro-N-(2-chloroethyl)ethanamine hydrochloride (16.81 g, 62.6 mmol) in one portion. The reaction mixture was stirred at 50° C. for 18 h, then cooled to r.t. and partitioned between water (50 mL) and DCM (50 mL). The aqueous phase was extracted with DCM (2×50 mL). The combined organic phases were dried over $Na_2SO_4$, filtered and concentrated in vacuo. The residue was purified by flash column chromatography, eluting with a gradient of 0-100% EtOAc in heptanes. The resulting yellow-orange oil was stirred in DCM (10 mL) and TFA (20 mL) at r.t. for 96 h. The reaction mixture was concentrated in vacuo, and saturated aqueous $NaHCO_3$ solution was carefully added. The aqueous phase was extracted with DCM (3×50 mL). The resulting off-white precipitate was filtered, then dried in vacuo at 40° C. for 1 h, to afford the title compound (2.15 g, 18%) as an off-white solid. $\delta_H$ (500 MHz, DMSO-$d_6$) 7.45 (d, J 8.5 Hz, 1H), 7.37-7.15 (m, 16H), 4.12 (s, 4H), 3.49 (s, 2H), 2.91 (d, J 11.3 Hz, 1H), 2.82-2.69 (m, 1H), 2.47-2.41 (m, 1H), 2.40-2.29 (m, 1H), 2.11-2.01 (m, 1H), 1.96-1.83 (m, 1H), 1.75-1.52 (m, 2H). LCMS (Method 1): $[M+H]^+$ m/z 554, RT 1.83 minutes.

Intermediate 39

{1-Benzyl-4-[3-(dibenzylamino)-2-fluoro-4-nitrophenyl]piperidin-4-yl}(3,3-difluoro-azetidin-1-yl) methanone To a stirred solution of Intermediate 38 (2.14 g, 3.72 mmol) and HATU (1.85 g, 4.86 mmol) in DCM (20 mL) at r.t. was added DIPEA (3.2 mL, 18.6 mmol). The reaction mixture was stirred for 15 minutes, then 3,3-difluoroazetidine hydrochloride (0.65 g, 5.02 mmol) was added. The reaction mixture was stirred for 18 h, then diluted with saturated aqueous $NaHCO_3$ solution (30 mL) and DCM (50 mL). The phases were separated, and the aqueous phase was extracted with DCM (2×50 mL). The combined organic phases were dried over $Na_2SO_4$, then filtered and concentrated in vacuo. The residue was purified by flash column chromatography, eluting with a 0-100% gradient of EtOAc in heptanes, to afford the title compound (2.15 g, 89%) as an orange foam. $\delta_H$ (500 MHz, DMSO-$d_6$) 7.58 (d, J 8.6 Hz, 1H), 7.45-7.35 (m, 1H), 7.35-7.15 (m, 15H), 4.85-4.18 (m, 2H), 4.16 (s, 4H), 3.72 (s, 2H), 3.39 (s, 2H), 2.58-2.41 (m, 2H), 2.32-2.20 (m, 2H), 2.20-2.08 (m, 2H), 1.96-1.80 (m, 2H). LCMS (Method 1): $[M+H]^+$ m/z 629, RT 1.84 minutes.

Intermediate 40

{4-[3-(Dibenzylamino)-2-fluoro-4-nitrophenyl]piperidin-4-yl}(3,3-difluoroazetidin-1-yl)-methanone To a stirred solution of Intermediate 39 (2.04 g, 3.15 mmol) in anhydrous toluene (50 mL) was added methyl chloroformate (0.85 mL, 7.87 mmol). The reaction mixture was stirred at 100° C. for 18 h, then cooled to r.t. and concentrated in vacuo. The residue was dissolved in MeOH (25 mL) and heated at 85° C. for 2 h. The reaction mixture was cooled to r.t., then concentrated in vacuo. The residue was partitioned between saturated aqueous $NaHCO_3$ solution (50 mL) and EtOAc (50 mL). The phases were separated, and the aqueous phase was extracted with EtOAc (2×50 mL). The combined organic phases were dried over $Na_2SO_4$, then filtered and concentrated in vacuo. The residue was purified by flash column chromatography, eluting with a gradient of 0-20% MeOH in DCM, to afford the title compound (0.45 g, 24%) as a yellow oil. $\delta_H$ (500 MHz, DMSO-$d_6$) 8.26 (br s, 1H), 7.65 (d, J 8.5 Hz, 1H), 7.42-7.30 (m, 1H), 7.33-7.12 (m, 10H), 4.56-4.24 (m, 2H), 4.17 (s, 4H), 3.94-3.61 (m, 2H), 3.20-3.10 (m, 2H), 3.06-2.95 (m, 2H), 2.38-2.23 (m, 2H), 2.07-1.92 (m, 2H). LCMS (Method 1): $[M+H]^+$ m/z 539, RT 1.79 minutes.

Intermediate 41 tert-Butyl 4-[3-(dibenzylamino)-2-fluoro-4-nitrophenyl]-4-(3,3-difluoroazetidine-1-carbonyl)piperidine-1-carboxylate To a stirred solution of Intermediate 40 (91%, 400 mg) in DCM (10 mL) was added di-tert-butyl dicarbonate (148 mg, 0.68 mmol), followed by triethylamine (0.19 mL, 1.35 mmol). The reaction mixture was stirred at r.t. for 40 minutes, then concentrated in vacuo. The residue was purified by flash column chromatography, eluting with a gradient of 0-100% EtOAc in heptanes, to afford the title compound (474 mg, 99%) as a yellow-orange gum. $\delta_H$ (400 MHz, DMSO-$d_6$) 7.58 (d, J 8.0 Hz, 1H), 7.42-7.33 (m, 1H), 7.32-7.15 (m, 10H), 4.57-4.11 (m, 6H), 3.98-3.51 (m, 2H), 3.47-3.24 (m, 1H, obs.), 2.21-2.04 (m, 2H), 1.86-1.73 (m, 2H), 1.69-1.56 (m, 1H), 1.39 (s, 9H), 0.98-0.77 (m, 2H). LCMS (Method 1): $[M+H]^+$ m/z 639, RT 2.20 minutes.

Intermediate 42 tert-Butyl 4-(3,4-diamino-2-fluorophenyl)-4-(3,3-difluoroazetidine-1-carbonyl)-piperidine-1-carboxylate To a stirred solution of Intermediate 41 (470 mg, 0.66 mmol) in EtOH (10 mL) was added 10% Pd/C (50% wet, 0.141 g, 0.13 mmol) in one portion. The reaction mixture was purged and stirred vigorously under a hydrogen atmosphere at r.t. for 3 h. The reaction mixture was filtered through a pad of Celite®, then washed with EtOH (2×20 mL) and concentrated in vacuo, to afford the title compound (0.3 g, 92%) as a brown solid. $\delta_H$ (500 MHz, DMSO-$d_6$) 6.43-6.29 (m, 2H), 4.87 (s, 2H), 4.46 (s, 2H), 4.29-4.03 (m, 2H), 3.70 (s, 2H), 3.56-3.48 (m, 2H), 3.38-3.20 (m, 2H, obs.), 2.20-2.06 (m, 2H), 1.82-1.71 (m, 2H), 1.39 (s, 9H). LCMS (Method 1): $[M-^tBu+H]^+$ m/z 373, RT 1.71 minutes.

Intermediate 43 tert-Butyl 4-(3-amino-4-{[(2S)-2-(benzyloxycarbonylamino)-2-(4,4-difluorocyclohexyl)-acetyl]amino}-2-fluorophenyl)-4-(3,3-difluoroazetidine-1-carbonyl)piperidine-1-carboxylate To a stirred suspension of Intermediate 1 (255 mg, 0.779 mmol) and HATU (296 mg, 0.779 mmol) in DCM (3 mL) at r.t. was added DIPEA (0.26 mL, 1.50 mmol). The reaction mixture was stirred at r.t. for 15 minutes, then Intermediate 42 (295 mg, 0.60 mmol) in DCM (3 mL) was added. The reaction mixture was stirred for 18 h, then diluted with saturated aqueous $NaHCO_3$ solution (30 mL) and DCM (30 mL). The phases were separated, and the aqueous phase was extracted with DCM (2×30 mL). The combined organic phases were separated using a phase separator, then concentrated in vacuo. The residue was purified by flash column chromatography, eluting with a gradient of 0-100% EtOAc in heptanes, to afford the title compound (0.44 g, 75%) as a red-brown oil. LCMS (Method 1): $[M-BOC+H]^+$ m/z 638, RT 2.02 minutes.

Intermediate 44 tert-Butyl 4-{2-[(S)-benzyloxycarbonylamino(4,4-difluorocyclohexyl)methyl]-4-fluoro-1H-benzimidazol-5-yl}-4-(3,3-difluoroazetidine-1-carbonyl)piperidine-1-carboxylate Intermediate 43 (0.44 g, 0.45 mmol) was stirred in acetic acid (7.8 mL) at 75° C. for 3 h. The reaction mixture was cooled to r.t. and concentrated in vacuo, then saturated aqueous $NaHCO_3$ solution (30 mL) was carefully added until effervescence subsided. The aqueous phase was extracted with EtOAc (3×30 mL). The combined organic phases were dried over $Na_2SO_4$, then filtered and concentrated in vacuo. The residue was purified by flash column chromatography, eluting with a gradient of 0-100% EtOAc in heptanes, to afford the title compound (0.32 g, 70%) as a light brown solid. $\delta_H$ (500 MHz, DMSO-$d_6$) 12.71 (br s, 1H), 7.99 (br s, 1H), 7.48-7.24 (m, 6H), 7.24-7.15 (m, 1H), 5.06 (d, J 12.6 Hz, 1H), 5.01 (d, J 12.6 Hz, 1H), 4.74 (t, J 8.2 Hz, 1H), 4.43-4.08 (m, 2H), 3.93-3.45 (m, 4H), 2.34-2.22 (m, 2H), 2.21-2.08 (m, 1H), 2.08-1.61 (m, 9H), 1.57-1.44 (m, 1H), 1.44-1.31 (m, 11H). LCMS (Method 1): $[M-^tBu+H]^+$ m/z 664, RT 2.01 minutes.

Intermediate 45 tert-Butyl 4-{2-[(S)-amino(4,4-difluorocyclohexyl)methyl]-4-fluoro-1H-benzimidazol-5-yl}-4-(3,3-difluoroazetidine-1-carbonyl)piperidine-1-carboxylate To a stirred solution of Intermediate 44 (0.31 g) in EtOH (5 mL) was added 10% Pd/C (50% wet, 0.129 g, 0.122 mmol) in one portion. The reaction mixture was purged and stirred vigorously under a hydrogen atmosphere at r.t. for 3.5 h. The reaction mixture was filtered through a pad of Celite®, then washed with EtOH (2×20 mL) and concentrated in vacuo, to afford the title compound (0.28 g, 100%) as a light brown oil. $\delta_H$ (500 MHz, DMSO-$d_6$) 12.57 (br s, 1H), 7.31 (d, J 8.5 Hz, 1H), 7.22-7.10 (m, 1H), 4.57-4.00 (m, 3H), 3.87 (d, J 6.2 Hz, 1H), 3.80-3.52 (m, 4H), 2.34-2.19 (m, 2H), 2.10-1.62 (m, 9H), 1.58-1.48 (m, 1H), 1.40 (s, 11H). LCMS (Method 1): $[M-^tBu+H]^+$ m/z 530, RT 1.35 minutes.

Intermediate 46 tert-Butyl 4-(3,3-difluoroazetidine-1-carbonyl)-4-(2-{(S)-(4,4-difluorocyclohexyl)[(4-methyl-1,2,5-oxadiazole-3-carbonyl)amino]methyl}-4-fluoro-1H-benzimidazol-5-yl)-piperidine-1-carboxylate To a stirred suspension of 4-methyl-1,2,5-oxadiazole-3-carboxylic acid (76 mg, 0.59 mmol) and HATU (227 mg, 0.60 mmol) in DCM (2.5 mL) at r.t. was added DIPEA (226 µL, 1.3 mmol). The reaction mixture was stirred at r.t. for 15 minutes, then Intermediate 45 (275 mg, 0.44 mmol) in DCM (2.5 mL) was added. The reaction mixture was stirred for 2 h, then diluted with saturated aqueous $NaHCO_3$ solution (20 mL) and DCM (20 mL). The phases were separated, and the aqueous phase was extracted with DCM (2×20 mL). The combined organic phases were dried over $Na_2SO_4$, then filtered and concentrated in vacuo. The residue was purified by flash column chromatography, eluting with a gradient of 0-100% EtOAc in heptanes, to afford the title compound (0.24 g, 73%) as a yellow oil. $\delta_H$ (500 MHz, DMSO-$d_6$) 12.90 (br s, 1H), 9.65 (br s, 1H), 7.36 (br s, 1H), 7.21 (t, J 7.6 Hz, 1H), 5.20 (d, J 8.1 Hz, 1H), 4.47-4.10 (m, 2H), 3.95-3.54 (m, 4H), 3.50-3.34 (m, 1H), 2.48 (s, 3H), 2.38-2.19 (m, 3H), 2.15-1.88 (m, 5H), 1.89-1.73 (m, 2H), 1.64-1.53 (m, 1H), 1.48-1.35 (m, 11H), 1.34-1.25 (m, 1H). LCMS (Method 1): $[M-^tBu+H]^+$ m/z 640, RT 1.97 minutes.

Intermediate 47

N,N-Dibenzyl-2,3-difluoro-6-nitroaniline

To a stirred solution of 2,3,4-trifluoronitrobenzene (200 g, 1.13 mol) in acetonitrile (2 L) were added DIPEA (296 g, 2.29 mol) and dibenzylamine (245 g, 1.20 mol). The reaction mixture was stirred at 65° C. for 18 h, then TBME (2 L) and water (1 L) were added. The phases were separated, and the organic fractions were washed with water (1 L), 5% HCl solution (1.6 L), 50% brine (1 L) and brine (600 mL). The organic fraction was dried over $Na_2SO_4$ and concentrated in vacuo. The residue was dissolved in TBME (500 mL) with heating, and isohexane (700 mL) was added. The mixture was allowed to cool to r.t., and crystallisation afforded the title compound (310 g, 77%). $\delta_H$ (300 MHz, DMSO-$d_6$) 7.69 (m, 1H), 7.45-7.20 (m, 11H), 4.20 (s, 4H). LCMS (Method 9): $[M+H]^+$ m/z 355.0, RT 3.03 minutes.

Intermediate 48

1-[3-(Dibenzylamino)-2-fluoro-4-nitrophenyl]-3,3-difluorocyclobutanecarbonitrile To a stirred solution of 3,3-difluorocyclobutanecarbonitrile (700 mg, 5.98 mmol) in THF (15 mL) in an ice bath was added 1M LiHMDS in THF (6.0 mL, 5.98 mmol), followed by Intermediate 47 (1.41 g, 3.99 mmol). The mixture was allowed to warm to r.t. and stirred for 16 h, then quenched with saturated aqueous $NH_4Cl$ solution and extracted with EtOAc (2×20 mL). The organic fractions were combined, and dried over $Na_2SO_4$. The residue was purified by flash column chromatography, eluting with a gradient of 0-100% EtOAc in heptanes, to afford the title compound (242 mg, 12%) as a yellow oil. $\delta_H$ (400 MHz, DMSO-$d_6$) 7.66 (dd, J 8.5, 1.3 Hz, 1H), 7.45 (dd, J 8.4, 7.4 Hz, 1H), 7.31-7.19 (m, 10H), 4.16 (s, 4H), 3.56 (tt, J 13.3, 5.9 Hz, 2H), 3.47-3.34 (m, 2H). LCMS (Method 4): $[M+H]^+$ m/z 452.1, RT 4.5 minutes.

Intermediate 49

1-[3-(Dibenzylamino)-2-fluoro-4-nitrophenyl]-3,3-difluorocyclobutanecarboxylic Acid Aqueous sodium hydroxide solution (5M, 0.77 mL, 3.86 mmol) and Intermediate 48 (242 mg, 0.48 mmol) were stirred in EtOH (5 mL) at 70° C. for 4 h, then stirred at r.t. for 40 h. The solution was concentrated in vacuo, adjusted to pH 1 using 1M HCl (5 mL), and extracted with DCM (3×5 mL). The organic fractions were combined, then passed through a phase separator and concentrated in vacuo, to give the title compound (226 mg, 95%) as an orange solid. $\delta_H$ (500 MHz, DMSO-$d_6$) 7.47 (d, J 8.4 Hz, 1H), 7.33-7.17 (m, 11H), 4.09 (s, 4H), 3.00-2.88 (m, 2H). LCMS (Method 3): $[M+H]^+$ m/z 471, RT 1.74 minutes.

Intermediate 50

[1-[3-(Dibenzylamino)-2-fluoro-4-nitrophenyl]-3,3-difluorocyclobutyl](3,3-difluoro-azetidin-1-yl) methanone To a stirred solution of DIPEA (239 μL, 1.37 mmol), Intermediate 49 (226 mg, 0.46 mmol) and 3,3-difluoroazetidine hydrochloride (65 mg, 0.50 mmol) in DCM (3 mL) at r.t. was added HATU (208 mg, 0.55 mmol). The reaction mixture was stirred at r.t. for 45 minutes, then washed with water (1×5 mL). The aqueous layer was extracted with DCM (2×5 mL). The organic layers were combined, passed through a phase separator and concentrated in vacuo. The residue was purified by flash column chromatography, eluting with a gradient of 0-100% EtOAc in heptanes, to afford the title compound (247 mg, 86%) as a yellow oil. $\delta_H$ (400 MHz, DMSO-$d_6$) 7.64-7.53 (m, 2H), 7.32-7.15 (m, 10H), 4.41-4.25 (m, 2H), 4.15 (s, 4H), 3.84-3.68 (m, 2H), 3.54-3.40 (m, 2H), 3.10-2.97 (m, 2H). LCMS (Method 1): $[M+H]^+$ m/z 546, RT 2.11 minutes.

Intermediate 51

[1-(3,4-Diamino-2-fluorophenyl)-3,3-difluorocyclobutyl](3,3-difluoroazetidin-1-yl)-methanone To a stirred solution of Intermediate 50 (247 mg, 0.45 mmol) in EtOH (4 mL) was added 10% Pd/C (50% wet with water, 80 mg, 0.04 mmol) in one portion. The reaction mixture was purged and stirred vigorously under a hydrogen atmosphere at r.t. for 18 h. The reaction mixture was filtered through a pad of Celite®, then washed with EtOH (2×10 mL) and concentrated in vacuo, to afford the title compound (129 mg, 85%) as a brown solid. $\delta_H$ (400 MHz, DMSO-$d_6$) 6.52 (t, J 8.4 Hz, 1H), 6.35 (d, J 8.3 Hz, 1H), 4.92 (s, 2H), 4.49 (s, 2H), 4.35-4.19 (m, 2H), 3.98-3.80 (m, 2H), 3.45-3.34 (m, 2H), 3.00-2.85 (m, 2H). LCMS (Method 1): $[M+H]^+$ m/z 336, RT 1.45 minutes.

Intermediate 52

Benzyl N—[(S)-{5-[1-(3,3-difluoroazetidine-1-carbonyl)-3,3-difluorocyclobutyl]-4-fluoro-1H-benzimidazol-2-yl}(4,4-difluorocyclohexyl)methyl]carbamate HATU (176 mg, 0.46 mmol) was added to a stirred solution of Intermediate 51 (129 mg, 0.39 mmol), Intermediate 1 (150 mg, 0.46 mmol) and DIPEA (134 μL, 0.77 mmol) in DCM (2 mL) at r.t. The reaction mixture was stirred for 2 h, then washed with water (5 mL). The aqueous layer was extracted with DCM (5 mL). The organic layers were combined, passed through a phase separator and concentrated in vacuo. The resulting crude oil was stirred in acetic acid (2.5 mL) at 50° C. for 16 h. The solution was concentrated in vacuo, then diluted with EtOAc (10 mL) and water (5 mL). The organic layer was separated and washed with saturated brine (1×5 mL), then dried over $Na_2SO_4$ and concentrated in vacuo. The residue was purified by flash column chromatography, eluting with a gradient of 0-100% EtOAc in heptanes, to afford the title compound (180 mg, 67%) as a brown solid. $\delta_H$ (400 MHz, DMSO-$d_6$) 13.11-12.52 (m, 1H), 8.04-7.89 (m, 1H), 7.41-7.27 (m, 6H), 5.09-4.96 (m, 2H), 4.72 (t, J 8.2 Hz, 1H), 4.38-4.20 (m, 2H), 4.01-3.88 (m, 2H), 3.63-3.47 (m, 2H), 3.24-3.07 (m, 2H), 2.17-1.92 (m, 3H), 1.91-1.56 (m, 4H), 1.52-1.28 (m, 3H). LCMS (Method 1): $[M+H]^+$ m/z 627, RT 1.94 minutes.

Intermediate 53

(1-{2-[(S)-Amino(4,4-difluorocyclohexyl)methyl]-4-fluoro-1H-benzimidazol-5-yl}-3,3-difluorocyclobutyl)(3,3-difluoroazetidin-1-yl)methanone To a stirred solution of Intermediate 52 (180 mg, 0.26 mmol) in EtOH (4 mL) was added 10% Pd/C (50% wet with water, 46 mg, 0.02 mmol) in one portion. The reaction mixture was purged and stirred vigorously under a hydrogen atmosphere at r.t. for 18 h. The reaction mixture was filtered through a pad of Celite®, then washed with EtOH (2×10 mL) and concentrated in vacuo. The resulting brown glass was purified by flash column chromatography (KP—NH), eluting with a gradient of MeOH in DCM, to afford the title compound (64 mg, 43%) as a colourless glass. LCMS (Method 1): $[M+H]^+$ m/z 493, RT 1.54 minutes.

Intermediate 54 tert-Butyl 4-[3-(dibenzylamino)-2-fluoro-4-nitrophenyl]tetrahydropyran-4-carboxylate To a stirred solution of NaH (60% purity, 9.23 g, 0.23 mol) in DMA (400 mL) was added Intermediate 5 (40 g, 88.8 mmol) at 5° C. in portions. The mixture was stirred for 10 minutes, then 1-iodo-2-(2-iodoethoxy)ethane (14 mL, 0.10 mol) was added dropwise. The resulting mixture was stirred at r.t. for 16 h, then cooled in an ice bath and quenched with saturated aqueous $NH_4Cl$ solution. The mixture was extracted with TBME (2×300 mL). The organic fractions were combined and washed with saturated brine (50 mL), then dried over $Na_2SO_4$ and concentrated in vacuo. The residue was purified by flash column chromatography, eluting with a gradient of EtOAc in heptanes, to afford the title compound (37.6 g, 67%) as a yellow solid. $\delta_H$ (500 MHz, $CDCl_3$) 7.36 (dd, J 8.7, 1.4 Hz, 1H), 7.30-7.17 (m, 10H), 7.15-7.10 (m, 1H), 4.21-4.15 (m, 4H), 3.86-3.76 (m, 4H), 2.33 (d, J 13.5 Hz, 2H), 2.01-1.92 (m, 2H), 1.44 (s, 9H). LCMS (Method 1): $[M+H]^+$ m/z 521, RT 2.26 minutes.

Intermediate 55 tert-Butyl 4-[4-amino-3-(dibenzylamino)-2-fluorophenyl]tetrahydropyran-4-carboxylate Intermediate 54 (36.9 g, 65.9 mmol) was dissolved in EtOH (700 mL) and EtOAc (300 mL), and 10% Pd/C (50% wet, 21.1 g, 9.89 mmol) was added. The reaction mixture was purged and stirred vigorously under a hydrogen atmosphere at r.t. for 20 h. The reaction mixture was filtered through a pad of Celite®, then washed with EtOH (2×100 mL) and concentrated in vacuo. The residue was purified by flash column chromatography, eluting with a gradient of EtOAc in heptanes, to afford the title compound (21.6 g, 67%) as an off-white solid. $\delta_H$ (400 MHz, DMSO-$d_6$) 7.28-7.16 (m, 10H), 6.78 (t, J 8.6 Hz, 1H), 6.32 (d, J 8.5 Hz, 1H), 5.03 (s, 2H), 4.11-3.90 (m, 4H), 3.70-3.49 (m, 4H), 2.15-2.05 (m, 2H), 1.86-1.75 (m, 2H), 1.33 (s, 9H). LCMS (Method 1): $[M+H]^+$ m/z 491, RT 2.19 minutes.

Intermediate 56 tert-Butyl 4-(3,4-diamino-2-fluorophenyl)tetrahydropyran-4-carboxylate

Intermediate 55 (21.6 g, 44.0 mmol) was dissolved in EtOH (300 mL) and 10% Pd/C (50% wet, 9.37 g, 4.40 mmol) was added. The reaction mixture was purged and stirred vigorously under a hydrogen atmosphere at r.t. for 16 h. The reaction mixture was filtered through a pad of Celite®, then washed with EtOH (2×100 mL) and concentrated in vacuo, to give the title compound (12.93 g, 90%) as a pale pink powder. $\delta_H$ (400 MHz, DMSO-$d_6$) 6.38-6.27 (m, 2H), 4.59 (s, 4H), 3.71 (dt, J 11.5, 3.9 Hz, 2H), 3.59-3.48 (m, 2H), 2.23-2.11 (m, 2H), 1.92-1.78 (m, 2H), 1.35 (s, 9H). LCMS (Method 1): $[M-^tBu+H]^+$ m/z 255, RT 1.63 minutes.

Intermediate 57 tert-Butyl 4-(3-amino-4-{[(2S)-2-(benzyloxycarbonylamino)-2-(4,4-difluorocyclohexyl)-acetyl]amino}-2-fluorophenyl)tetrahydropyran-4-carboxylate HATU (6.89 g, 18.1 mmol) was added portionwise to a stirred solution of Intermediate 1 (5.19 g, 15.8 mmol), Intermediate 56 (4.93 g, 15.1 mmol) and DIPEA (5.3 mL, 30.2 mmol) in DCM (50 mL) at r.t. The reaction mixture was stirred for 2 h, then washed with water (25 mL). The aqueous layer was extracted with DCM (15 mL). The organic layers were combined, passed through a phase separator and evaporated in vacuo. The residue was purified by flash column chromatography, eluting with a gradient of EtOAc in heptanes, to afford the title compound (9.5 g, 91%) as a pale pink solid. $\delta_H$ (500 MHz, DMSO-$d_6$) 9.49 (s, 1H), 7.68 (d, J 8.1 Hz, 1H), 7.39-7.29 (m, 5H), 7.07 (d, J 8.5 Hz, 1H), 6.57 (t, J 8.4 Hz, 1H), 5.05 (s, 2H), 4.84 (s, 2H), 4.14 (t, J 8.0 Hz, 1H), 3.77-3.69 (m, 2H), 3.64-3.56 (m, 2H), 2.20 (d, J 13.5 Hz, 2H), 2.10-1.99 (m, 2H), 1.97-1.67 (m, 7H), 1.46-1.30 (m, 11H). LCMS (Method 1): $[M+H]^+$ m/z 620, RT 2.03 minutes.

Intermediate 58 tert-Butyl 4-{2-[(S)-benzyloxycarbonylamino(4,4-difluorocyclohexyl)methyl]-4-fluoro-1H-benzimidazol-5-yl}tetrahydropyran-4-carboxylate Intermediate 57 (17.08 g, 27.6 mmol) was stirred in acetic acid (170 mL) at 75° C. for 4 h, then the mixture was cooled to r.t. and concentrated in vacuo. The resulting gum was partitioned between saturated aqueous $NaHCO_3$ solution (150 mL) and EtOAc (200 mL). The phases were separated, and the aqueous layer was further extracted with EtOAc (200 mL). The organic fractions were combined, washed with saturated brine (50 mL) and concentrated in vacuo. The residue was suspended in 1:1 EtOAc:heptanes, filtered and washed with heptanes. The filtrate was concentrated in vacuo and purified by flash column chromatography, eluting with a gradient of EtOAc in heptanes, to afford the title compound (13.29 g, 80%) as a white powder. $\delta_H$ (400 MHz, DMSO-$d_6$) 12.79 (s, 1H), 7.96 (d, J 8.3 Hz, 1H), 7.44-7.24 (m, 5H), 7.23-7.14 (m, 1H), 5.10-4.97 (m, 2H), 4.72 (t, J 8.2 Hz, 1H), 3.82-3.72 (m, 2H), 3.61 (t, J 10.2 Hz, 2H), 2.32 (d, J 12.4 Hz, 2H), 2.16-1.64 (m, 8H), 1.54-1.42 (m, 1H), 1.36 (s, 10H), 1.27-1.21 (m, 1H). LCMS (Method 4): $[M+H]^+$ m/z 602.3, RT 3.82 minutes.

Intermediate 59 tert-Butyl 4-{2-[(S)-amino(4,4-difluorocyclohexyl)methyl]-4-fluoro-1H-benzimidazol-5-yl}tetrahydropyran-4-carboxylate To a stirred solution of Intermediate 58 (2.0 g, 3.32 mmol) in EtOH (40 mL) and EtOAc (60 mL) was added 10% Pd/C (50% wet with water, 700 mg, 0.33 mmol). The reaction mixture was purged and stirred vigorously under a hydrogen atmosphere at r.t. for 1 h. The reaction mixture was filtered through a pad of Celite®, then washed with EtOH (2×20 mL) and concentrated in vacuo, to give the title compound (1.65 g, 100%) as a white solid. $\delta_H$ (400 MHz, DMSO-$d_6$) 7.27 (d, J 8.4 Hz, 1H), 7.18-7.09 (m, 1H), 3.86 (d, J 6.1 Hz, 1H), 3.82-3.72 (m, 2H), 3.66-3.56 (m, 2H), 2.31 (d, J 11.3 Hz, 2H), 2.08-1.91 (m, 4H), 1.91-1.62 (m, 4H), 1.52 (d, J 10.2 Hz, 1H), 1.35 (br s, 11H). LCMS (Method 1): $[M+H]^+$ m/z 468, RT 1.59 minutes.

Intermediate 60 tert-Butyl 4-(2-{(S)-(4,4-difluorocyclohexyl)[(4-methyl-1,2,5-oxadiazole-3-carbonyl)-amino]methyl}-4-fluoro-1H-benzimidazol-5-yl)tetrahydropyran-4-carboxylate DIPEA (1.5 mL, 8.43 mmol) was added to a stirred solution of 4-methyl-1,2,5-oxadiazole-3-carboxylic acid (0.49 g, 3.86 mmol) and HATU (1.48 g, 3.88 mmol) in DCM (26 mL) at r.t. The reaction mixture was stirred for 15 minutes, then Intermediate 59 (1.60 g, 2.84 mmol) was added. The reaction mixture was stirred at r.t. for 18 h, then quenched with saturated aqueous $NaHCO_3$ solution and extracted with EtOAc (3×20 mL). The combined organic layers were dried over $MgSO_4$, filtered and concentrated in vacuo. The residue was purified by flash column chromatography, eluting with a gradient of 0-70% EtOAc in heptanes, to afford the title compound (1.20 g, 66%) as a yellow oil. $\delta_H$ (500 MHz, DMSO-$d_6$) 12.69 (s, 1H), 9.66 (s, 1H), 7.30 (d, J 7.0 Hz, 1H), 7.20 (t, J 7.7 Hz, 1H), 5.29-5.08 (m, 1H), 3.84-3.68 (m, 2H), 3.61 (t, J 10.9 Hz, 2H), 2.47 (s, 3H), 2.31 (d, J 12.8 Hz, 2H), 2.10-1.90 (m, 5H), 1.88-1.70 (m, 2H), 1.62-1.50 (m, 1H), 1.45-1.21 (m, 12H). LCMS (Method 1): $[M+H]^+$ m/z 578, RT 1.98 minutes.

Intermediate 61

4-(2-{(S)-(4,4-Difluorocyclohexyl)[(4-methyl-1,2,5-oxadiazole-3-carbonyl)amino]-methyl}-4-fluoro-1H-benzimidazol-5-yl)tetrahydropyran-4-carboxylic Acid, Trifluoroacetate Salt Intermediate 60 (1.20 g, 1.87 mmol) was stirred in DCM (9 mL) and TFA (9 mL) at r.t. for 18 h. The reaction mixture was concentrated in vacuo to afford the title compound (1.46 g, 100%) as an off-white solid. LCMS (Method 1): $[M+H]^+$ m/z 522.0, RT 1.75 minutes.

Intermediate 62 tert-Butyl 2-[3-(dibenzylamino)-2-fluoro-4-nitrophenyl]propanoate

A mixture of Intermediate 4 (7.00 g, 16.2 mmol), XPhos (2.31 g, 4.85 mmol) and $Pd_2(dba)_3$ (2.22 g, 2.43 mmol) in dry THF (150 mL) was degassed under nitrogen for 2 minutes at r.t. A solution of bromo(2-tert-butoxy-1-methyl-2-oxoethyl)zinc in THF (0.5M, 97 mL, 48.5 mmol) was added. The reaction mixture was stirred at 50° C. for 1 h, then cooled to r.t., quenched with saturated aqueous ammonium chloride solution (30 mL) and extracted with EtOAc (3×30 mL). The organic fractions were combined, dried over sodium sulfate and concentrated. The residue was purified by flash column chromatography, eluting with a gradient of 0-10% EtOAc in heptanes, followed by acidic reverse phase column chromatography, eluting with a gradient of 70-85% acetonitrile in water (with 0.1% formic acid), to afford the title compound (7.24 g, 96%) as an orange oil. $\delta_H$ (500 MHz, $CDCl_3$) 7.31 (dd, J 8.5, 1.5 Hz, 1H), 7.28-7.25 (m, 8H), 7.25-7.20 (m, 2H), 7.07 (dd, J 8.5, 6.7 Hz, 1H), 4.22-4.17 (m, 4H), 3.89 (q, J 7.2 Hz, 1H), 1.45-1.39 (m, 12H). LCMS (Method 1): $[M+H]^+$ m/z 465, RT 2.32 minutes.

Intermediate 63

2-[3-(Dibenzylamino)-2-fluoro-4-nitrophenyl]-1-(3,3-difluoroazetidin-1-yl)propan-1-one Intermediate 62 (7.20 g, 15.5 mmol) was stirred in DCM (30 mL) and TFA (30 mL) for 18 h. The reaction mixture was concentrated in vacuo. The resulting brown oil was taken up in DCM (100 mL). 3,3-Difluoroazetidine hydrochloride (2.40 g, 18.6 mmol), DIPEA (11 mL, 61.9 mmol) and HATU (7.06 g, 18.6 mmol) were added. The reaction mixture was stirred for 2 h, then washed with water (2×50 mL) and brine (30 mL), dried over $Na_2SO_4$ and concentrated in vacuo. The residue was purified by flash column chromatography, eluting with a gradient of 0-40% EtOAc in heptanes, to afford the title compound (7.7 g, 99%) as an orange oil. $\delta_H$ (400 MHz, DMSO-$d_6$) 7.52 (dd, J 8.5, 1.2 Hz, 1H), 7.31-7.13 (m, 11H), 4.65 (q, J 11.8 Hz, 1H), 4.38-4.20 (m, 2H), 4.17 (s, 4H), 3.96 (q, J 6.9 Hz, 1H), 3.74 (q, J 11.4 Hz, 1H), 1.25 (d, J 7.0 Hz, 3H). LCMS (Method 1): $[M+H]^+$ m/z 484.0, RT 2.11 minutes.

Intermediate 64

2-(3,4-Diamino-2-fluorophenyl)-1-(3,3-difluoroazetidin-1-yl)propan-1-one

Intermediate 63 (7.7 g, 15.29 mmol) was dissolved in EtOH (100 mL) and 10% Pd/C (50% wet, 1.63 g, 0.80 mmol) was added. The reaction mixture was purged and stirred vigorously under a hydrogen atmosphere at r.t. for 16 h. The reaction mixture was filtered through a pad of Celite®, then washed with EtOH (2×100 mL) and concentrated in vacuo, to give the title compound (3.82 g, 88%) as a purple solid. $\delta_H$ (400 MHz, DMSO-$d_6$) 6.36-6.15 (m, 2H), 4.77-4.59 (m, 3H), 4.38 (s, 2H), 4.36-4.13 (m, 2H), 4.05-3.91 (m, 1H), 3.76 (q, J 6.9 Hz, 1H), 1.22 (d, J 7.0 Hz, 3H). LCMS (Method 1): $[M+H]^+$ m/z 274.0, RT 0.93 minutes.

Intermediate 65 tert-Butyl N—[(S)-{5-[2-(3,3-difluoroazetidin-1-yl)-1-methyl-2-oxoethyl]-4-fluoro-1H-benzimidazol-2-yl}(4,4-difluorocyclohexyl)methyl]carbamate To a solution of Intermediate 64 (2.32 g, 7.90 mmol) and Intermediate 2 (2.66 g, 9.06 mmol) in DCM (50 mL) was added DIPEA (2.9 mL, 16.5 mmol), followed by HATU (3.44 g, 9.06 mmol). The mixture was stirred at r.t. for 45 minutes, then diluted with DCM (50 mL) and washed with water (2×50 mL). The combined organic fractions were dried over $Na_2SO_4$ and concentrated in vacuo. The residue was purified by flash column chromatography, eluting with a gradient of 0-100% EtOAc in heptanes. The resulting pink solid was stirred in acetic acid (50 mL, 0.873 mol) at 60° C. for 9 h. The reaction mixture was concentrated in vacuo. The residue was diluted with EtOAc (100 mL) and washed with saturated aqueous $NaHCO_3$ solution (3×50 mL) and brine (30 mL), then dried over $Na_2SO_4$ and concentrated in vacuo. The residue was purified by flash column chromatography, eluting with a gradient of 0-90% EtOAc in heptanes, followed by further purification by flash column chromatography (KP—NH), eluting with a gradient of 0-100% EtOAc in heptanes, to afford the title compound (3.3 g, 78%) as a white solid. $\delta_H$ (400 MHz, DMSO-$d_6$) 12.95-12.27 (m, 1H), 7.46-7.17 (m, 2H), 7.17-6.88 (m, 1H), 4.89-4.71 (m, 1H), 4.71-4.49 (m, 1H), 4.41-3.90 (m, 4H), 2.14-1.91 (m, 3H), 1.91-1.63 (m, 3H), 1.56-1.09 (m, 15H). LCMS (Method 1): $[M+H]^+$ m/z 531.1, RT 1.86 minutes.

Intermediate 66

2-{2-[(S)-Amino(4,4-difluorocyclohexyl)methyl]-4-fluoro-1H-benzimidazol-5-yl}-1-(3,3-difluoroazetidin-1-yl)propan-1-one Intermediate 65 (3.30 g, 5.60 mmol) was stirred in DCM (30 mL) and TFA (10 mL) at r.t. for 1 h. The reaction mixture was concentrated in vacuo. The residue was dissolved in DCM (150 mL) and washed carefully with saturated aqueous $NaHCO_3$ solution (3×50 mL). The aqueous layer was extracted with DCM (2×50 mL). The combined organic layers were dried over $Na_2SO_4$, and concentrated in vacuo, to afford the title compound (2.6 g, 97%) as a white solid. $\delta_H$ (400 MHz, DMSO-$d_6$) 7.27 (d, J 8.3 Hz, 1H), 7.11-6.95 (m, 1H), 4.77 (q, J 11.9 Hz, 1H), 4.32 (q, J 13.0, 12.3 Hz, 1H), 4.21 (q, J 12.7 Hz, 1H), 4.10 (q, J 6.9 Hz, 1H), 4.07-3.91 (m, 1H), 3.87 (d, J 5.9 Hz, 1H), 2.08-1.91 (m, 2H), 1.91-1.63 (m, 4H), 1.57-1.45 (m, 1H), 1.42-1.21 (m, 5H). LCMS (Method 1): $[M+H]^+$ m/z 431.5, RT 0.84 minutes.

Intermediate 67 tert-Butyl 8-[3-(dibenzylamino)-2-fluoro-4-nitrophenyl]-1,4-dioxaspiro[4.5]decane-8-carboxylate To KOH pellets (785 mg, 14 mmol), KOH in water (60%, 20 mL), Intermediate 5 (900 mg, 2 mmol) and tetrabutylammonium bromide (1.95 g, 6 mmol) was added 2,2-bis (2-bromoethyl)-1,3-dioxolane (3.45 g, 12 mmol) in one portion. The reaction mixture was stirred at 50° C. for 24 h, then diluted with DCM (30 mL) and washed with water (10 mL). The organic fractions were combined, passed through a phase separator and concentrated in vacuo. The residue was purified by flash column chromatography, eluting with a gradient of 0-100% EtOAc in hexanes, to afford the title compound (550 mg, 48%) as a yellow oil. LCMS (Method 7): $[M+H]^+$ m/z 577.0, RT 1.73 minutes.

Intermediate 68

8-[3-(Dibenzylamino)-2-fluoro-4-nitrophenyl]-1,4-dioxaspiro[4.5]decane-8-carboxylic Acid, Trifluoroacetate Salt Intermediate 67 (550 mg, 0.954 mmol) was stirred in DCM (6 mL) and TFA (5 mL) at r.t. for 3 h. The reaction mixture was concentrated in vacuo to afford the title compound (450 mg, 100%) as a brown oil. LCMS (Method 7): $[M+H]^+$ m/z 521.0, RT 1.11 minutes.

Intermediate 69

4-[3-(Dibenzylamino)-2-fluoro-4-nitrophenyl]-4-(3,3-difluoroazetidine-1-carbonyl)-cyclohexanone To Intermediate 68 (450 mg, 0.864 mmol), HATU (395 mg, 1.04 mmol) and DIPEA (0.82 mL, 4.72 mmol) in DCM (5 mL) was added 3,3-difluoroazetidine hydrochloride (147 mg, 1.13 mmol). The reaction mixture was stirred at r.t. for 18 h, then purified by flash column chromatography, eluting with a gradient of 0-100% EtOAc in hexanes, to afford the title compound (370 mg, 78%) as a cream solid. LCMS (Method 7): $[M+H]^+$ m/z 552.0, RT 1.51 minutes.

Intermediate 70

{1-[3-(Dibenzylamino)-2-fluoro-4-nitrophenyl]-4,4-difluorocyclohexyl}(3,3-difluoro-azetidin-1-yl) methanone To a solution of Intermediate 69 (370 mg, 0.67 mmol) in DCM (6 mL) was added DAST (0.24 mL, 1.76 mmol) dropwise. The reaction mixture was stirred at r.t. for 18 h, then poured onto ice and neutralised with saturated aqueous $Na_2CO_3$ solution (1 mL). The mixture was extracted with DCM (2×30 mL). The combined organic fractions were dried over $MgSO_4$ and concentrated in vacuo. The residue was purified by flash column chromatography, eluting with a gradient of 0-100% EtOAc in hexanes, to afford the title compound (200 mg, 52%) as a yellow oil. LCMS (Method 7): $[M+H]^+$ m/z 574.0, RT 1.62 minutes.

Intermediate 71

[1-(3,4-Diamino-2-fluorophenyl)-4,4-difluorocyclohexyl](3,3-difluoroazetidin-1-yl)-methanone Intermediate 70 (200 mg, 0.35 mmol) was dissolved in EtOH (5 mL) and 10% Pd/C (74 mg, 0.070 mmol) was added. The reaction mixture was purged and stirred vigorously under a hydrogen atmosphere at r.t. for 18 h. The reaction mixture was filtered through a pad of Celite®, then washed with MeOH (2×20 mL) and concentrated in vacuo, to give the title compound (90 mg, 71%) as a brown solid. LCMS (Method 7): $[M+H]^+$ m/z 364.0, RT 1.07 minutes.

Intermediate 72

Benzyl N—[(S)-{5-[1-(3,3-difluoroazetidine-1-carbonyl)-4,4-difluorocyclohexyl]-4-fluoro-1H-benzimidazol-2-yl}(4,4-difluorocyclohexyl)methyl]carbamate To a solution of Intermediate 71 (90 mg, 0.25 mmol) and Intermediate 1 (97 mg, 0.297 mmol) in DCM (5 mL) at r.t. was added DIPEA (0.13 mL, 0.743 mmol), followed by HATU (113.0 mg, 0.297 mmol). The reaction mixture was stirred at r.t. for 18 h, then diluted with DCM (40 mL) and washed with water (10 mL). The aqueous fraction was extracted with DCM (2×20 mL). The organic fractions were combined, dried over $MgSO_4$ and concentrated in vacuo. The residue was dissolved in acetic acid (8 mL) and heated at 70° C. for 4 h, then allowed to cool to r.t. and concentrated in vacuo. The residue was purified by flash column chromatography, eluting with a gradient of 0-100% EtOAc in hexanes, to afford the title compound (160 mg, 99%) as a pale-yellow solid. LCMS (Method 7): $[M+H]^+$ m/z 655.0, RT 1.41 minutes.

Intermediate 73

(1-{2-[(S)-Amino(4,4-difluorocyclohexyl)methyl]-4-fluoro-1H-benzimidazol-5-yl}-4,4-difluorocyclohexyl)(3,3-difluoroazetidin-1-yl)methanone Intermediate 72 (160 mg, 0.24 mmol) was dissolved in EtOH (8 mL) and 10% Pd/C (52 mg, 0.05 mmol) was added. The reaction mixture was purged and stirred vigorously under a hydrogen atmosphere at r.t. for 18 h. The reaction mixture was filtered through a pad of Celite®, then washed with EtOH (2×20 mL) and concentrated in vacuo, to give the title compound (125 mg, 98%) as a purple solid. LCMS (Method 7): $[M+H]^+$ m/z 521.0, RT 1.20 minutes.

Intermediate 74

N,N-Dibenzyl-6-chloro-3-nitropyridin-2-amine

To a stirred solution of 2,6-dichloro-3-nitropyridine (3.00 g, 15.5 mmol) in DCM (50 mL) were added triethylamine (4.3 mL, 31.1 mmol) and dibenzylamine (3.1 mL, 15.5 mmol). The reaction mixture was stirred at r.t. for 18 h, then diluted with DCM (50 mL), washed with water (2×50 mL) and brine (50 mL), dried over $Na_2SO_4$ and concentrated in vacuo. The resulting yellow oil was purified by flash column chromatography, eluting with a gradient of 0-28% EtOAc/ heptane, to afford the title compound (6 g, 100%) as a yellow oil. LCMS (Method 1): $[M+H]^+$ m/z 354.0, RT 2.19 minutes.

Intermediate 75

Methyl 2-[6-(dibenzylamino)-5-nitropyridin-2-yl] acetate

To a solution of Intermediate 74 (19.9 g, 54.0 mmol) and dimethyl malonate (9.45 mL, 81.0 mmol) in DMF (110 mL) was added $K_2CO_3$ (18.7 g, 135 mmol). The mixture was heated at 70° C. for 20 h, then cooled to r.t., poured into water (400 mL) and acidified with 10% HCl solution (<pH 4). The mixture was extracted with TBME (400 mL). The organic fraction was washed with water (300 mL) and brine (300 mL), then passed through a phase separator and concentrated in vacuo. The residue was dissolved in DMSO (216 mL) and water (21.6 mL), then lithium chloride (6.9 g, 160 mmol) was added. The mixture was heated at 120° C. for 18 h and cooled to r.t., then diluted with water (600 mL) and extracted with TBME (2×300 mL). The combined organic fractions were washed with water (200 mL), dried over $Na_2SO_4$ and concentrated in vacuo. The residue was purified by flash column chromatography, eluting with a gradient of 0-25% EtOAc in isohexane, to afford the title compound (8.44 g, 34%). LCMS (Method 9): $[M+H]^+$ m/z 392.0, RT 2.81 minutes.

Intermediate 76

Methyl 4-[6-(dibenzylamino)-5-nitropyridin-2-yl] tetrahydropyran-4-carboxylate

To a stirred suspension of NaH (60%, 1.04 g, 26.0 mmol) in DMF (25 mL) at 0° C. was added Intermediate 75 (4.24 g, 10.8 mmol) in DMF (15 mL) dropwise. The red mixture was stirred for 5 minutes, then 1-iodo-2-(2-iodoethoxy) ethane (2.3 mL, 16.3 mmol) was added dropwise. The reaction mixture was stirred for 3 h with warming to r.t., then diluted with EtOAc (50 mL) and poured into saturated aqueous $NH_4Cl$ solution (50 mL). Water (50 mL) and EtOAc (150 mL) were added, and the mixture was separated. The organic fractions were washed sequentially with water (100 mL), saturated aqueous $NH_4Cl$ solution (100 mL), water (100 mL) and brine (50 mL). The organic fraction was dried over $Na_2SO_4$ and concentrated in vacuo. The residue was purified by flash column chromatography, eluting with a gradient of 0-30% EtOAc in heptanes, to afford the title compound (5.9 g, 100%) as a yellow oil. $\delta_H$ (400 MHz, $CDCl_3$) 8.11 (d, J 8.4 Hz, 1H), 7.26 (s, 6H), 7.21-7.10 (m, 4H), 6.76 (d, J 8.4 Hz, 1H), 4.59 (s, 4H), 3.79 (t, J 4.2 Hz, 1H), 3.76 (t, J 4.2 Hz, 1H), 3.64 (s, 3H), 3.62-3.49 (m, 2H), 2.38-2.27 (m, 2H), 2.09 (ddd, J 14.0, 10.2, 4.1 Hz, 2H). LCMS (Method 2): $[M+H]^+$ m/z 462.0, RT 3.43 minutes.

Intermediate 77

Methyl 4-[5-amino-6-(benzylamino)pyridin-2-yl] tetrahydropyran-4-carboxylate

Intermediate 76 (5.90 g, 10.9 mmol) was dissolved in EtOH (40 mL) and 10% Pd/C (50% wet, 2.32 g, 1.10 mmol) was added. The reaction mixture was purged and stirred vigorously under a hydrogen atmosphere at r.t. for 23 h. The reaction mixture was filtered through a pad of Celite®, then washed with EtOAc (2×50 mL) and concentrated in vacuo. The residue was purified by flash column chromatography, eluting with a gradient of 0-100% EtOAc in heptanes. The resulting orange oil (the nitro-reduced intermediate, 4.6 g) was re-dissolved in EtOH (40 mL) and 10% Pd/C (50% wet, 2.39 g, 1.12 mmol) was added. The reaction mixture was purged and stirred vigorously under a hydrogen atmosphere at r.t. for 21 h. The reaction mixture was filtered through a pad of Celite®, then washed with EtOH (2×50 mL) and concentrated in vacuo. The residue was dissolved in DCM (50 mL) and washed with saturated aqueous $NaHCO_3$ solution (20 mL). The aqueous fraction was extracted with 20% MeOH in DCM (2×40 mL). The organic fractions were combined, then dried over $Na_2SO_4$ and concentrated in vacuo, to afford the title compound (2.8 g, 52%) as a red/brown solid. LCMS (Method 6): $[M+H]^+$ m/z 342.3, RT 0.56 minutes.

Intermediate 78

Methyl 4-(5,6-diaminopyridin-2-yl)tetrahydropyran-4-carboxylate

Intermediate 77 (2.80 g, 8.20 mmol) was dissolved in MeOH (100 mL) and 10% Pd/C (50% wet, 1.75 g, 0.82 mmol) was added. The reaction mixture was purged and stirred vigorously under a hydrogen atmosphere at r.t. for 18 h. Aqueous HCl (6M, 1.4 mL, 8.20 mmol) was added, and the reaction mixture was stirred under a hydrogen atmosphere for 20 h. The reaction mixture was filtered through a pad of Celite®, then washed with MeOH (2×50 mL) and concentrated in vacuo. The residue was dissolved in 20% MeOH in DCM (50 mL), then washed with saturated aqueous $NaHCO_3$ solution (20 mL). The aqueous layer was extracted with 20% MeOH in DCM (50 mL). The combined organic layers were dried over $Na_2SO_4$, then concentrated in vacuo, to afford the title compound (1.98 g, 72%) as a red/brown solid. $\delta_H$ (500 MHz, DMSO-$d_6$) 6.66 (d, J 7.8 Hz, 1H), 6.35 (d, J 7.8 Hz, 1H), 5.32 (s, 2H), 4.62 (s, 2H), 3.75-3.63 (m, 2H), 3.57 (s, 3H), 3.47-3.36 (m, 2H), 2.21-2.10 (m, 2H), 1.96 (ddd, J 13.7, 10.0, 3.9 Hz, 2H). LCMS (Method 6): $[M+H]^+$ m/z 252.1, RT 0.34 minutes.

Intermediate 79

Methyl 4-[6-amino-5-(tert-butoxycarbonylamino) pyridin-2-yl]tetrahydropyran-4-carboxylate Intermediate 78 (1.98 g, 7.88 mmol), di-tert-butyl dicarbonate (2.06 g, 9.46 mmol) and guanidine hydrochloride (1:1) (150 mg, 1.58 mmol) were stirred in EtOH (40 mL) at r.t. for 18 h. The reaction mixture was concentrated in vacuo. The residue was separated between EtOAc (100 mL) and water (50 mL). The aqueous fraction was extracted with EtOAc (50 mL). The combined organic fractions were washed with brine (30 mL), dried over $Na_2SO_4$ and concentrated in vacuo. The residue was purified by flash column chromatography, eluting with a gradient of 0-60% EtOAc in heptanes, to afford the title compound (2.41 g, 82%) as a white solid. $\delta_H$ (500 MHz, DMSO-$d_6$) 8.40 (s, 1H), 7.55 (d, J 8.0 Hz, 1H), 6.54 (d, J 8.1 Hz, 1H), 5.70 (s, 2H), 3.70 (dt, J 11.5, 4.1 Hz, 2H), 3.60 (s, 3H), 3.48-3.39 (m, 2H), 2.24-2.14 (m, 2H), 2.05-1.92 (m, 2H), 1.46 (s, 9H). LCMS (Method 1): $[M+H]^+$ m/z 352.0, RT 1.62 minutes.

Intermediate 80

Methyl 4-[6-{[(2S)-2-(benzyloxycarbonylamino)-2-(4,4-difluorocyclohexyl)acetyl]-amino}-5-(tert-butoxycarbonylamino)pyridin-2-yl]tetrahydropyran-4-carboxylate To a stirred solution of Intermediate 79 (3.00 g, 8.11 mmol) and Intermediate 1 (2.92 g, 8.92 mmol) in EtOAc (50 mL) at 0° C. was added pyridine (3.0 mL, 36.5 mmol). T3P® in EtOAc (50%, 12 mL, 20.3 mmol) was added dropwise. The reaction mixture was stirred at r.t. for 1.5 h, then quenched with water (50 mL). The aqueous fraction was extracted with EtOAc (50 mL). The combined organic fractions were washed with saturated aqueous $NH_4Cl$ solution (50 mL) and water (50 mL), then dried over $Na_2SO_4$ and concentrated in vacuo. The residue was purified by flash column chromatography, eluting with a gradient of 0-30% EtOAc in heptanes, to afford the title compound (5.65 g, 95%) as a white solid. $\delta_H$ (400 MHz, DMSO-$d_6$) 10.67 (s, 1H), 8.03 (d, J 8.4 Hz, 1H), 7.87 (s, 1H), 7.74 (d, J 8.0 Hz, 1H), 7.42-7.24 (m, 6H), 5.06 (s, 2H), 4.41 (t, J 6.2 Hz, 1H), 3.77-3.65 (m, 2H), 3.62 (s, 3H), 3.55-3.42 (m, 2H), 2.31-2.23 (m, 2H), 2.18-1.96 (m, 4H), 1.96-1.65 (m, 5H), 1.42 (s, 11H). LCMS (Method 1): $[M+H]^+$ m/z 661.0, RT 2.08 minutes.

Intermediate 81

Methyl 4-(5-amino-6-{[(2S)-2-(benzyloxycarbonylamino)-2-(4,4-difluorocyclohexyl)-acetyl]amino}pyridin-2-yl)tetrahydropyran-4-carboxylate Intermediate 80 (5.65 g, 7.70 mmol) was stirred in 1,4-dioxane (25 mL) and 4M HCl in 1,4-dioxane (25 mL, 0.10 mol) for 5 h, then the reaction mixture was concentrated in vacuo. The residue was dissolved in EtOAc (100 mL) and washed with saturated aqueous $NaHCO_3$ solution (2×50 mL) and brine (20 mL), then dried over $Na_2SO_4$ and concentrated in vacuo, to afford the title compound (4.79 g, 94%) as a white foam. $\delta_H$ (400 MHz, DMSO-$d_6$) 10.17 (s, 1H), 7.61 (d, J 8.3 Hz, 1H), 7.43-7.25 (m, 5H), 7.17 (d, J 8.3 Hz, 1H), 7.08 (d, J 8.3 Hz, 1H), 5.05 (s, 2H), 4.91 (s, 2H), 4.39-4.20 (m, 1H), 3.77-3.64 (m, 2H), 3.59 (s, 3H), 3.52-3.37 (m, 2H), 2.29-2.15 (m, 2H), 2.15-1.94 (m, 4H), 1.94-1.61 (m, 5H), 1.60-1.30 (m, 2H). LCMS (Method 1): $[M+H]^+$ m/z 561.0, RT 1.87 minutes.

Intermediate 82

Methyl 4-{2-[(S)-benzyloxycarbonylamino(4,4-difluorocyclohexyl)methyl]-1H-imidazo-[4,5-b]pyridin-5-yl}tetrahydropyran-4-carboxylate Intermediate 81 (4.70 g, 7.13 mmol) was stirred in acetic acid (34 mL, 0.59 mol) at 50° C. for 2 h, then the reaction mixture was concentrated in vacuo. The residue was dissolved in EtOAc (150 mL) and washed with saturated aqueous $NaHCO_3$ solution (2×100 mL) and brine (20 mL), then dried over $Na_2SO_4$ and concentrated in vacuo. The residue was purified by flash column chromatography, eluting with a gradient of 0-80% EtOAc in heptanes, to afford the title compound (4.15 g, 97%) as a white solid foam. $\delta_H$ (500 MHz, DMSO-$d_6$) 13.27-12.36 (m, 1H), 8.03-7.76 (m, 2H), 7.39-7.28 (m, 5H), 7.25 (d, J 8.3 Hz, 1H), 5.11-4.94 (m, 2H), 4.78-4.67 (m, 1H), 3.80-3.71 (m, 2H), 3.60 (s, 3H), 3.55-3.45 (m, 2H), 2.41-2.32 (m, 2H), 2.21-2.07 (m, 2H), 2.07-1.91 (m, 3H), 1.91-1.66 (m, 3H), 1.57-1.47 (m, 1H), 1.44-1.31 (m, 1H), 1.31-1.20 (m, 1H). LCMS (Method 4): $[M+H]^+$ m/z 543.3, RT 3.12 minutes.

Intermediate 83

4-{2-[(S-Benzyloxycarbonylamino(4,4-difluorocyclohexyl)methyl]-1H-imidazo[4,5-b]-pyridin-5-yl}tetrahydropyran-4-carboxylic Acid Intermediate 82 (0.50 g, 0.92 mmol) was stirred in MeOH (10 mL) and 1M aqueous NaOH solution (6.0 mL, 6.00 mmol) at 50° C. for 7 h, followed by 16 h at r.t., then at 50° C. for 4 h. The reaction mixture was concentrated in vacuo. The remaining aqueous residue was washed with diethyl ether (2×20 mL), then acidified to pH 2-3 using 1M aqueous HCl, and extracted with EtOAc (2×50 mL). The organic fractions were combined, then dried over $Na_2SO_4$ and concentrated in vacuo, to afford the title compound (494 mg, 98%) as a yellow foam. LCMS (Method 1): $[M+H]^+$ m/z 529.0, RT 1.76 minutes.

Intermediate 84

Benzyl N—[(S)-(4,4-difluorocyclohexyl)(5-{4-[(2,2-difluorocyclopropyl)methylcarbamoyl]tetrahydropyran-4-yl}-1H-imidazo[4,5-b]pyridin-2-yl)methyl]carbamate To a stirred solution of Intermediate 83 (100.0 mg, 0.19 mmol) and (2,2-difluoro-cyclopropyl)methanamine hydrochloride (33.0 mg, 0.23 mmol) in DCM (3 mL) and DMF (2 mL) was added DIPEA (0.13 mL, 0.76 mmol), followed by HATU (86 mg, 0.23 mmol). The reaction mixture was stirred for 15 minutes, washed sequentially with water (2 mL), saturated aqueous $NH_4Cl$ solution (2 mL), water (2 mL) and brine (2 mL), then dried over $Na_2SO_4$ and concentrated in vacuo. The residue was purified by flash column chromatography, eluting with a gradient of 0-100% EtOAc in heptanes, to afford the title compound (172 mg, 68%) as a clear oil. LCMS (Method 1): $[M+H]^+$ m/z 618.0, RT 1.85 minutes.

Intermediate 85

4-{2-[(S)-Amino(4,4-difluorocyclohexyl)methyl]-1H-imidazo[4,5-b]pyridin-5-yl}-N-[(2,2-difluorocyclopropyl)methyl]tetrahydropyran-4-carboxamide Intermediate 84 (172 mg, 0.19 mmol) was dissolved in EtOH (5 mL) and 10% Pd/C (50% wet, 40 mg, 0.019 mmol) was added. The reaction mixture was purged and stirred vigorously under a hydrogen atmosphere at r.t. for 2 h. The reaction mixture was filtered through a pad of Celite®, then washed with EtOH (2×10 mL) and concentrated in vacuo, to afford the title compound (102 mg) as a clear oil. LCMS (Method 1): $[M+H]^+$ m/z 484.0, RT 1.43 minutes.

Intermediate 86

2-[3-(Dibenzylamino)-2-fluoro-4-nitrophenyl]acetic Acid

Intermediate 5 (2.00 g, 4.44 mmol) was dissolved in DCM (10 mL), and TFA (5 mL, 64.6 mmol) was added. The mixture was stirred at r.t. for 18 h. The solvent was removed in vacuo. The residue was azeotroped with EtOAc, then placed under high vacuum overnight, to give the title compound (1.74 g, 99.4%) as a yellow powder. $\delta_H$ (300 MHz, DMSO-$d_6$) 12.70 (br s, 1H), 7.50-7.20 (m, 12H), 4.15 (s, 4H), 3.76 (s, 2H). LCMS (Method 9): $[M+H]^+$ m/z 395, RT 1.28 minutes.

Intermediate 87

2-[3-(Dibenzylamino)-2-fluoro-4-nitrophenyl]-1-(3,3,4,4-tetrafluoropyrrolidin-1-yl)-ethanone Intermediate 86 (1.74 g, 4.41 mmol) and DIPEA (1.60 mL, 9.20 mmol) were stirred in DCM (20 mL) at r.t., then HATU (1.73 g, 4.41 mmol) and 3,3,4,4-tetrafluoropyrrolidine hydrochloride (832 mg, 4.63 mmol) were added. The mixture was stirred at r.t. for 18 h, then diluted with DCM (50 mL) and washed with saturated aqueous $NaHCO_3$ solution (50 mL). The organic layer was dried over $Na_2SO_4$ and concentrated in vacuo, then purified by chromatography (silica, DCM, 0-10% MeOH gradient). The relevant fractions were concentrated in vacuo. The resulting yellow oil was azeotroped with DCM/isohexane (~1:2) to give the title compound (2.17 g, 95%) as a yellow solid. $\delta_H$ (300 MHz, DMSO-$d_6$) 7.50-7.20 (m, 12H), 4.50 (m, 2H), 4.18 (s, 4H), 4.13 (m, 2H), 3.83 (s, 2H). LCMS (Method 9): $[M+H]^+$ m/z 520, RT 2.69 minutes.

Intermediate 88

2-[3-(Dibenzylamino)-2-fluoro-4-nitrophenyl]-4-(ethylsulfonyl)-1-(3,3,4,4-tetrafluoro-pyrrolidin-1-yl)butan-1-one Intermediate 87 (1.00 g, 1.92 mmol) was dissolved in dry DMF (5 mL), then NaH (81 mg, 2.02 mmol, 60% dispersion in oil) was added. The mixture was stirred at r.t. for 10 minutes, then ethyl vinyl sulfone (0.21 mL, 2.00 mmol) was added. The mixture was stirred at r.t. for 2 h, then quenched with saturated aqueous $NH_4Cl$ solution (20 mL) and extracted with TBME (20 mL). The organic layer was concentrated in vacuo, and purified by chromatography (silica, 0-15% EtOAc gradient in DCM), to give the title compound (590 mg, 48%) as a yellow solid. $\delta_H$ (300 MHz, DMSO-$d_6$) 7.42 (d, J 8 Hz, 1H), 7.35-7.20 (m, 10H), 7.07 (t, J 8 Hz, 1H), 4.35-4.30 (m, 1H), 4.27 (s, 4H), 4.20-3.80 (m, 3H), 3.23 (m, 1H), 3.11-2.96 (m, 4H), 2.47 (m, 1H), 2.21 (m, 1H), 1.43 (t, J 7.4 Hz, 3H). LCMS (Method 9): $[M+H]^+$ m/z 640, RT 2.68 minutes.

Intermediate 89

2-(3,4-Diamino-2-fluorophenyl)-4-(ethylsulfonyl)-1-(3,3,4,4-tetrafluoropyrrolidin-1-yl)-butan-1-one Intermediate 88 (580 mg, 0.91 mmol) was dissolved in EtOH (15 mL) and EtOAc (15 mL), and 10% Pd/C (80 mg) was added. The reaction mixture was degassed under vacuum and placed under a hydrogen atmosphere (balloon) with vigorous stirring for 18 h. The mixture was filtered through a Celite® plug, and washed with EtOH (20 mL). The combined organic fractions were concentrated in vacuo, then azeotroped with DCM/isohexanes twice, to give the title compound (289 mg, 97.8%) as a foamy off-white solid. $\delta_H$ (300 MHz, DMSO-$d_6$) 6.34 (d, J 8.2 Hz, 1H), 6.21 (t, J 8.0 Hz, 1H), 4.86 (s, 2H), 4.46 (m, 3H), 4.20-3.88 (m, 3H), 3.55 (q, J 13.7 Hz, 1H), 3.08 (q, J 7.4 Hz, 2H), 3.02-2.80 (m, 2H), 2.33-2.08 (m, 1H), 1.95 (tt, J 12.1, 10.7, 4.2 Hz, 1H), 1.18 (t, J 7.4 Hz, 3H). LCMS (Method 9): $[M+H]^+$ m/z 430, RT 1.24/1.27 minutes.

Intermediate 90

Benzyl N—[(S)-(4,4-difluorocyclohexyl){5-[3-(ethylsulfonyl)-1-(3,3,4,4-tetrafluoro-pyrrolidine-1-carbonyl)propyl]-4-fluoro-1H-benzimidazol-2-yl}methyl]carbamate Intermediate 1 (292 mg, 0.89 mmol) and HATU (350 mg, 0.89 mmol) were dissolved in dry DCM (50 mL) and DIPEA (0.31 mL, 1.785 mmol) was added, followed by Intermediate 89 (365 mg, 0.85 mmol). The mixture was stirred at r.t. for 6 h, then washed with saturated aqueous $NaHCO_3$ solution (50 mL). The organic fractions were dried over $Na_2SO_4$, then concentrated in vacuo. The residue was taken up DCM (40 mL), and TFA (0.2 mL, 3.0 mmol) was added. The mixture was stirred at 40° C. for 2 h, then allowed to cool to r.t. and washed with saturated aqueous $NaHCO_3$ solution (2×50 mL). The organic layer was separated and concentrated in vacuo. The residue was purified by chromatography (silica, DCM, 0-60% EtOAc gradient) to give the title compound (417 mg, 68%) as an off-white solid. $\delta_H$ (300 MHz, DMSO-$d_6$) 13.00-12.70 (s, 1H), 7.95 (m, 1H), 7.57-7.21 (m, 5H), 7.06 (m, 1H), 5.16-4.86 (m, 2H), 4.86-4.26 (m, 4H), 4.26-3.83 (m, 3H), 3.67 (t, J 13.8 Hz, 1H), 3.20-2.80 (m, 3H), 2.70 (s, 2H), 2.43-2.20 (m, 1H), 2.22-1.61 (m, 3H), 1.57-1.01 (m, 5H), 0.99-0.63 (m, 3H). LCMS (Method 9): $[M+H]^+$ m/z 721, RT 2.30 minutes.

Intermediate 91

2-{2-[(S)-Amino(4,4-difluorocyclohexyl)methyl]-4-fluoro-1H-benzimidazol-5-yl}-4-(ethylsulfonyl)-1-(3,3,4,4-tetrafluoropyrrolidin-1-yl)butan-1-one Intermediate 90 (410 mg, 0.57 mmol) was dissolved in EtOH (15 mL) and EtOAc (10 mL), and 10% Pd/C (50 mg) was added. The mixture was degassed and refilled with a hydrogen atmosphere (balloon), then stirred vigorously at r.t. for 4 h. The mixture was filtered through a Celite® pad, washing with EtOH (3×5 mL). The combined organic fractions were concentrated in vacuo to give the title compound (334 mg, 100%) as an off-white solid. LCMS (Method 9): $[M+H]^+$ m/z 587, RT 1.72 minutes.

Intermediate 92

Dimethyl 1-[6-(dibenzylamino)-5-nitropyridin-2-yl]-4-oxocyclohexane-1,3-dicarboxylate To a solution of Intermediate 75 (5 g, 12.39 mmol) in THF (25 mL) were added methyl acrylate (2.5 mL, 27 mmol) and DBU (9.5 mL, 62 mmol). The resulting mixture was stirred at r.t. for 3.5 h, then magnesium bromide (11.6 g, 61.7 mmol) was added in small portions. A cooling bath was introduced halfway through the addition to control the exothermic effect. The cooling bath was removed and the reaction mixture was stirred at r.t. for 20 h, then diluted with DCM (80 mL) and washed with 1N HCl (80 mL). The aqueous washings were re-extracted with DCM (50 mL). The combined organic extracts were washed with brine (50 mL), passed through a hydrophobic frit and concentrated in vacuo. Purification by flash chromatography (SNAP 100 g, 0-40% EtOAc in hexanes) afforded the title compound (6.5 g, 90%) as a yellow oil. LCMS (Method 9): $[M+H]^+$ m/z 564, RT 2.94 minutes.

Intermediate 93

Methyl 1-[6-(dibenzylamino)-5-nitropyridin-2-yl]-4-oxocyclohexanecarboxylate

To a solution of Intermediate 92 (6.5 g, 10 mmol) in DMSO (51 mL) were added NaCl (890 mg, 15.22 mmol) and water (5.1 mL). The resulting mixture was stirred at 110° C. for 2 days, then cooled to r.t., diluted with TBME (250 mL) and washed with water (250 mL) mixed with brine (20 mL). The aqueous washings were re-extracted with TBME (250 mL). The combined organic extracts were dried over $Na_2SO_4$, filtered and concentrated in vacuo. Purification by flash chromatography (SNAP 100 g, 0-50% EtOAc in hexane) afforded the title compound (3.0 g, 58%) as a yellow oil. LCMS (Method 7): $[M+H]^+$ m/z 474, RT 2.43 minutes.

Intermediate 94

Methyl 1-[6-(dibenzylamino)-5-nitropyridin-2-yl]-4,4-difluorocyclohexanecarboxylate To a solution of Intermediate 93 (2.5 g, 5.3 mmol) in dry DCM (26.4 mL) at −78° C. under $N_2$ was added bis(2-methoxyethyl)aminosulfur trifluoride (6.7 mL, 16 mmol). The cooling bath was removed, and the mixture was stirred at r.t. for 21 h, then diluted with DCM (150 mL) and washed with aqueous $NaHCO_3$ solution (150 mL). The organic extracts were passed through a hydrophobic frit and concentrated in vacuo. The residue was taken up in acetone (53 mL) and water (5.3 mL), then potassium osmate(VI) dihydrate (100 mg, 0.26 mmol) and 4-methylmorpholine N-oxide (1 g, 8.28 mmol) were added. The resulting mixture was stirred at r.t. for 22 h, then additional potassium osmate(VI) dihydrate (50 mg) was added. Stirring at r.t. was continued for 1.5 h, then additional 4-methylmorpholine N-oxide (300 mg) was added. After 1 h, the mixture was concentrated in vacuo. The residue was taken up in DCM (100 mL) and washed with water (100 mL). The aqueous washings were re-extracted with DCM (100 mL). The organic extracts were passed through a hydrophobic frit and concentrated in vacuo. Purification by flash chromatography (SNAP 100 g, 0-50% EtOAc in hexane) afforded a mixture of the title compound and vinyl fluoride, which was again dissolved in acetone (53 mL) and water (5.3 mL), to which potassium osmate(VI) dihydrate (100 mg, 0.26 mmol) and 4-methylmorpholine N-oxide (1 g, 8.28 mmol) were added. Stirring at r.t. was continued for 24 h, then the mixture was concentrated in vacuo. The residue was taken up in DCM (100 mL) and washed with water (100 mL). The aqueous washings were re-extracted with DCM (100 mL). The organic extracts were passed through a hydrophobic frit and concentrated in vacuo. Purification by flash chromatography (SNAP 100 g, 0-60% EtOAc in hexane) afforded the title compound (1.27 g, 48.5%) as a yellow oil that solidified on standing. LCMS (Method 7): $[M+H]^+$ m/z 496, RT 2.66 minutes.

Intermediate 95

Methyl 1-(5,6-diaminopyridin-2-yl)-4,4-difluorocyclohexanecarboxylate

To a stirred solution of Intermediate 94 (305 mg, 0.62 mmol) in a mixture of EtOH (4.6 mL) and DCM (4.6 mL) were added 6M HCl (0.21 mL) and 10% palladium on charcoal (50% wet) (64 mg, 0.30 mmol). The reaction mixture was evacuated with nitrogen gas (3 times), then placed under an atmosphere of hydrogen gas. The reaction mixture was stirred under 1 atmosphere of hydrogen gas (balloon) at ambient temperature for 20 h, then filtered over a pad of Celite®, rinsing the filter cake with EtOH (2×5 mL). The filtrates were combined, and the solvent was removed in vacuo. The residue was diluted with EtOAc (10 mL) and washed with saturated aqueous $NaHCO_3$ solution (5 mL) and brine (5 mL), then dried over anhydrous $Na_2SO_4$ and filtered. The solvent was removed in vacuo to afford the title compound (179 mg, 91%) as a purple oil, which was utilised without further purification. $\delta_H$ (400 MHz, $CDCl_3$) 6.85 (d, J 7.8 Hz, 1H), 6.63 (d, J 7.8 Hz, 1H), 4.18 (s, 2H), 3.67 (s, 3H), 3.25 (s, 2H), 2.47-2.36 (m, 2H), 2.26-2.16 (m, 2H), 2.09-1.83 (m, 4H).

Intermediate 96

Methyl 1-[6-amino-5-(tert-butoxycarbonylamino)pyridin-2-yl]-4,4-difluorocyclohexanecarboxylate To a stirred solution of Intermediate 95 (170 mg, 0.54 mmol) in EtOH (2.8 mL) were added di-tert-butyl dicarbonate (129 mg, 0.59 mmol) and guanidine hydrochloride (1:1) (11 mg, 0.11 mmol) portionwise. The reaction mixture was stirred at 50° C. for 16 h, then allowed to cool to ambient temperature. The solvent was removed in vacuo. Water (5 mL) was added, and the mixture was extracted with EtOAc (2×5 mL). The organic extracts were combined, washed with saturated aqueous $NaHCO_3$ solution (5 mL) and brine (5 mL), then dried over anhydrous $Na_2SO_4$ and filtered. The solvent was concentrated in vacuo. The residue was purified using automated chromatography (Isolera 4, 10 g SFAR Duo column), eluting with a gradient of EtOAc in heptane (5-50%), to afford the title compound (170 mg, 77%) as a clear gum. $\delta_H$ (400 MHz, $CDCl_3$) 7.51 (d, J 8.0 Hz, 1H), 6.72 (d, J 8.1 Hz, 1H), 6.00 (s, 1H), 4.51 (s, 2H), 3.67 (s, 3H), 2.47-2.37 (m, 2H), 2.28-2.15 (m, 2H), 2.08-1.85 (m, 4H), 1.51 (s, 9H).

Intermediate 97

Methyl 1-[6-{[(2S)-2-(benzyloxycarbonylamino)-2-(4,4-difluorocyclohexyl)acetyl]-amino}-5-(tert-butoxycarbonylamino)pyridin-2-yl]-4,4-difluorocyclohexanecarboxylate To a stirred solution of Intermediate 96 (170 mg, 0.44 mmol), Intermediate 1 (159 mg, 0.49 mmol) and pyridine (0.16 mL, 2.03 mmol) in EtOAc (1.5 mL), previously cooled using an ice bath, was added T3P® (50% in EtOAc) (0.65 mL, 1.10 mmol) dropwise, maintaining the temperature below 10° C. The reaction mixture was stirred at ambient temperature for 2 h, then diluted with EtOAc (4 mL), cooled to 0° C. and quenched with 1M HCl (2 mL). The aqueous phase was separated. The organic phase was washed with water (3 mL) and brine (2 mL), then dried over anhydrous $Na_2SO_4$ and filtered. The solvent was concentrated in vacuo to afford the title compound (315 mg, 95%) as a yellow foam. $\delta_H$ (400 MHz, $CDCl_3$) 8.48 (s, 1H), 8.17 (d, J 8.4 Hz, 1H), 7.83 (s, 1H), 7.40-7.30 (m, 5H), 7.26-7.21 (m, 1H), 5.48 (d, J 8.7 Hz, 1H), 5.14 (s, 2H), 4.46 (s, 1H), 3.65 (s, 3H), 2.45 (dd, J 12.9, 5.0 Hz, 2H), 2.23-2.10 (m, 4H), 2.06-1.62 (m, 11H), 1.48 (s, 9H).

Intermediate 98

Methyl 1-{2-[(S)-benzyloxycarbonylamino(4,4-difluorocyclohexyl)methyl]-1H-imidazo-[4,5-b]pyridin-5-yl}-4,4-difluorocyclohexanecarboxylate To a stirred solution of Intermediate 97 (310 mg, 0.45 mmol) in DCM (2 mL) was added TFA (0.33 mL, 4.46 mmol) portionwise. The reaction mixture was heated at 40° C. for 16 h, then allowed to cool to ambient temperature and washed with saturated aqueous $NaHCO_3$ solution (2 mL). The organic phase was collected, and the aqueous phase was extracted with DCM (2 mL). The organic layers were combined, dried over anhydrous $Na_2SO_4$ and filtered. The solvent was removed in vacuo. The residue was purified using automated chromatography (Isolera 4, 10 g KP-Sil column), eluting with a gradient of EtOAc in heptane (5-50%) to afford the title compound (137 mg, 51% yield) as a beige solid. $\delta_H$ (400 MHz, $CD_3OD$) 7.90 (d, J 8.2 Hz, 1H), 7.40-7.26 (m, 5H), 7.08-6.85 (m, 1H), 5.12 (d, J 12.5 Hz, 1H), 5.06 (d, J 12.5 Hz, 1H), 4.95 (d, J 20.1 Hz, 1H), 3.68 (s, 3H), 2.58-2.48 (m, 2H), 2.44-2.34 (m, 2H), 2.12-1.93 (m, 6H), 1.88-1.63 (m, 3H), 1.61-1.30 (m, 4H) (two NH signals exchanged with solvent).

Intermediate 99

Benzyl N—[(S)-(4,4-difluorocyclohexyl){5-[4,4-difluoro-1-(2,2,2-trifluoroethyl-carbamoyl)cyclohexyl]-1H-imidazo[4,5-b]pyridin-2-yl}methyl]carbamate To a stirred solution of Intermediate 98 (130 mg, 0.23 mmol) in MeOH (1 mL) was added 2M aqueous NaOH solution (0.56 mL, 1.13 mmol) portionwise. The reaction mixture was heated at 50° C. for 16 h, then cooled to ambient temperature. The pH was adjusted to ~2-3 with the slow addition of 1M HCl. The reaction mixture was diluted with EtOAc (10 mL) and washed with brine (2×2 mL), then dried over anhydrous $Na_2SO_4$ and filtered. The solvent was removed in vacuo. The resulting beige solid was taken up in EtOAc (0.7 mL) with 2,2,2-trifluoroethanamine (0.013 mL, 0.163 mmol) and pyridine (0.055 mL, 0.680 mmol). T3P® (50% in EtOAc) (0.22 mL, 0.37 mmol) was added dropwise at ambient temperature, and stirring was continued for a further 4.5 h. The reaction mixture was diluted with EtOAc (4 mL) and cooled to 0° C., then quenched with 1M HCl (2 mL). The aqueous phase was separated. The organic phase was washed with water (2 mL) and brine (2 mL), then dried over anhydrous $Na_2SO_4$ and filtered. The solvent was concentrated in vacuo. The residue was purified using automated chromatography (Isolera 4, 10 g SFAR Duo column), eluting with a gradient of EtOAc in heptane (5-100%), to afford the title compound (29.3 mg, 19%) as a grey solid. $\delta_H$ (400 MHz, $CD_3OD$) 7.99-7.80 (m, 1H), 7.40-7.21 (m, 5H), 7.17-6.90 (m, 1H), 5.12 (d, J 12.4 Hz, 1H), 5.06 (d, J 12.4 Hz, 1H), 4.80-4.75 (m, 1H), 3.83 (q, J 9.3 Hz, 2H), 2.59-2.35 (m, 4H), 2.10-1.93 (m, 6H), 1.87-1.65 (m, 3H), 1.58-1.36 (m, 4H) (three NH signals exchanged with solvent).

Intermediate 100

Methyl 2-[3-(dibenzylamino)-2-fluoro-4-nitrophenyl]acetate

To a solution of Intermediate 47 (15.0 g, 42.3 mmol) and dimethyl malonate (7.4 mL, 63 mmol) in DMF (85 mL) was added $K_2CO_3$ (14.6 g, 106 mmol). The mixture was heated at 60° C. for 24 h, then diluted with TBME (450 mL) and water (300 mL). The pH was adjusted to ~7 with 10% aqueous HCl. The organic layer was washed with water (2×300 mL), separated and concentrated in vacuo. The residue was dissolved in a mixture of DMSO (170 mL) and water (17 mL). Lithium chloride (5.4 g, 130 mmol) was added to the solution, and the mixture was heated at 115° C. for 20 h. Water (400 mL) was added to the mixture. The resulting yellow suspension was extracted with TBME (2×300 mL). The combined organic layers were washed with water (300 mL) and brine (300 mL), dried over $Na_2SO_4$ and concentrated. The residue was recrystallised from TBME and isohexane to give the title compound (11.26 g, 65%). LCMS (Method 8): $[M+H]^+$ m/z 409, RT 2.95 minutes.

Intermediate 101

Methyl 2-[3-(dibenzylamino)-2-fluoro-4-nitrophenyl]-4,4-difluorobutanoate

To a stirred solution of Intermediate 100 (10.60 g, 26.0 mmol) in THF was added NaH (60%, 1.15 g, 28.6 mmol) in one portion at −10° C. The mixture was stirred for 15 minutes, then a solution of 2,2-difluoroethyl trifluoromethanesulfonate (3.6 mL, 27.2 mmol) was added dropwise. The reaction mixture allowed to warm to r.t. and stirred for 18 h, then quenched with saturated aqueous $NH_4Cl$ solution (100 mL) and extracted with EtOAc (2×100 mL). The combined organic phases were washed with brine (2×50 mL) and dried over $MgSO_4$, then filtered and concentrated in vacuo. The resulting crude material was separated by flash column chromatography, eluting with EtOAc/heptane (0-100% gradient), to afford the title compound (7.4 g, 59%) as a yellow-orange solid. $\delta_H$ (500 MHz, DMSO-$d_6$) 7.53 (dd, J 8.4, 0.9 Hz, 1H), 7.38-7.13 (m, 11H), 5.97 (tt, J 56.1, 4.4 Hz, 1H), 4.21-4.06 (m, 5H), 3.63 (s, 3H), 2.77-2.55 (m, 1H), 2.23 (dtdd, J 19.2, 15.2, 8.2, 4.4 Hz, 1H). LCMS (Method 2): $[M+H]^+$ m/z 473, RT 3.66 minutes.

Intermediate 102

Methyl 2-(3,4-diamino-2-fluorophenyl)-4,4-difluorobutanoate

To a stirred solution of Intermediate 101 (7.3 g, 14.99 mmol) in EtOH (50 mL) was added 10% palladium on carbon (50% wet) (1.60 g, 1.50 mmol) in one portion. The reaction mixture was stirred under 1 atmosphere of $H_2$ for 18 h, then filtered through Celite® and concentrated in vacuo, to afford the title compound (4.25 g, 85%) as a purple oil. $\delta_H$ (400 MHz, DMSO-$d_6$) 6.38-6.24 (m, 2H), 5.96 (tt, J 56.4, 4.6 Hz, 1H), 4.81 (s, 2H), 4.44 (s, 2H), 3.88 (t, J 7.4 Hz, 1H), 3.59 (s, 3H), 2.66-2.52 (m, 1H), 2.24-2.06 (m, 1H). LCMS (Method 1): $[M+H]^+$ m/z 263, RT 1.50 minutes.

Intermediate 103

Methyl 2-(3-amino-4-{[(2S)-2-(benzyloxycarbonylamino)-2-(4,4-difluorocyclohexyl)-acetyl]amino}-2-fluorophenyl)-4,4-difluorobutanoate To a stirred solution of Intermediate 1 (5.48 g, 16.74 mmol) and HATU (6.36 g, 16.74 mmol) in DCM (30 mL) at r.t. was added DIPEA (5.62 mL, 32.19 mmol). The reaction mixture was stirred for 15 minutes, then Intermediate 102 (4.22 g, 12.87 mmol) was added as a solution in DCM (30 mL). The reaction mixture was stirred for 18 h, then diluted with saturated aqueous $NaHCO_3$ solution (50 mL) and DCM (50 mL). The phases were separated, and the aqueous phase was extracted with DCM (2×50 mL). The combined organic phases were separated using a hydrophobic frit, then concentrated in vacuo. The residue was separated by flash column chromatography, eluting with EtOAc/heptane (0-100% gradient), to afford the title compound (8.78 g, quantitative) as a pale pink solid. $\delta_H$ (500 MHz, DMSO-$d_6$) 9.51 (s, 1H), 7.70 (d, J 8.0 Hz, 1H), 7.42-7.27 (m, 5H), 7.07 (d, J 8.4 Hz, 1H), 6.52 (t, J 8.0 Hz, 1H), 6.04 (tt, J 56.3, 4.4 Hz, 1H), 5.06 (s, 2H), 4.96 (s, 2H), 4.14 (t, J 7.9 Hz, 1H), 4.08-3.99 (m, 1H), 3.62 (s, 3H), 2.72-2.58 (m, 1H), 2.32-2.17 (m, 1H), 2.14-1.96 (m, 2H), 1.95-1.56 (m, 5H), 1.50-1.28 (m, 2H). LCMS (Method 1): $[M+H]^+$ m/z 572, RT 2.02 minutes.

Intermediate 104

Methyl 2-{2-[(S)-benzyloxycarbonylamino(4,4-difluorocyclohexyl)methyl]-4-fluoro-1H-benzimidazol-5-yl}-4,4-difluorobutanoate Intermediate 103 (8.77 g, 13.66 mmol) was stirred in DCM (150 mL) and TFA (2.02 mL, 27.31 mmol) at 40° C. for 16 h. The reaction mixture was cooled to r.t., diluted with DCM (50 mL) and washed with 1M aqueous NaOH solution (50 mL). The layers were separated using a hydrophobic frit, and the organic phase was concentrated in vacuo. The residue was purified by flash column chromatography, eluting with EtOAc/heptane (0-100% gradient), to afford the title compound (7.25 g, 87%) as a pale pink solid. $\delta_H$ (500 MHz, DMSO-$d_6$) 12.68 (s, 1H), 8.01 (d, J 6.8 Hz, 1H), 7.40-7.24 (m, 6H), 7.16-7.08 (m, 1H), 6.18-5.88 (m, 1H), 5.06 (d, J 12.6 Hz, 1H), 5.01 (d, J 12.6 Hz, 1H), 4.71 (t, J 8.0 Hz, 1H), 4.23 (t, J 7.3 Hz, 1H), 3.60 (s, 3H), 2.85-2.60 (m, 1H), 2.40-2.23 (m, 1H), 2.17-2.07 (m, 1H), 2.07-1.93 (m, 2H), 1.92-1.85 (m, 1H), 1.85-1.61 (m, 2H), 1.54-1.43 (m, 1H), 1.42-1.31 (m, 1H), 1.31-1.20 (m, 1H). LCMS (Method 1): $[M+H]^+$ m/z 554, RT 2.00 minutes.

Intermediate 105

Methyl 2-{2-[(S)-amino(4,4-difluorocyclohexyl)methyl]-4-fluoro-1H-benzimidazol-5-yl}-4,4-difluorobutanoate Method 1

To a stirred solution of Intermediate 104 (2.50 g, 4.11 mmol) in EtOH (40 mL) was added 10% palladium on carbon (50% wet) (0.87 g, 0.41 mmol) in one portion. The reaction mixture was stirred under 1 atmosphere of $H_2$ for 18 h, then filtered through Celite® and concentrated in vacuo, to afford the title compound (2.02 g, quantitative) as a pale brown foam. $\delta_H$ (500 MHz, DMSO-$d_6$) 12.37 (br s, 1H), 7.30 (d, J 8.3 Hz, 1H), 7.08 (dd, J 8.2, 6.6 Hz, 1H), 6.03 (tt, J 56.3, 4.5 Hz, 1H), 4.22 (t, J 7.4 Hz, 1H), 3.97-3.80 (m, 1H), 3.60 (s, 3H), 2.81-2.63 (m, 1H), 2.40-2.22 (m, 1H), 2.08-1.92 (m, 2H), 1.93-1.63 (m, 4H), 1.61-1.48 (m, 1H), 1.42-1.22 (m, 2H) ($NH_2$ protons not observed in NMR spectrum). LCMS (Method 1): $[M+H]^+$ m/z 420, RT 1.55 minutes.

Method 2

To a stirred solution of Intermediate 104 (15.00 g, 27.1 mmol) in 1,4-dioxane (150 mL) was added 10% Pd/C (50% wet) (5.0%, 1.73 g, 0.81 mmol). The reaction mixture was cycled through vacuum and nitrogen three times, then stirred under an atmosphere of hydrogen at r.t. for 16 h. The mixture was filtered through a pad of Celite®, washing through with 1,4-dioxane (50 mL). The solvent was removed in vacuo to afford the title compound (12.8 g, quantitative) as a purple/brown foam. LCMS (Method 2): $[M+H]^+$ m/z 420, RT 2.07 minutes.

Intermediate 106

Methyl 2-(2-{(S)-(4,4-difluorocyclohexyl)[(4-methyl-1,2,5-oxadiazole-3-carbonyl)-amino]methyl}-4-fluoro-1H-benzimidazol-5-yl)-4,4-difluorobutanoate To a stirred suspension of 4-methyl-1,2,5-oxadiazole-3-carboxylic acid (0.67 g, 5.25 mmol) and HATU (2.00 g, 5.28 mmol) in DCM (20 mL) at r.t. was added DIPEA (2.00 mL, 11.47 mmol) The reaction mixture was stirred for 15 minutes, then Intermediate 105 (2.00 g, 3.86 mmol) in DCM (20 mL) was added. The reaction mixture was stirred for 18 h, then quenched with saturated aqueous $NaHCO_3$ solution (40 mL) and stirred at r.t. for 20 minutes. The phases separated using a hydrophobic frit, and the organic phase was concentrated in vacuo. The residue was separated by flash column chromatography, eluting with EtOAc/heptane (0-100% gradient), to afford the title compound (1.71 g, 79%) as a white solid. $\delta_H$ (500 MHz, DMSO-$d_6$) 12.78 (s, 1H), 9.68 (s, 1H), 7.51-7.23 (m, 1H), 7.20-7.06 (m, 1H), 6.17-5.90 (m, 1H), 5.23-5.13 (m, 1H), 4.24 (t, J 7.4 Hz, 1H), 3.60 (s, 3H), 2.80-2.63 (m, 1H), 2.48 (s, 3H), 2.41-2.24 (m, 2H), 2.14-1.92 (m, 3H), 1.91-1.71 (m, 2H), 1.68-1.52 (m, 1H), 1.48-1.23 (m, 2H). LCMS (Method 1): $[M+H]^+$ m/z 530, RT 1.96 minutes.

Intermediate 107

2-(2-{(S)-(4,4-Difluorocyclohexyl)[(4-methyl-1,2,5-oxadiazole-3-carbonyl)amino]-methyl}-4-fluoro-1H-benzimidazol-5-yl)-4,4-difluorobutanoic Acid To a stirred suspension of Intermediate 106 (1.7 g, 3.05 mmol) in THF (40 mL) and water (10 mL) was added $LiOH \cdot H_2O$ (0.32 g, 7.32 mmol) in one portion. The reaction mixture was stirred at r.t. for 18 h. Additional $LiOH \cdot H_2O$ (0.070 g, 1.62 mmol) was added, and stirring was continued at r.t. for another 2 h. The solvents were concentrated in vacuo and water (30 mL) was added, then the suspension was acidified to pH 2 with 1N HCl and extracted with DCM/IPA (4:1) (3×30 mL). The combined organic phases were dried over $MgSO_4$, then filtered and concentrated in vacuo, to afford, after drying in vacuo at 40° C. for 18 h, the title compound (1.60 g, 99%) as a white solid. $\delta_H$ (500 MHz, DMSO-$d_6$) 9.68 (d, J 8.4 Hz, 1H), 7.36 (d, J 8.4 Hz, 1H), 7.16 (dd, J 8.3, 6.6 Hz, 1H), 6.19-5.88 (m, 1H), 5.20 (t, J 8.4 Hz, 1H), 4.12 (t, J 7.4 Hz, 1H), 2.68 (dtdd, J 24.6, 16.7, 8.4, 4.8 Hz, 1H), 2.48 (s, 3H), 2.38-2.19 (m, 2H), 2.12-1.93 (m, 3H), 1.90-1.71 (m, 2H), 1.55 (d, J 12.5 Hz, 1H), 1.47-1.20 (m, 2H) ($CO_2H$ and benzimidazole NH protons not observed). LCMS (Method 1): $[M+H]^+$ m/z 516, RT 1.84 minutes.

Intermediate 108

Methyl 2-(2-{(S)-(4,4-difluorocyclohexyl)[(2-fluorobenzoyl)amino]methyl}-4-fluoro-1H-benzimidazol-5-yl)-4,4-difluorobutanoate To a stirred solution of Intermediate 105 (164 mg, 0.36 mmol), 2-fluorobenzoic acid (65 mg, 0.463 mmol) and DIPEA (186 µL, 1.07 mmol) in DMF (3 mL) was added HATU (176 mg, 0.463 mmol) in DMF (2 mL). The reaction mixture was stirred for 30 minutes at r.t., then concentrated in vacuo. The residue was dissolved in EtOAc (15 mL) and washed sequentially with saturated aqueous $NaHCO_3$ solution (10 mL) and brine (3×10 mL). The organic phase was dried over $MgSO_4$, then filtered and concentrated in vacuo. The residue was separated by flash column chromatography, eluting with EtOAc/heptane (0-100% gradient), to afford the title compound (165 mg, 81%) as a white solid. $\delta_H$ (400 MHz, DMSO-$d_6$) 13.08-12.71 (m, 1H), 9.00-8.76 (m, 1H), 7.62 (t, J 6.7 Hz, 1H), 7.59-7.50 (m, 1H), 7.35-7.22 (m, 3H), 7.20-7.08 (m, 1H), 6.22-5.86 (m, 1H), 5.20 (t, J 8.3 Hz, 1H), 4.23 (t, J 7.3 Hz, 1H), 3.60 (s, 3H), 3.48-2.21 (m, 1H, obs.), 2.83-2.63 (m, 1H), 2.39-2.18 (m, 1H), 2.15-1.93 (m, 3H), 1.94-1.69 (m, 2H), 1.60-1.50 (m, 1H), 1.48-1.22 (m, 2H). LCMS (Method 1): $[M+H]^+$ m/z 542, RT 1.97 minutes.

Intermediate 109

2-(2-{(S)-(4,4-Difluorocyclohexyl)[(2-fluorobenzoyl)amino]methyl}-4-fluoro-1H-benzimidazol-5-yl)-4,4-difluorobutanoic Acid To a stirred suspension Intermediate 108 (165 mg, 0.305 mmol) in THF (4 mL) and water (1 mL) was added $LiOH \cdot H_2O$ (31.4 mg, 0.731 mmol) in one portion. The reaction mixture was stirred at r.t. for 18 h. Additional $LiOH \cdot H_2O$ (10 mg, 0.233 mmol) was added, and stirring was continued at r.t. for another 2.5 h. The solvents were concentrated in vacuo and water (30 mL) was added, then the suspension was acidified to pH 2 with 1N HCl and extracted with DCM/IPA (4:1) (3×30 mL). The combined organic phases were dried over $MgSO_4$, then filtered and concentrated in vacuo, to afford, after drying in vacuo at 40° C. for 18 h, the title compound (191 mg, quantitative) as a white solid. $\delta_H$ (400 MHz, DMSO-$d_6$) 8.91 (d, J 6.5 Hz, 1H), 7.63 (t, J 7.6 Hz, 1H), 7.58-7.51 (m, 1H), 7.36 (d, J 8.4 Hz, 1H), 7.35-7.26 (m, 2H), 7.20-7.13 (m, 1H), 6.19-5.86 (m, 1H), 5.22 (t, J 8.4 Hz, 1H), 4.12 (t, J 7.4 Hz, 1H), 3.94-3.02 (m, 1H, obs.), 2.78-2.60 (m, 1H), 2.37-2.18 (m, 1H), 2.15-1.94 (m, 3H), 1.91-1.68 (m, 2H), 1.60-1.50 (m, 1H), 1.47-1.21 (m, 2H). LCMS (Method 1): $[M+H]^+$ m/z 528, RT 1.85 minutes.

Intermediate 110

2-{2-[(S)-Benzyloxycarbonylamino(4,4-difluorocyclohexyl)methyl]-4-fluoro-1H-benzimidazol-5-yl}-4,4-difluorobutanoic Acid Lithium hydroxide monohydrate (0.26 g, 6.08 mmol) in water (8 mL) was added to a solution of Intermediate 104 (1.54 g, 2.53 mmol) in THF (33 mL). The reaction mixture was stirred at r.t. for 64 h, then the solvents were concentrated in vacuo. The residue was diluted with water (50 mL), and the pH was adjusted to 2 using 1M HCl. The resulting material was extracted with DCM:IPA (4:1) (3×50 mL). The combined organic layers were washed with brine (50 mL), then dried over $MgSO_4$ and filtered. The solvent was concentrated in vacuo. The residue was dried in vacuo at 40° C. for 18 h to give the title compound (1.57 g, quantitative) as a yellow foam. LCMS (Method 1): $[M+H]^+$ m/z 540, RT 1.88 minutes.

Intermediate 111

Benzyl N—[(S)-(4,4-difluorocyclohexyl){5-[1-(2,2-difluoropropylcarbamoyl)-3,3-difluoropropyl]-4-fluoro-1H-benzimidazol-2-yl}methyl]carbamate HATU (202 mg, 0.53 mmol) was added to a stirred solution of Intermediate 110 (250 mg, 0.41 mmol) and 2,2-difluoropropan-1-amine hydrochloride (70 mg, 0.53 mmol). The mixture was stirred for 15 minutes, then DIPEA (356 µL, 2.04 mmol) in DCM (1 mL) was added. The reaction mixture was stirred at r.t. for 18 h, then diluted with EtOAc (30 mL) and quenched with saturated aqueous $NaHCO_3$ solution (30 mL) and water (30 mL). The biphasic mixture was stirred at r.t. for 10 minutes, then the phases were separated. The aqueous phase was washed with EtOAc (2×30 mL), and the combined organic phases were washed with brine (3×30 mL), then dried over $MgSO_4$, filtered and concentrated in vacuo. The resulting crude material was purified by normal phase flash column chromatography (Isolera 4, Sfar Duo 50 g, eluting with 0-100% EtOAc in heptane) to afford the title compound (207 mg, 80%) as a yellow solid. LCMS (Method 1): $[M+H]^+$ m/z 617, RT 1.97 minutes.

Intermediate 112

2-{2-[(S-Amino(4,4-difluorocyclohexyl)methyl]-4-fluoro-1H-benzimidazol-5-yl}-N-(2,2-difluoropropyl)-4,4-difluorobutanamide To a stirred solution of Intermediate 111 (200 mg, 0.32 mmol) in 1,4-dioxane (4 mL), placed under nitrogen (three cycles of vacuum/nitrogen gas), was added 10% Pd/C (50% wet) (5.0%, 134 mg, 0.06 mmol) in a single portion. The reaction mixture was stirred under hydrogen (three cycles of vacuum/nitrogen gas, followed by three cycles of vacuum/hydrogen gas) for 21 h, then filtered through Celite®. The plug was washed with additional MeOH. The combined filtrates were concentrated in vacuo to afford the title compound (182 mg, quantitative) as a brown foam. LCMS (Method 1): $[M+H]^+$ m/z 483, RT 1.60 minutes.

Intermediate 113

Methyl 2-(2-{(S)-(4,4-difluorocyclohexyl)[(2-isopropyl-1,2,4-triazole-3-carbonyl)amino]-methyl}-4-fluoro-1H-benzimidazol-5-yl)-4,4-difluorobutanoate To a stirred solution of Intermediate 105 (12.58 g, 27.0 mmol) and lithium 2-isopropyl-1,2,4-triazole-3-carboxylate (4.78 g, 29.7 mmol) in DMF (100 mL) was added HATU (12.32 g, 32.4 mmol), followed by DIPEA (10 mL, 56.7 mmol). The resulting mixture was stirred under an atmosphere of nitrogen at r.t. for 1.5 h, then partitioned between EtOAc (50 mL) and water (50 mL) and stirred for 10 minutes. The layers were separated, and the aqueous layer was further extracted with EtOAc (50 mL). The combined organic extracts were washed with saturated aqueous $NH_4Cl$ solution (20 mL), water (15 mL), saturated aqueous $NH_4Cl$ solution (15 mL), water (15 mL), saturated aqueous $NaHCO_3$ solution (15 mL), water (15 mL) and brine (15 mL), then dried over $MgSO_4$, filtered and concentrated in vacuo. The crude material was purified by flash chromatography (Isolera 4, Sfar Duo 350 g), eluting with a gradient 0-100% EtOAc in heptane, to give the title compound (9.8 g, 65%) as a yellow solid. LCMS (Method 2): $[M+H]^+$ m/z 557, RT 3.03 minutes.

Intermediate 114

2-(2-{(S)-(4,4-Difluorocyclohexyl)[(2-isopropyl-1,2,4-triazole-3-carbonyl)amino]-methyl}-4-fluoro-1H-benzimidazol-5-yl)-4,4-difluorobutanoic Acid To a solution of Intermediate 113 (9.82 g, 17.6 mmol) in THF (150 mL) was added 1M aqueous lithium hydroxide solution (53 mL, 52.9 mmol). The reaction mixture was stirred under an atmosphere of nitrogen at r.t. for 20 h. The THF was removed in vacuo. The aqueous phase was washed with TBME (20 mL), then acidified with 1N aqueous HCl and extracted with EtOAc (2×50 mL). The combined organic extracts were washed with water (15 mL) and brine (15 mL), then dried over $MgSO_4$, filtered and concentrated in vacuo, to afford the title compound (9 g, 61% over two steps) as a yellow solid. LCMS (Method 2): $[M+H]^+$ m/z 543, RT 2.75 minutes.

Intermediate 115

2-{2-[(S-Benzyloxycarbonylamino(4,4-difluorocyclohexyl)methyl]-4-fluoro-1H-benzimidazol-5-yl}-4,4,4-trifluorobutanoic Acid To a stirred solution of Intermediate 32 (1 g, 1.71 mmol) in a mixture of THF (4 mL) and MeOH (4 mL) was added 2M aqueous NaOH solution (4.0 mL, 8.00 mmol) portion-wise. The reaction mixture was stirred at ambient temperature for 3 h, then 1M HCl (9 mL) was added dropwise and the resulting material was extracted EtOAc (2×20 mL). The organic extracts were combined and washed with brine (20 mL), then dried over anhydrous $Na_2SO_4$ and filtered. The solvent was concentrated in vacuo to afford the title compound (932 mg, 98%) as a pink solid. LCMS (Method 2): $[M+H]^+$ m/z 558, RT 2.96 minutes.

Intermediate 116

Benzyl N—[(S)-(4,4-difluorocyclohexyl)(4-fluoro-5-{3,3,3-trifluoro-1-[(2-fluoro-2-methyl-propyl)carbamoyl]propyl}-1H-benzimidazol-2-yl)methyl]carbamate To a solution of Intermediate 115 (1.18 g, 2.00 mmol) and 2-fluoro-2-methyl-propan-1-amine hydrochloride (0.28 g, 2.20 mmol) in DMF (6 mL) was added DIPEA (1.0 mL, 6.01 mmol), followed by HATU (0.91 g, 2.40 mmol) in DMF (6 mL). The reaction mixture was stirred at r.t. for 18 h, then concentrated in vacuo. The resulting brown oil was taken up in EtOAc (50 mL). The organic layer was washed with saturated aqueous $NaHCO_3$ solution (25 mL) and brine (3×25 mL), then dried over $MgSO_4$ and filtered. The solvent was evaporated. Purification of the resulting brown foam by flash column chromatography (Biotage Isolera Sfar Duo 50 g, eluting with a gradient of 0-55% EtOAc in heptane) gave the title compound (1.37 g, quantitative) as a pale brown solid. LCMS (Method 2): $[M+H]^+$ m/z 631.2, RT 3.22 minutes.

Intermediate 117

2-{2-[(S)-Amino(4,4-difluorocyclohexyl)methyl]-4-fluoro-1H-benzimidazol-5-yl}-4,4,4-trifluoro-N-(2-fluoro-2-methylpropyl)butanamide To a stirred solution of Intermediate 116 (1.37 g, 2.05 mmol) in 1,4-dioxane (45 mL), placed under nitrogen (three cycles of vacuum/nitrogen gas), was added 10% Pd/C (50% wet) (5.0%, 0.87 g, 0.41 mmol) in a single portion. The reaction mixture was stirred under hydrogen (three cycles of vacuum/nitrogen gas, followed by three cycles of vacuum/hydrogen gas) for 22 h, then filtered through Celite®, washing with MeOH. The filtrate was concentrated in vacuo, then azeotroped with DCM, to give the title compound (1.16 g, 99.7%) as a grey/brown foam. LCMS (Method 1): $[M+H]^+$ m/z 497.2, RT 1.62 minutes.

Intermediate 118

Benzyl N—[(S)-(4,4-difluorocyclohexyl){5-[1-(2,2-difluoropropylcarbamoyl)-3,3,3-trifluoropropyl]-4-fluoro-1H-benzimidazol-2-yl}methyl]carbamate To a solution of Intermediate 115 (1.10 g, 1.87 mmol) and 2,2-difluoropropan-1-amine hydrochloride (1:1) (0.27 g, 2.05 mmol) in DMF (6 mL) was added DIPEA (0.98 mL, 5.60 mmol), followed by HATU (0.85 g, 2.24 mmol) in DMF (5 mL). The reaction mixture was stirred at r.t., then concentrated in vacuo. The resulting brown oil was taken up in EtOAc (50 mL). The organic layer was washed with saturated aqueous $NaHCO_3$ solution (25 mL) and brine (3×25 mL), then dried over $MgSO_4$ and filtered. The solvent was evaporated. Purification of the resulting pale brown foam was carried out by flash column chromatography (Biotage Isolera Sfar Duo 50 g, eluting with a gradient of 0-60% EtOAc in heptane) to give the title compound (1.23 g, quantitative) as a pale brown foam. LCMS (Method 2): $[M+H]^+$ m/z 635.2, RT 3.22 minutes.

Intermediate 119

2-{2-[(S)-Amino(4,4-difluorocyclohexyl)methyl]-4-fluoro-1H-benzimidazol-5-yl}-N-(2,2-difluoropropyl)-4,4,4-trifluorobutanamide To a stirred solution of Intermediate 118 (1.23 g, 1.86 mmol) in 1,4-dioxane (40 mL), placed under nitrogen (three cycles of vacuum/nitrogen gas), was added 10% Pd/C (50% wet) (5.0%, 0.79 g, 0.37 mmol) in a single portion. The reaction mixture was stirred under hydrogen (three cycles of vacuum/nitrogen gas, followed by three cycles of vacuum/hydrogen gas) for 20 h, then filtered through Celite®, washing with MeOH. The filtrate was concentrated in vacuo, then azeotroped with DCM, to give the title compound 1.02 g, quantitative) as a grey/brown foam. LCMS (Method 1): $[M+H]^+$ m/z 501.2, RT 1.63 minutes.

Intermediate 120

Methyl 2-[3-(dibenzylamino)-2-fluoro-4-nitrophenyl]prop-2-enoate

To a stirred solution of Intermediate 100 (1 g, 2.45 mmol) in DMSO (4.8969 mL) was added acetic anhydride (0.69 mL, 7.35 mmol), followed by N,N,N',N'-tetramethylmethanediamine (0.50 mL, 3.67 mmol). The resulting solution was stirred at r.t. for 2 h, then partitioned between EtOAc (15 mL) and water (10 mL) and stirred for 10 minutes. The layers were separated, and the organic phase was washed with brine (10 mL), dried over $MgSO_4$, filtered and concentrated to dryness. The crude material was purified by flash column chromatography (Isolera 4, Sfar Duo 25 g), eluting with a gradient 0-20% EtOAc in heptane, to afford the title compound (860 mg, 84%) as a yellow oil, which crystallised to a yellow solid upon standing. LCMS (Method 1): $[M+H]^+$ m/z 421, RT 2.21 minutes.

Intermediate 121

Methyl 2-[3-(dibenzylamino)-2-fluoro-4-nitrophenyl]-3-methoxypropanoate

To a stirred solution of Intermediate 120 (850 mg, 2.02 mmol) in anhydrous MeOH (20 mL) was added sodium methoxide (109 mg, 2.02 mmol). The resulting solution was stirred at r.t. under an atmosphere of nitrogen for 16 h. The volume was reduced to about 5 mL, then the resulting material was diluted with DCM (15 mL) and quenched with saturated aqueous $NH_4Cl$ solution (10 mL). After stirring for 5 minutes, the layers were separated, and the aqueous layer was extracted with DCM (10 mL). The combined organic extracts were washed with brine (10 mL) and dried over $MgSO_4$, then filtered and concentrated to dryness, to afford the title compound (950 mg, quantitative) as a yellow oil. LCMS (Method 1): $[M+H]^+$ m/z 453, RT 2.15 minutes.

Intermediate 122

Methyl 2-(3,4-diamino-2-fluorophenyl)-3-methoxypropanoate

To a stirred solution of Intermediate 121 (500 mg, 1.11 mmol) in EtOH (10 mL) was added 10% Pd/C (50% wet) (5.0%, 470 mg, 0.22 mmol). The reaction mixture was cycled through vacuum and nitrogen three times, then stirred under an atmosphere of hydrogen at r.t. for 16 h. The mixture was filtered through a pad of Celite®, washing through with EtOAc (10 mL). The solvent was removed in vacuo. The crude material (260 mg) was purified by FCC (Isolera4, Sfar Duo 10 g), eluting with a 0-100% gradient of EtOAc in heptane, to afford the title compound (215 mg, 80%) as a purple oil, which crystallised upon standing. LCMS (Method 1): $[M+H]^+$ m/z 243, RT 0.98 minutes.

Intermediate 123

Methyl 2-{2-[(S)-benzyloxycarbonylamino(4,4-difluorocyclohexyl)methyl]-4-fluoro-1H-benzimidazol-5-yl}-3-methoxypropanoate To a stirred solution of Intermediate 122 (190 mg, 0.784 mmol) and Intermediate 1 (257 mg, 0.78 mmol) in DMF (2.8 mL) was added HATU (328 mg, 0.86 mmol), followed by DIPEA (0.29 mL, 1.65 mmol). The resulting mixture was stirred under an atmosphere of nitrogen at r.t. for 16 h, then partitioned between EtOAc (20 mL) and water (10 mL) and stirred for 10 minutes. The layers were separated, and the aqueous layer was further extracted with EtOAc (10 mL). The combined organic extracts were washed with saturated aqueous $NH_4Cl$ solution (10 mL), water (10 mL), saturated aqueous $NaHCO_3$ solution (10 mL) and brine (10 mL), then dried over $MgSO_4$, filtered and concentrated in vacuo. The crude material (550 mg) was purified by FCC (Isolera 4, Sfar Duo 25 g), eluting with a 0-100% gradient of EtOAc in heptane, and the isolated material was taken up in DCM (10 mL), to which was added TFA (0.20 mL, 2.72 mmol). The reaction mixture was stirred under an atmosphere of nitrogen at 40° C. for 18 h, then cooled to r.t. and diluted with DCM (20 mL). Saturated aqueous $NaHCO_3$ solution was added until effervescence ceased. The layers were separated, and the aqueous layer was extracted with DCM (15 mL). The combined organic extracts were washed with brine (15 mL) and dried over $MgSO_4$, then filtered and concentrated in vacuo, to afford the title compound (350 mg, 84%) as a beige solid. LCMS (Method 1): $[M+H]^+$ m/z 534, RT 1.94 minutes.

Intermediate 124

2-{2-[(S-Benzyloxycarbonylamino(4,4-difluorocyclohexyl)methyl]-4-fluoro-1H-benzimidazol-5-yl}-3-methoxypropanoic Acid To a stirred solution of Intermediate 123 (150 mg, 0.28 mmol) in THF (5 mL) was added 1M aqueous lithium hydroxide solution (1.1 mL, 1.12 mmol). The reaction mixture was stirred under an atmosphere of nitrogen at r.t. for 40 h, then diluted with water, acidified with 1N aqueous HCl until pH 2, and extracted with EtOAc (2×15 mL). The combined organic extracts were washed with brine (10 mL) and dried over $MgSO_4$, then filtered and concentrated in vacuo, to yield the title compound (150 mg, quantitative) as a white solid. LCMS (Method 1): $[M+H]^+$ m/z 520, RT 1.83 minutes.

Intermediate 125

Benzyl N—[(S)-(4,4-difluorocyclohexyl){4-fluoro-5-[1-(methoxymethyl)-2-oxo-2-(2,2,2-trifluoroethylamino)ethyl]-1H-benzimidazol-2-yl}methyl]carbamate To a stirred solution of Intermediate 124 (150 mg, 0.289 mmol) and 2,2,2-trifluoroethanamine (34 mg, 0.346 mmol) in DMF (3 mL) was added HATU (132 mg, 0.346 mmol), followed by DIPEA (0.11 mL, 0.606 mmol). The resulting mixture was stirred under an atmosphere of nitrogen at r.t. for 15 h, then partitioned between EtOAc (10 mL) and water (5 mL) and stirred for 10 minutes. The layers were separated, and the aqueous layer was further extracted with EtOAc (10 mL). The combined organic extracts were washed with saturated aqueous $NH_4Cl$ solution (10 mL), water (10 mL), saturated aqueous $NaHCO_3$ solution (10 mL) and brine (10 mL), then dried over $MgSO_4$, filtered and concentrated in vacuo. The crude material was purified by flash column chromatography (Isolera 4, Sfar Duo 10 g), eluting with a 0-100% gradient of EtOAc in heptane, to afford the title compound (120 mg, 60%) as a white solid. LCMS (Method 2): $[M+H]^+$ m/z 601, RT 2.98 minutes.

Intermediate 126

2-{2-[(S-Amino(4,4-difluorocyclohexyl)methyl]-4-fluoro-1H-benzimidazol-5-yl}-3-methoxy-N-(2,2,2-trifluoroethyl)propanamide To a stirred solution of Intermediate 125 (120 mg, 0.20 mmol) in EtOH (4 mL) was added 10% Pd/C (50% wet) (5.0%, 85 mg, 0.04 mmol). The reaction mixture was cycled through vacuum and nitrogen three times, then stirred under an atmosphere of hydrogen at r.t. for 1.5 h. The mixture was filtered through a pad of Celite®, washing through with EtOAc (10 mL) and EtOH (10 mL). The solvent was removed in vacuo to afford the title compound (106 mg, quantitative) as a colourless film. LCMS (Method 2): $[M+H]^+$ m/z 467, RT 1.97 minutes.

Intermediate 127

1-{2-[(S)-Amino(4,4-difluorocyclohexyl)methyl]-1H-imidazo[4,5-b]pyridin-5-yl}-4,4-difluoro-N-(2,2,2-trifluoroethyl)cyclohexanecarboxamide To a nitrogen-purged solution of Intermediate 99 (2 g, 3.05 mmol) in EtOH (20 mL) was added Pd/C (0.15 g). The flask was evacuated and purged with hydrogen, then stirred overnight. The reaction mixture was filtered through Celite®, and the plug was washed with DCM. The resulting material was concentrated in vacuo. The resulting dark gum was purified using silica gel chromatography, eluting with 100% EtOAc and a MeOH gradient (0-10%), to yield the title compound (1.2 g, 70%) as a purple/grey foam. LCMS (Method 3): $[M+H]^+$ m/z 510, RT 1.19 minutes.

Intermediate 128

2,2-Difluoropropyl Trifluoromethanesulfonate

To a solution of 2,2-difluoropropanol (85 mL, 1050 mmol) and triethylamine (290 mL, 2080 mmol) in DCM (2 L) at −15° C. (internal temperature) was added trifluoromethanesulfonic anhydride (200 mL, 1200 mmol) over 40 minutes, maintaining the temperature below 10° C. The colourless solution became dark brown during the addition. After 1 h, the material was washed with 10% HCl solution and analysed by $^1H$ NMR, which showed complete conversion. 10% HCl solution (1 L) was added, and the mixture was warmed to 20° C. The organic layers were washed with water (2×1 L), then passed through a hydrophobic frit and concentrated in vacuo, to give the title compound (80 mass %) (231 g, 77%) as a dark brown oil. $^{19}F$ NMR (282 MHz, $CDCl_3$) δ −74.28, −98.69 to −101.35 (m). $\delta_H$ (300 MHz, $CDCl_3$) 4.53 (t, J 10.9 Hz, 2H), 1.77 (t, J 18.6 Hz, 3H).

Intermediate 129

Diethyl 2-(2,2-difluoropropyl)propanedioate

To a solution of diethyl malonate (61 mL, 400 mmol) at 0° C. in THF (800 mL) was added potassium tert-butoxide (55 g, 480 mmol) in three portions (exothermic). A thick suspension formed. After 30 minutes, Intermediate 128 (80 mass %) (231 g, 810 mmol) in THF (150 mL) was added. The mixture was warmed to 25° C. After 92 h, isohexane (200 mL) was added, followed by 10% HCl solution (400 mL). The aqueous layer was extracted with TBME (300 mL). The organic phases were combined and washed with saturated aqueous $NaHCO_3$ solution (2×500 mL) (effervescence observed), then dried over $Na_2SO_4$ and concentrated under reduced pressure. The resulting dark brown oil was purified by flash chromatography (gradient elution of 0-20% TBDME in isohexane) to give the title compound (90.0 g, 86%) as a pale-yellow oil. $\delta_H$ (300 MHz, $CDCl_3$) 4.39-4.09 (m, 4H), 3.68 (tt, J 6.8, 0.7 Hz, 1H), 2.57 (td, J 16.7, 6.8 Hz, 2H), 1.65 (t, J 18.4 Hz, 3H), 1.29 (t, J 7.1 Hz, 6H).

Intermediate 130

Diethyl 2-[3-(dibenzylamino)-2-fluoro-4-nitrophenyl]-2-(2,2-difluoropropyl)propanedioate To a solution of Intermediate 4 (20 g, 56 mmol) and Intermediate 129 (90 mass %) (26 g, 98 mmol) in DMF (110 mL) was added $K_2CO_3$ (24 g, 174 mmol). The mixture was heated at 90° C. (external temperature) for 30 h. The resulting dark brown/black mixture was cooled to ambient temperature and poured into water (200 mL). The aqueous phase was extracted with TBME (2×200 mL). The combined extracts were dried over $Na_2SO_4$ and concentrated under reduced pressure. The resulting dark brown oil crystallised slowly. The residue was recrystallised from isohexane: TBME (3:2) (150 mL). The crystals were recovered on a sinter, then washed with isohexane (200 mL) and dried, to give the title compound (22.3 g, 69%) as a yellow-brown solid. $\delta_H$ (300 MHz, DMSO-$d_6$) 7.82-7.68 (m, 1H), 7.55 (dd, J 8.8, 1.4 Hz, 1H), 7.38-7.12 (m, 10H), 4.34-4.12 (m, 4H), 4.10 (s, 4H), 2.96 (t, J 16.6 Hz, 2H), 1.52 (t, J 19.3 Hz, 3H), 1.17 (t, J 7.1 Hz, 6H).

Intermediate 131

2-[3-(Dibenzylamino)-2-fluoro-4-nitrophenyl]-4,4-difluoropentanoic Acid

To a solution of Intermediate 130 (4.1 g, 7.2 mmol) in THF (30 mL) was added $LiOH \cdot H_2O$ (1.2 g, 29 mmol) dissolved in $H_2O$ (10 mL). The mixture was stirred for 12 h at 35° C., then diethyl ether (50 mL) was added and the layers were separated. The aqueous layer was made acidic using 0.5M HCl solution. The material was extracted into EtOAc (2×50 mL), then passed through a hydrophobic frit and evaporated in vacuo, to give the title compound (3.3 g, 95%) as an orange gum. LCMS (Method 3): $[M+H]^+$ m/z 573, RT 1.55 minutes.

Intermediate 132

Methyl 2-[3-(dibenzylamino)-2-fluoro-4-nitrophenyl]-4,4-difluoropentanoate

To a solution of Intermediate 131 (10.0 g, 21.2 mmol) in MeOH (21 mL) was added $H_2SO_4$ (18.18M) in $H_2O$ (4.4 mL). The reaction mixture was heated at the reflux temperature (75° C.) for 18 h, then concentrated in vacuo and dissolved in EtOAc (100 mL). The organic layer was washed with saturated aqueous $NaHCO_3$ solution (100 mL), and the aqueous layer was extracted with EtOAc (2×50 mL). The combined organic extracts were dried over $Na_2SO_4$, then passed through a phase separator and concentrated in vacuo, to give the title compound (9.09 g, 88%) as an orange oil. LCMS (Method 3): $[M+H]^+$ m/z 487.2, RT 1.48 minutes.

Intermediate 133

Methyl 2-(3,4-diamino-2-fluorophenyl)-4,4-difluoropentanoate

To a solution of Intermediate 132 (9.0 g, 18.7 mmol) in EtOH (187 mL) under $N_2$ was added Pd/C (10 mass %) (909 mg, 0.85 mmol). The reaction flask was placed under an atmosphere of $H_2$. After 18 h, the reaction mixture was filtered through a pad of Celite®, then concentrated in vacuo, to give the title compound (5.3 g, quantitative) as an orange oil. LCMS (Method 9): $[M+H]^+$ m/z 277.2, RT 1.31 minutes.

Intermediate 134

Methyl 2-(3-amino-4-{[(2S)-2-(benzyloxycarbonylamino)-2-(4,4-difluorocyclohexyl)-acetyl]amino}-2-fluorophenyl)-4,4-difluoropentanoate To a mixture of Intermediate 133 (5.16 g, 18.7 mmol), Intermediate 1 (7.34 g, 22.4 mmol) and HATU (8.70 g, 22.4 mmol) in DCM (190 mL) was added DIPEA (6.0 g, 46.7 mmol). The reaction mixture was stirred at r.t. for 2.5 h, then washed with water (200 mL). The aqueous layer was extracted with DCM (2×100 mL). The combined organic extracts were passed through a phase separator and concentrated in vacuo. The crude material was purified by column chromatography (Biotage SFAR HC DUO, 200 g, Isolera), eluting with a gradient of 0-80% EtOAc in isohexane, to give title compound (10.86 g, 99%) as a pink amorphous solid. LCMS (Method 3): $[M+H]^+$ m/z 586.2, RT 1.22 minutes.

Intermediate 135

Methyl 2-{2-[(S)-benzyloxycarbonylamino(4,4-difluorocyclohexyl)methyl]-4-fluoro-1H-benzimidazol-5-yl}-4,4-difluoropentanoate To a solution of Intermediate 134 (10.9 g, 18.54 mmol) in DCM (185 mL) was added TFA (5.6 mL, 74.16 mmol). The reaction mixture was heated at 40° C. overnight, then quenched with saturated aqueous $NaHCO_3$ solution (200 mL). The aqueous layer was extracted with DCM (2×100 mL). The combined organic extracts were passed through a phase separator and concentrated in vacuo. The crude material was purified by column chromatography (Biotage SFAR HC DUO, 200 g, Isolera), eluting with a gradient of 0-80% EtOAc in isohexane, followed by crystallisation from hot TBME, to give the title compound (7.18 g, 68%) as a colourless amorphous solid. LCMS (Method 3): $[M+H]^+$ m/z 568.2, RT 1.21 minutes.

Intermediate 136

2-{2-[(S-Benzyloxycarbonylamino(4,4-difluorocyclohexyl)methyl]-4-fluoro-1H-benzimidazol-5-yl}-4,4-difluoropentanoic Acid To a solution of Intermediate 135 in 1,4-dioxane (50 mL) was added $LiOH·H_2O$ (880 mg, 21 mmol) dissolved in $H_2O$ (20 mL). MeOH (10 mL) was also added to facilitate the dissolution of the starting material, and the reaction mixture was left to stir overnight. Additional $LiOH·H_2O$ (0.5 g, 12 mmol) in water (10 mL) was added. The reaction mixture was left overnight, then the volatiles were removed in vacuo and the remainder was freeze-dried overnight, to afford the title compound (lithium salt) (~80% pure) (3.9 g, 79%) as a white solid. LCMS (Method 3): $[M+H]^+$ m/z 544.2, RT 1.44 minutes.

Intermediate 137

Benzyl N—[(S)-(4,4-difluorocyclohexyl)(5-{(1S)-3,3-difluoro-1-[(2-fluoro-2-methyl-propyl)carbamoyl]butyl}-4-fluoro-1H-benzimidazol-2-yl)methyl]carbamate To a stirred solution of Intermediate 136 (2 g, 3.25 mmol) in DCM (50 mL) and DIPEA (1.7 mL, 9.7 mmol) was added 2-fluoro-2-methylpropan-1-amine hydrochloride (622 mg, 4.88 mmol), followed by HATU (1.6 g, 4.1 mmol). The reaction mixture was stirred for 2 h at r.t., then diluted with DCM (100 mL) and brine (10 mL). The layers were separated, and aqueous layer was re-extracted with DCM (100 mL). The combined organic extracts were passed through a phase separator and concentrated in vacuo. The resulting off-white solid was purified by flash column chromatography on silica, eluting with 1-80% EtOAc/hexane, to afford a white solid (mixture of stereoisomers) (1.65 g). A portion of that material (300 mg) was subject to chiral purification (Method 25), yielding Peak 1 (100 mg) and Peak 2, the latter arbitrarily assigned as the title compound (100 mg). LCMS (Method 8): $[M+H]^+$ m/z 672.4, RT 2.05 minutes. Chiral analysis (Method 26): RT 5.140 minutes, 100% d.e.

Intermediate 138

(2S)-2-{2-[(S)-Amino(4,4-difluorocyclohexyl)methyl]-4-fluoro-1H-benzimidazol-5-yl}-4,4-difluoro-N-(2-fluoro-2-methylpropyl)pentanamide Intermediate 137 (420 mg, 0.67 mmol) was dissolved in EtOH (10 mL) and ammonium formate (0.9 g, 13.56 mmol) was added. The reaction flask was degassed and nitrogen flushed, then Pd/C (70 mg, 0.07 mmol) was added. The reaction mixture was stirred for 5 h, then filtered through a pad of Celite® and washed with DCM. The filtrate was washed with water (10 mL), then re-extracted with DCM (10 mL). The combined organic extracts were washed once again with water (10 mL), then passed through a hydrophobic frit and concentrated in vacuo, to afford the title compound (330 mg, 90%) as a white solid. LCMS (Method 9): $[M+H]^+$ m/z 493.2, RT 1.69 minutes.

Intermediate 139

2-[3-(Dibenzylamino)-2-fluoro-4-nitrophenyl]-4,4-difluorobutanoic Acid

To a stirred solution of Intermediate 101 (10.00 g, 21.2 mmol) in THF (100 mL) was added a solution of $LiOH·H_2O$ (2.20 g, 51.2 mmol) in water (25 mL) portionwise at ambient temperature. The reaction mixture was stirred for 16 h, then cooled with an ice bath. 6M HCl (10 mL) was added dropwise. The resulting solution was diluted with water (20 mL) and extracted with EtOAc (200 mL). The organic layer was washed with water (2×50 mL) and brine (50 mL), then dried over anhydrous $Na_2SO_4$ and filtered. The solvent was concentrated in vacuo to afford the title compound (9.77 g, 96%) as a yellow solid. LCMS (Method 1): $[M+H]^+$ m/z 459, RT 2.05 minutes.

Intermediate 140

2-[3-(Dibenzylamino)-2-fluoro-4-nitrophenyl]-4,4-difluoro-N-(2,2,2-trifluoroethyl)-butanamide To a stirred solution of Intermediate 139 (800 mg, 1.75 mmol) in DCM (8 mL) was added DIPEA (0.46 mL, 2.62 mmol). To the resulting solution was added 2,2,2-trifluoroethylamine (0.17 mL, 2.10 mmol), followed by HATU (821 mg, 2.09 mmol). The reaction mixture was stirred at r.t. for 18 h, then diluted with DCM (50 mL) and washed with brine. The aqueous layer was re-extracted with DCM (50 mL). The combined organic extracts were washed with saturated aqueous $NH_4Cl$ solution (50 mL) and concentrated in vacuo. The resulting orange oil was purified by column chromatography on silica (25 G SFar column), eluting with 1-100% EtOAc in hexane, to yield the title compound (900 mg, 96%) as a yellow oil. LCMS (Method 3): $[M+H]^+$ m/z 540, RT 1.55 minutes.

Intermediate 141

2-(3,4-Diamino-2-fluorophenyl)-4,4-difluoro-N-(2,2,2-trifluoroethyl)butanamide

To a stirred solution of Intermediate 140 (1.5 g, 2.78 mmol) in EtOH (20 mL) at r.t. was added Pd/C (592 mg, 0.56 mmol). The reaction mixture was placed under a hydrogen gas atmosphere (three cycles of vacuum/nitrogen gas, followed by three cycles of vacuum/hydrogen gas) and stirred at r.t. for 18 h. The material was filtered through a plug of Celite®, and concentrated in vacuo. The resulting dark brown oil was purified by column chromatography (25 g Si cartridge, pre-conditioned with hexane and eluted with 0-60% EtOAc/hexane) to yield the title compound (717 mg, 78%) as a light brown solid. LCMS (Method 3): $[M+H]^+$ m/z 330, RT 1.10 minutes.

Intermediates 142 & 143

(2R)-2-(3,4-Diamino-2-fluorophenyl)-4,4-difluoro-N-(2,2,2-trifluoroethyl)butanamide (Intermediate 142)

(2S)-2-(3,4-Diamino-2-fluorophenyl)-4,4-difluoro-N-(2,2,2-trifluoroethyl)butanamide (Intermediate 143)

Intermediate 141 (717 mg) was subject to chiral HPLC (Method 27) to yield the title compounds (Peak 1, 270 mg, 38%; and Peak 2, 270 mg, 38%). Chiral analysis (Method 28): Peak 1, RT 3.96 minutes (100%); and Peak 2, RT 4.93 minutes (100%).

Intermediate 144

Benzyl N-[(1S)-2-{2-amino-4-[(1S)-3,3-difluoro-1-(2,2,2-trifluoroethylcarbamoyl)-propyl]-3-fluoroanilino}-1-(4,4-difluorocyclohexyl)-2-oxoethyl]carbamate To a stirred solution of Intermediate 143 (50.00 g, 0.152 mol) and Intermediate 1 (49.71 g, 0.152 mol) in DMF (500 mL) was added HATU (69.00 g, 0.181 mol) portionwise, followed by DIPEA (53 mL, 0.304 mol). The reaction mixture was stirred at ambient temperature for 2.5 h, then poured into water (3 L). The resulting suspension was stirred for a further 20 minutes. The solid was collected by filtration, rinsing the filter cake with water (2×400 mL) and diethyl ether (400 mL). The wet solid was transferred to a 5 L flask and MeOH (3 L) was added. The slurry was heated at 50° C. for 1 h (resulting in partial crystallisation of the product, although full dissolution was never achieved). The solid (a wet cake) was collected by filtration, and further dried in a vacuum oven to give a fudge like solid. The MeOH filtrate was concentrated in vacuo to give a brown solid. Both solids were recombined and dissolved (with gentle heating) in EtOAc (6 L). The solvent was removed in vacuo, and the solid was further dried in a vacuum oven (40° C.) for 16 h, to afford the title compound (85.34 g, 86%) as a dark beige solid. LCMS (Method 2): $[M+H]^+$ m/z 639, RT 3.24 minutes.

Intermediate 145

Benzyl N—[(S)-(4,4-difluorocyclohexyl){5-[(1S)-3,3-difluoro-1-(2,2,2-trifluoroethyl-carbamoyl)propyl]-4-fluoro-1H-benzimidazol-2-yl}methyl]carbamate To a stirred solution of Intermediate 144 (85.00 g, 0.133 mol) in DCM (3400 mL) was added TFA (40 mL, 0.539 mol) dropwise. The reaction mixture was stirred at 40° C. for 20 h, then cooled to ambient temperature. 1M aqueous NaOH solution (0.5 L) was added portionwise. Saturated aqueous NaOH solution (200 mL) was then carefully added portionwise. The organic phase was collected and washed with water (1 L), then dried over anhydrous $Na_2SO_4$ and filtered. The solvent was concentrated in vacuo. The residue was purified by dry flash chromatography (1 kg of silica), eluting with a 10-40% gradient of EtOAc in heptane, to afford the title compound (100% e.e.) (74.36 g, 88%) as a pale pink solid. LCMS (Method 2): $[M+H]^+$ m/z 621, RT 3.19 minutes.

Intermediate 146

(2S)-2-{2-[(S)-Amino(4,4-difluorocyclohexyl)methyl]-4-fluoro-1H-benzimidazol-5-yl}-N-(2,2,2-difluoroethyl)-4,4-difluorobutanamide To a stirred solution of Intermediate 145 (0.7 g, 1 mmol) in EtOH (10 mL), degassed and nitrogen flushed, was added Pd/C (100 mg, 0.09 mmol). The material was further degassed, and hydrogen was added via a balloon. The reaction mixture was stirred overnight, then filtered through a pad of Celite®. The filtrate was concentrated in vacuo to afford the title compound (0.6 g, quantitative) as a grey solid. LCMS (Method 3): $[M+H]^+$ m/z 487.0, RT 1.22 minutes.

Intermediate 147

Benzyl N—[(S)-(4,4-difluorocyclohexyl){5-[1-(2,2-difluoropropylcarbamoyl)-3,3-difluorobutyl]-4-fluoro-1H-benzimidazol-2-yl}methyl]carbamate Into a vial were introduced Intermediate 136 (150 mg, 0.27 mmol), 2,2-difluoro-propan-1-amine hydrochloride (53 mg, 0.41 mmol), DIPEA (0.14 mL, 0.81 mmol) and DMF (3 mL) at r.t. under N, then HATU (155 mg, 0.41 mmol) was added. The reaction mixture was stirred for 2 h, then quenched with water (12 mL) and brine (6 mL). The mixture was extracted with EtOAc (12 mL). The organic layer was washed with brine (6 mL), then dried over $MgSO_4$, filtered and concentrated in vacuo. The resulting crude material was purified by silica flash column chromatography, eluting with a gradient of between 10% EtOAc:90% heptane and 70% EtOAc:30% heptane, to give the title compound (141 mg, 83%) as a white solid. LCMS (Method 1): $[M+H]^+$ 631.2, RT 1.96 minutes.

Intermediate 148

2-{2-[(S)-Amino(4,4-difluorocyclohexyl)methyl]-4-fluoro-1H-benzimidazol-5-yl}-N-(2,2-difluoropropyl)-4,4-difluoropentanamide Into a round-bottomed flask were introduced Intermediate 147 (141 mg, 0.203 mmol) and EtOH (6 mL) at r.t. The mixture was stirred, evacuated and purged with $N_2$, and the cycle was repeated three times. Pd/C (10 wt %, 50% wet) (5.0%, 43 mg, 0.02 mmol) was added. The mixture was stirred, evacuated and purged with $N_2$, and the cycle was repeated three times. The evacuate-purge cycle was repeated three times with $H_2$, and the reaction mixture was left for 2 h. The reaction mixture was evacuated and purged with $N_2$, and the cycle was repeated three times. The reaction mixture was filtered through glass-fibre filter paper, and the filter cake was washed with MeOH (~10 mL). The filtrate was concentrated in vacuo to give the title compound (106 mg, 95%) as a grey solid. LCMS (Method 1): $[M+H]^+$ 497.2, RT 1.61 minutes.

Examples 1 & 2

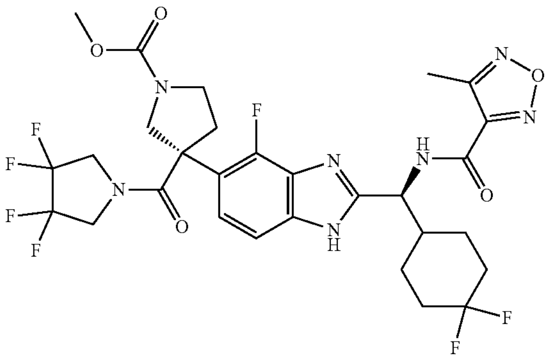

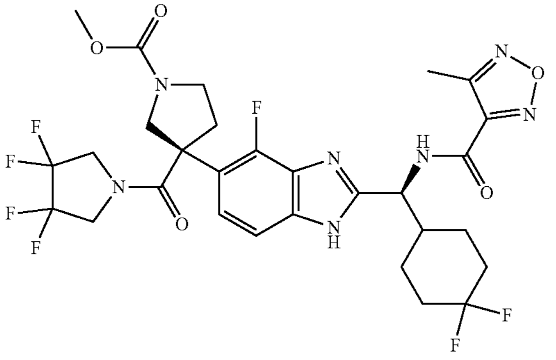

Methyl (3S)-3-(2-{(S)-(4,4-difluorocyclohexyl)[(4-methyl-1,2,5-oxadiazole-3-carbonyl)-amino]methyl}-4-fluoro-1H-benzimidazol-5-yl)-3-(3,3,4,4-tetrafluoropyrrolidine-1-carbonyl)pyrrolidine-1-carboxylate (Example 1)

Methyl (3R)-3-(2-{(S)-(4,4-difluorocyclohexyl)[(4-methyl-1,2,5-oxadiazole-3-carbonyl)-amino]methyl}-4-fluoro-1H-benzimidazol-5-yl)-3-(3,3,4,4-tetrafluoropyrrolidine-1-carbonyl)pyrrolidine-1-carboxylate (Example 2)

To a stirred solution of 3,3,4,4-tetrafluoropyrrolidine hydrochloride (53 mg, 0.30 mmol) and 2-chloro-1-methylpyridinium iodide (75 mg, 0.29 mmol) in DMA (1 mL) was added DIPEA (100 μL, 0.57 mmol), followed by dropwise addition of a solution of Intermediate 16 (100 mg, 0.15 mmol) in DMA (1 mL). The reaction mixture was stirred at r.t. for 25 minutes, then added dropwise to a further solution of 2-chloro-1-methylpyridinium iodide (37 mg, 0.14 mmol), 3,3,4,4-tetrafluoropyrrolidine hydrochloride (26 mg, 0.15 mmol) and DIPEA (50 μL, 0.28 mmol) in DMA (0.2 mL) at r.t and stirred for 30 minutes. The reaction mixture was diluted with saturated aqueous $NH_4Cl$ solution (5 mL) and extracted with EtOAc (3×5 mL). The combined organic layers were dried over $Na_2SO_4$, then filtered and concentrated in vacuo. The residue was purified by flash column chromatography, eluting with a gradient of 0-10% MeOH in DCM. The resulting material was purified by chiral preparative HPLC (Method 10) to afford the title compounds (Peak 1, 23 mg, 22%; and Peak 2, 22 mg, 21%) as off-white solids.

Peak 1 (arbitrarily assigned 3S at pyrrolidine): $\delta_H$ (500 MHz, DMSO-$d_6$) 12.79 (br s, 1H), 9.61 (br s, 1H), 7.33 (br s, 1H), 7.24-7.12 (m, 1H), 5.21-5.10 (m, 1H), 4.13-3.84 (m, 3H), 3.75-3.55 (m, 2H), 3.55-3.49 (m, 3H), 3.48-3.29 (m, 3H), 2.65-2.50 (m, 1H), 2.41 (s, 3H), 2.30-2.18 (m, 1H), 2.06-1.84 (m, 3H), 1.83-1.65 (m, 2H), 1.51 (d, J 12.2 Hz, 1H), 1.41-1.14 (m, 3H). LCMS (Method 4): $[M+H]^+$ m/z 690.3, RT 3.31 minutes.

Peak 2 (arbitrarily assigned 3R at pyrrolidine): $\delta_H$ (500 MHz, DMSO-$d_6$) 12.80 (br s, 1H), 9.59 (br s, 1H), 7.34 (br s, 1H), 7.23-7.13 (m, 1H), 5.15 (d, J 7.9 Hz, 1H), 4.16-3.87 (m, 3H), 3.77-3.55 (m, 2H), 3.53 (d, J 2.9 Hz, 3H), 3.48-3.31 (m, 3H), 2.65-2.50 (m, 1H), 2.41 (s, 3H), 2.29-2.19 (m, 1H), 2.06-1.84 (m, 3H), 1.83-1.66 (m, 2H), 1.56-1.46 (m, 1H), 1.41-1.14 (m, 3H). LCMS (Method 4): $[M+H]^+$ m/z 690.3, RT 3.31 minutes.

Example 3

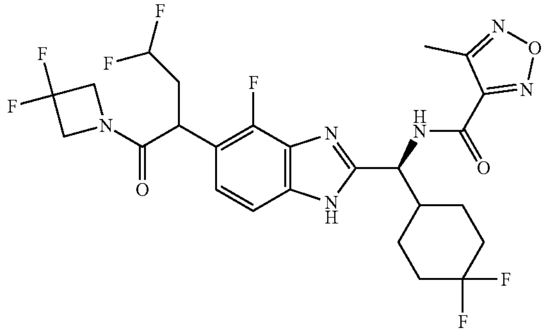

N—[(S)-{5-[1-(3,3-Difluoroazetidine-1-carbonyl)-3,3-difluoropropyl]-4-fluoro-1H-benzimidazol-2-yl}(4,4-difluorocyclohexyl)methyl]-4-methyl-1,2,5-oxadiazole-3-carboxamide To a stirred solution of 4-methyl-1,2,5-oxadiazole-3-carboxylic acid (31.0 mg, 0.24 mmol) and HATU (93.0 mg, 0.25 mmol) in DCM (4 mL) at r.t. was added DIPEA (140 μL, 0.80 mmol), followed by Intermediate 22 (100 mg, 0.21 mmol). The reaction mixture was stirred for 18 h, then concentrated in vacuo. The residue was purified by preparative HPLC (Method 5) to afford the title compound (60 mg, 49%) as an off-white solid. $\delta_H$ (500 MHz, $CD_3OD$) 7.57-7.28 (m, 1H), 7.28-7.18 (m, 1H), 5.87 (tt, J 56.5, 4.5 Hz, 1H), 5.26 (d, J 8.6 Hz, 1H), 4.77-4.65 (m, 1H), 4.44-4.28 (m, 2H), 4.28-4.17 (m, 1H), 4.14-3.99 (m, 1H), 2.80-2.65 (m, 1H), 2.53 (s, 3H), 2.40-2.19 (m, 2H), 2.18-1.99 (m, 3H), 1.95-1.72 (m, 2H), 1.65-1.35 (m, 3H). LCMS (Method 4): $[M+H]^+$ m/z 591.3, RT 3.32 minutes.

Examples 4 & 5

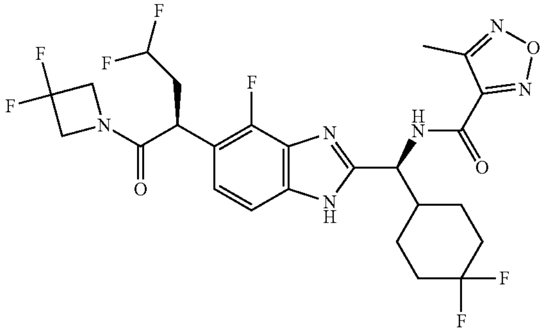

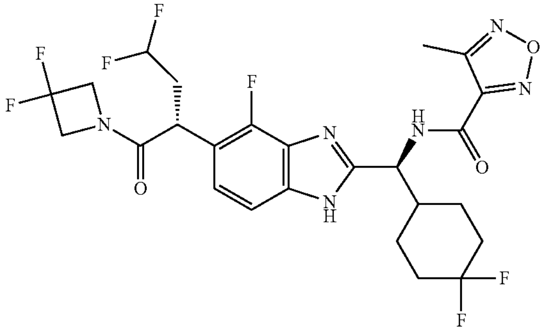 [SMILES: Cc1nonc1C(=O)N[C@H](c1nc2c(F)c(C(CC(F)F)C(=O)N3CC(F)(F)C3)ccc2[nH]1)C1CCC(F)(F)CC1]

N—[(S)-{5-[(1S)-1-(3,3-Difluoroazetidine-1-carbonyl)-3,3-difluoropropyl]-4-fluoro-1H-benzimidazol-2-yl}(4,4-difluorocyclohexyl)methyl]-4-methyl-1,2,5-oxadiazole-3-carboxamide (Example 4)

N—[(S)-{5-[(1R)-1-(3,3-Difluoroazetidine-1-carbonyl)-3,3-difluoropropyl]-4-fluoro-1H-benzimidazol-2-yl}(4,4-difluorocyclohexyl)methyl]-4-methyl-1,2,5-oxadiazole-3-carboxamide (Example 5)

Example 3 (55 mg) was subjected to chiral preparative HPLC (Method 11) to afford the title compounds (Peak 1, 9 mg, 16%; and Peak 2, 10 mg, 18%) as white solids.

Peak 1 (arbitrarily assigned S): $\delta_H$ (400 MHz, DMSO-$d_6$) 12.93 (s, 1H), 9.69 (s, 1H), 7.34 (d, J 8.4 Hz, 1H), 7.09 (d, J 7.6 Hz, 1H), 5.98 (tt, J 56.4, 4.5 Hz, 1H), 5.19 (d, J 8.0 Hz, 1H), 4.80 (q, J 11.9 Hz, 1H), 4.56-4.11 (m, 3H), 3.98 (q, J 11.8 Hz, 1H), 3.33 (br s, 3H), 2.67 (d, J 1.9 Hz, 1H), 2.42-2.13 (m, 3H), 2.13-1.90 (m, 2H), 1.78 (dd, J 31.8, 13.4 Hz, 1H), 1.58 (d, J 13.4 Hz, 1H), 1.50-1.15 (m, 2H), 1.03-0.73 (m, 1H). LCMS (Method 8): $[M+H]^+$ m/z 591.4, RT 1.89 minutes.

Peak 2 (arbitrarily assigned R): $\delta_H$ (400 MHz, DMSO-$d_6$) 13.05 (s, 1H), 9.73 (s, 1H), 7.33 (d, J 8.4 Hz, 1H), 7.08 (s, 1H), 6.34-5.49 (m, 1H), 5.19 (d, J 8.1 Hz, 1H), 4.80 (q, J 11.9 Hz, 1H), 4.46-4.10 (m, 3H), 3.97 (q, J 11.4 Hz, 1H), 3.33 (br s, 3H), 2.84-2.56 (m, 1H), 2.40-2.14 (m, 2H), 2.14-1.91 (m, 2H), 1.91-1.67 (m, 1H), 1.58 (d, J 13.4 Hz, 1H), 1.48-1.09 (m, 3H), 0.85 (d, J 7.7 Hz, 1H). LCMS (Method 8): $[M+H]^+$ m/z 591.2, RT 1.89 minutes.

Example 6

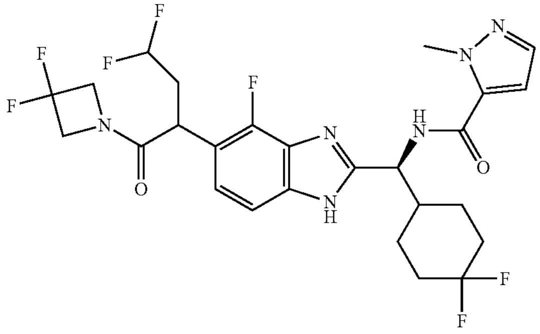 [SMILES: Cn1nccc1C(=O)N[C@H](c1nc2c(F)c(C(CC(F)F)C(=O)N3CC(F)(F)C3)ccc2[nH]1)C1CCC(F)(F)CC1]

N—[(S)-{5-[1-(3,3-Difluoroazetidine-1-carbonyl)-3,3-difluoropropyl]-4-fluoro-1H-benzimidazol-2-yl}(4,4-difluorocyclohexyl)methyl]-2-methylpyrazole-3-carboxamide To a stirred solution of Intermediate 22 (100 mg, 0.21 mmol), 2-methylpyrazole-3-carboxylic acid (31 mg, 0.25 mmol) and DIPEA (140 µL, 0.80 mmol) in DCM (4 mL) at r.t. was added HATU (99.0 mg, 0.260 mmol). The mixture was stirred at r.t. for 2 h, then concentrated in vacuo and purified by preparative HPLC, to afford the title compound (77 mg, 63%) as an off-white solid. $\delta_H$ (500 MHz, $CD_3OD$) 7.49 (d, J 2.1 Hz, 1H), 7.38 (br s, 1H), 7.28-7.18 (m, 1H), 6.95 (t, J 2.2 Hz, 1H), 5.87 (tt, J 56.6, 4.4 Hz, 1H), 5.21 (d, J 8.7 Hz, 1H), 4.77-4.65 (m, 1H), 4.45-4.28 (m, 2H), 4.28-4.18 (m, 1H), 4.09 (s, 3H), 4.08-4.01 (m, 1H), 2.80-2.65 (m, 1H), 2.36-2.20 (m, 2H), 2.18-1.99 (m, 3H), 1.94-1.70 (m, 2H), 1.64-1.35 (m, 3H). LCMS (Method 4): $[M+H]^+$ m/z 589.3, RT 2.94 minutes.

Example 7

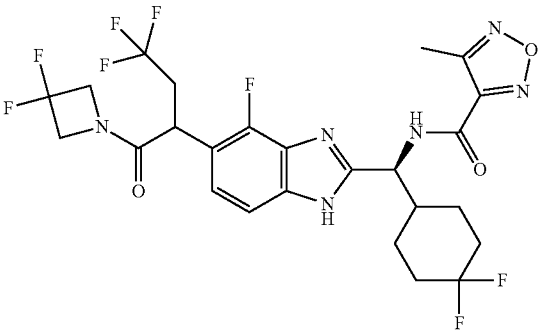 [SMILES: Cc1nonc1C(=O)N[C@H](c1nc2c(F)c(C(CC(F)(F)F)C(=O)N3CC(F)(F)C3)ccc2[nH]1)C1CCC(F)(F)CC1]

N—[(S)-{5-[1-(3,3-Difluoroazetidine-1-carbonyl)-3,3,3-trifluoropropyl]-4-fluoro-1H-benzimidazol-2-yl}(4,4-difluorocyclohexyl)methyl]-4-methyl-1,2,5-oxadiazole-3-carboxamide To a stirred suspension of 4-methyl-1,2,5-oxadiazole-3-carboxylic acid (16 mg, 0.12 mmol) and HATU (44 mg, 0.12 mmol) in DCM (0.5 mL) at r.t. was added DIPEA (44 µL, 0.25 mmol). The reaction mixture was stirred at r.t. for 15 minutes, then Intermediate 29 (50 mg, 0.09 mmol) in DCM (0.5 mL) was added. The reaction mixture was stirred for 18 h, then concentrated in vacuo. The residue was purified by preparative HPLC (Method 5) to afford the title compound (33 mg, 55%) as a white powder. $\delta_H$ (500 MHz, $CD_3OD$) 7.38 (dd, J 8.4, 3.2 Hz, 1H), 7.27-7.18 (m, 1H), 5.27 (d, J 8.7 Hz, 1H), 4.77-4.67 (m, 1H), 4.44-4.31 (m, 2H), 4.21 (q, J 11.9 Hz, 1H), 4.12-4.02 (m, 1H), 3.20-3.06 (m, 1H), 2.70-2.57 (m, 1H), 2.50 (s, 3H), 2.39-2.28 (m, 1H), 2.17-1.99 (m, 3H), 1.91-1.69 (m, 2H), 1.63-1.37 (m, 3H). LCMS (Method 4): $[M+H]^+$ m/z 609, RT 3.46 minutes.

Example 8

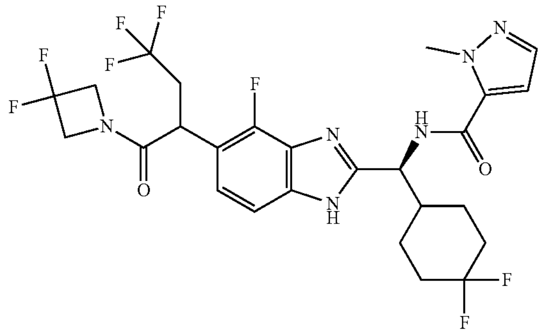 [SMILES: Cn1nccc1C(=O)N[C@H](c1nc2c(F)c(C(CC(F)(F)F)C(=O)N3CC(F)(F)C3)ccc2[nH]1)C1CCC(F)(F)CC1]

N—[(S)-{5-[1-(3,3-Difluoroazetidine-1-carbonyl)-3,3,3-trifluoropropyl]-4-fluoro-1H-benzimidazol-2-yl}(4,4-difluorocyclohexyl)methyl]-2-methylpyrazole-3-carboxamide To a stirred solution of 1-methyl-1H-pyrazole-5-carboxylic acid (16.0 mg, 0.13 mmol) and HATU (49.5 mg, 0.13 mmol) in DCM (1.1 mL) at r.t. was added DIPEA (49 μL, 0.28 mmol). The reaction mixture was stirred for 15 minutes, then Intermediate 29 (50 mg, 0.10 mmol) was added. The reaction mixture was stirred at r.t. for 18 h, then concentrated in vacuo. The residue was purified by preparative HPLC (Method 5) to afford the title compound (23 mg, 39%) as a white solid. $\delta_H$ (500 MHz, $CD_3OD$) 7.47 (d, J 2.2 Hz, 1H), 7.38 (d, J 8.4 Hz, 1H), 7.25-7.20 (m, 1H), 6.93 (t, J 2.3 Hz, 1H), 5.21 (d, J 8.7 Hz, 1H), 4.77-4.65 (m, 1H), 4.45-4.31 (m, 2H), 4.27-4.16 (m, 1H), 4.13-4.01 (m, 4H), 3.21-3.07 (m, 1H), 2.71-2.57 (m, 1H), 2.36-2.24 (m, 1H), 2.16-1.97 (m, 3H), 1.90-1.69 (m, 2H), 1.62-1.35 (m, 3H). LCMS (Method 4): $[M+H]^+$ m/z 607, RT 3.10 minutes.

Examples 9 & 10

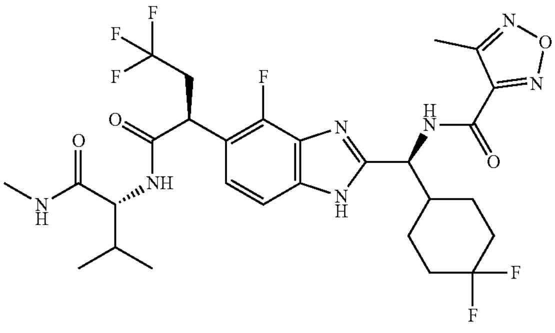

-continued

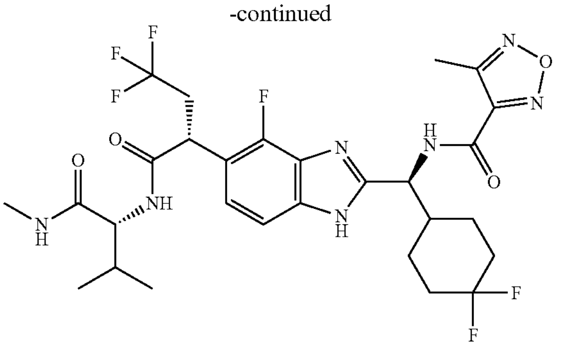

N—[(S)-(4,4-Difluorocyclohexyl){4-fluoro-5-[(1S)-3,3,3-trifluoro-1-{[(1R)-2-methyl-1-(methylcarbamoyl)propyl]carbamoyl}propyl]-1H-benzimidazol-2-yl}methyl]-4-methyl-1,2,5-oxadiazole-3-carboxamide (Example 9)

N—[(S)-(4,4-Difluorocyclohexyl){4-fluoro-5-[(1R)-3,3,3-trifluoro-1-{[(1R)-2-methyl-1-(methylcarbamoyl)propyl]carbamoyl}propyl]-1H-benzimidazol-2-yl}methyl]-4-methyl-1,2,5-oxadiazole-3-carboxamide (Example 10)

To a stirred suspension of Intermediate 37 (40 mg, 0.06 mmol) and HATU (29 mg, 0.08 mmol) in DCM (1 mL) at r.t. was added DIPEA (52 μL, 0.30 mmol). The reaction mixture was stirred at r.t. for 15 minutes, then methylamine (2M in THF, 39 μL, 0.08 mmol) was added. The reaction mixture was stirred for 64 h, then quenched with saturated aqueous $NaHCO_3$ solution (1 mL) and stirred at r.t. for 20 minutes. The phases were separated using a phase separator, and the organic phase was concentrated in vacuo. The residue was purified by acidic preparative HPLC (Method 5) to afford the title compounds (Peak 1, 7 mg, 18%; and Peak 2, 1.6 mg, 4%) as white solids.

Peak 1 (arbitrarily assigned as S): $\delta_H$ (500 MHz, DMSO-$d_6$) 12.70 (s, 1H), 9.67 (d, J 8.5 Hz, 1H), 8.13 (d, J 9.0 Hz, 1H), 7.92-7.79 (m, 1H), 7.46-7.20 (m, 2H), 5.25-5.14 (m, 1H), 4.40 (t, J 6.8 Hz, 1H), 4.10-4.01 (m, 1H), 3.19-3.02 (m, 1H), 2.72-2.61 (m, 1H), 2.59 (d, J 4.5 Hz, 3H), 2.48 (s, 3H), 2.36-2.23 (m, 1H), 2.14-1.93 (m, 3H), 1.90-1.70 (m, 3H), 1.61-1.50 (m, 1H), 1.47-1.35 (m, 1H), 1.36-1.22 (m, 1H), 0.70-0.53 (m, 6H). LCMS (Method 4): $[M+H]^+$ m/z 646, RT 3.13 minutes.

Peak 2 (arbitrarily assigned as R): $\delta_H$ (500 MHz, $CD_3OD$) 7.54-7.19 (m, 2H), 5.26 (d, J 8.5 Hz, 1H), 4.55-4.42 (m, 1H), 4.09 (d, J 8.1 Hz, 1H), 3.28-3.11 (m, 1H), 2.61 (s, 3H), 2.58-2.44 (m, 4H), 2.42-2.25 (m, 1H), 2.19-1.96 (m, 4H), 1.96-1.70 (m, 2H), 1.69-1.36 (m, 3H), 1.01-0.86 (m, 6H). LCMS (Method 4): $[M+H]^+$ m/z 646, RT 3.26 minutes.

Examples 11 & 12

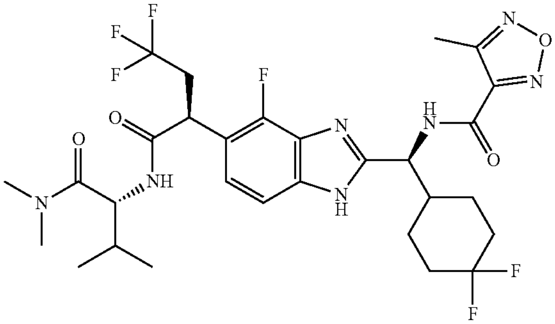

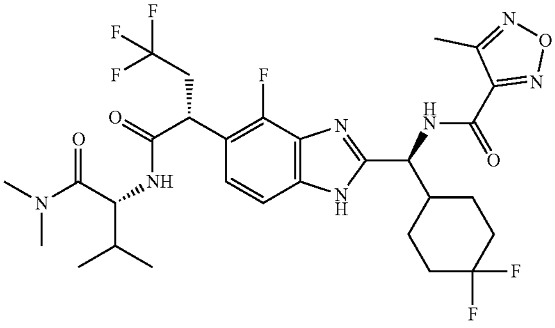

N—[(S)-(4,4-Difluorocyclohexyl){5-[(1S)-1-{[(1R)-1-(dimethylcarbamoyl)-2-methyl-propyl]carbamoyl}-3,3,3-trifluoropropyl]-4-fluoro-1H-benzimidazol-2-yl}methyl]-4-methyl-1,2,5-oxadiazole-3-carboxamide (Example 11)

N—[(S)-(4,4-Difluorocyclohexyl)-{5-[(1R)-1-{[(1R)-1-(dimethylcarbamoyl)-2-methyl-propyl]carbamoyl}-3,3,3-trifluoro-propyl]-4-fluoro-1H-benzimidazol-2-yl}methyl]-4-methyl-1,2,5-oxadiazole-3-carboxamide (Example 12)

To a stirred suspension of Intermediate 37 (40 mg, 0.06 mmol) and HATU (29 mg, 0.08 mmol) in DCM (1 mL) at r.t. was added DIPEA (52 μL, 0.30 mmol). The reaction mixture was stirred at r.t. for 15 minutes, then dimethylamine (2M in THF, 39 μL, 0.08 mmol) was added. The reaction mixture was stirred for 64 h, then quenched with saturated aqueous $NaHCO_3$ solution (1 mL) and stirred at r.t. for 20 minutes. The phases were separated using a phase separator, and the organic phase was concentrated in vacuo. The residue was purified by acidic preparative HPLC (Method 5) to afford the title compounds (Peak 1, 7.8 mg, 20%; and Peak 2, 9 mg, 22%) as white solids.

Peak 1 (arbitrarily assigned S): $\delta_H$ (500 MHz, DMSO-$d_6$) 12.77 (s, 1H), 9.69 (s, 1H), 8.43 (d, J 8.8 Hz, 1H), 7.52-7.09 (m, 2H), 5.24-5.10 (m, 1H), 4.56 (t, J 8.4 Hz, 1H), 4.43 (dd, J 8.7, 4.9 Hz, 1H), 3.18-3.02 (m, 1H), 2.97 (s, 3H), 2.72 (s, 3H), 2.64-2.53 (m, 1H), 2.48 (s, 3H), 2.36-2.21 (m, 1H), 2.15-1.91 (m, 4H), 1.90-1.66 (m, 2H), 1.62-1.48 (m, 1H), 1.47-1.20 (m, 2H), 0.87 (d, J 6.7 Hz, 3H), 0.83 (d, J 6.7 Hz, 3H). LCMS (Method 4): $[M+H]^+$ m/z 646, RT 3.46 minutes.

Peak 2 (arbitrarily assigned as R): $\delta_H$ (500 MHz, DMSO-$d_6$) 12.72 (s, 1H), 9.78-9.64 (m, 1H), 8.39 (d, J 8.3 Hz, 1H), 7.47-7.22 (m, 2H), 5.25-5.15 (m, 1H), 4.49 (t, J 8.5 Hz, 1H), 4.43-4.31 (m, 1H), 3.20-3.01 (m, 4H), 2.84 (s, 3H), 2.73-2.57 (m, 1H), 2.48 (s, 3H), 2.36-2.25 (m, 1H), 2.13-1.92 (m, 3H), 1.92-1.71 (m, 3H), 1.61-1.51 (m, 1H), 1.47-1.35 (m, 1H), 1.36-1.21 (m, 1H), 0.70 (d, J 6.7 Hz, 3H), 0.64-0.50 (m, 3H). LCMS (Method 4): $[M+H]^+$ m/z 660, RT 3.32 minutes.

Example 13

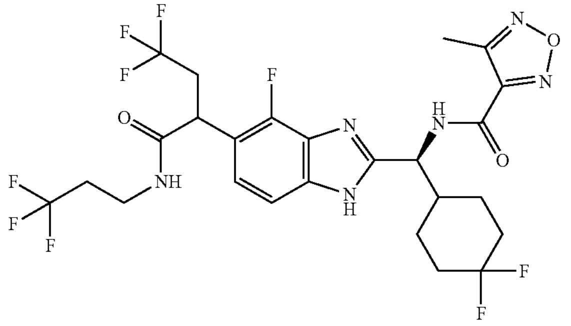 [SMILES: Cc1nonc1C(=O)N[C@H](c1nc2c(F)c(C(CC(F)(F)F)C(=O)NCCC(F)(F)F)ccc2[nH]1)C1CCC(F)(F)CC1]

N—[(S)-(4,4-Difluorocyclohexyl){4-fluoro-5-[3,3,3-trifluoro-1-(3,3,3-trifluoropropyl-carbamoyl)propyl]-1H-benzimidazol-2-yl}methyl]-4-methyl-1,2,5-oxadiazole-3-carboxamide To a stirred solution of Intermediate 35 (50 mg, 0.07 mmol) and HATU (36 mg, 0.10 mmol) in DCM (1 mL) at r.t. was added DIPEA (64 μL, 0.37 mmol). The reaction mixture was stirred for 15 minutes, then 3,3,3-trifluoropropan-1-amine (11 mg, 0.10 mmol) was added. The reaction mixture was stirred for 64 h, then concentrated in vacuo. The residue was purified by acidic preparative HPLC (Method 5) to afford the title compound (23 mg, 50%) as a cream solid. $\delta_H$ (500 MHz, DMSO-$d_6$) 12.74 (s, 1H), 9.69 (d, J 8.4 Hz, 1H), 8.36 (t, J 5.1 Hz, 1H), 7.30 (d, J 8.4 Hz, 1H), 7.25-7.12 (m, 1H), 5.18 (t, J 8.3 Hz, 1H), 4.18 (t, J 6.8 Hz, 1H), 3.31-3.26 (m, 1H), 3.26-3.18 (m, 1H), 3.17-3.02 (m, 1H), 2.79-2.56 (m, 1H), 2.48 (s, 3H), 2.42-2.24 (m, 3H), 2.13-1.93 (m, 3H), 1.91-1.70 (m, 2H), 1.61-1.50 (m, 1H), 1.47-1.35 (m, 1H), 1.35-1.22 (m, 1H). LCMS (Method 4): $[M+H]^+$ m/z 629, RT 3.52 minutes.

Example 14

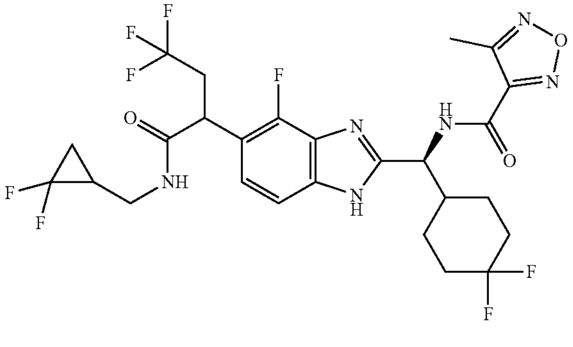 [SMILES: Cc1nonc1C(=O)N[C@H](c1nc2c(F)c(C(CC(F)(F)F)C(=O)NCC3CC3(F)F)ccc2[nH]1)C1CCC(F)(F)CC1]

N—[(S)-(4,4-Difluorocyclohexyl)(5-{1-[(2,2-difluorocyclopropyl)methylcarbamoyl]-3,3,3-trifluoropropyl}-4-fluoro-1H-benzimidazol-2-yl)methyl]-4-methyl-1,2,5-oxadiazole-3-carboxamide To a stirred solution of Intermediate 35 (150 mg, 0.22 mmol) and HATU (109 mg, 0.22 mmol) in DCM (3.5 mL) at r.t. was added DIPEA (192 µL, 1.10 mmol). The reaction mixture was stirred for 15 minutes, then (2,2-difluorocyclopropyl)methanamine (31 mg, 0.29 mmol) was added. The reaction mixture was stirred for 64 h, then diluted with DCM (15 mL), quenched with saturated aqueous $NaHCO_3$ solution (20 mL) and stirred at r.t. for 10 minutes. The phases were separated, and the aqueous phase was extracted with DCM (2×15 mL). The combined organic phases were dried over $Na_2SO_4$, then filtered and concentrated in vacuo. The residue was purified by flash column chromatography, eluting with a gradient of 0-100% EtOAc in heptanes, to afford the title compound (85 mg, 58%) as a pale pink solid. $\delta_H$ (400 MHz, DMSO-$d_6$) 13.16-12.57 (m, 1H), 9.85-9.42 (m, 1H), 8.51-8.36 (m, 1H), 7.50-7.26 (m, 1H), 7.27-7.04 (m, 1H), 5.18 (t, J 7.7 Hz, 1H), 4.23 (t, J 6.5 Hz, 1H), 3.21-2.97 (m, 3H), 2.66-2.55 (m, 1H), 2.48 (s, 3H), 2.37-2.19 (m, 1H), 2.15-1.92 (m, 3H), 1.90-1.65 (m, 3H), 1.61-1.03 (m, 5H). LCMS (Method 4): $[M+H]^+$ m/z 623, RT 3.49 minutes.

Example 15

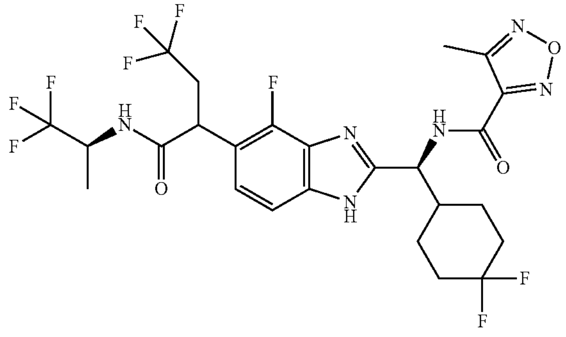 [SMILES: Cc1nonc1C(=O)N[C@H](c1nc2c(F)c(C(CC(F)(F)F)C(=O)N[C@@H](C)C(F)(F)F)ccc2[nH]1)C1CCC(F)(F)CC1]

N—{(S)-(4,4-Difluorocyclohexyl)[4-fluoro-5-(3,3,3-trifluoro-1-{[(1S)-2,2,2-trifluoro-1-methylethyl]carbamoyl}propyl)-1H-benzimidazol-2-yl]methyl}-4-methyl-1,2,5-oxadiazole-3-carboxamide To a stirred solution of Intermediate 35 (50 mg, 0.07 mmol) and HATU (36 mg, 0.10 mmol) in DCM (1 mL) at r.t. was added DIPEA (64 µL, 0.38 mmol). The reaction mixture was stirred for 15 minutes, then (2S)-1,1,1-trifluoropropan-2-amine (11 mg, 0.10 mmol) was added. The reaction mixture was stirred for 64 h, then concentrated in vacuo. The residue was purified by acidic preparative HPLC (Method 5) to afford the title compound (4.7 mg, 10%). $\delta_H$ (500 MHz, DMSO-$d_6$) 13.46-12.31 (m, 1H), 9.74-9.54 (m, 1H), 9.00-8.66 (m, 1H), 7.48-7.28 (m, 1H), 7.27-7.12 (m, 1H), 5.18 (q, J 7.8 Hz, 1H), 4.68-4.51 (m, 1H), 4.37-4.24 (m, 1H), 3.21-3.02 (m, 1H), 2.72-2.57 (m, 1H), 2.48 (s, 3H), 2.36-2.24 (m, 1H), 2.13-1.93 (m, 3H), 1.91-1.71 (m, 2H), 1.61-1.50 (m, 1H), 1.47-1.36 (m, 1H), 1.35-1.25 (m, 1H), 1.25-1.09 (m, 3H). LCMS (Method 4): $[M+H]^+$ m/z 629, RT 3.63 minutes.

Example 16

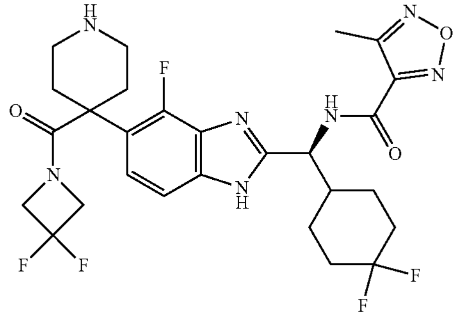 [SMILES: Cc1nonc1C(=O)N[C@H](c1nc2c(F)c(C3(C(=O)N4CC(F)(F)C4)CCNCC3)ccc2[nH]1)C1CCC(F)(F)CC1]

N—[(S)-{5-[4-(3,3-Difluoroazetidine-1-carbonyl)piperidin-4-yl]-4-fluoro-1H-benzimidazol-2-yl}(4,4-difluorocyclohexyl)methyl]-4-methyl-1,2,5-oxadiazole-3-carboxamide Intermediate 46 (0.23 g, 0.31 mmol) was stirred in DCM (5 mL) and TFA (0.46 mL, 6.18 mmol) at r.t. for 40 minutes. The reaction mixture was quenched with saturated aqueous $NaHCO_3$ solution (20 mL) and extracted with DCM:isopropanol (4:1, 2×20 mL). The combined organic phases were dried over $Na_2SO_4$, then filtered and concentrated in vacuo, to afford the title compound (0.21 g, 100%) as an off-white solid. $\delta_H$ (500 MHz, DMSO-$d_6$) 9.66 (s, 1H), 7.39 (d, J 8.2 Hz, 1H), 7.33-7.09 (m, 1H), 5.21 (d, J 6.0 Hz, 1H), 4.79-4.31 (m, 1H), 4.31-4.05 (m, 2H), 3.84-3.58 (m, 2H), 3.03-2.92 (m, 2H), 2.91-2.78 (m, 2H), 2.48 (s, 3H), 2.40-2.20 (m, 3H), 2.18-1.91 (m, 5H), 1.90-1.73 (m, 2H), 1.63-1.54 (m, 1H), 1.48-1.25 (m, 2H). LCMS (Method 1): $[M+H]^+$ m/z 596, RT 1.58 minutes.

Example 17

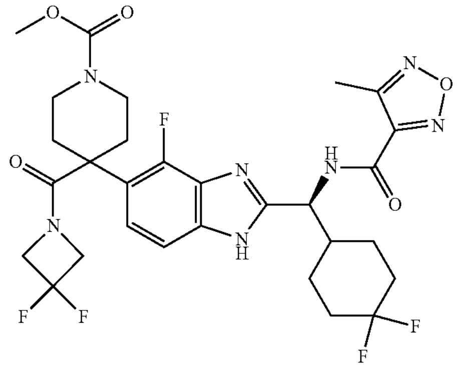 [SMILES: COC(=O)N1CCC(C(=O)N2CC(F)(F)C2)(c2ccc3[nH]c([C@@H](NC(=O)c4nonc4C)C4CCC(F)(F)CC4)nc3c2F)CC1]

Methyl 4-(3,3-difluoroazetidine-1-carbonyl)-4-(2-{(S)-(4,4-difluorocyclohexyl)[(4-methyl-1,2,5-oxadiazole-3-carbonyl)amino]methyl}-4-fluoro-1H-benzimidazol-5-yl)-piperidine-1-carboxylate Methyl chloroformate (6.2 µL, 0.08 mmol) in DCM (1 mL) was added to an ice-cooled solution of Example 16 (50 mg, 0.08 mmol) and DIPEA (28 µL, 0.16 mmol) in DCM (1 mL). The reaction mixture was stirred at 0° C. for 20 minutes, then allowed to warm to r.t. and stirred for 30 minutes. The reaction mixture was quenched with water (7 mL) and stirred vigorously for 15 minutes. Saturated aqueous $NH_4Cl$ solution (7 mL) was added, and the mixture was stirred vigorously for a further 15 minutes. The phases were separated, and the combined organic layers were concentrated in vacuo. The residue was purified by acidic preparative HPLC (Method 5) to afford the title compound (25 mg, 48%) as a white solid. $\delta_H$ (500 MHz, DMSO-$d_6$) 12.86 (br s, 1H), 9.69 (br s, 1H), 7.36 (br s, 1H), 7.26-7.14 (m, 1H), 5.21 (d, J 8.1 Hz, 1H), 4.69-4.03 (m, 2H), 3.95-3.62 (m, 4H), 3.59 (s, 3H), 3.33 (m, 2H, obs.), 2.47 (s, 3H), 2.35-2.22 (m, 3H), 2.13-1.88 (m, 5H), 1.87-1.72 (m, 2H), 1.63-1.52 (m, 1H), 1.48-1.25 (m, 2H). LCMS (Method 4): $[M+H]^+$ m/z 654, RT 3.10 minutes.

Example 18

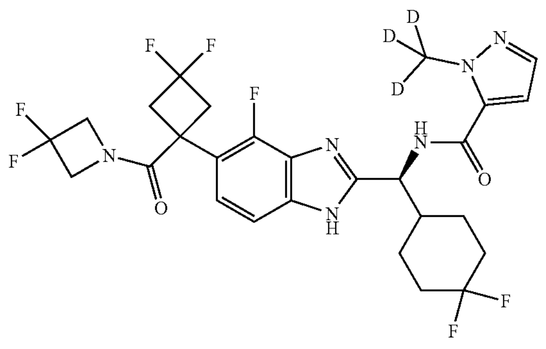 [SMILES: [2H]C([2H])([2H])n1nccc1C(=O)N[C@H](c1nc2c(F)c(C3(C(=O)N4CC(F)(F)C4)CC(F)(F)C3)ccc2[nH]1)C1CCC(F)(F)CC1]

N—[(S)-{5-[1-(3,3-Difluoroazetidine-1-carbonyl)-3,3-difluorocyclobutyl]-4-fluoro-1H-benzimidazol-2-yl}(4,4-difluorocyclohexyl)methyl]-2-(trideuteriomethyl)pyrazole-3-carboxamide HATU (51 mg, 0.13 mmol) was added to a stirred solution of DIPEA (117 μL, 0.67 mmol), Intermediate 53 (64 mg, 0.11 mmol) and 2-(trideuteriomethyl)pyrazole-3-carboxylic acid (16 mg, 0.12 mmol) in DCM (2 mL). The reaction mixture was stirred at r.t. for 16 h, then washed with water (5 mL). The aqueous layer was extracted with DCM (5 mL). The organic layers were combined, dried over $Na_2SO_4$ and concentrated in vacuo. The residue was purified by flash column chromatography, eluting with a gradient of EtOAc in heptanes. To the resulting colourless glass was added diethyl ether (1 mL), followed by EtOAc (2 mL) and heptanes (8 mL), until a white precipitate was observed. The mixture was filtered and washed with heptanes. The solid was further purified by reverse-phase column chromatography, eluting with a gradient of acetonitrile in water (+0.1% formic acid), to afford the title compound (21 mg, 31%) as a white powder. $\delta_H$ (400 MHz, $CD_3OD$) 7.48 (d, J 2.2 Hz, 1H), 7.46-7.35 (m, 2H), 6.94 (d, J 2.2 Hz, 1H), 5.21 (d, J 8.7 Hz, 1H), 4.30 (s, 2H), 3.93 (s, 2H), 3.62-3.46 (m, 2H), 3.23-3.08 (m, 2H), 2.38-2.23 (m, 1H), 2.19-1.97 (m, 3H), 1.94-1.68 (m, 2H), 1.62-1.34 (m, 3H). LCMS (Method 4): $[M+H]^+$ m/z 604, RT 2.98 minutes.

Example 19

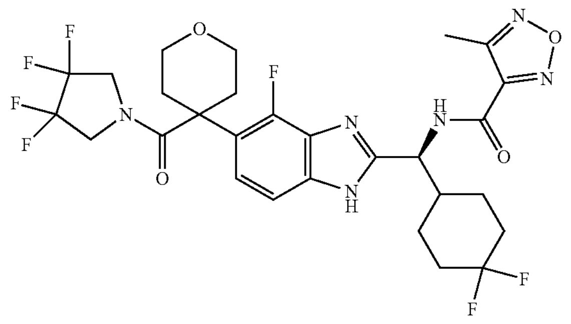 [SMILES: Cc1nonc1C(=O)N[C@H](c1nc2c(F)c(C3(C(=O)N4CC(F)(F)C(F)(F)C4)CCOCC3)ccc2[nH]1)C1CCC(F)(F)CC1]

N—[(S)-(4,4-Difluorocyclohexyl){4-fluoro-5-[4-(3,3,4,4-tetrafluoropyrrolidine-1-carbonyl)tetrahydropyran-4-yl]-1H-benzimidazol-2-yl}methyl]-4-methyl-1,2,5-oxadiazole-3-carboxamide To a stirred solution of 3,3,4,4-tetrafluoropyrrolidine hydrochloride (28.0 mg, 0.16 mmol) and 2-chloro-1-methylpyridinium iodide (40.0 mg, 0.16 mmol) in DMA (0.3 mL) was added DIPEA (52 μL, 0.30 mmol), followed by a solution of Intermediate 61 (50.0 mg, 0.08 mmol) in DMA (0.3 mL). The reaction mixture was stirred at r.t. for 15 minutes, then concentrated in vacuo. The residue was purified by acidic preparative HPLC (Method 5) to afford the title compound (21 mg, 41%) as an off-white solid. $\delta_H$ (400 MHz, $CD_3OD$) 7.65-7.34 (m, 2H), 5.28 (d, J 8.4 Hz, 1H), 4.20-3.78 (m, 6H), 3.65-3.34 (m, 2H), 2.53 (s, 3H), 2.44-2.28 (m, 3H), 2.26-2.01 (m, 5H), 1.93-1.73 (m, 2H), 1.64-1.39 (m, 3H). LCMS (Method 4): $[M+H]^+$ m/z 647.14, RT 3.33 minutes.

Example 20

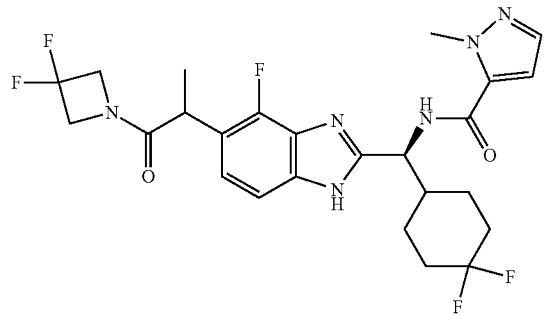 [SMILES: CC(C(=O)N1CC(F)(F)C1)c1ccc2[nH]c([C@@H](NC(=O)c3ccnn3C)C3CCC(F)(F)CC3)nc2c1F]

N—[(S)-{5-[2-(3,3-Difluoroazetidin-1-yl)-1-methyl-2-oxoethyl]-4-fluoro-1H-benzimidazol-2-yl}(4,4-difluorocyclohexyl)methyl]-2-methylpyrazole-3-carboxamide To a solution of Intermediate 66 (1.70 g, 3.52 mmol) and 2-methylpyrazole-3-carboxylic acid (532 mg, 4.22 mmol) in DCM (50 mL) was added DIPEA (2.5 mL, 14.1 mmol), followed by HATU (1.6 g, 4.22 mmol). The reaction mixture was stirred at r.t. for 1 h, diluted with DCM (50 mL) and washed with water (4×50 mL) and brine (30 mL), then dried over $Na_2SO_4$ and concentrated in vacuo. The residue was purified by flash column chromatography, eluting with a gradient of 0-100% EtOAc in DCM, followed by trituration with cold diethyl ether, to afford the title compound (1.4 g, 70%) as a white solid. $\delta_H$ (500 MHz, DMSO-$d_6$) 13.01-12.67 (m, 1H), 9.02-8.85 (m, 1H), 7.50-7.45 (m, 1H), 7.43-7.23 (m, 1H), 7.13-7.02 (m, 2H), 5.20-5.07 (m, 1H), 4.86-4.68 (m, 1H), 4.38-4.26 (m, 1H), 4.26-4.15 (m, 1H), 4.15-4.08 (m, 1H), 4.08-3.91 (m, 4H), 2.35-2.22 (m, 1H), 2.12-1.92 (m, 3H), 1.89-1.68 (m, 2H), 1.60-1.47 (m, 1H), 1.45-1.20 (m, 5H). LCMS (Method 4): $[M+H]^+$ m/z 539.3, RT 2.73 minutes.

Examples 21 & 22

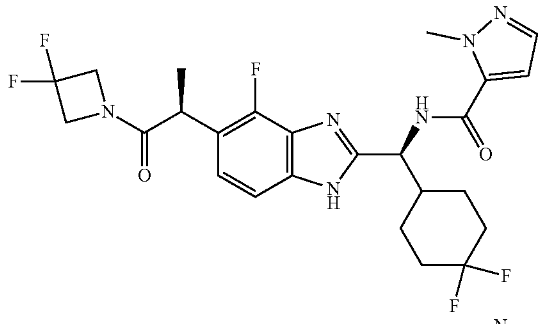

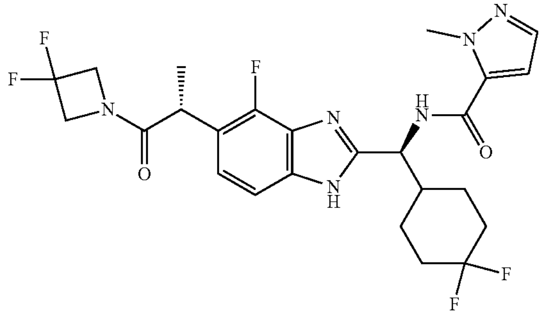

N—[(S)-{5-[(1S)-2-(3,3-Difluoroazetidin-1-yl)-1-methyl-2-oxoethyl]-4-fluoro-1H-benzimidazol-2-yl}(4,4-difluorocyclohexyl)methyl]-2-methylpyrazole-3-carboxamide (Example 21)

N—[(S)-{5-[(1R)-2-(3,3-Difluoroazetidin-1-yl)-1-methyl-2-oxoethyl]-4-fluoro-1H-benzimidazol-2-yl}(4,4-difluorocyclohexyl)methyl]-2-methylpyrazole-3-carboxamide (Example 22)

Example 20 (1.4 g) was subject to chiral separation (Method 12) to afford the title compounds (Peak 1, 423 mg, 30%; and Peak 2, 427 mg, 30%) as white solids.

Peak 1 (arbitrarily assigned S): $\delta_H$ (400 MHz, DMSO-$d_6$) 12.82 (s, 1H), 8.97 (d, J 8.5 Hz, 1H), 7.48 (d, J 2.1 Hz, 1H), 7.31 (d, J 8.3 Hz, 1H), 7.18-6.82 (m, 2H), 5.15 (t, J 8.6 Hz, 1H), 4.78 (q, J 12.1 Hz, 1H), 4.43-4.11 (m, 2H), 4.03 (s, 3H), 3.33 (s, 2H), 2.51 (p, J 1.9 Hz, 3H), 2.30 (q, J 10.5, 10.1 Hz, 1H), 2.19-1.96 (m, 2H), 1.54 (d, J 13.3 Hz, 1H), 1.46-1.04 (m, 5H). LCMS (Method 8): $[M+H]^+$ m/z 539.2, RT 1.61 minutes.

Peak 2 (arbitrarily assigned R): $\delta_H$ (400 MHz, DMSO-$d_6$) 12.82 (s, 1H), 8.97 (d, J 8.5 Hz, 1H), 7.47 (d, J 2.1 Hz, 1H), 7.31 (d, J 8.4 Hz, 1H), 7.18-6.80 (m, 2H), 5.15 (t, J 8.6 Hz, 1H), 4.79 (d, J 12.1 Hz, 1H), 4.49-3.77 (m, 6H), 3.33 (s, 2H), 2.51 (s, 1H), 2.30 (q, J 10.9, 10.5 Hz, 1H), 2.15-1.91 (m, 2H), 1.91-1.66 (m, 1H), 1.66-1.46 (m, 1H), 1.46-0.97 (m, 5H). LCMS (Method 8): $[M+H]^+$ m/z 539.2, RT 1.60 minutes.

Example 23

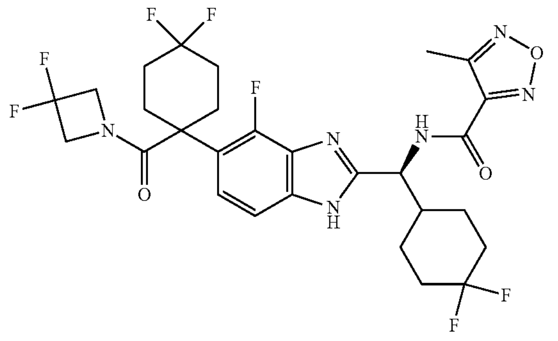 [SMILES: Cc1nonc1C(=O)N[C@H](c1nc2c(F)c(C3(C(=O)N4CC(F)(F)C4)CCC(F)(F)CC3)ccc2[nH]1)C1CCC(F)(F)CC1]

N—[(S)-{5-[1-(3,3-Difluoroazetidine-1-carbonyl)-4,4-difluorocyclohexyl]-4-fluoro-1H-benzimidazol-2-yl}(4,4-difluorocyclohexyl)methyl]-4-methyl-1,2,5-oxadiazole-3-carboxamide To a solution of 4-methyl-1,2,5-oxadiazole-3-carboxylic acid (8.1 mg, 0.06 mmol) in DCM (0.5 mL) were added DIPEA (21 μL, 0.23 mmol) and HATU (25 mg, 0.06 mmol). The mixture was stirred at r.t. for 10 minutes, then Intermediate 73 (30 mg, 0.06 mmol) in DCM (0.5 mL) was added. The mixture was stirred at r.t. for 1 h, then diluted with DCM (10 mL), washed with water (2×5 mL) and passed through a phase separator. The organic fractions were combined and concentrated in vacuo. The residue was purified by reverse-phase preparative HPLC (Method 13) to afford the title compound (3.5 mg, 9.5%) as an off white solid. $\delta_H$ (400 MHz, DMSO-$d_6$) 12.80 (s, 1H), 9.59 (s, 1H), 7.35 (s, 1H), 7.19 (s, 1H), 5.20 (d, J 8.0 Hz, 1H), 4.27 (s, 2H), 3.59 (d, J 63.0 Hz, 2H), 2.68 (p, J 1.8 Hz, 1H), 2.46-2.36 (m, 1H), 2.36-2.13 (m, 2H), 2.13-1.90 (m, 7H), 1.81 (dt, J 29.9, 13.2 Hz, 2H), 1.60 (d, J 13.3 Hz, 2H), 1.53-1.19 (m, 4H), 0.95 (dd, J 6.6, 1.6 Hz, 1H). LCMS (Method 8): $[M+H]^+$ m/z 631.4, RT 2.00 minutes.

Example 24

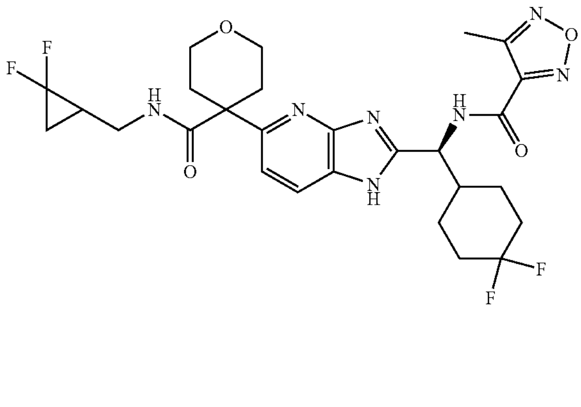 [SMILES: Cc1nonc1C(=O)N[C@H](c1nc2nc(C3(C(=O)NCC4CC4(F)F)CCOCC3)ccc2[nH]1)C1CCC(F)(F)CC1]

N—[(S)-(4,4-Difluorocyclohexyl)(5-{4-[(2,2-difluorocyclopropyl)methylcarbamoyl]-tetrahydropyran-4-yl}-1H-imidazo[4,5-b]pyridin-2-yl)methyl]-4-methyl-1,2,5-oxadiazole-3-carboxamide To a stirred solution of Intermediate 85 (102 mg, 0.19 mmol) and 4-methyl-1,2,5-oxadiazole-3-carboxylic acid (29 mg, 0.23 mmol) in DCM (3 mL) was added DIPEA (66 μL, 0.38 mmol), followed by HATU (87 mg, 0.23 mmol). The reaction mixture was stirred at r.t. for 1.5 h, washed with water (2×2 mL) and brine (1 mL), then concentrated under $N_2$ stream. The residue was purified by preparative HPLC (Method 14) to afford the title compound (26 mg, 23%) as a white solid. $\delta_H$ (400 MHz, DMSO-$d_6$) 13.25-12.38 (m, 1H), 9.56 (br s, 1H), 7.93 (br s, 1H), 7.85-7.74 (m, 1H), 7.22 (d, J 8.4 Hz, 1H), 5.29-5.11 (m, 1H), 3.78-3.61 (m, 2H), 3.61-3.48 (m, 2H), 3.23-3.14 (m, 1H), 3.14-3.02 (m, 1H), 2.48 (s, 3H), 2.41-2.34 (m, 2H), 2.34-2.25 (m, 1H), 2.19-2.10 (m, 2H), 2.10-1.91 (m, 3H), 1.91-1.72 (m, 3H), 1.66-1.55 (m, 1H), 1.50-1.37 (m, 2H), 1.37-1.26 (m, 1H), 1.19-1.10 (m, 1H). LCMS (Method 4): $[M+H]^+$ m/z 594.3, RT 2.93 minutes.

Examples 25 & 26

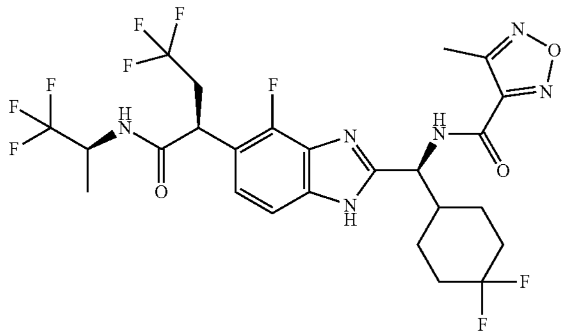

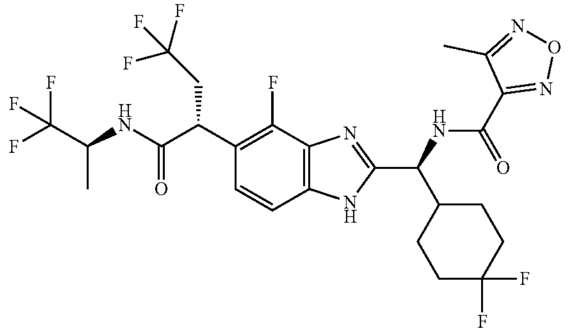

N—[(S)-(4,4-Difluorocyclohexyl){4-fluoro-5-[(1S)-3,3,3-trifluoro-1-{[(1S)-2,2,2-trifluoro-1-methylethyl]carbamoyl}propyl]-1H-benzimidazol-2-yl}methyl]-4-methyl-1,2,5-oxadiazole-3-carboxamide (Example 25)

N—[(S)-(4,4-Difluorocyclohexyl){4-fluoro-5-[(1R)-3,3,3-trifluoro-1-{[(1S)-2,2,2-trifluoro-1-methylethyl]carbamoyl}propyl]-1H-benzimidazol-2-yl}methyl]-4-methyl-1,2,5-oxadiazole-3-carboxamide (Example 26)

Example 15 (110 mg) was subjected to chiral preparative HPLC (Method 15) to afford the title compounds (Peak 1, 31 mg; and Peak 2, 33 mg) as white solids.

Peak 1 (arbitrarily assigned S): $\delta_H$ (400 MHz, DMSO-$d_6$) 12.80 (br s, 1H), 9.63 (br s, 1H), 8.78 (d, J 8.8 Hz, 1H), 7.29 (d, J 8.0 Hz, 1H), 7.14 (t, J 7.4 Hz, 1H), 5.18 (d, J 8.1 Hz, 1H), 4.62 (dt, J 15.5, 7.7 Hz, 1H), 4.31 (dd, J 8.4, 5.4 Hz, 1H), 3.12 (m, 1H), 2.74-2.56 (m, 1H), 2.48 (s, 3H), 2.34-2.25 (m, 1H), 2.09-1.90 (m, 3H), 1.90-1.68 (m, 2H), 1.56 (d, J 13.4 Hz, 1H), 1.46-1.27 (m, 2H), 1.23 (d, J 7.0 Hz, 3H). LCMS (Method 8): $[M+H]^+$ m/z 629.4, RT 2.06 minutes. Chiral LC (Method 16): RT 3.52 minutes, 100%.

Peak 2 (arbitrarily assigned R): $\delta_H$ (400 MHz, DMSO-$d_6$) 9.67 (br s, 1H), 8.88 (d, J 8.9 Hz, 1H), 7.31 (br s, 1H), 7.23 (m, 1H), 5.18 (t, J 7.7 Hz, 1H), 4.57 (dq, J 15.6, 7.5 Hz, 1H), 4.28 (dd, J 9.1, 4.7 Hz, 1H), 3.12 (dt, J 15.0, 11.1 Hz, 1H), 2.68-2.59 (m, 1H), 2.48 (s, 3H), 2.36-2.23 (m, 1H), 2.09-1.96 (m, 3H), 1.88-1.70 (m, 2H), 1.55 (d, J 13.5 Hz, 1H), 1.47-1.18 (m, 2H), 1.11 (d, J 7.1 Hz, 3H). LCMS (Method 8): $[M+H]^+$ m/z 629.4, RT 2.08 minutes. Chiral LC (Method 16): RT 4.22 minutes, 100%.

Example 27

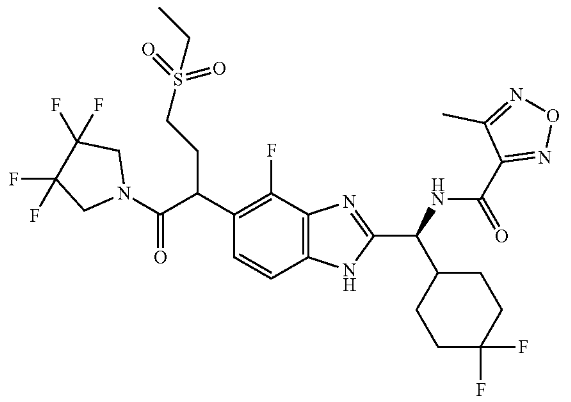 [SMILES: CCS(=O)(=O)CCC(C(=O)N1CC(F)(F)C(F)(F)C1)c1ccc2[nH]c([C@@H](NC(=O)c3nonc3C)C3CCC(F)(F)CC3)nc2c1F]

N—[(S)-(4,4-Difluorocyclohexyl){5-[3-(ethylsulfonyl)-1-(3,3,4,4-tetrafluoropyrrolidine-1-carbonyl)propyl]-4-fluoro-1H-benzimidazol-2-yl}methyl]-4-methyl-1,2,5-oxadiazole-3-carboxamide 4-Methyl-1,2,5-oxadiazole-3-carboxylic acid (40 mg, 0.30 mmol) and HATU (117 mg, 0.30 mmol) were dissolved in DCM (3 mL) and DIPEA (0.10 mL, 0.58 mmol) was added, followed by Intermediate 91 (167 mg, 0.28 mmol) in DCM (4 mL). The mixture was stirred at r.t. overnight, then washed with saturated aqueous $NH_4Cl$ solution (10 mL) and concentrated in vacuo. The residue was purified by chromatography (silica, DCM, 0-65% EtOAc gradient) to give the title compound (187 mg, 94%) as an off-white solid. $\delta_H$ (300 MHz, DMSO-$d_6$) 13.05 (d, J 4.4 Hz, 0.25H), 12.80 (s, 0.75H), 9.68 (d, J 8.4 Hz, 0.75H), 9.59 (d, J 8.6 Hz, 0.25H), 7.47 (d, J 8.4 Hz, 0.25H), 7.36 (d, J 8.4 Hz, 0.75H), 7.09 (ddd, J 8.6, 6.4, 2.8 Hz, 1H), 5.21 (q, J 8.3 Hz, 1H), 4.56 (q, J 13.5 Hz, 1H), 4.36 (q, J 6.1, 5.1 Hz, 1H), 4.25-3.86 (m, 2H), 3.86-3.50 (m, 1H), 3.22-2.81 (m, 4H), 2.50 (s, 3H), 2.32 (q, J 11.1, 10.5 Hz, 2H), 2.15-1.00 (m, 13H). LCMS (Method 9): $[M+H]^+$ m/z 697, RT 2.11 minutes.

Examples 28 & 29

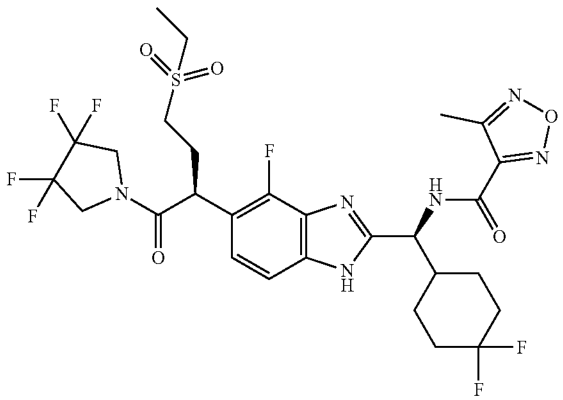

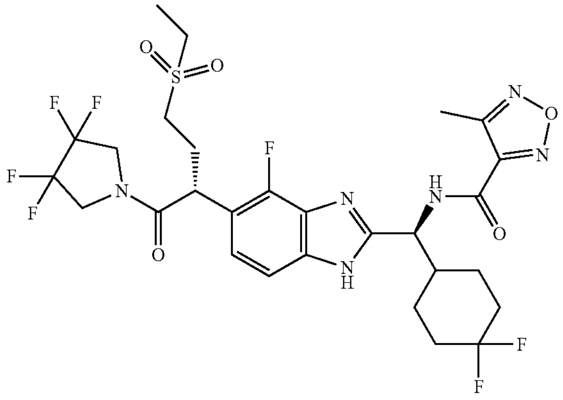

N—[(S)-(4,4-Difluorocyclohexyl){5-[(1S)-3-(ethylsulfonyl)-1-(3,3,4,4-tetrafluoro-pyrrolidine-1-carbonyl)propyl]-4-fluoro-1H-benzimidazol-2-yl}methyl]-4-methyl-1,2,5-oxadiazole-3-carboxamide (Example 28)

N—[(S)-(4,4-Difluorocyclohexyl){5-[(1R)-3-(ethylsulfonyl)-1-(3,3,4,4-tetrafluoro-pyrrolidine-1-carbonyl)propyl]-4-fluoro-1H-benzimidazol-2-yl}methyl]-4-methyl-1,2,5-oxadiazole-3-carboxamide (Example 29)

Example 27 (120 mg) was subjected to chiral preparative HPLC (Method 17) to afford the title compounds (Peak 1, 37 mg; and Peak 2, 32 mg) as white solids.

Peak 1 (arbitrarily assigned S): $\delta_H$ (400 MHz, DMSO-$d_6$) 13.04 (s, 0.2H), 12.92-12.68 (m, 0.8H), 9.68 (d, J 8.5 Hz, 0.8H), 9.59 (d, J 8.6 Hz, 0.2H), 7.47 (d, J 8.4 Hz, 0.2H), 7.36 (d, J 8.4 Hz, 0.8H), 7.07 (dt, J 8.2, 6.0 Hz, 1H), 5.29-5.06 (m, 1H), 4.56 (q, J 13.2 Hz, 1H), 4.37 (t, J 7.2 Hz, 1H), 4.05 (dt, J 47.6, 14.4 Hz, 2H), 3.65 (p, J 13.5, 13.0 Hz, 1H), 3.22-2.81 (m, 4H), 2.50 (s, 3H), 2.43-2.16 (m, 1H), 2.17-1.67 (m, 6H), 1.67-1.02 (m, 7H). LCMS (Method 9): $[M+H]^+$ m/z 697, RT 2.11 minutes. Chiral LC (Method 18): RT 3.48 minutes, 100%.

Peak 2 (arbitrarily assigned R): $\delta_H$ (400 MHz, DMSO-$d_6$) 12.86 (s, 1H), 9.64 (s, 1H), 7.36 (d, J 8.3 Hz, 1H), 7.05 (t, J 7.4 Hz, 1H), 5.19 (s, 1H), 4.56 (q, J 13.5 Hz, 1H), 4.36 (t, J 7.2 Hz, 1H), 4.07 (dq, J 46.8, 14.3 Hz, 2H), 3.65 (q, J 13.5 Hz, 1H), 3.17-2.80 (m, 4H), 2.49 (s, 3H), 2.42-2.15 (m, 1H), 2.18-1.24 (m, 8H), 1.17 (t, J 7.4 Hz, 5H). LCMS (Method 9): $[M+H]^+$ m/z 697, RT 2.11 minutes. Chiral LC (Method 18): RT 5.09 minutes, 99.7%.

Example 30

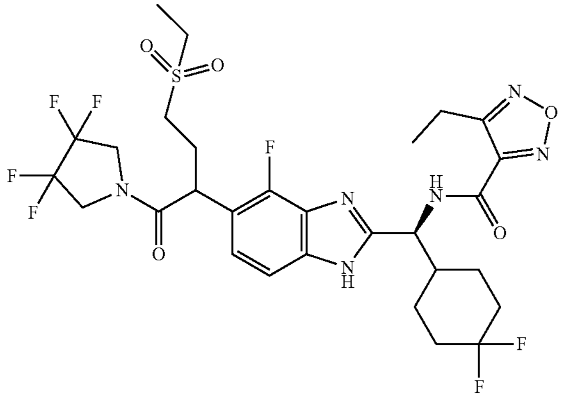 [SMILES: CCc1nonc1C(=O)N[C@H](c1nc2c(F)c(C(CCS(=O)(=O)CC)C(=O)N3CC(F)(F)C(F)(F)C3)ccc2[nH]1)C1CCC(F)(F)CC1]

N—[(S)-(4,4-Difluorocyclohexyl){5-[3-(ethylsulfonyl)-1-(3,3,4,4-tetrafluoropyrrolidine-1-carbonyl)propyl]-4-fluoro-1H-benzimidazol-2-yl}methyl]-4-ethyl-1,2,5-oxadiazole-3-carboxamide 4-Ethyl-1,2,5-oxadiazole-3-carboxylic acid (43 mg, 0.30 mmol) and HATU (117 mg, 0.30 mmol) were dissolved in DCM (3 mL) and DIPEA (0.10 mL, 0.58 mmol) was added, followed by Intermediate 91 (167 mg, 0.28 mmol) in DCM (4 mL). The mixture was stirred at r.t. overnight, then washed with saturated aqueous $NH_4Cl$ solution (10 mL) and concentrated in vacuo. Purification by chromatography (silica, DCM, 0-65% EtOAc gradient) gave the title compound (195 mg, 96%) as an off-white solid. $\delta_H$ (300 MHz, DMSO-$d_6$) 12.92-12.80 (m, 1H), 9.70 (d, J 8.4 Hz, 1H), 8.16 (s, 0.2H), 7.08 (dd, J 8.8, 6.7 Hz, 1H), 5.20 (m, 1H), 4.81-4.25 (m, 2H), 4.25-3.82 (m, 2H), 3.82-3.48 (m, 2H), 3.23-2.70 (m, 6H), 2.45-2.20 (m, 2H), 2.20-1.63 (m, 5H), 1.24-0.95 (m, 10H). LCMS (Method 9): $[M+H]^+$ m/z 711, RT 2.37 minutes.

Examples 31 & 32

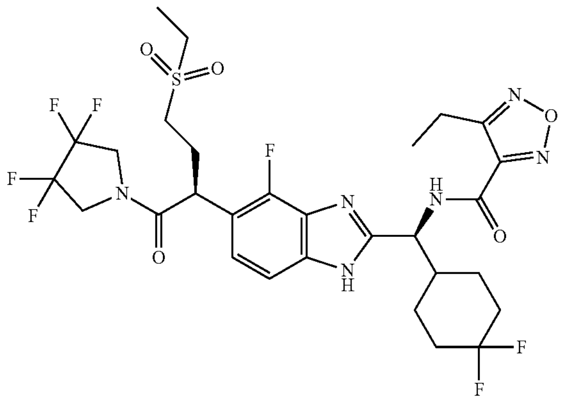

-continued

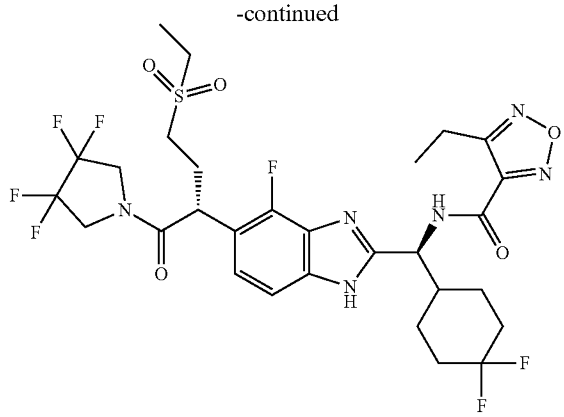

N—[(S)-(4,4-Difluorocyclohexyl){5-[(1S)-3-(ethylsulfonyl)-1-(3,3,4,4-tetrafluoro-pyrrolidine-1-carbonyl)propyl]-4-fluoro-1H-benzimidazol-2-yl}methyl]-4-ethyl-1,2,5-oxadiazole-3-carboxamide (Example 31)

N—[(S)-(4,4-Difluorocyclohexyl){5-[(1R)-3-(ethylsulfonyl)-1-(3,3,4,4-tetrafluoro-pyrrolidine-1-carbonyl)propyl]-4-fluoro-1H-benzimidazol-2-yl}methyl]-4-ethyl-1,2,5-oxadiazole-3-carboxamide (Example 32)

Example 30 (130 mg) was subjected to chiral preparative HPLC (Method 17) to afford the title compounds (Peak 1, 35 mg; and Peak 2, 32 mg) as white solids.

Peak 1 (arbitrarily assigned S): $\delta_H$ (400 MHz, DMSO-$d_6$) 13.06 (s, 0.2H), 12.82 (s, 0.8H), 9.71 (d, J 8.4 Hz, 0.8H), 9.63 (d, J 8.4 Hz, 0.2H), 7.47-7.35 (m, 1H), 7.18-6.97 (m, 1H), 5.29-5.12 (m, 1H), 4.56 (q, J 13.3 Hz, 1H), 4.37 (t, J 7.2 Hz, 1H), 4.20-3.90 (m, 2H), 3.63 (q, J 13.6 Hz, 1H), 3.20-2.83 (m, 7H), 2.44-2.22 (m, 1H), 2.14-1.48 (m, 6H), 1.49-1.07 (m, 9H). LCMS (Method 9): $[M+H]^+$ m/z 711, RT 2.37 minutes. Chiral LC (Method 18): RT 3.31 minutes, 100%.

Peak 2 (arbitrarily assigned R): $\delta_H$ (400 MHz, DMSO-$d_6$) 12.97 (s, 1H), 9.47 (s, 1H), 7.28 (d, J 8.3 Hz, 1H), 6.88 (s, 1H), 5.16 (d, J 7.5 Hz, 1H), 4.53 (q, J 13.2 Hz, 1H), 4.32 (t, J 7.2 Hz, 1H), 4.06 (dq, J 43.3, 14.3 Hz, 2H), 3.59 (q, J 13.6 Hz, 1H), 3.16-2.76 (m, 7H), 2.44-2.14 (m, 2H), 2.14-1.54 (m, 6H), 1.21 (dt, J 29.8, 7.4 Hz, 8H). LCMS (Method 9): $[M+H]^+$ m/z 711, RT 2.37 minutes. Chiral LC (Method 18): RT 4.83 minutes, 99.6%.

Example 33

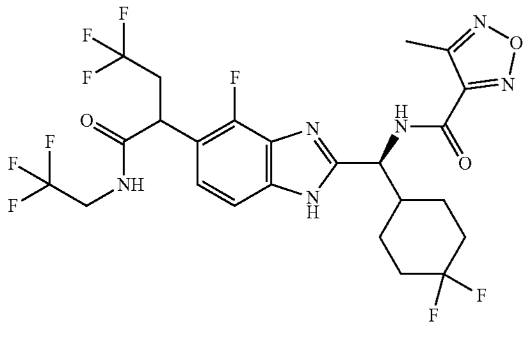 [SMILES: Cc1nonc1C(=O)N[C@H](c1nc2c(F)c(C(CC(F)(F)F)C(=O)NCC(F)(F)F)ccc2[nH]1)C1CCC(F)(F)CC1]

N—[(S)-(4,4-Difluorocyclohexyl){4-fluoro-5-[3,3,3-trifluoro-1-(2,2,2-trifluoroethyl-carbamoyl)propyl]-1H-benzimidazol-2-yl}methyl]-4-methyl-1,2,5-oxadiazole-3-carboxamide To a stirred suspension of Intermediate 35 (100 mg, 0.147 mmol) and HATU (73 mg, 0.191 mmol) in DCM (1 mL) at r.t. was added DIPEA (128 μL, 0.734 mmol). The reaction mixture was stirred at r.t. for 15 minutes, then 2,2,2-trifluoroethanamine (19 mg, 0.191 mmol) was added. The reaction mixture was stirred at r.t. for 64 h, then diluted with DCM, quenched with saturated aqueous $NaHCO_3$ solution (8 mL) and stirred at r.t. for 10 minutes. The phases were separated using a hydrophobic frit, and the organic phase was concentrated in vacuo. The residue was separated by acidic preparative HPLC (Method 5) to afford the title compound (29 mg, 44%) as a white solid. $\delta_H$ (500 MHz, DMSO-$d_6$) 13.39-12.19 (m, 1H), 9.69 (s, 1H), 8.91-8.85 (m, 1H), 7.52-7.25 (m, 1H), 7.24-7.17 (m, 1H), 5.18 (d, J 7.9 Hz, 1H), 4.30 (dd, J 8.3, 5.6 Hz, 1H), 3.95-3.83 (m, 2H), 3.22-3.08 (m, 1H), 2.72-2.58 (m, 1H), 2.48 (s, 3H), 2.35-2.24 (m, 1H), 2.12-1.91 (m, 3H), 1.89-1.71 (m, 2H), 1.58-1.49 (m, 1H), 1.46-1.35 (m, 1H), 1.35-1.23 (m, 1H). LCMS (Method 4): $[M+H]^+$ m/z 615, RT 3.52 minutes.

Examples 34 & 35

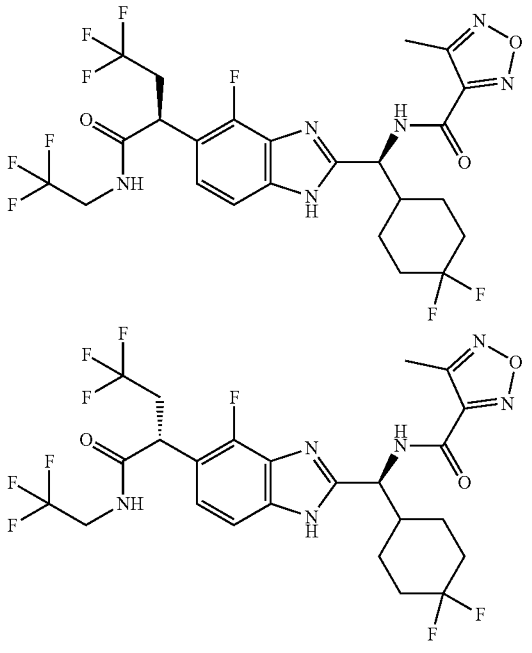

N—[(S)-(4,4-Difluorocyclohexyl){4-fluoro-5-[(1S)-3,3,3-trifluoro-1-(2,2,2-trifluoroethyl-carbamoyl)propyl]-1H-benzimidazol-2-yl}methyl]-4-methyl-1,2,5-oxadiazole-3-carboxamide (Example 34)

N—[(S)-(4,4-Difluorocyclohexyl){4-fluoro-5-[(1R)-3,3,3-trifluoro-1-(2,2,2-trifluoroethyl-carbamoyl)propyl]-1H-benzimidazol-2-yl}methyl]-4-methyl-1,2,5-oxadiazole-3-carboxamide (Example 35)

Example 33 (25 mg) was subjected to chiral preparative purification (Method 19) to afford the title compounds (Peak 1, 7.5 mg, 38%; and Peak 2, 8.1 mg, 41%) as white solids.

Peak 1 (arbitrarily assigned S): $\delta_H$ (500 MHz, DMSO-$d_6$) 12.81 (br s, 1H), 9.67 (br s, 1H), 8.87 (t, J 6.3 Hz, 1H), 7.49-7.25 (m, 1H), 7.23-7.14 (m, 1H), 5.18 (d, J 8.2 Hz, 1H), 4.30 (dd, J 8.3, 5.5 Hz, 1H), 3.94-3.84 (m, 2H), 3.22-3.08 (m, 1H), 2.76-2.57 (m, 1H), 2.48 (s, 3H), 2.35-2.25 (m, 1H), 2.12-1.92 (m, 3H), 1.90-1.70 (m, 2H), 1.60-1.51 (m, 1H), 1.46-1.35 (m, 1H), 1.35-1.23 (m, 1H). LCMS (Method 4): $[M+H]^+$ m/z 615, RT 3.51 minutes.

Peak 2 (arbitrarily assigned R): $\delta_H$ (500 MHz, DMSO-$d_6$) 12.81 (br s, 1H), 9.65 (br s, 1H), 8.87 (t, J 6.3 Hz, 1H), 7.48-7.26 (m, 1H), 7.23-7.15 (m, 1H), 5.18 (d, J 8.2 Hz, 1H), 4.30 (dd, J 8.3, 5.5 Hz, 1H), 3.94-3.83 (m, 2H), 3.22-3.06 (m, 1H), 2.72-2.58 (m, 1H), 2.48 (s, 3H), 2.35-2.25 (m, 1H), 2.12-1.92 (m, 3H), 1.89-1.71 (m, 2H), 1.60-1.50 (m, 1H), 1.47-1.35 (m, 1H), 1.35-1.23 (m, 1H). LCMS (Method 4): $[M+H]^+$ m/z 615, RT 3.52 minutes.

Example 36

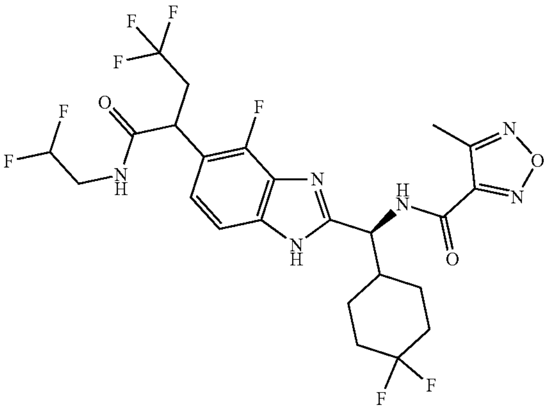

N—[(S)-(4,4-Difluorocyclohexyl){5-[1-(2,2-difluoroethylcarbamoyl)-3,3,3-trifluoro-propyl]-4-fluoro-1H-benzimidazol-2-yl}methyl]-4-methyl-1,2,5-oxadiazole-3-carboxamide To a stirred suspension of Intermediate 35 (95%, 50 mg, 0.0734 mmol) and HATU (36 mg, 0.0954 mmol) in DCM (1 mL) at r.t. was added DIPEA (64 μL, 0.367 mmol). The reaction mixture was stirred at r.t. for 15 minutes, then 2,2-difluoroethan-amine (7.7 mg, 0.10 mmol) was added. The reaction mixture was stirred at r.t. for 18 h, then diluted with DCM (4 mL), quenched with saturated aqueous $NaHCO_3$ solution (4 mL) and stirred at r.t. for 10 minutes. The phases were separated using a hydrophobic frit, and the organic phase was concentrated in vacuo. The residue was separated by acidic preparative HPLC (Method 5) to afford, after freeze-drying, the title compound (14.8 mg, 44%) as a white solid. $\delta_H$ (500 MHz, DMSO-$d_6$) 12.74 (br s, 1H), 9.74-9.65 (m, 1H), 8.62-8.53 (m, 1H), 7.30 (d, J 8.4 Hz, 1H), 7.25-7.15 (m, 1H), 6.09-5.79 (m, 1H), 5.18 (t, J 8.4 Hz, 1H), 4.28 (t, J 6.9 Hz, 1H), 3.53-3.40 (m, 2H), 3.23-3.04 (m, 1H), 2.75-2.58 (m, 1H), 2.48 (s, 3H), 2.35-2.24 (m, 1H), 2.13-1.92 (m, 3H), 1.92-1.70 (m, 2H), 1.60-1.50 (m, 1H), 1.48-1.35 (m, 1H), 1.35-1.22 (m, 1H). LCMS (Method 4): $[M+H]^+$ m/z 597, RT 3.36 minutes.

Examples 37 & 38

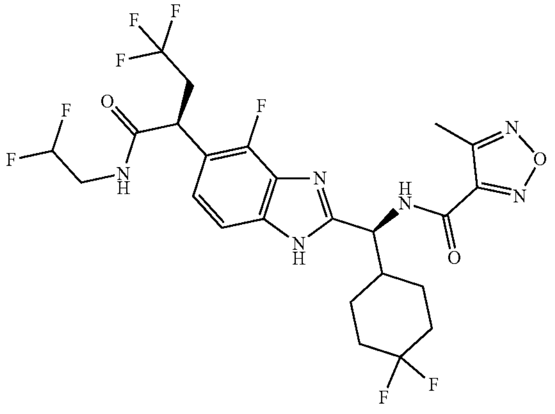

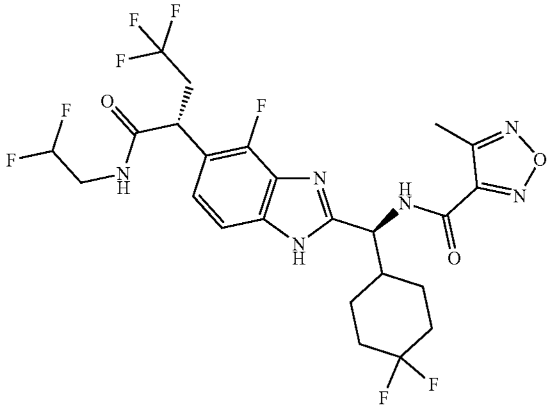 [SMILES: Cc1nonc1C(=O)N[C@H](c1nc2c(F)c(C(CC(F)(F)F)C(=O)NCC(F)F)ccc2[nH]1)C1CCC(F)(F)CC1]

N—[(S)-(4,4-Difluorocyclohexyl){5-[(1S)-1-(2,2-difluoroethylcarbamoyl)-3,3,3-trifluoro-propyl]-4-fluoro-1H-benzimidazol-2-yl}methyl]-4-methyl-1,2,5-oxadiazole-3-carboxamide (Example 37)

N—[(S)-(4,4-Difluorocyclohexyl){5-[(1R)-1-(2,2-difluoroethylcarbamoyl)-3,3,3-trifluoro-propyl]-4-fluoro-1H-benzimidazol-2-yl}methyl]-4-methyl-1,2,5-oxadiazole-3-carboxamide (Example 38)

Example 36 (27 mg) was subjected to chiral basic preparative HPLC (Method 23) to afford the title compounds (Peak 1, 3 mg; and Peak 2, 3 mg) as white solids.

Peak 1 (arbitrarily assigned S): LCMS (Method 9): $[M+H]^+$ m/z 597, RT 1.91 minutes. LCMS (Method 24): $[M+H]^+$ m/z 597, RT 1.96 minutes.

Peak 2 (arbitrarily assigned R): LCMS (Method 9): $[M+H]^+$ m/z 597, RT 1.89 minutes. LCMS (Method 24): $[M+H]^+$ m/z 597, RT 1.94 minutes.

Example 39

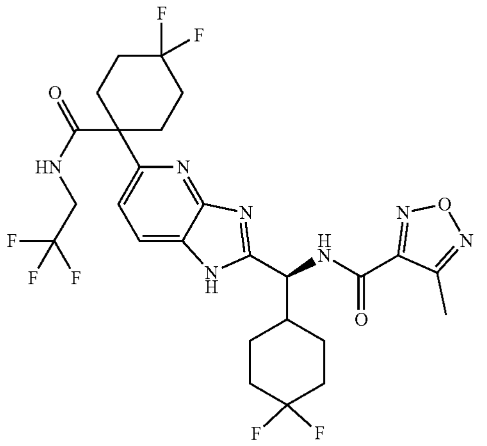 [SMILES: Cc1nonc1C(=O)N[C@H](c1nc2nc(C3(C(=O)NCC(F)(F)F)CCC(F)(F)CC3)ccc2[nH]1)C1CCC(F)(F)CC1]

N—[(S)-(4,4-Difluorocyclohexyl){5-[4,4-difluoro-1-(2,2,2-trifluoroethylcarbamoyl)-cyclohexyl]-1H-imidazo[4,5-b]pyridin-2-yl}methyl]-4-methyl-1,2,5-oxadiazole-3-carboxamide Monoformate Salt To a stirred solution of Intermediate 99 (25 mg, 0.04 mmol) in EtOH (0.5 mL) and DCM (0.5 mL) were added ammonium formate (24 mg, 0.388 mmol) and 10% palladium on charcoal (50% wet) (4.1 mg, 0.02 mmol). The reaction mixture was stirred at r.t. for 16 h, then placed under an atmosphere of hydrogen gas. Stirring was continued at r.t. for a further 2 h. The catalyst was removed by filtration, and the filtrate was concentrated in vacuo. The residue was diluted with DCM (5 mL) and washed with water (2 mL), then filtered through phase separator. The DCM was removed in vacuo. The residue was diluted with EtOH (1 mL) and 10% palladium on charcoal (50% wet) (4.1 mg, 0.02 mmol) was added. The mixture was stirred under an atmosphere of hydrogen for a further 20 h, then diluted with EtOH (2 mL) and filtered through a pad of Celite®, rinsing the filter cake with EtOH (2×1 mL). The filtrates were combined, and the solvent was removed in vacuo. The resulting clear gum was taken up in EtOAc (0.48 mL) with 4-methyl-1,2,5-oxadiazole-3-carboxylic acid (5 mg, 0.04 mmol) and pyridine (11 μL, 0.14 mmol). T3P® (50% in EtOAc) (45 μL, 0.08 mmol) was added dropwise at r.t., and stirring was continued for a further 5 h. The reaction mixture was diluted with EtOAc (4 mL) and cooled to 0° C., then quenched with 1M HCl (0.5 mL). The aqueous phase was separated. The organic phase was washed with water (1 mL) and brine (1 mL), then dried over anhydrous $Na_2SO_4$ and filtered. The solvent was concentrated in vacuo. The residue was purified using flash column chromatography (2 g silica), eluting with a gradient of EtOAc in heptane (10-60%). The resulting white solid was further purified by preparative HPLC to afford the title compound (4.5 mg, 22%) as a white solid. $\delta_H$ (400 MHz, $CD_3OD$) 8.54 (s, 1H), 7.93 (d, J 8.3 Hz, 1H), 7.36 (d, J 8.5 Hz, 1H), 5.27 (d, J 8.5 Hz, 1H), 3.83 (q, J 9.3 Hz, 2H), 2.54 (s, 1H), 2.52 (s, 3H), 2.47-2.30 (m, 3H), 2.13-1.96 (m, 7H), 1.92-1.71 (m, 2H), 1.67-1.59 (m, 1H), 1.60-1.32 (m, 3H) (formate salt, 3×NH signals exchanged with solvent). LCMS (Method 4): $[M+H]^+$ m/z 620, RT 3.52 minutes.

Example 40

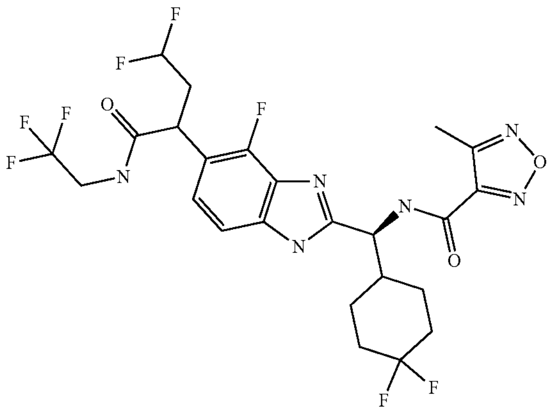 [SMILES: Cc1nonc1C(=O)N[C@H](c1nc2c(F)c(C(CC(F)F)C(=O)NCC(F)(F)F)ccc2[nH]1)C1CCC(F)(F)CC1]

N—[(S)-(4,4-Difluorocyclohexyl){5-[3,3-difluoro-1-(2,2,2-trifluoroethylcarbamoyl)-propyl]-4-fluoro-1H-benzimidazol-2-yl}methyl]-4-methyl-1,2,5-oxadiazole-3-carboxamide To a stirred solution of Intermediate 107 (500 mg, 0.94 mmol), 2,2,2-trifluoroethanamine (121 mg, 1.22 mmol) and DIPEA (0.82 mL, 4.70 mmol) in DCM (15 mL) at r.t. was added HATU (465 mg, 1.22 mmol) in one portion. The reaction mixture was stirred at r.t. for 16 h, then diluted with DCM (20 mL) and quenched with saturated aqueous $NaHCO_3$ solution (20 mL). The biphasic mixture was stirred at r.t. for 10 minutes, and the phases were separated using a hydrophobic frit. The organic phase was concentrated in vacuo. The residue was separated by flash column chromatography, eluting with EtOAc/heptane (0-100% gradient), to afford the title compound as a white solid (361 mg, 61%). $\delta_H$ (500 MHz, DMSO-$d_6$) 12.73 (s, 1H), 9.74-9.62 (m, 1H), 8.84-8.66 (m, 1H), 7.30 (d, J 8.4 Hz, 1H), 7.22-7.08 (m, 1H), 6.11-5.82 (m, 1H), 5.17 (t, J 8.3 Hz, 1H), 4.19 (t, J 7.2 Hz, 1H), 3.97-3.77 (m, 2H), 2.71-2.56 (m, 1H), 2.47 (s, 3H), 2.32-2.15 (m, 2H), 2.10-1.97 (m, 3H), 1.88-1.71 (m, 2H), 1.54 (d, J 11.8 Hz, 1H), 1.45-1.24 (m, 2H). LCMS (Method 4): $[M+H]^+$ m/z 597, RT 3.39 minutes.

Examples 41 & 42

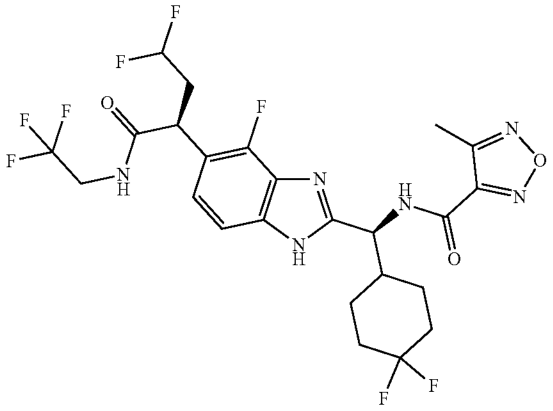

-continued

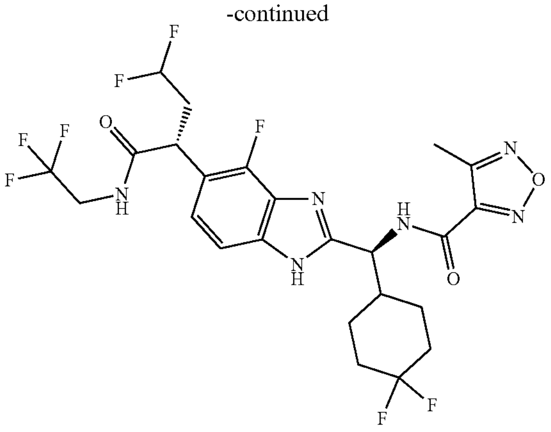

N—[(S)-(4,4-Difluorocyclohexyl){5-[(1S)-3,3-difluoro-1-(2,2,2-trifluoroethylcarbamoyl)-propyl]-4-fluoro-1H-benzimidazol-2-yl}methyl]-4-methyl-1,2,5-oxadiazole-3-carboxamide (Example 41)

N—[(S)-(4,4-Difluorocyclohexyl){5-[(1R)-3,3-difluoro-1-(2,2,2-trifluoroethylcarbamoyl)-propyl]-4-fluoro-1H-benzimidazol-2-yl}methyl]-4-methyl-1,2,5-oxadiazole-3-carboxamide (Example 42)

Example 40 (350 mg) was subjected to chiral basic preparative HPLC (Method 15) to afford the title compounds (Peak 1, 100 mg, 29%; and Peak 2, 100 mg, 29%) as white solids.

Peak 1 (arbitrarily assigned S): $\delta_H$ (300 MHz, DMSO-$d_6$) 12.80 (s, 1H), 9.64 (s, 1H), 8.74 (t, J 6.3 Hz, 1H), 7.31 (d, J 8.4 Hz, 1H), 7.14 (dd, J 8.4, 6.5 Hz, 1H), 5.96 (tt, J 56.5, 4.4 Hz, 1H), 5.17 (d, J 8.0 Hz, 1H), 4.35-4.03 (m, 1H), 4.05-3.67 (m, 2H), 2.65 (dtt, J 19.7, 9.3, 4.5 Hz, 1H), 2.47 (s, 3H), 2.40-2.15 (m, 2H), 2.11-1.97 (m, 3H), 1.88-1.71 (m, 2H), 1.54 (m, 1H), 1.45-1.20 (m, 2H). LCMS (Method 9): $[M+H]^+$ m/z 597, RT 1.89 minutes. Chiral LC (Method 16): RT 5.37 minutes, 100%.

Peak 2 (arbitrarily assigned R): $\delta_H$ (300 MHz, DMSO-$d_6$) 12.83 (s, 1H), 9.65 (s, 1H), 8.75 (t, J 6.3 Hz, 1H), 7.32 (d, J 8.4 Hz, 1H), 7.15 (dd, J 8.4, 6.5 Hz, 1H), 5.96 (tt, J 56.4, 4.5 Hz, 1H), 5.18 (d, J 8.0 Hz, 1H), 4.36-4.02 (m, 1H), 3.88 (dq, J 15.4, 9.3 Hz, 2H), 2.65 (m, 1H), 2.47 (s, 3H), 2.39-2.10 (m, 2H), 2.10-1.97 (m, 3H), 1.88-1.71 (m, 2H), 1.64-1.15 (m, 3H). LCMS (Method 9): $[M+H]^+$ m/z 597, RT 1.88 minutes. Chiral LC (Method 16): RT 6.46 minutes, 99%.

Example 43

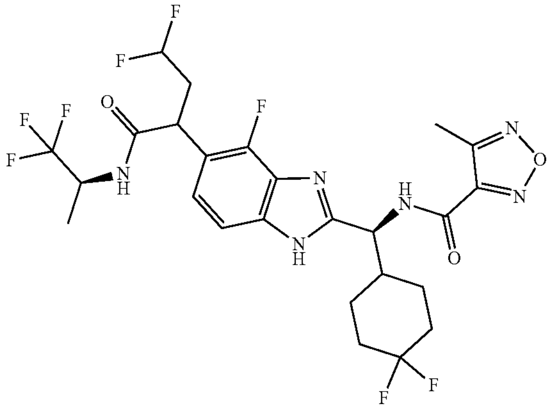 [SMILES: Cc1nonc1C(=O)N[C@H](c1nc2c(F)c(C(CC(F)F)C(=O)N[C@@H](C)C(F)(F)F)ccc2[nH]1)C1CCC(F)(F)CC1]

N—{(S)-(4,4-Difluorocyclohexyl)[5-(3,3-difluoro-1-{[(1S)-2,2,2-trifluoro-1-methylethyl]-carbamoyl}propyl)-4-fluoro-1H-benzimidazol-2-yl]methyl}-4-methyl-1,2,5-oxadiazole-3-carboxamide To a stirred solution of (2S)-1,1,1-trifluoropropan-2-amine (96 mg, 0.85 mmol) and 2-chloro-1-methylpyridinium iodide (157 mg, 0.612 mmol) in DMA (2.5 mL) was added DIPEA (411 μL, 2.35 mmol), followed by the dropwise addition of a solution of Intermediate 107 (250 mg, 0.47 mmol) in DMA (2.5 mL). The reaction mixture was stirred at 50° C. for 18 h, then diluted with water (10 mL) and extracted with EtOAc (3×15 mL). The combined organic layers were washed with brine (2×15 mL) and dried over $MgSO_4$, then filtered and concentrated in vacuo. The residue was separated by flash column chromatography, eluting with EtOAc/heptane (0-100% gradient), to afford the title compound (219 mg, 74%) as a white solid. $\delta_H$ (500 MHz, DMSO-$d_6$) 12.75 (br s, 1H), 9.67 (br s, 1H), 8.83-8.65 (m, 1H), 7.49-7.25 (m, 1H), 7.24-7.12 (m, 1H), 6.15-5.79 (m, 1H), 5.28-5.10 (m, 1H), 4.68-4.52 (m, 1H), 4.25-4.13 (m, 1H), 2.72-2.55 (m, 1H), 2.48 (s, 3H), 2.36-2.24 (m, 1H), 2.24-2.12 (m, 1H), 2.11-1.94 (m, 3H), 1.89-1.72 (m, 2H), 1.60-1.51 (m, 1H), 1.46-1.36 (m, 1H), 1.35-1.23 (m, 1H), 1.25-1.07 (m, 3H). LCMS (Method 4): $[M+H]^+$ m/z 611, RT 3.53 minutes.

Examples 44 & 45

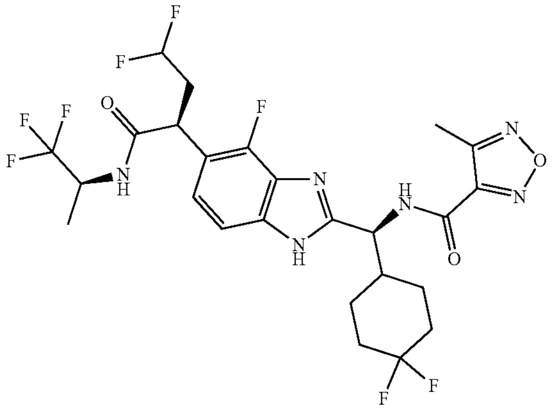

-continued

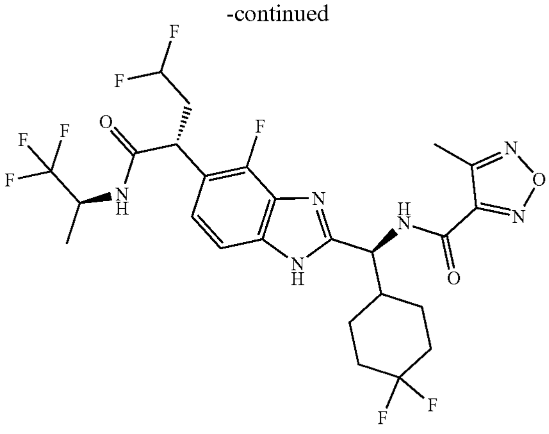

N—[(S)-(4,4-Difluorocyclohexyl){5-[(1S)-3,3-difluoro-1-{[(1S)-2,2,2-trifluoro-1-methylethyl]carbamoyl}propyl]-4-fluoro-1H-benzimidazol-2-yl}methyl]-4-methyl-1,2,5-oxadiazole-3-carboxamide (Example 44)

N—[(S)-(4,4-Difluorocyclohexyl){5-[(1R)-3,3-difluoro-1-{[(1S)-2,2,2-trifluoro-1-methylethyl]carbamoyl}propyl]-4-fluoro-1H-benzimidazol-2-yl}methyl]-4-methyl-1,2,5-oxadiazole-3-carboxamide (Example 45)

Example 43 (80 mg) was subjected to chiral basic preparative HPLC (Method 15) to afford the title compounds (Peak 1, 25 mg, 31%; and Peak 2, 24 mg, 31%) as white solids.

Peak 1 (arbitrarily assigned S): $\delta_H$ (400 MHz, DMSO-$d_6$) 12.83 (br s, 1H), 9.70 (br s, 1H), 8.68 (d, J 8.8 Hz, 1H), 7.64-7.22 (m, 1H), 7.19-7.09 (m, 1H), 6.15-5.80 (m, 1H), 5.19 (d, J 7.2 Hz, 1H), 4.67-4.53 (m, 1H), 4.25-4.14 (m, 1H), 2.71-2.55 (m, 1H), 2.48 (s, 3H), 2.37-2.25 (m, 1H), 2.23-1.93 (m, 4H), 1.91-1.68 (m, 2H), 1.60-1.50 (m, 1H), 1.49-1.26 (m, 2H), 1.23 (d, J 7.1 Hz, 3H). LCMS (Method 4): $[M+H]^+$ m/z 611, RT 3.49 minutes.

Peak 2 (arbitrarily assigned R): $\delta_H$ (400 MHz, DMSO-$d_6$) 12.90 (s, 1H), 9.72 (s, 1H), 8.77 (d, J 8.9 Hz, 1H), 7.67-7.26 (m, 1H), 7.20 (dd, J 8.3, 6.6 Hz, 1H), 6.12-5.73 (m, 1H), 5.18 (d, J 8.1 Hz, 1H), 4.66-4.48 (m, 1H), 4.18 (dd, J 8.4, 6.3 Hz, 1H), 2.71-2.55 (m, 1H), 2.48 (s, 3H), 2.35-2.14 (m, 2H), 2.12-1.92 (m, 3H), 1.91-1.68 (m, 2H), 1.60-1.51 (m, 1H), 1.47-1.20 (m, 2H), 1.12 (d, J 7.1 Hz, 3H). LCMS (Method 4): $[M+H]^+$ m/z 611, RT 3.52 minutes.

Example 46

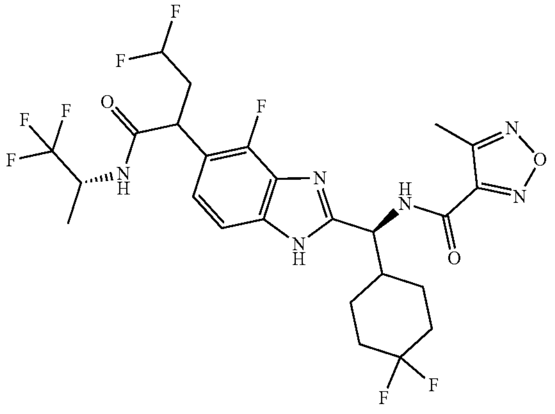 [SMILES: Cc1nonc1C(=O)N[C@H](c1nc2c(F)c(C(CC(F)F)C(=O)N[C@H](C)C(F)(F)F)ccc2[nH]1)C1CCC(F)(F)CC1]

N—{(S)-(4,4-Difluorocyclohexyl)[5-(3,3-difluoro-1-{[(1R)-2,2,2-trifluoro-1-methylethyl]-carbamoyl}propyl)-4-fluoro-1H-benzimidazol-2-yl]methyl}-4-methyl-1,2,5-oxadiazole-3-carboxamide To a stirred solution of (2R)-1,1,1-trifluoropropan-2-amine (96 mg, 0.85 mmol) and 2-chloro-1-methylpyridinium iodide (157 mg, 0.612 mmol) in DMA (2.5 mL) was added DIPEA (411 μL, 2.35 mmol), followed by dropwise addition of a solution of Intermediate 107 (250 mg, 0.47 mmol) in DMA (2.5 mL). The reaction mixture was stirred at 50° C. for 24 h, then diluted with water (10 mL) and extracted with EtOAc (3×15 mL). The combined organic layers were washed with brine (2×15 mL) and dried over $MgSO_4$, then filtered and concentrated in vacuo. The residue was separated by flash column chromatography, eluting with EtOAc/heptane (0-100% gradient), to afford the title compound (215 mg, 69%) as a white solid. $\delta_H$ (500 MHz, DMSO-$d_6$) 12.75 (br s, 1H), 9.66 (br s, 1H), 8.86-8.65 (m, 1H), 7.46-7.26 (m, 1H), 7.23-7.11 (m, 1H), 6.15-5.78 (m, 1H), 5.24-5.12 (m, 1H), 4.68-4.51 (m, 1H), 4.25-4.14 (m, 1H), 2.70-2.56 (m, 1H), 2.48 (s, 3H), 2.35-2.25 (m, 1H), 2.25-2.13 (m, 1H), 2.11-1.93 (m, 3H), 1.91-1.69 (m, 2H), 1.60-1.49 (m, 1H), 1.47-1.35 (m, 1H), 1.35-1.25 (m, 1H), 1.26-1.07 (m, 3H). LCMS (Method 4): $[M+H]^+$ m/z 611, RT 3.48 minutes.

Examples 47 & 48

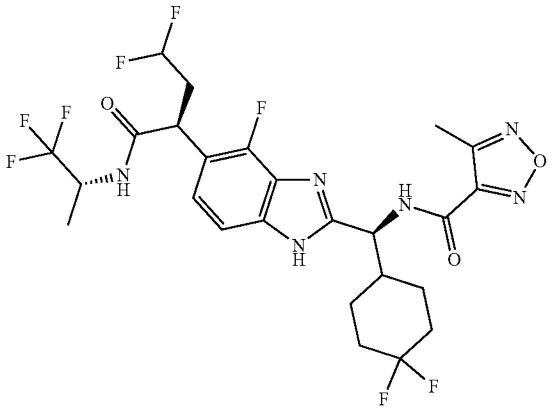

-continued

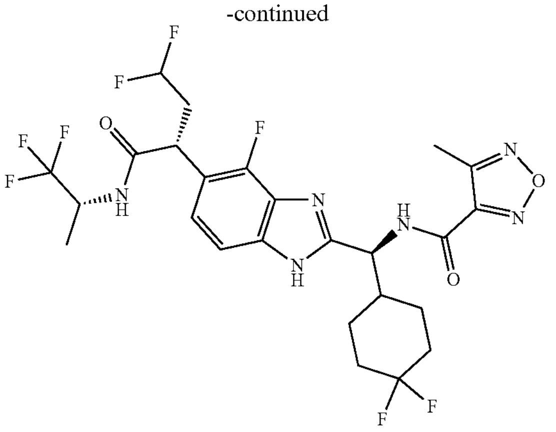

N—[(S)-(4,4-Difluorocyclohexyl){5-[(1S)-3,3-difluoro-1-{[(1R)-2,2,2-trifluoro-1-methylethyl]carbamoyl}propyl]-4-fluoro-1H-benzimidazol-2-yl}methyl]-4-methyl-1,2,5-oxadiazole-3-carboxamide (Example 47)

N—[(S)-(4,4-Difluorocyclohexyl){5-[(1R)-3,3-difluoro-1-{[(1R)-2,2,2-trifluoro-1-methylethyl]carbamoyl}propyl]-4-fluoro-1H-benzimidazol-2-yl}methyl]-4-methyl-1,2,5-oxadiazole-3-carboxamide (Example 48)

Example 46 (110 mg) was subjected to chiral basic preparative HPLC (Method 15) to afford the title compounds (Peak 1, 66 mg; and Peak 2, 35 mg) as white solids.

Peak 1 (arbitrarily assigned S): $\delta_H$ (500 MHz, DMSO-$d_6$) 13.24 (br s, 1H), 9.91 (br s, 1H), 8.70 (d, J 8.8 Hz, 1H), 7.40-7.22 (m, 1H), 7.20-7.08 (m, 1H), 6.14-5.84 (m, 1H), 5.20 (d, J 8.0 Hz, 1H), 4.68-4.53 (m, 1H), 4.24-4.15 (m, 1H), 2.70-2.54 (m, 1H), 2.48 (s, 3H), 2.35-2.25 (m, 1H), 2.24-2.10 (m, 1H), 2.10-1.91 (m, 3H), 1.89-1.70 (m, 2H), 1.61-1.50 (m, 1H), 1.47-1.35 (m, 1H), 1.35-1.25 (m, 1H), 1.23 (d, J 7.1 Hz, 3H). LCMS (Method 4): $[M+H]^+$ m/z 611, RT 3.48 minutes.

Peak 2 (arbitrarily assigned R): $\delta_H$ (500 MHz, DMSO-$d_6$) 13.18 (br s, 1H), 9.91 (br s, 1H), 8.78 (d, J 8.9 Hz, 1H), 7.56-7.25 (m, 1H), 7.23-7.16 (m, 1H), 6.09-5.80 (m, 1H), 5.19 (d, J 8.0 Hz, 1H), 4.65-4.51 (m, 1H), 4.21-4.15 (m, 1H), 2.68-2.54 (m, 1H), 2.47 (s, 3H), 2.35-2.24 (m, 1H), 2.24-2.14 (m, 1H), 2.12-1.91 (m, 3H), 1.89-1.70 (m, 2H), 1.58-1.50 (m, 1H), 1.48-1.36 (m, 1H), 1.35-1.22 (m, 1H), 1.11 (d, J 7.1 Hz, 3H). LCMS (Method 4): $[M+H]^+$ m/z 611, RT 3.53 minutes.

Example 49

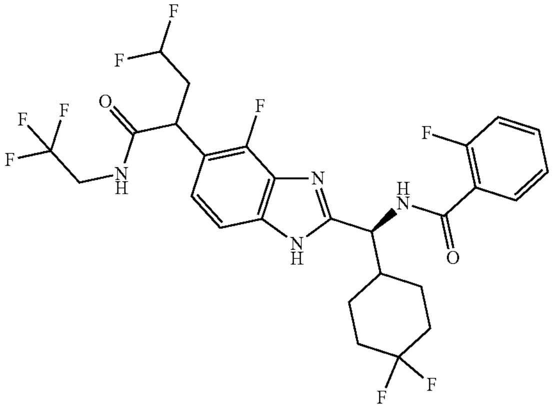 [SMILES: O=C(N[C@H](c1nc2c(F)c(C(CC(F)F)C(=O)NCC(F)(F)F)ccc2[nH]1)C1CCC(F)(F)CC1)c1ccccc1F]

N—[(S)-(4,4-Difluorocyclohexyl){5-[3,3-difluoro-1-(2,2,2-trifluoroethylcarbamoyl)-propyl]-4-fluoro-1H-benzimidazol-2-yl}methyl]-2-fluorobenzamide To a stirred suspension of Intermediate 109 (191 mg, 0.28 mmol) and HATU (137 mg, 0.36 mmol) in DCM (2 mL) at r.t. was added DIPEA (242 µL, 1.39 mmol) The reaction mixture was stirred at r.t. for 15 minutes, then 2,2,2-trifluoroethanamine (36 mg, 0.36 mmol) in DCM (2 mL) was added. The reaction mixture was stirred for 18 h, then diluted with DCM (4 mL) and quenched with saturated aqueous $NaHCO_3$ solution (4 mL). The biphasic mixture was stirred at r.t. for 10 minutes, then the phases were separated using a hydrophobic frit. The organic phase was concentrated in vacuo. The residue was separated by preparative HPLC (Method 21) to afford the title compound (88 mg, 50%) as a white solid. $\delta_H$ (400 MHz, DMSO-$d_6$) 12.70 (br s, 1H), 8.88 (d, J 7.9 Hz, 1H), 8.75 (t, J 6.3 Hz, 1H), 7.69-7.60 (m, 1H), 7.58-7.50 (m, 1H), 7.41-7.23 (m, 3H), 7.21-7.12 (m, 1H), 6.15-5.80 (m, 1H), 5.21 (t, J 8.4 Hz, 1H), 4.26-4.15 (m, 1H), 4.01-3.76 (m, 2H), 2.75-2.55 (m, 1H), 2.30-2.14 (m, 2H), 2.13-1.92 (m, 3H), 1.91-1.67 (m, 2H), 1.58-1.49 (m, 1H), 1.48-1.21 (m, 2H)._LCMS (Method 4): $[M+H]^+$ m/z 609, RT 3.37 minutes.

Examples 50 & 51

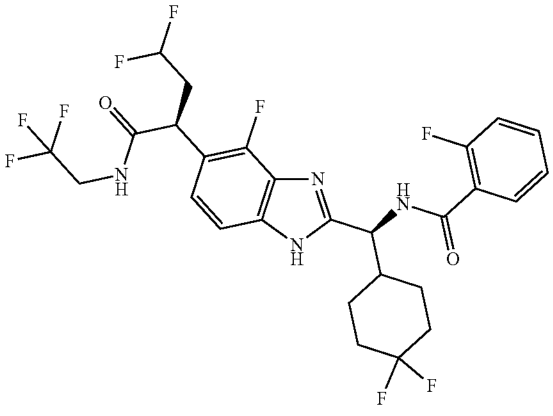

-continued

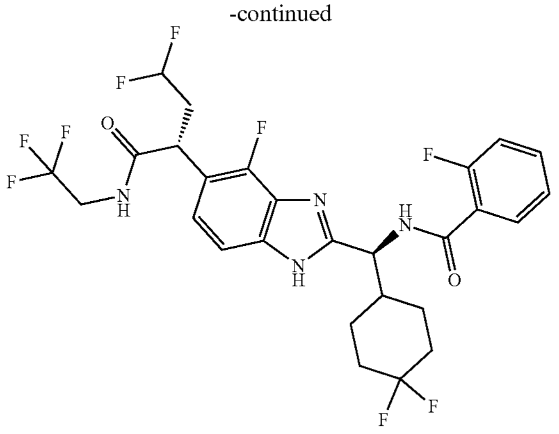

N—[(S)-(4,4-Difluorocyclohexyl){5-[(1S)-3,3-difluoro-1-(2,2,2-trifluoroethylcarbamoyl)-propyl]-4-fluoro-1H-benzimidazol-2-yl}methyl]-2-fluorobenzamide (Example 50)

N—[(S)-(4,4-Difluorocyclohexyl){5-[(1R)-3,3-difluoro-1-(2,2,2-trifluoroethylcarbamoyl)-propyl]-4-fluoro-1H-benzimidazol-2-yl}methyl]-2-fluorobenzamide (Example 51)

Example 49 (85 mg) was subjected to chiral purification (Method 22) to afford the title compounds (Peak 1, 43 mg; and Peak 2, 21 mg) as white solids.

Peak 1 (arbitrarily assigned S): $\delta_H$ (400 MHz, DMSO-$d_6$) 12.74 (br s, 1H), 9.00-8.83 (m, 1H), 8.74 (t, J 6.3 Hz, 1H), 7.67-7.59 (m, 1H), 7.59-7.49 (m, 1H), 7.45-7.23 (m, 3H), 7.18-7.09 (m, 1H), 6.15-5.79 (m, 1H), 5.21 (t, J 8.3 Hz, 1H), 4.24-4.14 (m, 1H), 3.98-3.75 (m, 2H), 2.75-2.58 (m, 1H), 2.30-2.14 (m, 2H), 2.12-1.93 (m, 3H), 1.92-1.63 (m, 2H), 1.58-1.49 (m, 1H), 1.49-1.15 (m, 2H). LCMS (Method 4): $[M+H]^+$ m/z 609, RT 3.37 minutes.

Peak 2 (arbitrarily assigned R): $\delta_H$ (400 MHz, DMSO-$d_6$) 12.90 (s, 1H), 9.72 (s, 1H), 8.77 (d, J 8.9 Hz, 1H), 7.67-7.26 (m, 1H), 7.20 (dd, J 8.3, 6.6 Hz, 1H), 6.12-5.73 (m, 1H), 5.18 (d, J 8.1 Hz, 1H), 4.66-4.48 (m, 1H), 4.18 (dd, J 8.4, 6.3 Hz, 1H), 2.71-2.55 (m, 1H), 2.48 (s, 3H), 2.35-2.14 (m, 2H), 2.12-1.92 (m, 3H), 1.91-1.68 (m, 2H), 1.60-1.51 (m, 1H), 1.47-1.20 (m, 2H), 1.12 (d, J 7.1 Hz, 3H). LCMS (Method 4): $[M+H]^+$ m/z 609, RT 3.37 minutes.

Example 52

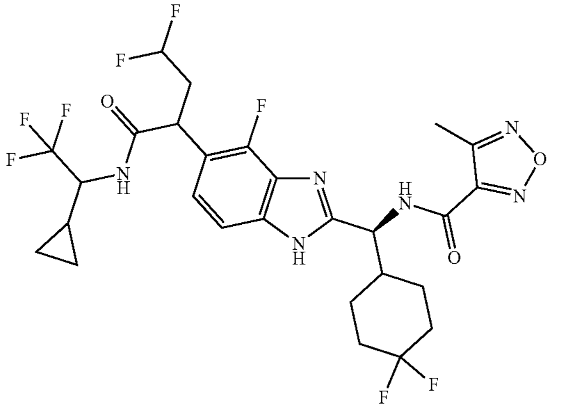 [SMILES: Cc1nonc1C(=O)N[C@H](c1nc2c(F)c(C(CC(F)F)C(=O)NC(C3CC3)C(F)(F)F)ccc2[nH]1)C1CCC(F)(F)CC1]

N—[(S)-(5-{1-[(1-Cyclopropyl-2,2,2-trifluoroethyl)carbamoyl]-3,3-difluoropropyl}-4-fluoro-1H-benzimidazol-2-yl)(4,4-difluorocyclohexyl)methyl]-4-methyl-1,2,5-oxadiazole-3-carboxamide To a stirred solution of 1-cyclopropyl-2,2,2-trifluoroethan-1-amine hydrochloride (45 mg, 0.26 mmol) and 2-chloro-1-methylpyridinium iodide (48 mg, 0.19 mmol) in DMA (1 mL) was added DIPEA (125 µL, 0.72 mmol), followed by the dropwise addition of a solution of Intermediate 107 (100 mg, 0.14 mmol) in DMA (1 mL). The reaction mixture was stirred at 50° C. for 18 h, then diluted with water (7 mL) and extracted with EtOAc (3×7 mL). The combined organic layers were dried over $MgSO_4$, filtered and concentrated in vacuo. The residue was separated by flash column chromatography, eluting with EtOAc/heptane (0-100% gradient). The relevant fractions were combined and concentrated in vacuo. The residue was further purified by acidic preparative HPLC (Method 21) to afford the title compound (57 mg, 61%) as a white solid. $\delta_H$ (400 MHz, DMSO-$d_6$) 12.63 (br s, 1H), 9.56 (br s, 1H), 8.72 (d, J 9.0 Hz, 1H), 7.43-7.12 (m, 1H), 7.12-6.98 (m, 1H), 6.08-5.65 (m, 1H), 5.08 (d, J 7.5 Hz, 1H), 4.22-4.09 (m, 1H), 3.99-3.79 (m, 1H), 3.61-2.97 (m, 1H, obs.), 2.65-2.45 (m, 1H), 2.37 (s, 3H), 2.27-1.81 (m, 4H), 1.81-1.58 (m, 2H), 1.50-1.40 (m, 1H), 1.38-1.24 (m, 1H), 1.24-1.10 (m, 1H), 1.04-0.79 (m, 1H), 0.55-0.33 (m, 2H), 0.26 to −0.06 (m, 2H). LCMS (Method 4): $[M+H]^+$ m/z 637, RT 3.68, 3.70 minutes (mixture of stereoisomers).

Example 53

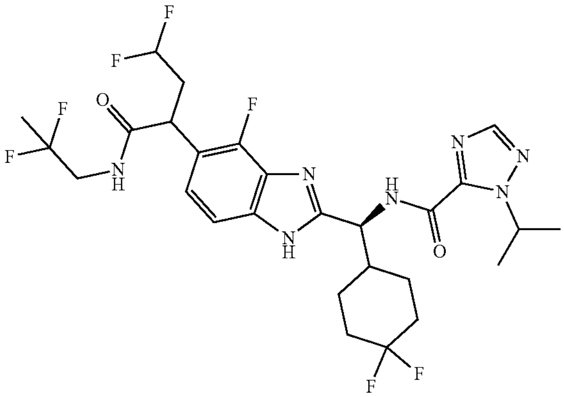 [SMILES: CC(C)n1ncnc1C(=O)N[C@H](c1nc2c(F)c(C(CC(F)F)C(=O)NCC(C)(F)F)ccc2[nH]1)C1CCC(F)(F)CC1]

N—[(S)-(4,4-Difluorocyclohexyl){5-[1-(2,2-difluoropropylcarbamoyl)-3,3-difluoropropyl]-4-fluoro-1H-benzimidazol-2-yl}methyl]-2-isopropyl-1,2,4-triazole-3-carboxamide DIPEA (79 μL, 0.46 mmol) was added to a stirred solution of lithium 2-isopropyl-1,2,4-triazole-3-carboxylate (27 mg, 0.17 mmol) and HATU in DMF (1 mL) at r.t. The material was stirred for 5 minutes, then Intermediate 112 (87 mg, 0.15 mmol) in DMF (1 mL) was added. The reaction mixture was stirred at r.t. for 18 h, then left standing at r.t. for 4 days. The mixture was diluted with EtOAc (20 mL) and quenched with saturated aqueous $NaHCO_3$ solution (20 mL), then the biphasic mixture was stirred at r.t. for 20 minutes. The layers were separated, and the aqueous phase was extracted with EtOAc (2×20 mL). The combined organic extracts were dried over $MgSO_4$, then filtered and concentrated in vacuo. The residue was purified by low pH HPLC to afford the title compound (mixture of stereoisomers) (20 mg, 21%) as an off-white solid. $\delta_H$ (500 MHz, DMSO-$d_6$) 13.21-12.49 (m, 1H), 9.18-8.92 (m, 1H), 8.53 (t, J 6.2 Hz, 1H), 8.13 (s, 1H), 7.52-7.24 (m, 1H), 7.25-7.15 (m, 1H), 6.13-5.79 (m, 1H), 5.60-5.46 (m, 1H), 5.16 (t, J 8.4 Hz, 1H), 4.25-4.14 (m, 1H), 3.62-3.39 (m, 2H), 2.71-2.55 (m, 1H), 2.32-2.11 (m, 2H), 2.10-1.88 (m, 3H), 1.88-1.68 (m, 2H), 1.58-1.18 (m, 12H). LCMS (Method 4): $[M+H]^+$ m/z 620, RT 3.36 minutes.

Examples 54 & 55

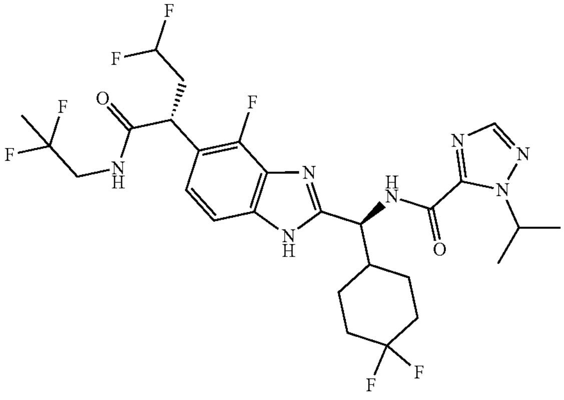

-continued

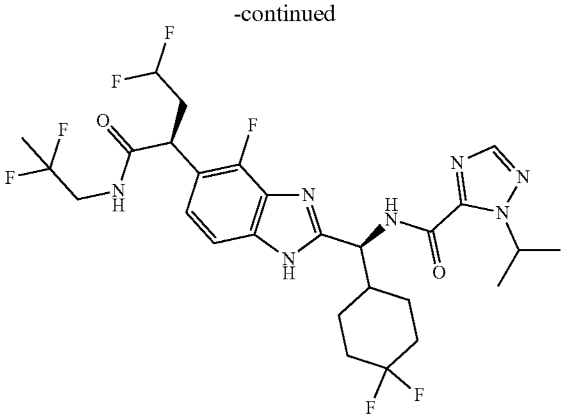

N—[(S)-(4,4-Difluorocyclohexyl){5-[(1R)-1-(2,2-difluoropropylcarbamoyl)-3,3-difluoropropyl]-4-fluoro-1H-benzimidazol-2-yl}methyl]-2-isopropyl-1,2,4-triazole-3-carboxamide N—[(S)-(4,4-Difluorocyclohexyl){5-[(1S)-1-(2,2-difluoropropylcarbamoyl)-3,3-difluoropropyl]-4-fluoro-1H-benzimidazol-2-yl}methyl]-2-isopropyl-1,2,4-triazole-3-carboxamide Example 53 (12 mg) was subjected to chiral purification (Method 29) to afford the title compounds (Peak 1, 5 mg, 41%; and Peak 2, 5 mg, 41%) as white solids.

Peak 1 (arbitrarily assigned R): NMR and LCMS retention times identical to those described for Example 53. Chiral LC (Method 30): RT 2.74 minutes, 95%.

Peak 2 (arbitrarily assigned S): NMR and LCMS retention times identical to those described for Example 53. Chiral LC (Method 30): RT 4.14 minutes, 98%.

Example 56

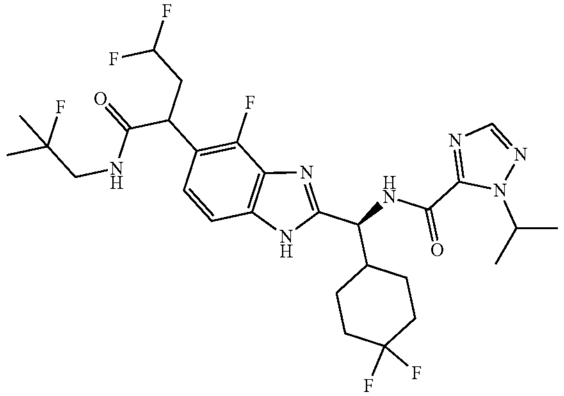 [SMILES: CC(C)n1ncnc1C(=O)N[C@H](c1nc2c(F)c(C(CC(F)F)C(=O)NCC(C)(C)F)ccc2[nH]1)C1CCC(F)(F)CC1]

N—[(S)-(4,4-Difluorocyclohexyl)(5-{3,3-difluoro-1-[(2-fluoro-2-methylpropyl)-carbamoyl]propyl}-4-fluoro-1H-benzimidazol-2-yl)methyl]-2-isopropyl-1,2,4-triazole-3-carboxamide To a stirred solution of Intermediate 114 (126 mg, 0.23 mmol) and 2-fluoro-2-methylpropan-1-amine hydrochloride (47 mg, 0.37 mmol) in DMF (2 mL) and DIPEA (0.12 mL, 0.69 mmol) was added HATU (114 mg, 0.29 mmol). The reaction mixture was stirred for 90 h, then partitioned between EtOAc (20 mL) and brine (20 mL). The layers were separated, and the aqueous layer was back-extracted with EtOAc (3×20 mL). The combined organic extracts were dried, filtered and concentrated in vacuo. Purification by flash chromatography (KP—NH, sample pre-adsorbed onto KP—NH silica and dry loaded), eluting with a 0-80% gradient of EtOAc/isohexane, yielded the title compound (25 mg, 18%) as a white solid. $\delta_H$ (400 MHz, DMSO-$d_6$) 12.74 (s, 1H), 9.06 (d, J 8.6 Hz, 1H), 8.30 (t, J 6.2 Hz, 1H), 8.13 (s, 1H), 7.38-7.24 (m, 1H), 7.18 (t, J 7.6 Hz, 1H), 5.94 (tt, J 56.6, 4.5 Hz, 1H), 5.55 (hept, J 6.6 Hz, 1H), 5.16 (t, J 8.2 Hz, 1H), 4.21 (dd, J 8.5, 6.3 Hz, 1H), 3.36-3.34 (m, 1H), 3.31-3.14 (m, 2H), 2.67-2.52 (m, 2H), 2.32-2.11 (m, 1H), 2.10-1.67 (m, 3H), 1.60-1.50 (m, 1H), 1.43 (d, J 6.6 Hz, 3H), 1.38 (d, J 6.6 Hz, 3H), 1.37-1.25 (m, 1H), 1.21 (d, J 21.4 Hz, 3H), 1.13 (d, J 21.4 Hz, 3H). LCMS (Method 8): $[M+H]^+$ m/z 616, RT 2.69 minutes.

Examples 57 & 58

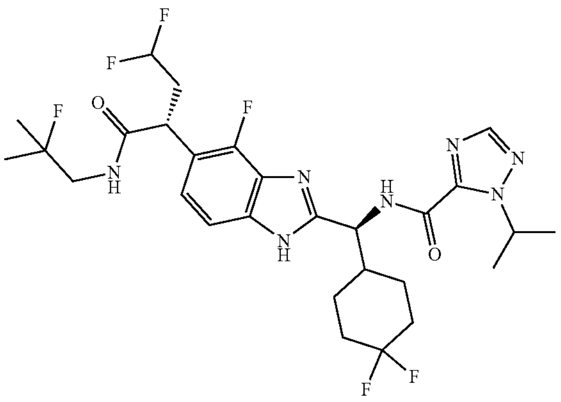

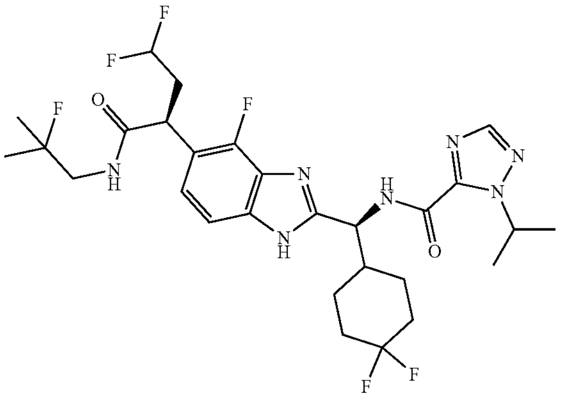

N—[(S)-(4,4-Difluorocyclohexyl)(5-{(1R)-3,3-difluoro-1-[(2-fluoro-2-methylpropyl)-carbamoyl]propyl}-4-fluoro-1H-benzimidazol-2-yl)methyl]-2-isopropyl-1,2,4-triazole-3-carboxamide N—[(S)-(4,4-Difluorocyclohexyl)(5-{(1S)-3,3-difluoro-1-[(2-fluoro-2-methylpropyl)-carbamoyl]propyl}-4-fluoro-1H-benzimidazol-2-yl)methyl]-2-isopropyl-1,2,4-triazole-3-carboxamide Example 56 (115 mg) was subjected to chiral purification (Method 31) to afford, after lyophilisation, the title compounds (Peak 1, 7 mg, 4.9%; and Peak 2, 13 mg, 9.1%) as white solids.

Peak 1 (arbitrarily assigned R): NMR and LCMS retention times identical to those described for Example 56. Chiral LC (Method 32): RT 4.33 minutes, 100%.

Peak 2 (arbitrarily assigned S): NMR and LCMS retention times identical to those described for Example 56. Chiral LC (Method 32): RT 4.79 minutes, 100%.

Example 59

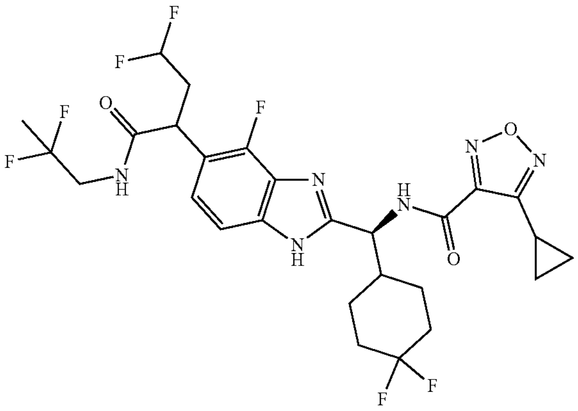 [SMILES: CC(F)(F)CNC(=O)C(CC(F)F)c1ccc2[nH]c([C@@H](NC(=O)c3nonc3C3CC3)C3CCC(F)(F)CC3)nc2c1F]

4-Cyclopropyl-N—[(S)-(4,4-difluorocyclohexyl){5-[1-(2,2-difluoropropylcarbamoyl)-3,3-difluoropropyl]-4-fluoro-1H-benzimidazol-2-yl}methyl]-1,2,5-oxadiazole-3-carboxamide DIPEA (79 μL, 0.455 mmol) was added to a stirred solution of 4-cyclopropyl-1,2,5-oxadiazole-3-carboxylic acid (29 mg, 0.169 mmol) and HATU (79 mg, 0.208 mmol) in DMF (1 mL) at r.t. The resulting mixture was stirred for 5 minutes then Intermediate 112 in DMF (1 mL) was added. The reaction mixture was stirred at r.t. for 18 h, then left standing at r.t. for 4 days. The mixture was diluted with EtOAc (20 mL), then quenched with saturated aqueous $NaHCO_3$ solution (20 mL). The biphasic mixture was stirred at r.t. for 20 minutes. The layers were separated, and the aqueous phase was extracted with EtOAc (2×20 mL). The combined organic extracts were dried over $MgSO_4$, then filtered and concentrated in vacuo. The residue was purified by low pH HPLC to afford the title compound (mixture of stereoisomers) (32 mg, 34%) as an off-white solid. $\delta_H$ (500 MHz, DMSO-$d_6$) 13.14-12.58 (m, 1H), 9.84-9.58 (m, 1H), 8.53 (t, J 6.3 Hz, 1H), 7.47-7.25 (m, 1H), 7.24-7.14 (m, 1H), 6.13-5.80 (m, 1H), 5.24-5.15 (m, 1H), 4.20 (dd, J 8.2, 6.5 Hz, 1H), 3.61-3.39 (m, 2H), 2.74-2.56 (m, 1H), 2.33-2.12

(m, 3H), 2.12-1.91 (m, 3H), 1.90-1.69 (m, 2H), 1.59-1.50 (m, 1H), 1.50-1.25 (m, 5H), 1.18-1.05 (m, 2H). LCMS (Method 4): $[M+H]^+$ m/z 619, RT 3.57 minutes.

Examples 60 & 61

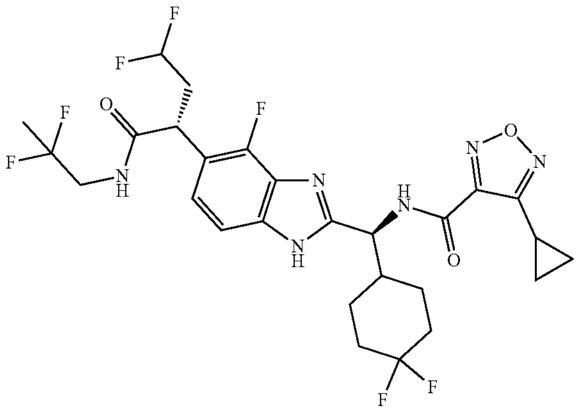

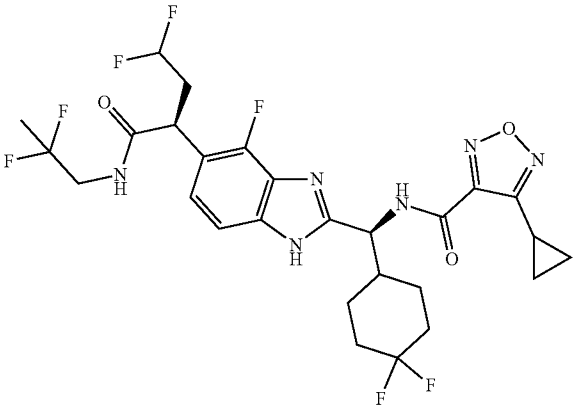

4-Cyclopropyl-N—[(S)-(4,4-difluorocyclohexyl){5-[(1R)-1-(2,2-difluoropropylcarbamoyl)-3,3-difluoropropyl]-4-fluoro-1H-benzimidazol-2-yl}methyl]-1,2,5-oxadiazole-3-carboxamide 4-Cyclopropyl-N—[(S)-(4,4-difluorocyclohexyl){5-[(1S)-1-(2,2-difluoropropylcarbamoyl)-3,3-difluoropropyl]-4-fluoro-1H-benzimidazol-2-yl}methyl]-1,2,5-oxadiazole-3-carboxamide Example 59 (30 mg) was subjected to chiral purification (Method 33) to afford the title compounds (Peak 1, 13 mg, 43%; and Peak 2, 12 mg, 40%) as white solids.

Peak 1 (arbitrarily assigned R): NMR and LCMS retention times identical to those described for Example 59. Chiral LC (Method 34): RT 1.70 minutes, 100%.

Peak 2 (arbitrarily assigned S): NMR and LCMS retention times identical to those described for Example 59. Chiral LC (Method 34): RT 2.55 minutes, 100%.

Example 62

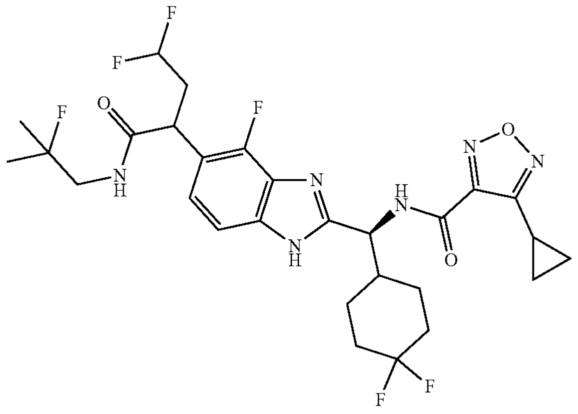 [SMILES: CC(C)(F)CNC(=O)C(CC(F)F)c1ccc2[nH]c([C@@H](NC(=O)c3nonc3C3CC3)C3CCC(F)(F)CC3)nc2c1F]

4-Cyclopropyl-N—[(S)-(4,4-difluorocyclohexyl)(4-fluoro-5-{3,3,3-trifluoro-1-[(2-fluoro-2-methylpropyl)carbamoyl]propyl}-1H-benzimidazol-2-yl)methyl]-1,2,5-oxadiazole-3-carboxamide DIPEA (46 µL, 0.27 mmol) was added to a solution of Intermediate 117 (50 mg, 0.09 mmol) and 4-cyclopropyl-1,2,5-oxadiazole-3-carboxylic acid (20 mg, 0.12 mmol) in DMF (0.5 mL), then HATU (40 mg, 0.11 mmol) in DMF (0.5 mL) was added. The reaction mixture was stirred at r.t. for 2.5 h, then diluted with saturated aqueous $NaHCO_3$ solution (2 mL) and water (2 mL). The aqueous mixture was extracted with EtOAc (5×2 mL). The combined organic layers were dried over $MgSO_4$ and filtered, then the solvent was concentrated in vacuo. Purification of the resulting brown oil by low pH HPLC gave the title compound (29 mg, 65%) as an off-white solid. $\delta_H$ (500 MHz, $CD_3OD$) 7.41-7.24 (m, 2H), 5.27 (d, J 8.7 Hz, 1H), 4.43 (dd, J 8.5, 5.2 Hz, 1H), 3.41 (dd, J 20.7, 14.1 Hz, 1H), 3.30-3.16 (m, 2H), 2.62-2.49 (m, 1H), 2.45-2.38 (m, 1H), 2.38-2.27 (m, 1H), 2.17-2.00 (m, 3H), 1.92-1.70 (m, 2H), 1.62-1.37 (m, 3H), 1.24 (d, J 21.1 Hz, 3H), 1.17-1.09 (m, 5H), 1.06-0.98 (m, 2H). Three exchangeable proton signals were not observed. LCMS (Method 4): $[M+H]^+$ m/z 633.3, RT 3.74 minutes.

Examples 63 & 64

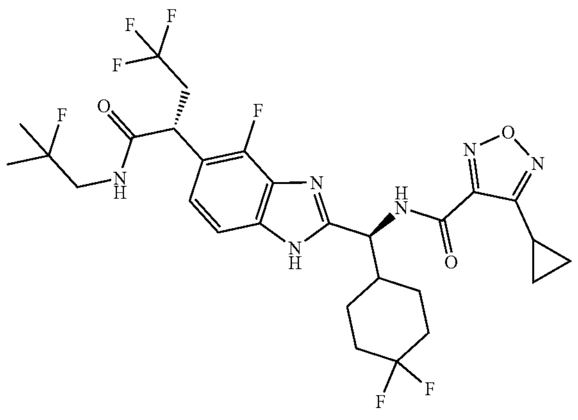

-continued

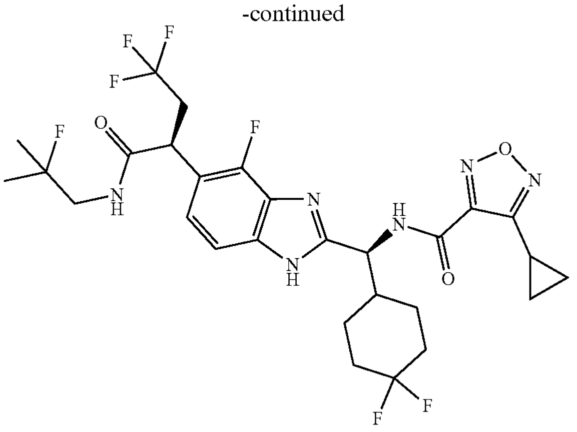

4-Cyclopropyl-N—[(S)-(4,4-difluorocyclohexyl)(4-fluoro-5-{(1R)-3,3,3-trifluoro-1-[(2-fluoro-2-methyl-propyl)carbamoyl]propyl}-1H-benzimidazol-2-yl) methyl]-1,2,5-oxadiazole-3-carboxamide 4-Cyclopropyl-N—[(S)-(4,4-difluorocyclohexyl)(4-fluoro-5-{(1S)-3,3,3-trifluoro-1-[(2-fluoro-2-methyl-propyl)carbamoyl]propyl}-1H-benzimidazol-2-yl) methyl]-1,2,5-oxadiazole-3-carboxamide Example 62 (27 mg) was subjected to chiral purification (Method 35) to afford the title compounds (Peak 1, 6 mg, 22%; and Peak 2, 6 mg, 22%) as white solids.

Peak 1 (arbitrarily assigned R): NMR and LCMS retention times identical to those described for Example 62. Chiral LC (Method 36): RT 5.87 minutes, 100%.

Peak 2 (arbitrarily assigned S): NMR and LCMS retention times identical to those described for Example 62. Chiral LC (Method 36): RT 8.06 minutes, 100%.

Example 65

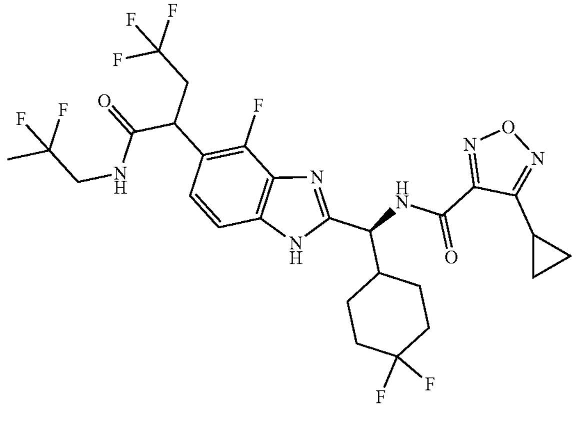 [SMILES: CC(F)(F)CNC(=O)C(CC(F)(F)F)c1ccc2[nH]c([C@@H](NC(=O)c3nonc3C3CC3)C3CCC(F)(F)CC3)nc2c1F]

4-Cyclopropyl-N—[(S)-(4,4-difluorocyclohexyl){5-[1-(2,2-difluoropropylcarbamoyl)-3,3,3-trifluoropropyl]-4-fluoro-1H-benzimidazol-2-yl}methyl]-1,2,5-oxadiazole-3-carboxamide To a stirred solution of DIPEA (38 µL, 0.218 mmol) was added a solution of Intermediate 119 (40 mg, 0.07 mmol) and 4-cyclopropyl-1,2,5-oxadiazole-3-carboxylic acid (16 mg, 0.09 mmol) in DMF (0.4 mL), then HATU (33 mg, 0.09 mmol) in DMF (0.4 mL) was added. The reaction mixture was stirred at r.t. for 2.5 h, then diluted with saturated aqueous $NaHCO_3$ solution (2 mL) and water (2 mL). The aqueous mixture was extracted with EtOAc (5×2 mL). The combined organic layers were dried over $MgSO_4$ and filtered, then the solvent was concentrated in vacuo. The resulting brown oil was purified by low pH HPLC to give the title compound (34 mg, 80%) as an off-white solid. $\delta_H$ (500 MHz, $CD_3OD$) 7.38-7.27 (m, 2H), 5.26 (d, J 8.7 Hz, 1H), 4.41 (dd, J 8.4, 5.3 Hz, 1H), 3.65-3.46 (m, 2H), 3.26-3.14 (m, 1H), 2.62-2.50 (m, 1H), 2.45-2.39 (m, 1H), 2.37-2.28 (m, 1H), 2.18-1.99 (m, 3H), 1.92-1.70 (m, 2H), 1.62-1.49 (m, 2H), 1.48-1.35 (m, 4H), 1.18-1.07 (m, 2H), 1.07-0.98 (m, 2H). Three exchangeable proton signals were not observed. LCMS (Method 4): $[M+H]^+$ m/z 637.3, RT 3.71 minutes.

Examples 66 & 67

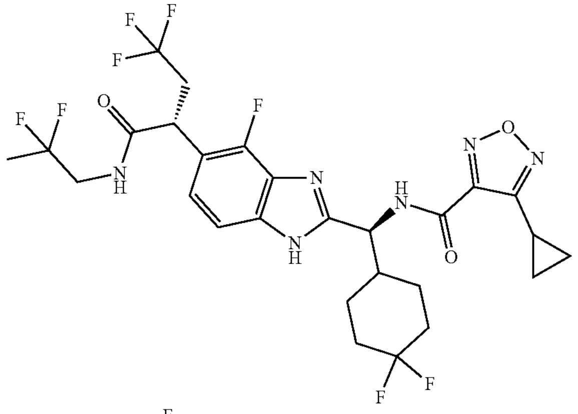

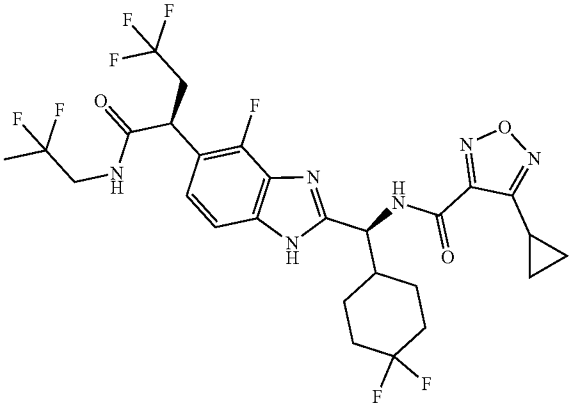

4-Cyclopropyl-N—[(S)-(4,4-difluorocyclohexyl){5-[(1R)-1-(2,2-difluoropropylcarbamoyl)-3,3,3-trifluoropropyl]-4-fluoro-1H-benzimidazol-2-yl}methyl]-1,2,5-oxadiazole-3-carboxamide 4-Cyclopropyl-N—[(S)-(4,4-difluorocyclohexyl){5-[(1S)-1-(2,2-difluoropropylcarbamoyl)-3,3,3-trifluoropropyl]-4-fluoro-1H-benzimidazol-2-yl}methyl]-1,2,5-oxadiazole-3-carboxamide Example 65 (28 mg) was subjected to chiral purification (Method 37) to afford the title compounds (Peak 1, 10 mg, 35%; and Peak 2, 10 mg, 35%) as white solids.

Peak 1 (arbitrarily assigned R): NMR and LCMS retention times identical to those described for Example 65. Chiral LC (Method 38): RT 2.53 minutes, 100%.

Peak 2 (arbitrarily assigned S): NMR and LCMS retention times identical to those described for Example 65. Chiral LC (Method 38): RT 4.09 minutes, 98%.

Example 68

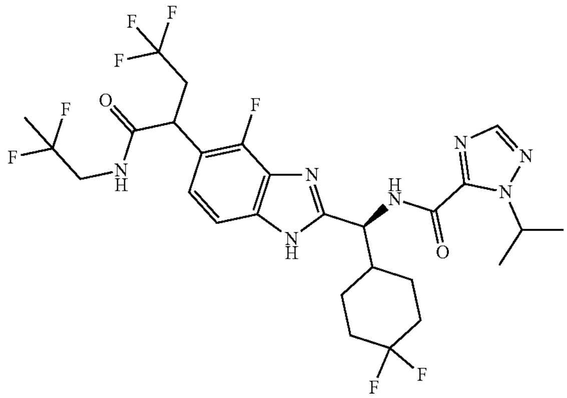 [SMILES: CC(C)n1ncnc1C(=O)N[C@H](c1nc2c(F)c(C(CC(F)(F)F)C(=O)NCC(C)(F)F)ccc2[nH]1)C1CCC(F)(F)CC1]

N—[(S)-(4,4-Difluorocyclohexyl){5-[1-(2,2-difluoropropylcarbamoyl)-3,3,3-trifluoro-propyl]-4-fluoro-1H-benzimidazol-2-yl}methyl]-2-isopropyl-1,2,4-triazole-3-carboxamide DIPEA (299 μL, 1.71 mmol) was added to a solution of Intermediate 119 (470 mg, 0.86 mmol) and lithium 2-isopropyl-1,2,4-triazole-3-carboxylate (151 mg, 0.94 mmol) in DMF (5 mL), then HATU (390 mg, 1.03 mmol) in DMF (5 mL) was added. The reaction mixture was stirred at r.t. for 18 h, then concentrated in vacuo. The resulting brown oil was partitioned between EtOAc (50 mL) and saturated aqueous $NaHCO_3$ solution (10 mL). The aqueous layer was extracted with EtOAc (20 mL). The combined organic layers were dried over $MgSO_4$ and filtered, then the solvent was concentrated in vacuo. The resulting orange/brown viscous oil (0.82 g) was purified by flash column chromatography (Biotage Isolera, Sfar HC 25 g, eluting with a gradient of 0-3% MeOH-DCM), followed by further flash column chromatography (Biotage Isolera, Sfar Amino Duo 28 g, eluting with a gradient of 0-100% EtOAc-heptane), then further purified by low pH HPLC, to afford the title compound (mixture of diastereomers) (327 mg, 56%) as a cream solid. $\delta_H$ (400 MHz, $CD_3OD$) 7.98 (s, 1H), 7.39-7.24 (m, 2H), 5.69-5.55 (m, 1H), 5.24 (d, J 8.3 Hz, 1H), 4.40 (dd, J 8.4, 5.3 Hz, 1H), 3.67-3.43 (m, 2H), 3.28-3.15 (m, 1H), 2.62-2.48 (m, 1H), 2.34-2.23 (m, 1H), 2.16-1.98 (m, 3H), 1.92-1.69 (m, 2H), 1.58 (s, 1H), 1.53-1.37 (m, 11H). Three exchangeable proton signals were not observed. LCMS (Method 8): $[M+H]^+$ m/z 636.4, RT 1.99 minutes.

Examples 69 & 70

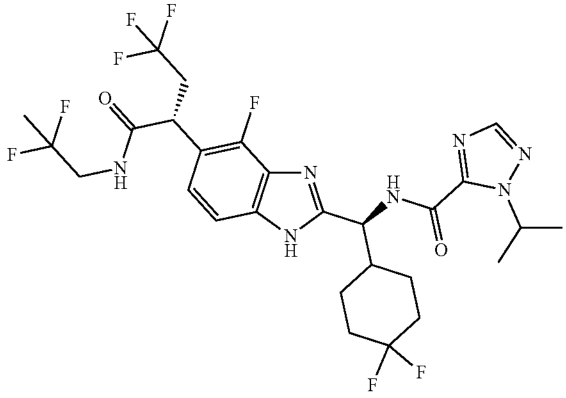

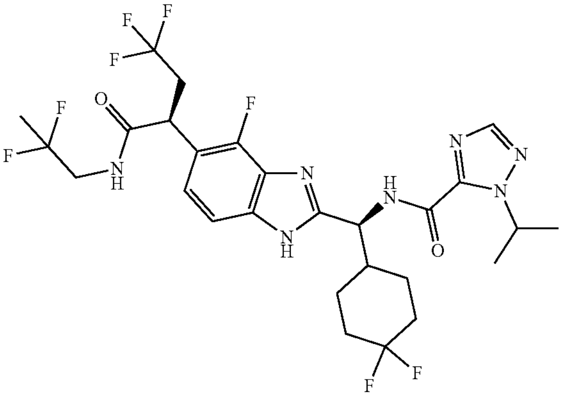

N—[(S)-(4,4-Difluorocyclohexyl){5-[(1S)-1-(2,2-difluoropropylcarbamoyl)-3,3,3-trifluoro-propyl]-4-fluoro-1H-benzimidazol-2-yl}methyl]-2-isopropyl-1,2,4-triazole-3-carboxamide N—[(S)-(4,4-Difluorocyclohexyl){5-[(1R)-1-(2,2-difluoropropylcarbamoyl)-3,3,3-trifluoro-propyl]-4-fluoro-1H-benzimidazol-2-yl}methyl]-2-isopropyl-1,2,4-triazole-3-carboxamide Example 68 (325 mg) was subjected to chiral purification (Method 25) to afford the title compounds (Peak 1, 90 mg, 27%; and Peak 2, 90 mg, 27%) as white solids.

Peak 1 (arbitrarily assigned R): NMR and LCMS retention times identical to those described for Example 68. Chiral LC (Method 26): RT 3.27 minutes, 100%.

Peak 2 (arbitrarily assigned S): NMR and LCMS retention times identical to those described for Example 68. Chiral LC (Method 26): RT 3.72 minutes, 99%.

Example 71

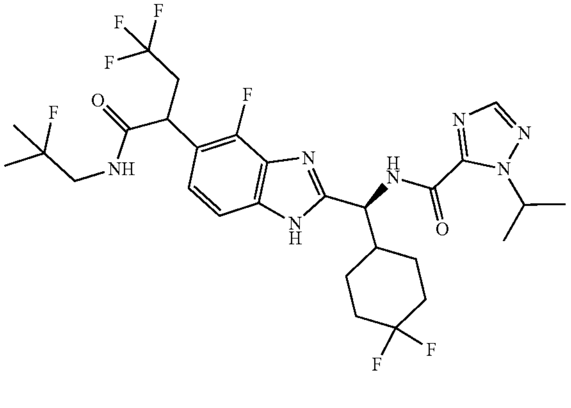 [SMILES: CC(C)n1ncnc1C(=O)N[C@H](c1nc2c(F)c(C(CC(F)(F)F)C(=O)NCC(C)(C)F)ccc2[nH]1)C1CCC(F)(F)CC1]

N—[(S)-(4,4-Difluorocyclohexyl)(4-fluoro-5-{3,3,3-trifluoro-1-[(2-fluoro-2-methyl-propyl)carbamoyl]propyl}-1H-benzimidazol-2-yl)methyl]-2-isopropyl-1,2,4-triazole-3-carboxamide DIPEA (290 μL, 1.66 mmol) was added to a stirred solution of Intermediate 117 (470 mg, 0.83 mmol) and lithium 2-isopropyl-1,2,4-triazole-3-carboxylate (160 mg, 0.99 mmol) in DMF (5 mL), then HATU (410 mg, 1.08 mmol) in DMF (5 mL) was added. The reaction mixture was stirred at r.t. for 18 h, then concentrated in vacuo. The resulting brown oil was partitioned between EtOAc (50 mL) and saturated aqueous $NaHCO_3$ solution (10 mL). The aqueous layer was extracted with EtOAc (20 mL). The combined organic layers were dried over $MgSO_4$ and filtered, then the solvent was concentrated in vacuo. The resulting orange/brown viscous oil was purified by flash column chromatography (Biotage Isolera, Sfar HC 25 g, eluting with a gradient of 0-3% MeOH-DCM), followed by further flash column chromatography (Biotage Isolera, Sfar Amino Duo 28 g, eluting with a gradient of 0-100% EtOAc-heptane), then further purified by low pH HPLC, to give the title compound (mixture of diastereomers) (294 mg, 53%) as a cream solid. $\delta_H$ (400 MHz, $CD_3OD$) 8.00-7.95 (m, 1H), 7.46-7.21 (m, 2H), 5.69-5.56 (m, 1H), 5.24 (d, J 8.4 Hz, 1H), 4.42 (dd, J 8.5, 5.1 Hz, 1H), 3.46-3.36 (m, 1H), 3.28-3.15 (m, 2H), 2.63-2.48 (m, 1H), 2.35-2.22 (m, 1H), 2.17-1.95 (m, 3H), 1.93-1.69 (m, 2H), 1.63-1.55 (m, 1H), 1.53-1.36 (m, 8H), 1.24 (dd, J 21.1, 1.1 Hz, 3H), 1.13 (dd, J 21.1, 2.4 Hz, 3H). Three exchangeable proton signals were not observed. LCMS (Method 8): $[M+H]^+$ m/z 632.4, RT 2.00 minutes.

Examples 72 & 73

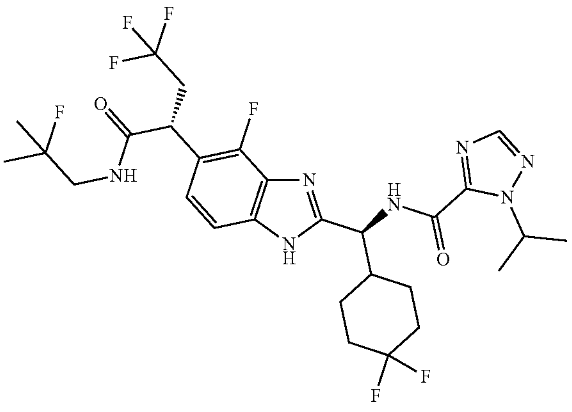

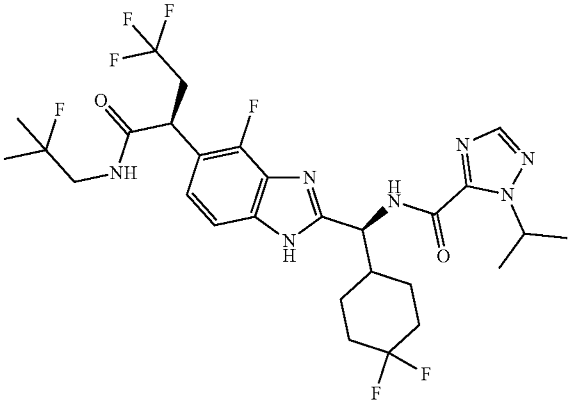

N—[(S)-(4,4-Difluorocyclohexyl)(4-fluoro-5-{(1R)-3,3,3-trifluoro-1-[(2-fluoro-2-methyl-propyl)carbamoyl]propyl}-1H-benzimidazol-2-yl)methyl]-2-isopropyl-1,2,4-triazole-3-carboxamide N—[(S)-(4,4-Difluorocyclohexyl)(4-fluoro-5-{(1S)-3,3,3-trifluoro-1-[(2-fluoro-2-methyl-propyl)carbamoyl]propyl}-1H-benzimidazol-2-yl)methyl]-2-isopropyl-1,2,4-triazole-3-carboxamide Example 71 (292 mg) was subjected to chiral purification (Method 25) to afford the title compounds (Peak 1, 95 mg, 33%; and Peak 2, 92 mg, 32%) as white solids.

Peak 1 (arbitrarily assigned R): NMR and LCMS retention times identical to those described for Example 71. Chiral LC (Method 26): RT 4.03 minutes, 100%.

Peak 2 (arbitrarily assigned S): NMR and LCMS retention times identical to those described for Example 71. Chiral LC (Method 26): RT 4.45 minutes, 99.7%.

Example 74

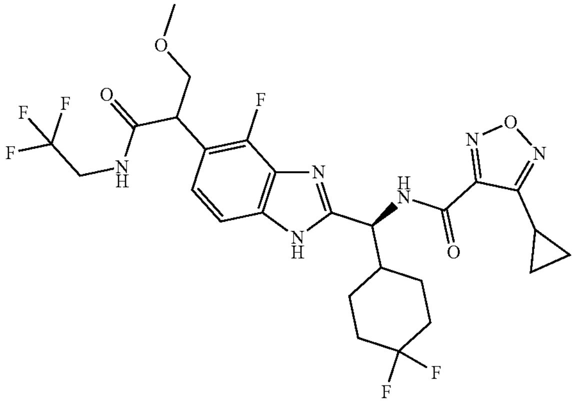

4-Cyclopropyl-N—[(S)-(4,4-difluorocyclohexyl){4-fluoro-5-[1-(methoxymethyl)-2-oxo-2-(2,2,2-trifluoroethylamino)ethyl]-1H-benzimidazol-2-yl}methyl]-1,2,5-oxadiazole-3-carboxamide To a stirred solution of Intermediate 126 (50 mg, 0.11 mmol) and 4-cyclopropyl-1,2,5-oxadiazole-3-carboxylic acid (18 mg, 0.12 mmol) in DMF (1.5 mL) was added HATU (49 mg, 0.13 mmol), followed by DIPEA (39 μL, 0.23 mmol). The reaction mixture was stirred under an atmosphere of nitrogen at r.t. for 1.5 h, then partitioned between EtOAc (10 mL) and water (10 mL), and stirred for 10 minutes. The layers were separated, and the aqueous layer was further extracted with EtOAc (10 mL). The combined organic extracts were washed with saturated aqueous $NH_4Cl$ solution (5 mL), water (5 mL), saturated aqueous $NaHCO_3$ solution (5 mL) and brine (5 mL), then dried over $MgSO_4$, filtered and concentrated. The crude material (130 mg) was purified by flash column chromatography (Isolera 4, Sfar Duo 10 g), eluting with a 0-100% gradient of EtOAc in heptane, to afford the title compound (32 mg, 44%) as a white solid. $\delta_H$ (400 MHz, DMSO-$d_6$) 12.80 (s, 1H), 9.71 (s, 1H), 8.76 (t, J 6.4 Hz, 1H), 7.38-7.25 (m, 1H), 7.24-7.16 (m, 1H), 5.19 (d, J 7.7 Hz, 1H), 4.26 (dd, J 8.7, 5.8 Hz, 1H), 4.04-3.74 (m, 3H), 3.54-3.44 (m, 1H), 3.24 (s, 3H), 2.32-2.22 (m, 2H), 2.13-1.90 (m, 3H), 1.90-1.69 (m, 2H), 1.60-1.49 (m, 1H), 1.47-1.33 (m, 1H), 1.33-1.20 (m, 1H), 1.16-1.07 (m, 2H), 1.00-0.93 (m, 2H). LCMS (Method 4): $[M+H]^+$ m/z 603, RT 3.41 minutes.

Examples 75 & 76

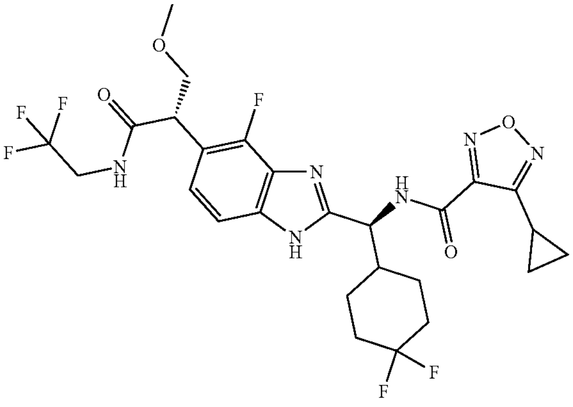 [SMILES: COCC(C(=O)NCC(F)(F)F)c1ccc2[nH]c([C@@H](NC(=O)c3nonc3C3CC3)C3CCC(F)(F)CC3)nc2c1F]

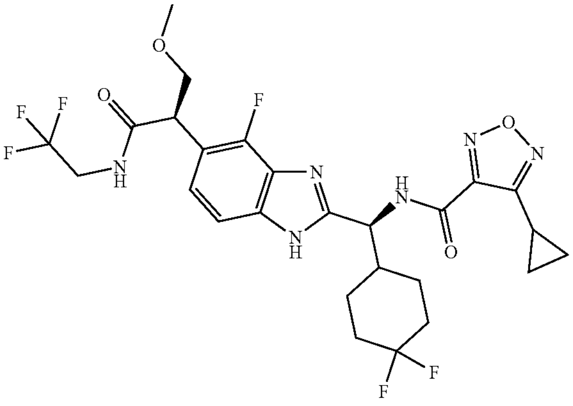

4-Cyclopropyl-N—[(S)-(4,4-difluorocyclohexyl){4-fluoro-5-[(1S)-1-(methoxymethyl)-2-oxo-2-(2,2,2-trifluoroethylamino)ethyl]-1H-benzimidazol-2-yl}methyl]-1,2,5-oxadiazole-3-carboxamide 4-Cyclopropyl-N—[(S)-(4,4-difluorocyclohexyl){4-fluoro-5-[(1R)-1-(methoxymethyl)-2-oxo-2-(2,2,2-trifluoroethylamino)ethyl]-1H-benzimidazol-2-yl}methyl]-1,2,5-oxadiazole-3-carboxamide Example 74 (25 mg) was subjected to chiral purification (Method 33) to afford the title compounds (Peak 1, 8 mg, 32%; and Peak 2, 7 mg, 28%) as white solids.

Peak 1 (arbitrarily assigned R): NMR and LCMS retention times identical to those described for Example 74. Chiral LC (Method 34): RT 4.38 minutes, 100% d.e.

Peak 2 (arbitrarily assigned S): NMR and LCMS retention times identical to those described for Example 74. Chiral LC (Method 34): RT 21.68 minutes, 100% d.e.

Example 77

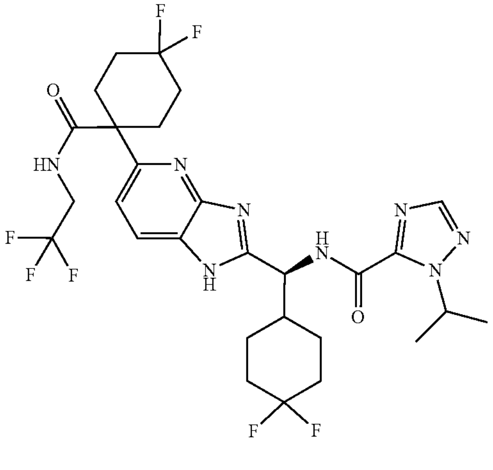 [SMILES: CC(C)n1ncnc1C(=O)N[C@H](c1nc2nc(C3(C(=O)NCC(F)(F)F)CCC(F)(F)CC3)ccc2[nH]1)C1CCC(F)(F)CC1]

N—[(S)-(4,4-Difluorocyclohexyl){5-[4,4-difluoro-1-(2,2,2-trifluoroethylcarbamoyl)-cyclohexyl]-1H-imidazo[4,5-b]pyridin-2-yl}methyl]-2-isopropyl-1,2,4-triazole-3-carboxamide Intermediate 127 (1.2 g, 2.4 mmol) and lithium 2-isopropyl-1,2,4-triazole-3-carboxylate (0.42 g, 2.5 mmol) were suspended in DMF (9.4 mL), then HATU (1.1 g, 2.8 mmol) was added portionwise. The reaction mixture was stirred at r.t. for 1 h, then partitioned between EtOAc and water. The organic portion was dried over $Na_2SO_4$, then filtered and concentrated in vacuo. The crude material was purified on silica gel (eluting with a gradient of 0-100% EtOAc in isohexanes). The resulting white solid was triturated with diethyl ether to give the title compound (96% purity) (0.71 g, 46%). $\delta_H$ (400 MHz, DMSO-$d_6$) 13.44-12.09 (m, 1H), 9.28-8.83 (m, 1H), 8.30-8.20 (m, 1H), 8.14 (s, 1H), 8.06-7.88 (m, 1H), 7.22 (d, J 8.4 Hz, 1H), 5.55 (hept, J 6.6 Hz, 1H), 5.25-5.13 (m, 1H), 4.04-3.68 (m, 2H), 2.48-2.43 (m, 2H), 2.37-2.14 (m, 3H), 2.16-1.66 (m, 9H), 1.67-1.53 (m, 1H), 1.43 (d, J 6.6 Hz, 3H), 1.39 (d, J 6.6 Hz, 3H), 1.37-1.18 (m, 2H). LCMS (Method 8): $[M+H]^+$ m/z 647, RT 2.37 minutes.

Example 78

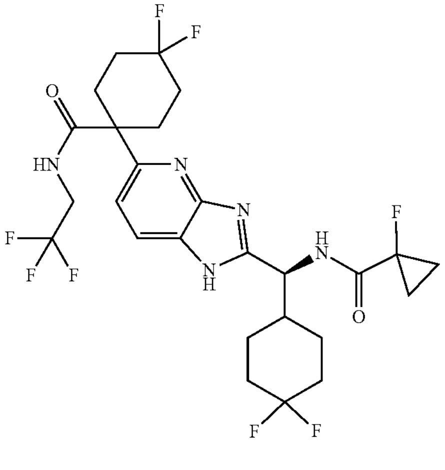 [SMILES: O=C(N[C@H](c1nc2nc(C3(C(=O)NCC(F)(F)F)CCC(F)(F)CC3)ccc2[nH]1)C1CCC(F)(F)CC1)C1(F)CC1]

1-(2-{(S)-(4,4-Difluorocyclohexyl)[(1-fluorocyclopropanecarbonyl)amino]methyl}-1H-imidazo[4,5-b]pyridin-5-yl)-4,4-difluoro-N-(2,2,2-trifluoroethyl)cyclohexanecarboxamide HATU (21.2 mg, 0.0541 mmol) was added to a solution of Intermediate 127 (25.0 mg, 0.0491 mmol) and 1-fluorocyclopropanecarboxylic acid (5.7 mg, 0.054 mmol) in DMF (0.25 mL), then DIPEA (0.026 mL, 0.15 mmol) was added. The reaction mixture was stirred at r.t. for 5 h, then purified by preparative basic reverse-phase HPLC and freeze-dried, to afford the title compound (12.5 mg, 43%) as a white solid. $\delta_H$ (400 MHz, DMSO-$d_6$) 12.82 (br s, 1H), 8.57 (br s, 1H), 8.20 (t, J 6.3 Hz, 1H), 7.88 (br s, 1H), 7.14 (br s, 1H), 5.03 (t, J 8.2 Hz, 1H), 3.84 (td, J 9.8, 6.3 Hz, 2H), 2.49-2.41 (obs. m, 2H), 2.32-2.13 (m, 3H), 2.11-1.65 (m, 9H), 1.60-1.47 (m, 1H), 1.42-1.11 (m, 6H). LCMS (Method 8): $[M+H]^+$ m/z 596, RT 1.90 minutes.

Example 79

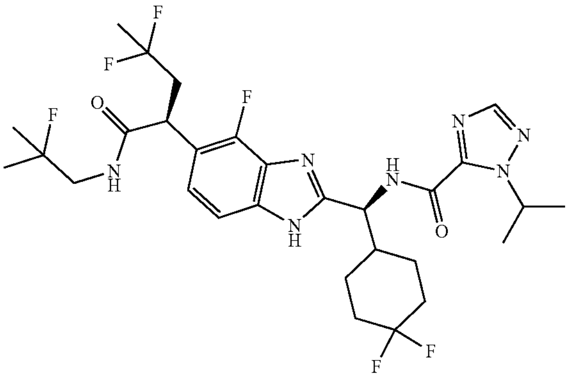 [SMILES: CC(C)n1ncnc1C(=O)N[C@H](c1nc2c(F)c([C@H](CC(C)(F)F)C(=O)NCC(C)(C)F)ccc2[nH]1)C1CCC(F)(F)CC1]

N—[(S)-(4,4-Difluorocyclohexyl)(5-{(1S)-3,3-difluoro-1-[(2-fluoro-2-methylpropyl)-carbamoyl]butyl}-4-fluoro-1H-benzimidazol-2-yl)methyl]-2-isopropyl-1,2,4-triazole-3-carboxamide Intermediate 138 (35 mg, 0.07 mmol) and lithium 2-isopropyl-1,2,4-triazole-3-carboxylate (15 mg, 0.084 mmol) were suspended in DCM (2 mL), and DIPEA (0.04 mL, 0.2 mmol) was added. After 2 minutes, HATU (35 mg, 0.09 mmol) was added. The reaction mixture was vigorously stirred at r.t. for 1 h, then diluted with DCM (10 mL) and washed with water (10 mL). The aqueous layer was extracted with DCM (10 mL). The combined organic phases were passed through a hydrophobic frit and evaporated in vacuo. The resulting off-white solid was purified by preparative HPLC to afford the title compound (15 mg, 33%) as a white solid. $\delta_H$ (300 MHz, DMSO-$d_6$) 12.50 (s, 1H), 9.09 (s, 1H), 8.32 (t, J 6.2 Hz, 1H), 8.13 (s, 1H), 7.29-7.18 (m, 1H), 5.54 (p, J 6.6 Hz, 1H), 5.18 (t, J 8.5 Hz, 1H), 4.29 (dd, J 8.7, 4.4 Hz, 1H), 3.26 (dd, J 6.1, 2.0 Hz, 1H), 3.23-3.15 (m, 1H), 2.98-2.73 (m, 1H), 2.43-1.76 (m, 7H), 1.60 (t, J 19.0 Hz, 5H), 1.50-1.27 (m, 3H), 1.42 (d, J 6.6 Hz, 3H), 1.38 (d, J 6.6 Hz, 3H), 1.21 (d, J 21.4 Hz, 3H), 1.12 (d, J 21.4 Hz, 3H). LCMS (Method 8): $[M+H]^+$ m/z 630.4, RT 1.96 minutes.

Example 80

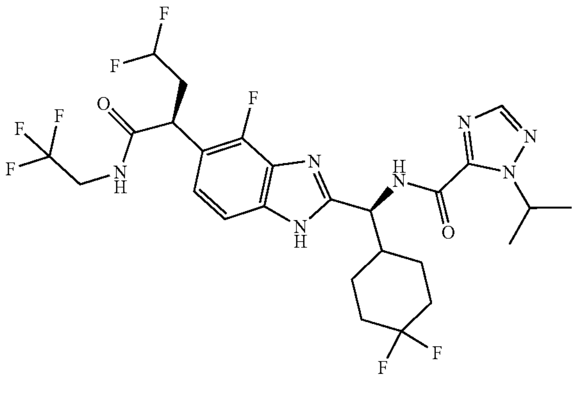 [SMILES: CC(C)n1ncnc1C(=O)N[C@H](c1nc2c(F)c([C@H](CC(F)F)C(=O)NCC(F)(F)F)ccc2[nH]1)C1CCC(F)(F)CC1]

N—[(S)-(4,4-Difluorocyclohexyl){5-[(1S)-3,3-difluoro-1-(2,2,2-trifluoroethylcarbamoyl)-propyl]-4-fluoro-1H-benzimidazol-2-yl}methyl]-2-isopropyl-1,2,4-triazole-3-carboxamide HATU (187 mg, 0.49 mmol) was added to a solution of Intermediate 146 (190 mg, 0.39 mmol) and lithium 2-isopropyl-1,2,4-triazole-3-carboxylate (72 mg, 0.43 mmol) in DMF (2 mL), then DIPEA (0.028 mL, 0.16 mmol) was added. The reaction mixture was stirred at r.t. for 48 h, then diluted with water. The white solid that precipitated was collected by filtration, then purified by preparative basic reverse-phase HPLC and freeze-dried, to afford the title compound (100 mg, 33%) as a white solid. $\delta_H$ (400 MHz, DMSO-$d_6$) 12.74 (br s, 1H), 9.09 (d, J 9.3 Hz, 1H), 8.75 (t, J 6.3 Hz, 1H), 8.13 (s, 1H), 7.33 (d, J 8.9 Hz, 1H), 7.16 (dd, J 8.4, 6.4 Hz, 1H), 5.97 (t, J 4.5 Hz, 1H), 5.53 (h, J 6.6 Hz, 1H), 5.17 (t, J 8.5 Hz, 1H), 4.20 (dd, J 8.2, 6.4 Hz, 1H), 3.86 (m, 2H), 2.62 (ddt, J 15.1, 11.0, 5.2 Hz, 1H), 2.23 (ddd, J 20.5, 13.4, 6.8 Hz, 2H), 2.12-1.64 (m, 4H), 1.54-1.20 (m, 10H). LCMS (Method 8): $[M+H]^+$ m/z 624, RT 2.25 minutes.

Example 81

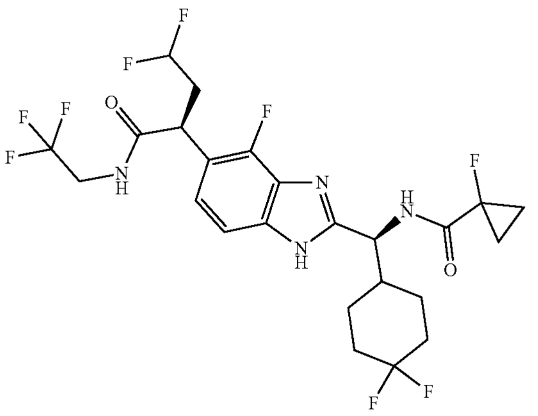 [SMILES: O=C(NCC(F)(F)F)[C@@H](CC(F)F)c1ccc2[nH]c([C@@H](NC(=O)C3(F)CC3)C3CCC(F)(F)CC3)nc2c1F]

N—[(S)-(4,4-Difluorocyclohexyl){5-[(1S)-3,3-difluoro-1-(2,2,2-trifluoroethylcarbamoyl)-propyl]-4-fluoro-1H-benzimidazol-2-yl}methyl]-1-fluorocyclopropanecarboxamide HATU (22.9 mg, 0.0584 mmol) was added to a solution of Intermediate 146 (25.8 mg, 0.05 mmol) and 1-fluorocyclopropanecarboxylic acid (6.1 mg, 0.06 mmol) in DMF (0.27 mL), then DIPEA (0.028 mL, 0.16 mmol) was added. The reaction mixture was stirred at r.t. for 5 h, then purified by preparative basic reverse-phase HPLC and freeze-dried, to afford the title compound (observed as a 0.8:0.2 ratio of two "tautomers" in the NMR spectrum) (10.6 mg, 35%) as a white solid. $\delta_H$ (400 MHz, DMSO-$d_6$) 12.96 (s, 0.2H), 12.65 (s, 0.8H), 8.86-8.70 (m, 1.8H), 8.66 (s, 0.2H), 7.45-7.36 (m, 0.2H), 7.30 (d, J 8.4 Hz, 0.8H), 7.16 (t, J 7.4 Hz, 1H), 5.97 (tt, J 56.4, 4.4 Hz, 1H), 5.04 (t, J 8.6 Hz, 1H), 4.24-4.15 (m, 1H), 3.98-3.76 (m, 2H), 2.73-2.54 (m, 1H), 2.31-2.12 (m, 2H), 2.12-1.89 (m, 3H), 1.89-1.66 (m, 2H), 1.49-1.10 (m, 7H). LCMS (Method 8): $[M+H]^+$ m/z 573, RT 1.80 minutes.

Example 82

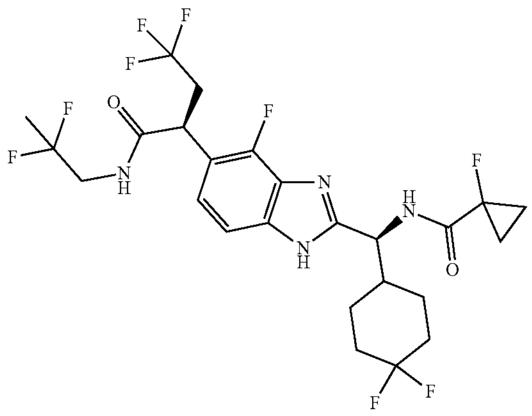 [SMILES: CC(F)(F)CNC(=O)[C@@H](CC(F)(F)F)c1ccc2[nH]c([C@@H](NC(=O)C3(F)CC3)C3CCC(F)(F)CC3)nc2c1F]

N—[(S)-(4,4-Difluorocyclohexyl){5-[1-(2,2-difluoropropylcarbamoyl)-3,3,3-trifluoro-propyl]-4-fluoro-1H-benzimidazol-2-yl}methyl]-1-fluorocyclopropanecarboxamide Into a vial were introduced Intermediate 119 (100 mg, 0.18 mmol), 1-fluoro-cyclopropane-1-carboxylic acid (23 mg, 0.22 mmol), DIPEA (0.06 mL, 0.36 mmol) and DMF (2 mL) at r.t. under $N_2$, followed by HATU (83 mg, 0.22 mmol). The reaction mixture was stirred for 1 h, then diluted with EtOAc (8 mL) and washed sequentially with water (2 mL) and brine (2 mL). The combined organic layers were dried over $MgSO_4$, filtered and concentrated in vacuo. The crude residue was purified by HPLC to give the title compound (81 mg, 74%) as a white solid. $\delta_H$ (500 MHz, DMSO-$d_6$) 13.13-12.52 (m, 1H), 8.84-8.70 (m, 1H), 8.63 (q, J 6.2 Hz, 1H), 7.44-7.25 (m, 1H), 7.25-7.16 (m, 1H), 5.04 (t, J 8.6 Hz, 1H), 4.36-4.27 (m, 1H), 3.55-3.45 (m, 2H), 3.16-3.06 (m, 1H), 2.68-2.56 (m, 1H), 2.29-2.17 (m, 1H), 2.10-2.01 (m, 1H), 2.01-1.89 (m, 2H), 1.87-1.65 (m, 2H), 1.51-1.38 (m, 4H), 1.38-1.11 (m, 6H). LCMS (Method 4): $[M+H]^+$ 587.2, RT 3.29 minutes.

Examples 83 & 84

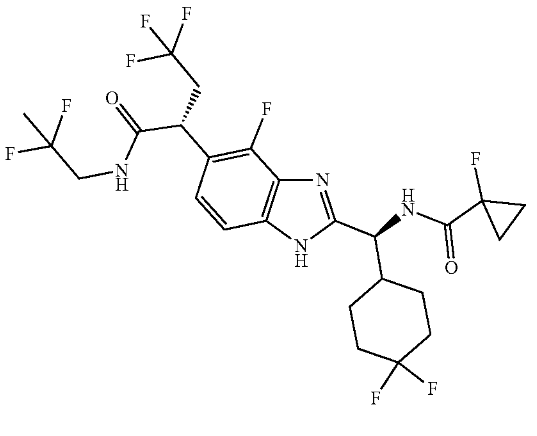

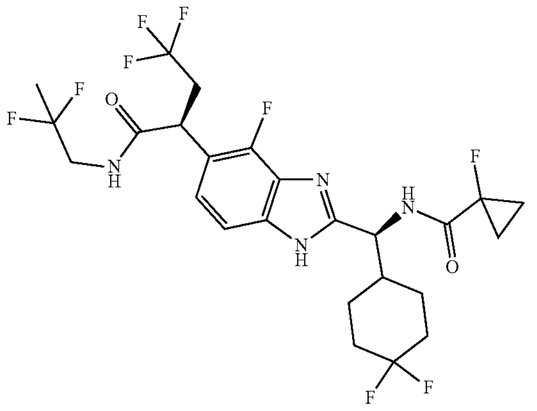

N—[(S)-(4,4-Difluorocyclohexyl){5-[(1R)-1-(2,2-difluoropropylcarbamoyl)-3,3,3-trifluoro-propyl]-4-fluoro-1H-benzimidazol-2-yl}methyl]-1-fluorocyclopropanecarboxamide N—[(S)-(4,4-Difluorocyclohexyl){5-[(1S)-1-(2,2-difluoropropylcarbamoyl)-3,3,3-trifluoro-propyl]-4-fluoro-1H-benzimidazol-2-yl}methyl]-1-fluorocyclopropanecarboxamide Example 82 (74 mg) was subjected to chiral purification (Method 39) to afford the title compounds (Peak 1, 27 mg, 36%; and Peak 2, 26 mg, 36%) as white solids.

Peak 1 (arbitrarily assigned R): NMR and LCMS retention times identical to those described for Example 82. Chiral LC (Method 40): RT 6.42 minutes, 100%.

Peak 2 (arbitrarily assigned S): NMR and LCMS retention times identical to those described for Example 82. Chiral LC (Method 40): RT 8.67 minutes, 100%.

Example 85

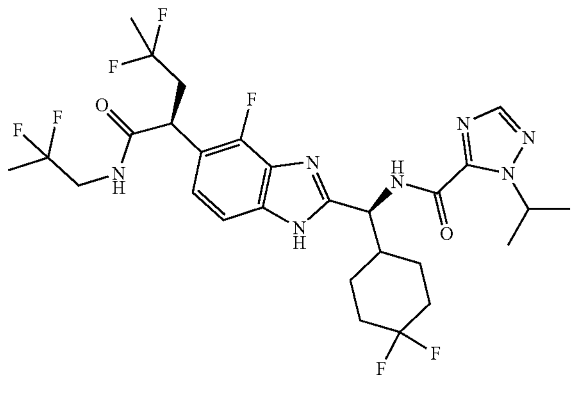 [SMILES: CC(C)n1ncnc1C(=O)N[C@H](c1nc2c(F)c([C@H](CC(C)(F)F)C(=O)NCC(C)(F)F)ccc2[nH]1)C1CCC(F)(F)CC1]

N—[(S)-(4,4-Difluorocyclohexyl){5-[1-(2,2-difluoropropylcarbamoyl)-3,3-difluorobutyl]-4-fluoro-1H-benzimidazol-2-yl}methyl]-2-isopropyl-1,2,4-triazole-3-carboxamide Into a vial were introduced Intermediate 148 (106 mg, 0.19 mmol), lithium 2-isopropyl-1,2,4-triazole-3-carboxylate (38 mg, 0.23 mmol), DIPEA (68 μL, 0.39 mmol) and DMF (2 mL) at r.t. under $N_2$, followed by HATU (89 mg, 0.23 mmol). The reaction mixture was stirred for 30 minutes, then diluted with EtOAc (6 mL) and washed sequentially with water (2 mL) and brine (2 mL). The combined organic layers were dried over $MgSO_4$, filtered and concentrated in vacuo. The residue was purified by preparative HPLC to give the title compound (69 mg, 55%) as a white solid. $\delta_H$ (400 MHz, DMSO-$d_6$) 13.14-12.46 (m, 1H), 9.17-8.90 (m, 1H), 8.62-8.43 (m, 1H), 8.12 (s, 1H), 7.52-7.03 (m, 2H), 5.65-5.42 (m, 1H), 5.17 (t, J 8.6 Hz, 1H), 4.34-4.17 (m, 1H), 3.55-3.41 (m, 2H), 2.98-2.75 (m, 1H), 2.30-2.11 (m, 2H), 2.11-1.87 (m, 3H), 1.87-1.67 (m, 2H), 1.66-1.47 (m, 4H), 1.47-1.35 (m, 9H), 1.35-1.20 (m, 2H). LCMS (Method 4): $[M+H]^+$ 634.3, RT 3.39 minutes.

Examples 86 & 87

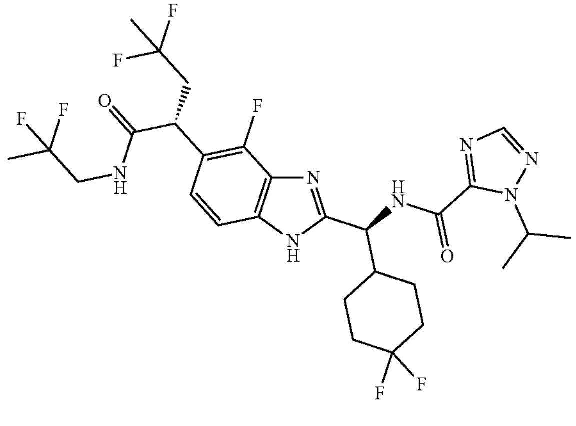

-continued

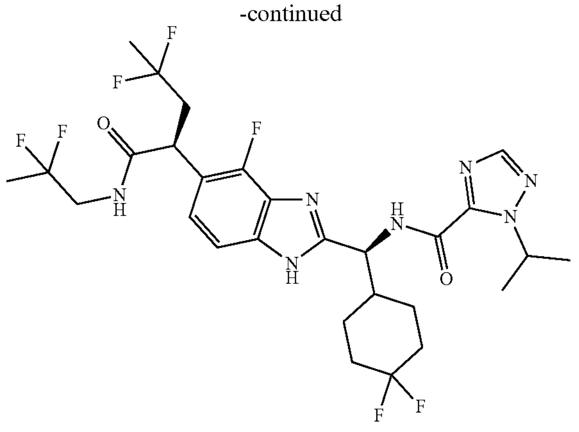

N—[(S)-(4,4-Difluorocyclohexyl){5-[(1R)-1-(2,2-difluoropropylcarbamoyl)-3,3-difluorobutyl]-4-fluoro-1H-benzimidazol-2-yl}methyl]-2-isopropyl-1,2,4-triazole-3-carboxamide N—[(S)-(4,4-Difluorocyclohexyl){5-[(1S)-1-(2,2-difluoropropylcarbamoyl)-3,3-difluorobutyl]-4-fluoro-1H-benzimidazol-2-yl}methyl]-2-isopropyl-1,2,4-triazole-3-carboxamide Example 85 (64 mg) was subjected to chiral purification (Method 33) to afford the title compounds (Peak 1, 20 mg, 31%; and Peak 2, 23 mg, 36%) as white solids.

Peak 1 (arbitrarily assigned R): NMR and LCMS retention times identical to those described for Example 85. Chiral LC (Method 41): RT 3.52 minutes, 100% d.e.

Peak 2 (arbitrarily assigned S): NMR and LCMS retention times identical to those described for Example 85. Chiral LC (Method 41): RT 6.78 minutes, 100% d.e.

The invention claimed is:

1. A compound of formula (IIA) or an N-oxide thereof, or a pharmaceutically acceptable salt thereof:

(IIA)

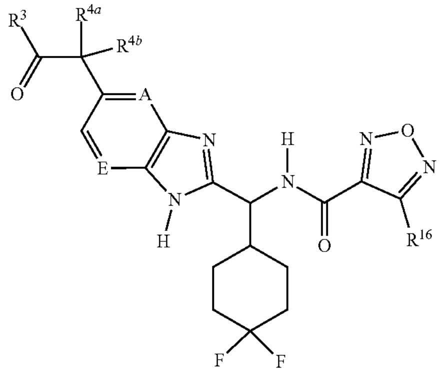

wherein

A represents C—$R^1$ or N;

E represents C—$R^2$ or N;

$R^1$ represents hydrogen or fluoro;

$R^2$ represents hydrogen or fluoro;

$R^3$ represents —$NR^{3a}R^{3b}$; or $R^3$ represents a group of formula (Wa):

(Wa)

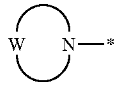

in which the asterisk (*) represents the point of attachment to the remainder of the molecule;

W represents the residue of an optionally substituted saturated monocyclic ring containing 3 to 6 carbon atoms, one nitrogen atom, and 0, 1, 2 or 3 additional heteroatoms independently selected from N, O and S, but containing no more than one O or S atom; or W represents the residue of an optionally substituted saturated bicyclic ring system containing 4 to 10 carbon atoms, one nitrogen atom, and 0, 1, 2 or 3 additional heteroatoms independently selected from N, O and S, but containing no more than one O or S atom; or W represents the residue of an optionally substituted saturated spirocyclic ring system containing 5 to 10 carbon atoms, one nitrogen atom, and 0, 1, 2 or 3 additional heteroatoms independently selected from N, O and S, but containing no more than one O or S atom;

$R^{3a}$ represents hydrogen or $C_{1-6}$ alkyl;

$R^{3b}$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^{4a}$ represents hydrogen, fluoro or hydroxy; or $R^{4a}$ represents $C_{1-6}$ alkyl, which group may be optionally substituted by one or more substituents; and $R^{4b}$ represents hydrogen, fluoro or $C_{1-6}$ alkyl; or $R^{4a}$ and $R^{4b}$, when taken together with the carbon atom to which they are both attached, represent $C_{3-9}$ cycloalkyl or $C_{3-7}$ heterocycloalkyl, either of which groups may be optionally substituted by one or more substituents; and $R^{16}$ represents methyl, ethyl, isopropyl or cyclopropyl.

2. A compound as claimed in claim 1 wherein $R^3$ represents —$NR^{3a}R^{3b}$; and $R^{3b}$ represents $C_{1-6}$ alkyl or $C_{3-7}$ cycloalkyl($C_{1-6}$)alkyl, either of which groups is optionally substituted by one or more substituents.

3. A compound as claimed in claim 1 wherein $R^3$ represents a group of formula (Wa), in which the group of formula (Wa) represents azetidin-1-yl or pyrrolidin-1-yl, either of which rings is optionally substituted by one or more substituents.

4. A compound as claimed in claim 1 wherein $R^{4a}$ represents $C_{1-6}$ alkyl, which group is optionally substituted by one, two or three substituents independently selected from halogen, $C_{1-6}$ alkoxy and $C_{1-6}$ alkylsulfonyl.

5. A compound as claimed in claim 1 wherein $R^{4a}$ and $R^{4b}$ together with the carbon atom to which they are both attached represent cyclobutyl, cyclohexyl, pyrrolidinyl, tetrahydropyranyl or piperidinyl, any of which groups is optionally substituted by one or more substituents.

6. A compound as claimed in claim 1 which is

Methyl (3S)-3-(2-{(S)-(4,4-difluorocyclohexyl)[(4-methyl-1,2,5-oxadiazole-3-carbonyl)-amino]methyl}-4-fluoro-1H-benzimidazol-5-yl)-3-(3,3,4,4-tetrafluoro-pyrrolidine-1-carbonyl)pyrrolidine-1-carboxylate;

Methyl (3R)-3-(2-{(S)-(4,4-difluorocyclohexyl)[(4-methyl-1,2,5-oxadiazole-3-carbonyl)-amino]methyl}-4-fluoro-1H-benzimidazol-5-yl)-3-(3,3,4,4-tetrafluoro-pyrrolidine-1-carbonyl)pyrrolidine-1-carboxylate;

N—[(S)-{5-[1-(3,3-Difluoroazetidine-1-carbonyl)-3,3-difluoropropyl]-4-fluoro-1H-benzimidazol-2-yl}(4,4-difluorocyclohexyl)methyl]-4-methyl-1,2,5-oxadiazole-3-carboxamide;

N—[(S)-{5-[(1S)-1-(3,3-Difluoroazetidine-1-carbonyl)-3,3-difluoropropyl]-4-fluoro-1H-benzimidazol-2-yl}(4,4-difluorocyclohexyl)methyl]-4-methyl-1,2,5-oxadiazole-3-carboxamide;

N—[(S)-{5-[(1R)-1-(3,3-Difluoroazetidine-1-carbonyl)-3,3-difluoropropyl]-4-fluoro-1H-benzimidazol-2-yl}(4,4-difluorocyclohexyl)methyl]-4-methyl-1,2,5-oxadiazole-3-carboxamide;

N—[(S)-{5-[1-(3,3-Difluoroazetidine-1-carbonyl)-3,3,3-trifluoropropyl]-4-fluoro-1H-benzimidazol-2-yl}(4,4-difluorocyclohexyl)methyl]-4-methyl-1,2,5-oxadiazole-3-carboxamide;

N—[(S)-(4,4-Difluorocyclohexyl){4-fluoro-5-[(1S)-3,3,3-trifluoro-1-{[(1R)-2-methyl-1-(methylcarbamoyl)propyl]carbamoyl}propyl]-1H-benzimidazol-2-yl}methyl]-4-methyl-1,2,5-oxadiazole-3-carboxamide;

N—[(S)-(4,4-Difluorocyclohexyl){4-fluoro-5-[(1R)-3,3,3-trifluoro-1-{[(1R)-2-methyl-1-(methylcarbamoyl)propyl]carbamoyl}propyl]-1H-benzimidazol-2-yl}methyl]-4-methyl-1,2,5-oxadiazole-3-carboxamide;

N—[(S)-(4,4-Difluorocyclohexyl){5-[(1S)-1-{[(1R)-1-(dimethylcarbamoyl)-2-methyl-propyl]carbamoyl}-3,3,3-trifluoropropyl]-4-fluoro-1H-benzimidazol-2-yl}methyl]-4-methyl-1,2,5-oxadiazole-3-carboxamide;

N—[(S)-(4,4-Difluorocyclohexyl)-{5-[(1R)-1-{[(1R)-1-(dimethylcarbamoyl)-2-methyl-propyl]carbamoyl}-3,3,3-trifluoro-propyl]-4-fluoro-1H-benzimidazol-2-yl}methyl]-4-methyl-1,2,5-oxadiazole-3-carboxamide;

N—[(S)-(4,4-Difluorocyclohexyl){4-fluoro-5-[3,3,3-trifluoro-1-(3,3,3-trifluoropropyl-carbamoyl)propyl]-1H-benzimidazol-2-yl}methyl]-4-methyl-1,2,5-oxadiazole-3-carboxamide;

N—[(S)-(4,4-Difluorocyclohexyl)(5-{1-[(2,2-difluorocyclopropyl)methylcarbamoyl]-3,3,3-trifluoropropyl}-4-fluoro-1H-benzimidazol-2-yl)methyl]-4-methyl-1,2,5-oxadiazole-3-carboxamide;

N—{(S)-(4,4-Difluorocyclohexyl)[4-fluoro-5-(3,3,3-trifluoro-1-{[(1S)-2,2,2-trifluoro-1-methylethyl]carbamoyl}propyl)-1H-benzimidazol-2-yl]methyl}-4-methyl-1,2,5-oxadiazole-3-carboxamide;

N—[(S)-{5-[4-(3,3-Difluoroazetidine-1-carbonyl)piperidin-4-yl]-4-fluoro-1H-benzimidazol-2-yl}(4,4-difluorocyclohexyl)methyl]-4-methyl-1,2,5-oxadiazole-3-carboxamide;

Methyl 4-(3,3-difluoroazetidine-1-carbonyl)-4-(2-{(S)-(4,4-difluorocyclohexyl)[(4-methyl-1,2,5-oxadiazole-3-carbonyl)amino]methyl}-4-fluoro-1H-benzimidazol-5-yl)-piperidine-1-carboxylate;

N—[(S)-(4,4-Difluorocyclohexyl){4-fluoro-5-[4-(3,3,4,4-tetrafluoropyrrolidine-1-carbonyl)tetrahydropyran-4-yl]-1H-benzimidazol-2-yl}methyl]-4-methyl-1,2,5-oxadiazole-3-carboxamide;

N—[(S)-{5-[1-(3,3-Difluoroazetidine-1-carbonyl)-4,4-difluorocyclohexyl]-4-fluoro-1H-benzimidazol-2-yl}(4,4-difluorocyclohexyl)methyl]-4-methyl-1,2,5-oxadiazole-3-carboxamide;

N—[(S)-(4,4-Difluorocyclohexyl)(5-{4-[(2,2-difluorocyclopropyl)methylcarbamoyl]-tetrahydropyran-4-yl}-1H-imidazo[4,5-b]pyridin-2-yl)methyl]-4-methyl-1,2,5-oxadiazole-3-carboxamide;

N—[(S)-(4,4-Difluorocyclohexyl){4-fluoro-5-[(1S)-3,3,3-trifluoro-1-{[(1S)-2,2,2-trifluoro-1-methylethyl]carbamoyl}propyl]-1H-benzimidazol-2-yl}methyl]-4-methyl-1,2,5-oxadiazole-3-carboxamide;

N—[(S)-(4,4-Difluorocyclohexyl){4-fluoro-5-[(1R)-3,3,3-trifluoro-1-{[(1S)-2,2,2-trifluoro-1-methylethyl]carbamoyl}propyl]-1H-benzimidazol-2-yl}methyl]-4-methyl-1,2,5-oxadiazole-3-carboxamide;

N—[(S)-(4,4-Difluorocyclohexyl){5-[3-(ethylsulfonyl)-1-(3,3,4,4-tetrafluoropyrrolidine-1-carbonyl)propyl]-4-fluoro-1H-benzimidazol-2-yl}methyl]-4-methyl-1,2,5-oxadiazole-3-carboxamide;

N—[(S)-(4,4-Difluorocyclohexyl){5-[(1S)-3-(ethylsulfonyl)-1-(3,3,4,4-tetrafluoro-pyrrolidine-1-carbonyl)propyl]-4-fluoro-1H-benzimidazol-2-yl}methyl]-4-methyl-1,2,5-oxadiazole-3-carboxamide;

N—[(S)-(4,4-Difluorocyclohexyl){5-[(1R)-3-(ethylsulfonyl)-1-(3,3,4,4-tetrafluoro-pyrrolidine-1-carbonyl)propyl]-4-fluoro-1H-benzimidazol-2-yl}methyl]-4-methyl-1,2,5-oxadiazole-3-carboxamide;

N—[(S)-(4,4-Difluorocyclohexyl){5-[3-(ethylsulfonyl)-1-(3,3,4,4-tetrafluoropyrrolidine-1-carbonyl)propyl]-4-fluoro-1H-benzimidazol-2-yl}methyl]-4-ethyl-1,2,5-oxadiazole-3-carboxamide;

N—[(S)-(4,4-Difluorocyclohexyl){5-[(1S)-3-(ethylsulfonyl)-1-(3,3,4,4-tetrafluoro-pyrrolidine-1-carbonyl)propyl]-4-fluoro-1H-benzimidazol-2-yl}methyl]-4-ethyl-1,2,5-oxadiazole-3-carboxamide;

N—[(S)-(4,4-Difluorocyclohexyl){5-[(1R)-3-(ethylsulfonyl)-1-(3,3,4,4-tetrafluoro-pyrrolidine-1-carbonyl)propyl]-4-fluoro-1H-benzimidazol-2-yl}methyl]-4-ethyl-1,2,5-oxadiazole-3-carboxamide;

N—[(S)-(4,4-Difluorocyclohexyl){4-fluoro-5-[3,3,3-trifluoro-1-(2,2,2-trifluoroethyl-carbamoyl)propyl]-1H-benzimidazol-2-yl}methyl]-4-methyl-1,2,5-oxadiazole-3-carboxamide;

N—[(S)-(4,4-Difluorocyclohexyl){4-fluoro-5-[(1S)-3,3,3-trifluoro-1-(2,2,2-trifluoroethyl-carbamoyl)propyl]-1H-benzimidazol-2-yl}methyl]-4-methyl-1,2,5-oxadiazole-3-carboxamide;

N—[(S)-(4,4-Difluorocyclohexyl){4-fluoro-5-[(1R)-3,3,3-trifluoro-1-(2,2,2-trifluoroethyl-carbamoyl)propyl]-1H-benzimidazol-2-yl}methyl]-4-methyl-1,2,5-oxadiazole-3-carboxamide;

N—[(S)-(4,4-Difluorocyclohexyl){5-[1-(2,2-difluoroethylcarbamoyl)-3,3,3-trifluoro-propyl]-4-fluoro-1H-benzimidazol-2-yl}methyl]-4-methyl-1,2,5-oxadiazole-3-carboxamide;

N—[(S)-(4,4-Difluorocyclohexyl){5-[(1S)-1-(2,2-difluoroethylcarbamoyl)-3,3,3-trifluoro-propyl]-4-fluoro-1H-benzimidazol-2-yl}methyl]-4-methyl-1,2,5-oxadiazole-3-carboxamide;

N—[(S)-(4,4-Difluorocyclohexyl){5-[(1R)-1-(2,2-difluoroethylcarbamoyl)-3,3,3-trifluoro-propyl]-4-fluoro-1H-benzimidazol-2-yl}methyl]-4-methyl-1,2,5-oxadiazole-3-carboxamide;

N—[(S)-(4,4-Difluorocyclohexyl){5-[4,4-difluoro-1-(2,2,2-trifluoroethylcarbamoyl)-cyclohexyl]-1H-imidazo[4,5-b]pyridin-2-yl}methyl]-4-methyl-1,2,5-oxadiazole-3-carboxamide monoformate salt;

N—[(S)-(4,4-Difluorocyclohexyl){5-[3,3-difluoro-1-(2,2,2-trifluoroethylcarbamoyl)-propyl]-4-fluoro-1H-benzimidazol-2-yl}methyl]-4-methyl-1,2,5-oxadiazole-3-carboxamide;

N—[(S)-(4,4-Difluorocyclohexyl){5-[(1S)-3,3-difluoro-1-(2,2,2-trifluoroethylcarbamoyl)-propyl]-4-fluoro-1H-benzimidazol-2-yl}methyl]-4-methyl-1,2,5-oxadiazole-3-carboxamide;

N—[(S)-(4,4-Difluorocyclohexyl){5-[(1R)-3,3-difluoro-1-(2,2,2-trifluoroethylcarbamoyl)-propyl]-4-fluoro-1H-benzimidazol-2-yl}methyl]-4-methyl-1,2,5-oxadiazole-3-carboxamide;

N—{(S)-(4,4-Difluorocyclohexyl)[5-(3,3-difluoro-1-{[(1S)-2,2,2-trifluoro-1-methylethyl]-carbamoyl}propyl)-4-fluoro-1H-benzimidazol-2-yl]methyl}-4-methyl-1,2,5-oxadiazole-3-carboxamide;

N—[(S)-(4,4-Difluorocyclohexyl){5-[(1S)-3,3-difluoro-1-{[(1S)-2,2,2-trifluoro-1-methylethyl]carbamoyl}propyl]-4-fluoro-1H-benzimidazol-2-yl}methyl]-4-methyl-1,2,5-oxadiazole-3-carboxamide;

N—[(S)-(4,4-Difluorocyclohexyl){5-[(1R)-3,3-difluoro-1-{[(1S)-2,2,2-trifluoro-1-methylethyl]carbamoyl}propyl]-4-fluoro-1H-benzimidazol-2-yl}methyl]-4-methyl-1,2,5-oxadiazole-3-carboxamide;

N—{(S)-(4,4-Difluorocyclohexyl)[5-(3,3-difluoro-1-{[(1R)-2,2,2-trifluoro-1-methylethyl]-carbamoyl}propyl)-4-fluoro-1H-benzimidazol-2-yl]methyl}-4-methyl-1,2,5-oxadiazole-3-carboxamide;

N—[(S)-(4,4-Difluorocyclohexyl){5-[(1S)-3,3-difluoro-1-{[(1R)-2,2,2-trifluoro-1-methylethyl]carbamoyl}propyl]-4-fluoro-1H-benzimidazol-2-yl}methyl]-4-methyl-1,2,5-oxadiazole-3-carboxamide;

N—[(S)-(4,4-Difluorocyclohexyl){5-[(1R)-3,3-difluoro-1-{[(1R)-2,2,2-trifluoro-1-methylethyl]carbamoyl}propyl]-4-fluoro-1H-benzimidazol-2-yl}methyl]-4-methyl-1,2,5-oxadiazole-3-carboxamide;

N—[(S)-(5-{1-[(1-Cyclopropyl-2,2,2-trifluoroethyl)carbamoyl]-3,3-difluoropropyl}-4-fluoro-1H-benzimidazol-2-yl)(4,4-difluorocyclohexyl)methyl]-4-methyl-1,2,5-oxadiazole-3-carboxamide;

4-Cyclopropyl-N—[(S)-(4,4-difluorocyclohexyl){5-[1-(2,2-difluoropropylcarbamoyl)-3,3-difluoropropyl]-4-fluoro-1H-benzimidazol-2-yl}methyl]-1,2,5-oxadiazole-3-carboxamide;

4-Cyclopropyl-N—[(S)-(4,4-difluorocyclohexyl){5-[(1R)-1-(2,2-difluoropropylcarbamoyl)-3,3-difluoropropyl]-4-fluoro-1H-benzimidazol-2-yl}methyl]-1,2,5-oxadiazole-3-carboxamide;

4-Cyclopropyl-N—[(S)-(4,4-difluorocyclohexyl){5-[(1S)-1-(2,2-difluoropropylcarbamoyl)-3,3-difluoropropyl]-4-fluoro-1H-benzimidazol-2-yl}methyl]-1,2,5-oxadiazole-3-carboxamide;

4-Cyclopropyl-N—[(S)-(4,4-difluorocyclohexyl)(4-fluoro-5-{3,3,3-trifluoro-1-[(2-fluoro-2-methylpropyl)carbamoyl]propyl}-1H-benzimidazol-2-yl)methyl]-1,2,5-oxadiazole-3-carboxamide;

4-Cyclopropyl-N—[(S)-(4,4-difluorocyclohexyl)(4-fluoro-5-{(1R)-3,3,3-trifluoro-1-[(2-fluoro-2-methylpropyl)carbamoyl]propyl}-1H-benzimidazol-2-yl)methyl]-1,2,5-oxadiazole-3-carboxamide;

4-Cyclopropyl-N—[(S)-(4,4-difluorocyclohexyl)(4-fluoro-5-{(1S)-3,3,3-trifluoro-1-[(2-fluoro-2-methylpropyl)carbamoyl]propyl}-1H-benzimidazol-2-yl)methyl]-1,2,5-oxadiazole-3-carboxamide;

4-Cyclopropyl-N—[(S)-(4,4-difluorocyclohexyl){5-[1-(2,2-difluoropropylcarbamoyl)-3,3,3-trifluoropropyl]-4-fluoro-1H-benzimidazol-2-yl}methyl]-1,2,5-oxadiazole-3-carboxamide;

4-Cyclopropyl-N—[(S)-(4,4-difluorocyclohexyl){5-[(1R)-1-(2,2-difluoropropylcarbamoyl)-3,3,3-trifluoropropyl]-4-fluoro-1H-benzimidazol-2-yl}methyl]-1,2,5-oxadiazole-3-carboxamide;

4-Cyclopropyl-N—[(S)-(4,4-difluorocyclohexyl){5-[(1S)-1-(2,2-difluoropropylcarbamoyl)-3,3,3-trifluoropropyl]-4-fluoro-1H-benzimidazol-2-yl}methyl]-1,2,5-oxadiazole-3-carboxamide;

4-Cyclopropyl-N—[(S)-(4,4-difluorocyclohexyl){4-fluoro-5-[1-(methoxymethyl)-2-oxo-2-(2,2,2-trifluoroethylamino)ethyl]-1H-benzimidazol-2-yl}methyl]-1,2,5-oxadiazole-3-carboxamide;

4-Cyclopropyl-N—[(S)-(4,4-difluorocyclohexyl){4-fluoro-5-[(1S)-1-(methoxymethyl)-2-oxo-2-(2,2,2-trifluoroethylamino)ethyl]-1H-benzimidazol-2-yl}methyl]-1,2,5-oxadiazole-3-carboxamide; or 4-Cyclopropyl-N—[(S)-(4,4-difluorocyclohexyl){4-fluoro-5-[(1R)-1-(methoxymethyl)-2-oxo-2-(2,2,2-trifluoroethylamino)ethyl]-1H-benzimidazol-2-yl}methyl]-1,2,5-oxadiazole-3-carboxamide.

7. A pharmaceutical composition comprising a compound of formula (I) as defined in claim 1 or an N-oxide thereof, or a pharmaceutically acceptable salt thereof, in association with a pharmaceutically acceptable carrier.

8. A pharmaceutical composition as claimed in claim 7 further comprising an additional pharmaceutically active ingredient.

9. A method for the treatment and/or prevention of an inflammatory or autoimmune disorder, which comprises administering to a patient in need of such treatment an effective amount of a compound of formula (I) as defined in claim 1 or an N-oxide thereof, or a pharmaceutically acceptable salt thereof.

* * * * *